(12) United States Patent
Brown et al.

(10) Patent No.: US 8,816,095 B2
(45) Date of Patent: Aug. 26, 2014

(54) NA CHANNELS, DISEASE, AND RELATED ASSAYS AND COMPOSITIONS

(75) Inventors: Milton L. Brown, Brookeville, MD (US); Scott Grindrod, Arlington, VA (US); Thomas H. Walls, Arlington, VA (US); Todd Hansen, Norfolk, VA (US); Simeng Suy, Fairfax, VA (US); Mikell A. Paige, Fairfax, VA (US)

(73) Assignee: Georgetown University, Washington, DC (US)

( * ) Notice: Subject to any disclaimer, the term of this patent is extended or adjusted under 35 U.S.C. 154(b) by 305 days.

(21) Appl. No.: 13/059,182

(22) PCT Filed: Aug. 17, 2009

(86) PCT No.: PCT/US2009/054079
§ 371 (c)(1),
(2), (4) Date: Jun. 8, 2011

(87) PCT Pub. No.: WO2010/019963
PCT Pub. Date: Feb. 18, 2010

(65) Prior Publication Data
US 2011/0230442 A1    Sep. 22, 2011

Related U.S. Application Data

(60) Provisional application No. 61/089,500, filed on Aug. 15, 2008.

(51) Int. Cl.
*C07D 233/76* (2006.01)
*A61K 31/69* (2006.01)

(52) U.S. Cl.
USPC ........ 548/319.1; 548/405; 548/507; 554/112; 564/112; 564/123; 514/64; 514/391

(58) Field of Classification Search
USPC ........ 554/112; 548/319.1, 405, 507; 564/112, 564/123; 514/64, 391
See application file for complete search history.

(56) References Cited

U.S. PATENT DOCUMENTS

| | | | |
|---|---|---|---|
| 3,610,795 A | 10/1969 | Metz |
| 5,084,824 A | 1/1992 | Lam |
| 5,135,917 A | 8/1992 | Burch |
| 5,288,514 A | 2/1994 | Ellman |
| 5,294,533 A | 3/1994 | Lupski |
| 5,449,754 A | 9/1995 | Nishioka |
| 5,476,766 A | 12/1995 | Gold |
| 5,503,978 A | 4/1996 | Schneider |
| 5,506,337 A | 4/1996 | Summerton |
| 5,539,083 A | 7/1996 | Cook |
| 5,545,568 A | 8/1996 | Ellman |
| 5,556,762 A | 9/1996 | Pinilla |
| 5,565,324 A | 10/1996 | Still |
| 5,565,332 A | 10/1996 | Hoogenboom |
| 5,573,905 A | 11/1996 | Lerner |
| 5,618,825 A | 4/1997 | Baldwin |
| 5,619,680 A | 4/1997 | Berkovich |
| 5,627,158 A | 5/1997 | Cho-Chung |
| 5,627,210 A | 5/1997 | Valerio |
| 5,631,146 A | 5/1997 | Szostak |
| 5,641,754 A | 6/1997 | Iversen |
| 5,646,042 A | 7/1997 | Stinchcomb |
| 5,646,285 A | 7/1997 | Baindur |
| 5,663,046 A | 9/1997 | Baldwin |
| 5,670,326 A | 9/1997 | Beutel |
| 5,677,195 A | 10/1997 | Winkler |
| 5,683,899 A | 11/1997 | Stuart |
| 5,688,696 A | 11/1997 | Lebl |
| 5,688,997 A | 11/1997 | Baldwin |
| 5,691,317 A | 11/1997 | Cho-Chung |
| 5,693,535 A | 12/1997 | Draper |
| 5,698,685 A | 12/1997 | Summerton |
| 5,712,146 A | 1/1998 | Khosla |
| 5,721,099 A | 2/1998 | Still |
| 5,723,598 A | 3/1998 | Lerner |
| 5,731,295 A | 3/1998 | Draper |
| 5,731,424 A | 3/1998 | Toothman |
| 5,741,713 A | 4/1998 | Brown |
| 5,780,228 A | 7/1998 | Parma |
| 5,780,607 A | 7/1998 | Goodnow, Jr. |
| 5,786,138 A | 7/1998 | Swenson |
| 5,792,431 A | 8/1998 | Moore |

(Continued)

OTHER PUBLICATIONS

Abrahmsen, et al., "Engineering subtilisin and its substrates for efficient ligation of peptide bonds in aqueous solution", Biochemistry, 30:4151-9 (1991).
Amaya, et al., "Diversity of expression of the sensory neuron-specific TTX-resistant voltage-gated sodium ion channels SNS and SNS2", Mol Cell Neurosci, 15:331-42 (2000).
Anderson, et al., "Voltage-gated sodium channel blockers as cytostatic inhibitors of the androgen-independent prostate cancer cell line PC-3", Mol Cancer Ther., 2:1149-54 (2003).
Anger, et al., "Medicinal Chemistry of Neuronal Voltage-Gated Sodium Channel Blockers", J. Med. Chem., 44:115-37 (2001).
Aronov, "Common pharmacophores for uncharged human ether-a-go-go-related gene (hERG) blockers", J Med Chem., 49(23):6917-21 (2006).

(Continued)

*Primary Examiner* — Shailendra Kumar
(74) *Attorney, Agent, or Firm* — Pabst Patent Group LLP

(57) ABSTRACT

Disclosed are molecules and their synthesis, for use in blocking gated ion channels such as voltage-gated sodium channels (VGSCs) and prostate voltage sodium channels (PVSCs). These inhibitors have superior blocking efficacy, for instance in displacing the radioligand [$^3$H]-Batrachotoxin-B ([$^3$H]-BTX-B) that binds to site 2 of a VGSC. The molecules of the invention comprise a moiety which increases the binding affinity of molecules for the protein binding site in prostate cancer cells (PCs), and which is also fluorescent. In one embodiment the invention molecules are an inhibition system that can be used to target over-abundant or hyperactive VGSCs selectively in pain, epilepsy or prostate cancer, inhibiting the proliferation of PCs. The fluorescent moiety also facilitates screening, tracking, and pharmacodynamic studies of the drug in a biological system both in vitro and in vivo.

21 Claims, 34 Drawing Sheets

(56) References Cited

U.S. PATENT DOCUMENTS

Figure 1:
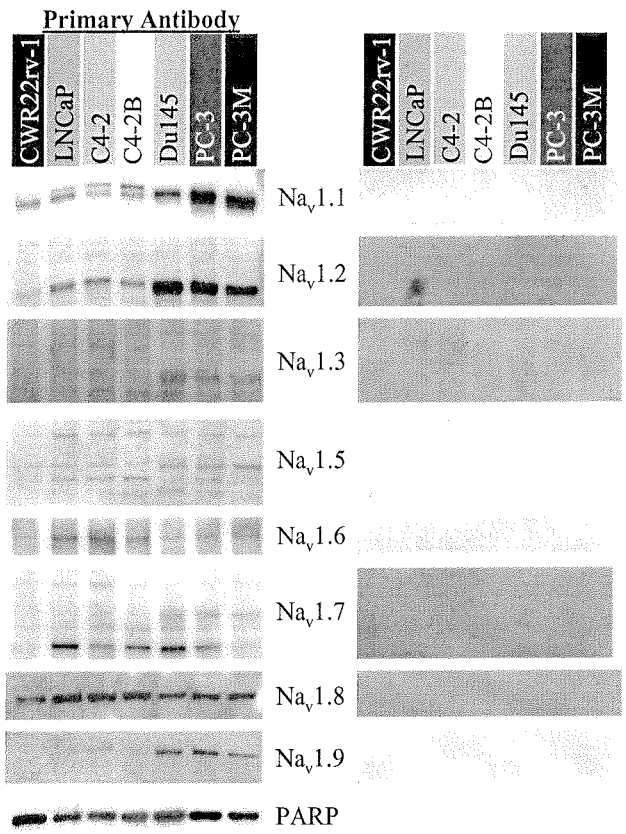

| | | |
|---|---|---|
| 5,792,613 A | 8/1998 | Schmidt |
| 5,795,721 A | 8/1998 | Rabin |
| 5,807,683 A | 9/1998 | Brenner |
| 5,807,754 A | 9/1998 | Zambias |
| 5,811,300 A | 9/1998 | Sullivan |
| 5,821,130 A | 10/1998 | Baldwin |
| 5,831,014 A | 11/1998 | Cook |
| 5,834,195 A | 11/1998 | Benkovic |
| 5,834,318 A | 11/1998 | Buettner |
| 5,834,588 A | 11/1998 | Wasserman |
| 5,837,855 A | 11/1998 | Chowrira |
| 5,840,500 A | 11/1998 | Pei |
| 5,846,713 A | 12/1998 | Pagratis |
| 5,847,150 A | 12/1998 | Dorwald |
| 5,849,903 A | 12/1998 | Pietrzkowski |
| 5,856,103 A | 1/1999 | Gray |
| 5,856,107 A | 1/1999 | Ostresh |
| 5,856,496 A | 1/1999 | Fagnola |
| 5,858,660 A | 1/1999 | Eaton |
| 5,859,190 A | 1/1999 | Meyer |
| 5,861,254 A | 1/1999 | Schneider |
| 5,864,010 A | 1/1999 | Cook |
| 5,864,026 A | 1/1999 | Jensen |
| 5,869,253 A | 2/1999 | Draper |
| 5,869,641 A | 2/1999 | Jayasena |
| 5,874,443 A | 2/1999 | Kiely |
| 5,877,021 A | 3/1999 | Stinchcomb |
| 5,877,022 A | 3/1999 | Stinchcomb |
| 5,877,214 A | 3/1999 | Kim |
| 5,880,972 A | 3/1999 | Horlbeck |
| 5,886,126 A | 3/1999 | Newkome |
| 5,886,127 A | 3/1999 | Newkome |
| 5,891,737 A | 4/1999 | Baindur |
| 5,916,899 A | 6/1999 | Kiely |
| 5,919,772 A | 7/1999 | Szyf |
| 5,919,955 A | 7/1999 | Fancelli |
| 5,925,527 A | 7/1999 | Hayes |
| 5,939,268 A | 8/1999 | Boger |
| 5,942,387 A | 8/1999 | Hollinshead |
| 5,945,070 A | 8/1999 | Kath |
| 5,948,696 A | 9/1999 | Dolle, III |
| 5,955,590 A | 9/1999 | Levina |
| 5,958,691 A | 9/1999 | Pieken |
| 5,958,702 A | 9/1999 | Benner |
| 5,958,792 A | 9/1999 | Desai |
| 5,962,337 A | 10/1999 | Ohlmeyer |
| 5,965,719 A | 10/1999 | Hindsgaul |
| 5,972,699 A | 10/1999 | Draper |
| 5,972,704 A | 10/1999 | Draper |
| 5,972,719 A | 10/1999 | Dolle, III |
| 5,976,894 A | 11/1999 | Dolle, III |
| 5,980,704 A | 11/1999 | Cherukuri |
| 5,985,356 A | 11/1999 | Schultz |
| 5,989,906 A | 11/1999 | Thompson |
| 5,990,088 A | 11/1999 | Ensoli |
| 5,994,320 A | 11/1999 | Low |
| 5,998,602 A | 12/1999 | Torrence |
| 5,999,086 A | 12/1999 | Ecker |
| 6,001,579 A | 12/1999 | Still |
| 6,001,988 A | 12/1999 | Parma |
| 6,004,617 A | 12/1999 | Schultz |
| 6,005,095 A | 12/1999 | Capaccioli |
| 6,007,995 A | 12/1999 | Baker |
| 6,008,321 A | 12/1999 | Li |
| 6,011,020 A | 1/2000 | Gold |
| 6,013,443 A | 1/2000 | Heilig |
| 6,013,522 A | 1/2000 | Monia |
| 6,017,756 A | 1/2000 | Draper |
| 6,017,768 A | 1/2000 | Baldwin |
| 6,017,898 A | 1/2000 | Pietrzkowski |
| 6,018,042 A | 1/2000 | Mett |
| 6,020,130 A | 2/2000 | Gold |
| 6,025,198 A | 2/2000 | Bennett |
| 6,025,371 A | 2/2000 | Gordeev |
| 6,028,186 A | 2/2000 | Tasset |
| 6,030,776 A | 2/2000 | Eaton |
| 6,030,917 A | 2/2000 | Weinberg |
| 6,033,910 A | 3/2000 | Monia |
| 6,040,193 A | 3/2000 | Winkler |
| 6,040,296 A | 3/2000 | Nyce |
| 6,045,671 A | 4/2000 | Wu |
| 6,045,755 A | 4/2000 | Lebl |
| 6,046,004 A | 4/2000 | Wu |
| 6,046,319 A | 4/2000 | Power |
| 6,051,698 A | 4/2000 | Janjic |
| 6,057,437 A | 5/2000 | Kamiya |
| 6,060,596 A | 5/2000 | Lerner |
| 6,061,636 A | 5/2000 | Horlbeck |
| 7,270,949 B2 | 9/2007 | Belardetti |
| 7,439,383 B2 * | 10/2008 | Brown ........................... 560/39 |
| 8,293,513 B2 * | 10/2012 | Brown et al. .................. 435/184 |
| 2005/0228033 A1 | 10/2005 | Brown |

OTHER PUBLICATIONS

Baggiolini, et al., "Interleukin-8, a chemotactic and inflammatory cytokine", FEBS Lett. 307:97-101 (1992).

Bagshawe, et al., "A cytotoxic agent can be generated selectively at cancer sites", Br, J. Cancer, 58:700-703 (1988).

Bagshawe, "The First Bagshawe lecture. Towards generating cytotoxic agents at cancer sites", Br. J. Cancer, 60:275-281 (1989).

Banidur, et al., "Selective fluorescent ligands for pharmacological receptors", Drug Dev. Res., 33:373-98 (1994).

Banerjee, et al, "Sulfonamide Drugs Binding to the Colchicine Site of Tubulin: Thermodynamic Analysis of the Drug-Tubulin Interactions by Isothermal Titration Calorimetry", J Med Chem., 48:547-55 (2005).

Battelli, et al., "T lymphocyte killing by a xanthine-oxidase-containing immunotoxin", Cancer Immunol.Immunother., 35:421-5 (1992).

Becher and Holland, et al., "Genetically engineered models have advantages over xenografts for preclinical studies", Cancer Res, 66:3355-9 (2006).

Bennet, et al., "Voltage-gated Na+ channels confer invasive properties on human prostate cancer cells", Pflugers Arch., 447:908-14 (2004).

Biton, "Clinical pharmacology and mechanism of action of zonisamide", Clin Neuropharm, 30:230 (2007).

Blay, et al., "Enantioselective synthesis of (S)-3-hydroxy-3-phenyl-3,4-dihydroquinolin-2(IH)-onering system", Synthesis, 1:108-12 (2007).

Blay, et al., "Enantioselective synthesis of 2-substituted-1,4-diketones from (S)-mandelic acid enolate and alpha ,beta-enones", Tetrahedron., 62:9174-82 (2006).

Brackenbury, et al., "An Emerging Role for Voltage-Gated Na+ Channels in Cellular Migration: Regulation of Central Nervous System Development and Potentiation of Invasive Cancers", The Neuroscientist,14:571-83 (2008).

Brackenbury and Djamgos, "Activity-dependent regulation of voltage-gated Na+ channel expression in Mat-LyLu rat prostate cancer cell line", J Physiol., 573:343-56 (2006).

Brackenbury and Djamgos, "Nerve growth factor enhances voltage-gated Na+ channel activity and Transwell migration in Mat-LyLu rat prostate cancer cell line", J Cell Physiol., 210:602-8 (2007).

Brown, et al., "Comparative molecular field analysis of hydantoin binding to the neuronal voltage-dependent sodium channel", J. Med. Chem., 42:1537-45 (1999).

Caine, et al., "Reactions of a 3(2H)-furanone lithium enolate with 4-halocrotonates", Synlett., 9:1391-4 (1999).

Catterall, "Molecular mechanisms of gating and drug block of sodium channels", Novartis Foundation Symposium, 241:206-25 (2002).

Cestèle and Catterall, "Molecular mechanisms of neurotoxin action on voltage-gated sodium channels", Biochimie., 82:883-92 (2000).

Choudhury-Mukherjee, et al., "Design, Synthesis, and Evaluation of Analogues of 3,3,3-Trifluoro-2-Hydroxy-2-Phenyl-Propionamide as Orally Available General Anesthetics", J Med Chem., 46:2495-2501(2003).

Clark-Lewis, et al, "Structural requirements for interleukin-8 function identified by design of analogs and CXC chemokine hybrids", J.Biol.Chem., 269:16075-81 (1994).

(56) References Cited

OTHER PUBLICATIONS

Clark-Lewis, et al., "Chemical synthesis, purification, and characterization of two inflammatory proteins, neutrophil activating peptide 1 (interleukin-8) and neutrophil activating peptide", Biochemistry, 30:3128-35 (1991).
Cohen, et al., "An artificial cell-cycle inhibitor isolated from a combinatorial library", PNAS, 95(24):14272-7 (1998).
Correa, et al., "Fluorescent Probes of o- and §-Biochemical and Histochemical Evaluation", Neurosci. Lett., 16:47-53 (1980).
Costa, et al., "Catalytic Asymmetric Synthesis of Homoallylic Alcohols", J Am Chem Soc. 115:7001 (1993).
Crane, et al., "Fluorescent Inhibitors for IspF, an Enzyme in the Non-Mevalonate Pathway for Isoprenoid Biosynthesis and a Potential Target for Antimalarial Therapy", Angew Chem. Int Ed, 45:1069-74 (2006).
Dawson, et al., "Synthesis of Proteins by Native Chemical Ligation", Science, 266:776-9 (1994).
deLisle, et al., "Techniques in Protein Chemistry", IV. Academic Press, New York, pp. 257-267 (1992).
Diss,, et al., "A potential novel marker for human prostate cancer: voltage-gated sodium channel expression in vivo", Prostate Cancer Prostatic Dis., 8:266-73 (2005).
Diss, et al.,"Expression profiles of voltage-gated Na+ channel—subunit genes in rat and human prostate cancer cell lines", Prostate, 48:165-78 (2001).
Djamgoz, et al., "Directional movement of rat prostate cancer cells in direct-current electric field: involvement of voltage-gated Na+ channel activity", J Cell Sci.,114:2697-705 (2001).
Drews, "Drug Discovery: a Historical Perspective", J Science, 287:1960-4 (2000).
Edwards, et al., "Structure and Biosynthesis of the Jamaicamides, New Mixed Polyketide-Peptide Neurotoxins from the Marine Cyanobacterium", *Lyngbya majuscula*. Chem. Biol., 11:817-33 (2004).
Felix, et al., "Functional Assay of Voltage-Gated Sodium Channels Using Membrane Potential-Sensitive Dyes", Assay and Drug Devel. Tech., 2:260-8 (2004).
Fraser, et al., "Effects of Voltage-Gated Ion Channel Modulators on Rat Prostatic Cancer Cell Proliferation: Comparison of Strongly and Weakly Metastatic Cell Lines", The Prostate, 44:61-76 (2000).
Fraser, et al., "Tetrodotoxin suppresses morphological enhancement of the metastatic MAT-LyLu rat prostate cancer cell line", Cell Tissue Res., 295:505-12 (1999).
Fraser,et al., "Contribution of functional voltage-gated Na+ channel expression to cell behaviors involved in the metastatic cascade in rat prostate cancer: I. lateral motility", J Cell Physiol., 195:479-87 (2003).
Fraser and Pardo, "Ion Channels: Functional Expression and Therapeutic Potential in Cancer", EMBO Reports, 9:512-5 (2008).
George, "Inherited disorders of voltage-gated sodium channels", J Clin. Invest.,115:I990-9 (2005).
Grimes, et al., "Differential expression of voltage-activated Na+ currents in two prostatic tumour cell lines: contribution to invasiveness in vitro", FEBS Lett., 369:290-4 (1995).
Grimes and Djamgos, "Electrophysiological Characterization of Voltage-Gated Na Current Expressed in the Highly Metastatic Mat-LyLu Cell Line of Rat Prostate Cancer", J. Cell. Physiol., 175:50-8 (1998).
Grimm, et al., "Design, Synthesis, and Development of Novel Caprolactam Anticonvulsants", Bioorg. Med Chrm., 11:4133-41 (2003).
Grover, et al., "Chiral mandelic acidvbTabtemplate provides a highly practical solution for (S)-oxybutynin synthesis", J Org Chem., 65:6283-7 (2000).
Gruzel, et al., "Carbonic Anhydrase Inhibitors. Interaction of 2-(hydrazinocarbonyl)-3-phenyl-IH-indole-5-sulfonamide with 12 Mammalian Isoforms: Kinetic and X-Ray Crystallographic Studies", Bioorg. Med Chem Lett., 18:152-8 (2008).
Haddad, et al., "Of Mice and (Wo)Men: Is This Any Way to Test a New", J Clin. Oncol. , 25:830-2 (2008).

Hammerer, et al., "Using prostate-specific antigen screening and nomograms to assess risk and predict outcomes in the management of prostate cancer", BJU Int., 98:11-9 (2006).
Haydon and Urban, "The Action of Alcohols and Other Non-Ionic Surface Active Substances on the Sodium Current of the Squid Giant Axon", Drug J Physiol, 341:411-27 (1983).
Hellerstedt and Pienta, "The current state of hormonal therapy for prostate cancer", CA Cancer J Clin., 52:154-79 (2002).
Hermetter, et al., "Powerful Probes for Glycosidases: Novel, Fluorescently Tagged Glycosidase Inhibitors", Bioorg. Med. Chem. Lett., 11:1339-42 (2001).
Hughes, et al., "Monoclonal antibody targeting of liposomes to mouse lung in vivo", Cancer Res, 49:6214-20, (1989).
Janout, et al al., "Molecular Umbrellas", J. Am. Chem. Soc., 118:1573-4 (1996).
Johnson, et al., "Relationships between drug activity in NCI preclinical in vitro and in vivo models and early clinical trials", British J of Cancer, 84:1424-31 (2001).
Ko, et al., "Reversal of neuropathic pain by alpha-hydroxyphenylamide: A novel sodium channel antagonist", Neuropharmacology., 50:865-73 (2006).
Kunkel, et al., "Rapid and efficient site-specific mutagenesis without phenotypic selection", Methods Enzymol., 154:367 (1987).
Laniado, et al., "Expression and functional analysis of voltage-activated Na+ channels in human prostate cancer cell lines and their contribution to invasion in vitro", Am J Pathol., 150:1213-21 (1997).
Lansdell, et al., "Design and Synthesis of Fluorescent SGLT2 Inhibitors", Bioorg. Med. Chem. Lett., 18:4944-7 (2008).
Lao, et al., "Adsorption of fluorescently labeled protein residues on poly(ethylene-co-acrylic acid) films modified with affinity functionalities", Colliods Surf B, 50:89-96 (2006).
Lavis and Raines, "Bright Ideas for Chemical Biology", ACS Chem. Biol., 3:142-55 (2008).
Lenkowski, et al., "A Pharmacophore Derived Phenytoin Analogue with Increased Affinity for Slow Inactiviated Sodium Channels Exhibits a Desired Anticonvulsant Profile", Neuropharmacology, 52:1044-54 (2007).
LePage, et al., "The neurotoxic lipopeptide kalkitoxin interacts with voltage-sensitive sodium channels in cerebellar granule neurons", Toxicol. Lett., 158:133-9 (2005).
Letsinger, et al., "Cholesteryl-conjugated oligonucleotides: synthesis, properties, and activity as inhibitors of replication of human immunodeficiency virus in cell culture", PNAS, 86:6553-6 (1989).
Li, et al., "Antillatoxin is a marine cyanobacterial toxin that potently activates voltage-gated sodium channels", PNAS, 98:7599-7604 (2001).
Li, et al., "A Stereoselective Synthesis of (4E,7S)-(-)-7-Methoxydodec-4-enoic Acid", Synlett., 320-324 (2006).
Li, et al., "Activation of signal transducer and activator of transcription 5 in human prostate cancer is associated with high histological grade", Cancer Res., 64:4774-82 (2004).
Linford, et al., "Interaction of batrachotoxin with the local anesthetic receptor site in transmembrane segment IVS6 of the voltage-gated sodium channel", PNAS, 95:13947-52 (1998).
Lipkind, et al., "Molecular modeling of local anesthetic drug binding by voltage-gated gated sodium channels", Mol Pharmacol, 68:1611-22 (2005).
Litzinger and Huang, "Biodistribution and immunotargetability of ganglioside-stabilized dioleoylphosphatidylethanolamine liposomes", Biochim Biophys Acta, 104:179-87, (1992).
Liu, et al., "Stereoselective synthesis of the optical isomers of a new muscarinic receptor antagonist, HL-031120", Synth Commun., 36 :1815-22 (2006).
Luo, et al., "Adsorption of Fluorescently Labeled Protein Residues on Poly (ethylene-co-acrylic acid) Films Modified with Affinity Functionalities", Colloids Surf. B., 50:89-96 (2006).
Mattei, et al., "Neurotoxins targetting receptor site 5 of voltage-dependent sodium channels increase the nodal volume of myelinated axons", J. Neurosci. Res., 55: 666-73 (1999).
McGrath, et al., "Do Fluorescent Drugs Show You More Than You Wanted to Know", Br. J Pharmacol., 139:187-9 (2003).

(56) References Cited

OTHER PUBLICATIONS

Misaki, et al., "Improved Practical Asymmetric Synthesis of alpha-Alkylmandelic Acids Utilizing Highly Diastereoselective Alkylation of 5-Aryl-2-(1-naphthyl)-1,3-dioxolan-4-ones", Org. Process Res Dev., 10:500-4 (2006).

Morris, et al., "Automated Docking Using a Lamarckian Genetic Algorithm and Empirical Binding Free Energy Function", J Computational Chem., 19:1639-62 (1998).

Mueller, et al., "Synthesis of (4E,7S)-(-)-methoxy-4-tetradecenoic acid, a major constituent of the marine cyanophyte Lyngbya majuscule", Liebigs Ann. Chem., 4:673-6 (1995).

Mycielska, et al., "Contribution of functional voltage-gated channel expression to cell behaviors involved in the metastatic cascade in rat prostate cancer: II. secretory membrane activity", J Cell Physiol. ,195:461-69 (2003).

Mycielska, et al., "Expression of Na+-dependent citrate transport in a strongly metastatic human prostate cancer PC-3M cell line: regulation by voltage-gated Na+ channel activity", J Physiol., 563:393-408 (2005).

Nagase, et al., "Practical and robust method for the preparation of Seebach and Frater's chiral template, cis-2-substituted 5-methyl(or phenyl)-1,3-dioxolan-4-ones", Synthesis, 22:3815-7 (2006).

Nau and Wang, "Interactions of Local Anesthetics with Voltage-Gated Na+ Channels", J. Membrane Biol., 201:1-8 (2004).

Palmer, et al., "Single Cell Adhesion Measuring Apparatus (SCAMA): Application to Cancer Cell Lines of Different Metastatic Potential and Voltage-Gated Na+ Channel Expression", Eur. Biophys J, 37:359-68 (2008).

Pietersz and McKenzie, "Antibody conjugates for the treatment of cancer", Immunolog. Reviews, 129:57-80, (1992).

Poupaert, et al., "Structure-Activity Relationships of Phenytoin-like Anticonvulsant Drugs", J Med. Chem., 27:76-8 (1989).

Preu At, "Expression of voltage-gated potassium channels Kv1.3 and Kv1.5 in human gliomas", Neurosci Lett., 346(1-2):33-6 (2003).

Ragsdale, et al., "Molecular Determinants of State-Dependent Block of Sodium Channels by Local Anesthetics", Science, 265:1724-28 (1994).

Rajarathnam, et al., "1H NMR studies of interleukin 8 analogs: characterization of the domains essential for function", Biochemistry, 33:6623-30 (1994).

Rizo and Gierasch, "Constrained peptides: models of bioactive peptides and protein substructures", Ann. Rev. Biochem., 61:387-418 (1992).

Roberts and Szostak, "RNA-peptide fusions for the in vitro selection of peptides and proteins", PNAS, 94(23)12997-302 (1997).

Roddam, et al., "Use of prostate-specific antigen (PSA) isoforms for the detection of prostate cancer in men with a PSA level of 2-10 ng/ml: systematic review and meta-analysis", Eur Urol, 48:386-99 (2005).

Roffler, et al., "Anti-neoplastic glucuronide prodrug treatment of human tumor cells targeted with a monoclonal antibody-enzyme conjugate", Biochem. Pharmacol, 42:2062-2 (1991).

Roger, et al., "Voltage-gated sodium channels: new targets in cancer therapy", Curr Pharm Des., 12:3681-95 (2006).

Roger, et al., "Voltage-Gated Sodium Channels Potentiate the Invasive Capacities of Human Non-Small-Cell Lung Cancer Cell Lines", Intl J Biochem Cell Biol., 39:774-86 (2007).

Sankaranarayanan, et al., "Convenient synthesis of (±): and (S)-antipode of (4E,7S)-7-methoxytetradec-4-enoic acid, the antimicrobial principle of marine cyanophyte", Tetrahedron Asymm., 7:2639-43 (1996).

Sausville, et al, "Contributions of Human Tumor Xenografts to Anticancer Drug Development", Cancer Res., 66:3351-4 (2006).

Schenck, et al., "Synthesis and Evaluation of Novel Hydroxyamides as Orally Available Anticonvulsants", Bioorg Med. Chem., 12:979-93 (2004).

Schnolzer, et al., "Constructing proteins by dovetailing unprotected synthetic peptides: backbone-engineered HIV protease", Science, 256:221-5 (1992).

Seebach, et al., "Self-Regeneration of Stereocenters (SRS) Applications, Limitations, and Abandonment of a Synthetic Principle", Angewandte Chemie Int Ed Engl., 23-24: 2708-48 (1996).

Senter, et al., "Generation of 5-fluorouracil from 5-fluorocytosine by monoclonal antibody-cytosine deaminase conjugates", Bioconju gate Chem., 2:447-51, (1991).

Senter, et al., "Generation of cytotoxic agents by targeted enzymes", Bioconjugate Chem., 4:3-9, (1993).

Shao, et al.. "Phenoxyphenyl Pyridines as Novel State-Dependent, High-Potency Sodium Channel Inhibitors", J Med. Chern., 4277-85 (2004).

Sharpless, et al., "The Mighty Mouse: Genetically EngineeredMouse Models in Cancer Drug Development", Nat Rev Drug Discov., 5:741-54 (2006).

Sikes, et al., "Therapeutic approaches targeting prostate cancer progression using novel voltage-gated ion channel blockers", Clin Prostate Cancer, 2:181-7 (2003).

Smith, et al., "Sodium channel protein expression enhances the invasiveness of rat and human prostate cancer cells", FEBS Lett, 423:19-24 (1998).

Szatkowski, et al., "Electrophysiological recordings from the rat prostate gland in vitro: identified single-cell and transepithelial (lumen) potentials", BJI Int., 86:1068-75 (2000).

Tan, et al., "Hermitamides A and B, Toxic Malyngamide-Type Natural Products from the Marine Cyanobacterium Lyngbya majuscule", J. Nat. Prod., 63:952-5 (2000).

The End of the Beginning?, no authors listed, Nat. Rev. Dru g. Discov., 5:705 (2006).

Toledo-Aral, et al., "Identification of PN1, a predominant voltage-dependent sodium channel expressed principally in peripheral neurons", PNAS , 94:1527-32 (1997).

Uysal-Onganer, et al., "Epidermal Growth Factor Potentiates /n vitro Metastatic Behaviour of Human Prostate Cancer PC-3M Cells: Involvement of Voltage-Gated Sodium Channel", Mol. Cancer, 6:76 (2007).

Virolleaud, et al., "Total and formal enantioselective synthesis of lyngbic acid and hermitamides A and B", Tetrahedron Lett., 47:5127-30 (2006).

Wang, et al., "Functional and pharmacological properties of canine ERC potassium channels", Am J. Physiol Heart Circ Physiol, 284:H256-H267 (2003).

Weber, et al., "Synthesis and Spectral Properties of a Hydrophobic Fluorescent Probe: 6-Propionyl-2-(dimethylamino)naphthalene", Biochemistry, 18:3074-78 (1979).

Yarov-Yarovoy, et al., "Molecular Determinants of Voltage-Dependent Gating and Binding of Pore-Blocking Drugs in Transmembrane Segment IIIS6 of the Sodium Channel o-Subunit", J Biol. Chem, 276:20-7 (2001).

Yarov-Yarovoy, et al., "The Role of Amino Acid Residues in Transmembrane Segments IS6 and IIS6 of the Sodium Channel o-Subunit in Voltage-Dependent Gating and Drug Block", J Biol. Chem, 277:35395-401 (2002).

Yu and Catterall, "Overview of the voltage-gated sodium channel family", Genome Biol., 4:207-14 (2003).

Zhang, et al., "A Genetic Mouse Model for Metastatic Lung Cancer with Gender Differences in Survival", Oncogene, 26:6896-6904 (2007).

* cited by examiner

Compounds were dosed ip once a day every other day for 26 days. Studies with N=6.

| VGSC | Channel I.D. | Former Name | Pharmacology | %mRNA Expression | |
|---|---|---|---|---|---|
| | | | | PC-3 | LNCaP |
| SCN1A | Nav1.1 | Brain type 1 | TTX-s | - | - |
| SCN2A | Nav1.2 | Brain type 2 | TTX-s | 11 ± 5 | 11 ± 7 |
| SCN3A | Nav1.3 | Brain type 3 | TTX-s | 1 ± 1 | 1 ± 1 |
| SCN4A | Nav1.4 | SkM1 | TTX-s | - | - |
| SCN5A | Nav1.5 | Cardiac | TTX-r | ND | ND |
| SCN8A | Nav1.6 | NaCh6 | TTX-s | - | 47 ± 15 |
| SCN9A | Nav1.7 | Neonatal | TTX-s | 41 ± 5 | - |
| SCN10A | Nav1.8 | SNS/PN3 | TTX-r | ND | ND |
| SCN11A | Nav1.9 | - | TTX-r | - | - |
| SCN6A SCN7A | Nax | NaG hNav2.1 | ? | - | 10 ± 7 |
| Non-NSVC | ? | ? | TTX-r | 2 ± 2 | 41 ± 7 |

Figure 27

| | $R_1$ | $R_2$ | $R_3$ | n | $^3$H-BTX $IC_{50}$ ($\mu$M) |
|---|---|---|---|---|---|
| 1 | $CH_3CH_2CH_2$ | H | H | | 162 |
| 2 | $CH_3(CH_2)_2CH_2$ | H | H | | 103 |
| 3 | $CH_3(CH_2)_2CH_2$ | H | $CH_3$ | | 285 |
| 4 | $CH_3(CH_2)_3CH_2$ | H | H | | 39 |
| 5 | $CH_3(CH_2)_4CH_2$ | H | H | | 13 |
| 6 | $CH_3(CH_2)_5CH_2$ | H | H | | 5 |
| 7 | $CH_3(CH_2)_7CH_2$ | H | H | | 5 |
| 8 | $CH_3$ | $CH_3CH_2$ | H | | 720 |
| DPH | Phenyl | H | H | | 40 |
| 9 | | | | 1 | 2112 |
| 10 | | | | 2 | 851 |
| 11 | | | | 3 | 251 |
| 12 | | | | 4 | 251 |
| 13 | | | | | 250 |

Figure 30

| compd | R₁ | R₂ | R₃ | R₄ | energy | NVSC -log IC₅₀ | | |
|---|---|---|---|---|---|---|---|---|
| | | | | | | obsd | pred | res |
| 14a | Butyl | Methyl | H | H | 10.8 | -2.35 | -2.27 | -0.08 |
| 14b | Butyl | Methyl | H | H | 12.4 | -2.35 | -2.37 | 0.02 |
| 15 | Butyl | H | Methyl | H | 8.2 | -1.76 | -2.03 | 0.26 |
| 16 | Butyl | H | H | Methyl | | -1.98 | -2.03 | 0.05 |
| 17 | Cyclohexyl | H | H | H | | -1.76 | -1.89 | 0.13 |
| 18a | | | | | 40.4 | -2.85 | -3.11 | 0.26 |
| 18b | | | | | 39.1 | -2.85 | -2.92 | 0.07 |
| 19a | | | | | 27 | -2.63 | 2.72 | 0.09 |
| 19b | | | | | 26.3 | | | |
| 20 | | | | | | -2.12 | -2.10 | -0.02 |

| | hNa$_v$1.7 IC$_{50}$ μM | hNa$_v$1.8 IC$_{50}$ μM | hNa$_v$1.5 IC$_{50}$ μM | L-type Ca$_v$1.2 IC$_{50}$ μM$^a$ | N-type Ca$_v$2.2 IC$_{50}$ μM | hERG IC$_{50}$ μM$^b$ |
|---|---|---|---|---|---|---|
| ICM-I-136 | 1.81 | 1.60 | 5.78 | 8.08 | 5.0 | 10 |
| Phenytoin | >100 | >100 | >100 | >20 | | >30 |

All Compounds @ 40μM

All Compounds @ 40μM

| Compound | $h\mathrm{Na}_v1.8$ $\mathrm{IC}_{50}$ µM |
|---|---|
| ICM-I-136 | 2.21 |
| (−)-ICM-I-136 | 1.87 |
| (+)-ICM-I-136 | 4.1 |

ICM-I-136

| Dose (mg/kg)[b] | Time (hours) | | | |
|---|---|---|---|---|
| | 0.25 | 0.5 | 1.0 | 4.0 |
| 30 | - | 0/4 | - | 0/2 |
| 100 | 0/4[a] | 1/8 | 1/8 | 0/4 |
| 300 | - | 3/4 | - | 0/2 |

NA CHANNELS, DISEASE, AND RELATED ASSAYS AND COMPOSITIONS

This application is a national phase filing under 35 U.S.C. §371 of PCT/US2009/054079 filed under the Patent Cooperation Treaty on Aug. 17, 2009, which claims the benefit of U.S. Provisional Application No. 61/089,500, filed on Aug. 15, 2008, the contents of each being hereby incorporated by reference in their entirety.

I. FEDERAL RIGHTS

This invention was developed using funds from federal NIH-R01 grant CA105534-04, 7CA105435 and NIH grant nos. NIH-R01 grant CA105534-04.

II. BACKGROUND

Hyperexcited neuronal voltage-gated sodium channels (VGSCs) play an integral role in seizure activity, a characteristic symptom of epilepsy. Neuronal VGSCs are heterotrimeric transmembrane proteins that allow sodium ions to permeate through the cell membrane in order to rapidly depolarize local electric fields (i.e., action potentials) across cardiac, neuronal, and skeletal-muscular cell membranes. (Lenkowski, P. W. et al. *Neuropharmacology*, 2007, 52, 1044-1054 and Lenkowski, P. W. et al. *Eur. J. Pharm. Sci.*, 2004, 21, 635-644).

Neuronal VGSCs exist in three distinct states: active, resting, and inactive. They can be blocked therapeutically in a state-dependent way to treat epilepsy. (Yu, F. H. and Catterall, W. A. *Genome Biology*, 2003, 4, 207, and Brown, M. L. et al. *J. Med. Chem.* 1999, 42, 1537-1545). Diphenylhydantoin (DPH) also known as phenyloin was a first-generation antiepileptic drug (AED) developed in 1938, and continues to serve a major role in treating epilepsy. (Scott, D. F. *J. Hist. Neurosci.*, 1992, 1, 111-118). DPH has shown inactivated state-dependent blocking activity ($IC_{50}$ 40 μM) in neuronal VGSCs. (Brown, M. L. et al. *J. Med. Chem.* 1997, 40, 602-607).

VGSCs are now known to have a much broader role in human health and disease. They are found most prominently in excitable tissues such as brain, heart, and skeletal muscle but have also been found in non-excitable prostate cancer (PCa) epithelial tissue. (Sikes, R. A, et al., *Clinical Prostate Cancer.* 2003, 2, 181-187; Fraser, S. P., et al., *The Prostate*, 2000, 44, 61-76; Shao, B., et al., *J Med. Chem.* 2004, 47, 4277-4285; and Poupaert, J. R., et al., *J Med. Chem.* 1989, 27, 76-78). Although the exact purpose of VGSC expression in prostate epithelial tissue is unknown, VGSC upregulation has been linked to prostate adenocarcinoma invasiveness and metastatic potential. (Anderson, J. D., et al., *Mol. Cancer. Ther.* 2003, 2, 1149-1154).

In addition, the role of ion channels in cancer is an emerging field. Recent studies have demonstrated that voltage-gated ion channels could play a role in the onset, proliferation and malignant progression of various types of cancer, such as prostate, colon, and glioma. (Anderson, James D. Mol Cancer Ther. 2003 November; 2(11):1149-54; Laniado, Marc E. Prostate. 2001 Mar. 1; 46(4):262-74; 154 Preussat, Katja Neurosci Lett. 2003 Jul. 31; 346(1-2):33-6; 155. Wang, Xi-Tao 2000) Specifically, the voltage-gated sodium channel has been shown to play a role in cancer cell proliferation, migration, and adhesion. (Smith, P FEBS Lett. 1998, 423, 19-24. However, the signaling pathways involved in cancer progression are yet to be elucidated. (Fiske, Jamie L. Cancer Metastasis Rev. 2006 September; 25(3):493-500)

Thus VGSC's are attractive targets for drug design, and their structure and interactions have been studied in detail. More specifically, VGSCs are heterotrimeric transmembrane are composed of a large pore-forming α-subunit (260 kDa) that participates in cell-cell interactions, and auxiliary β-subunits. (Catterall, William Neuron. 2000 April; 26(1):13-25). The α-subunit is further divided into four homologous domains (I to IV) containing six transmembrane α-helices (S1-S6); the S4 segments serve as voltage sensors which move outward in the form of a sliding helix to initiate activation of the channel (Catterall, W. A, *Novartis Foundation Symposium*, 2002, 241, 206-225). To date, nine α-subunit isoforms have been cloned along with four auxiliary β-subunit isoforms. (Goldin, A. L. Annu Rev Physiol. 2001; 63:871-94) These nine sodium channel isoforms are classified by their sensitivity to the neurotoxin tetrodotoxin (TTX). There are six TTX-sensitive isoforms: Nav1.1, Nav1.2, Nav1.3, Nav1.4, Nav1.6 and Nav1.7; and three TTX-resistant isoforms: Nav1.5, Nav1.8, and Nav1.9. (Baker M D. Trends Pharmacol. Sci. 2001, 22, 27-31)

Pharmacological modulation of voltage-gate sodium channels has proven clinically beneficial for the treatment of pain, epilepsy, depression, and cardiac arrhythmias. (Baker M D. Trends Pharmacol. Sci. 2001, 22, 27-3). Local anesthetics, antiarrhythmics, and anticonvulsants are known to act at the batrachotoxin (BTX) binding site located in S6 of domains I, III and IV. (Correa, F. M. A, et al., *Neurosci. Lett.* 1980, 16, 47-53). Compounds known to bind to the BTX site cause persistent inactivation of the VGSC, which has been measured by voltage (patch) clamp assays. (Sikes, R. A, Walls, A M., Brennen, W. N., Anderson, J. D., Choudhury-Mukherjee, I. Schenck, H. A, and Brown, M. L. Therapeutic Approaches Targeting Prostate Cancer Progression Using Novel Voltage-Gated Ion Channel Blockers. *Clinical Prostate Cancer.* 2003, 2, 181-187.) Fraser, S. P., Grimes, J. A and Djamgos, M. B. A Effects of Voltage-Gated Ion Channel Modulators on Rat Prostatic Cancer Cell Proliferation: Comparison of Strongly and Weakly Metastatic Cell Lines. *The Prostate*, 2000, 44, 61-76. Shao, B., Victory, S., Ilyin, V. I., Goehring, R. R., Sun, Q., Hogenkamp, D., Hodges, D. O., Islam, K., Sha, D., Zhang, C., Nguyen, P., Robledo, S., Sakellaropoulos, G., and Carter, R. B. Phenoxyphenyl Pyridines as Novel State-Dependent, High-Potency Sodium Channel Inhibitors. *J Med. Chem.* 2004, 47, 4277-4285. Poupaert, J. R, Vandervorst, D., Guiot, P., Moustafa, M. M. M., and Dumont, P. Structure-Activity Relationships of Phenyloin-like Anticonvulsant Drugs. *J Med. Chem.* 1989, 27, 76-78. Anderson, J. D., Hansen, T. P., Lenkowski, P. W., Walls, A M., Choudhury, I. M., Schenck, R A, Friehling, M., Holl, G. M., Patel, M. K., Sikes, R A, and Brown, M. L. Voltage-Gated Sodium Channel Blockers as Cytostatic Inhibitors of the Androgen-Independent Prostate Cancer Cell Line PC-3. *Mol. Cancer. Ther.* 2003, 2, 1149-1154).

However to date the efficacy of drugs in blocking VGSCs has not exceeded the level attained with DPH 70 years ago. Moreover it has been difficult to assess the activity of AEDs and VGSC-targeting drugs in general following administration. Thus it is an objective of this invention to provide compounds with improved efficacy for blocking targeted VGSC states, and with improved capacity for assessment of activity. However to date the efficacy of drugs in blocking VGSCs has not exceeded the level attained with DPH 70 years ago. Moreover it has been difficult to assess the activity of AEDs and VGSC-targeting drugs in general following administration. Thus it is an objective of this invention to provide compounds with improved efficacy for blocking targeted VGSC states, and with improved capacity for assessment of activity.

III. SUMMARY

Disclosed are methods and compositions related to Sodium channels, their use and activities and molecules that bind them, as well as molecules that interact with protein kinases.

IV. BRIEF DESCRIPTION OF THE DRAWINGS

The accompanying drawings, which are incorporated in and constitute a part of this specification, illustrate several embodiments and together with the description illustrate the disclosed compositions and methods.

FIG. 1. Sodium Channel Isotype Expression in Human Prostate Cancer Cell Lines. Nav1.1, 1.2, and 1.8 are ubiquitous. Nav1.1, 1.2 and 1.9 expression level increases in highly metastatic PCaNav.1.6, and 1.8 have steady levels. Nav1.7 decreases its expression level with progression and metastatic potential.

Figure 2:
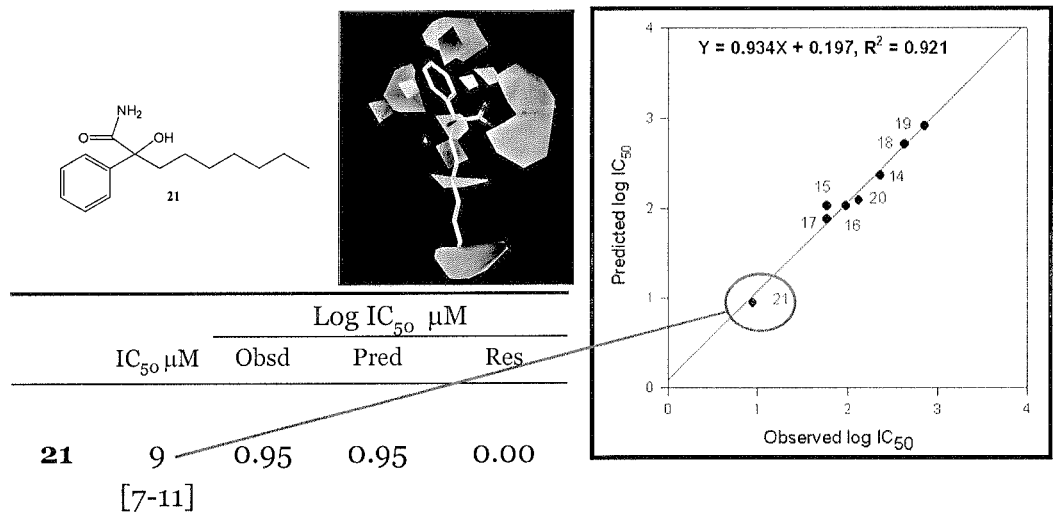

FIG. 2. Comparative Molecular Field Analysis (CoMFA) test set indicating the lead compound.

Figure 3:
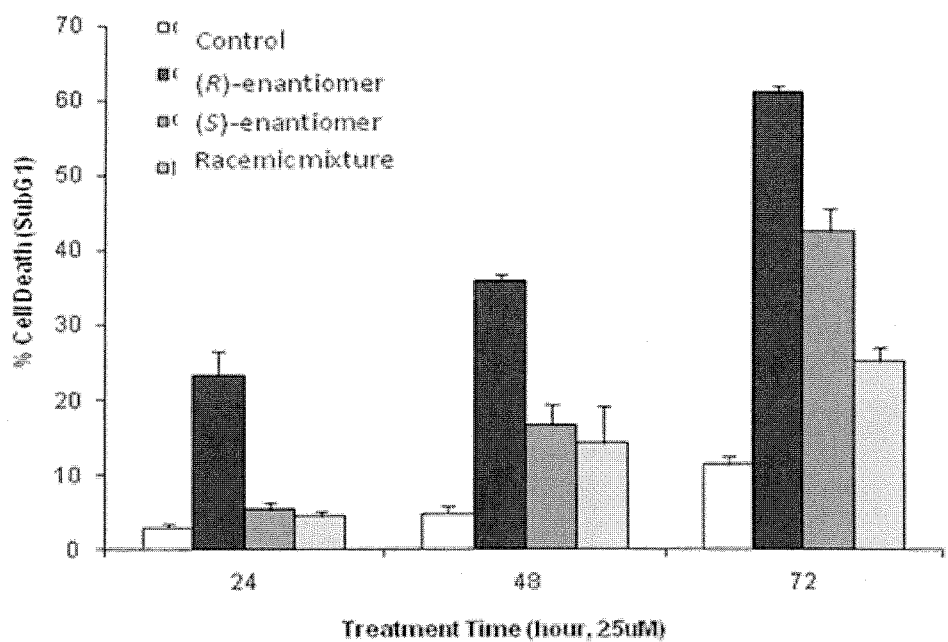

FIG. 3. (R)-(−)-2-(3-chloro-phenyl)-2-hydroxy-nonanoic acid amide induces cell death at 25 μM after 24 hrs.

Figure 4:
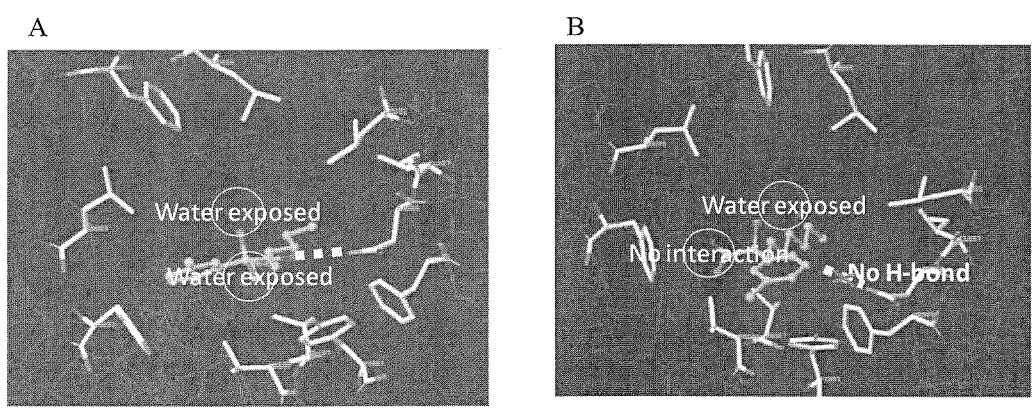

FIG. 4. A. Proposed binding model for the (R)-enantiomer of 2-(3-chloro-phenyl)-2-hydroxy-nonanoic acid amide. B. Proposed binding model for the (S)-enantiomer of 2-(3-chloro-phenyl)-2-hydroxy-nonanoic acid amide.

Figure 5:
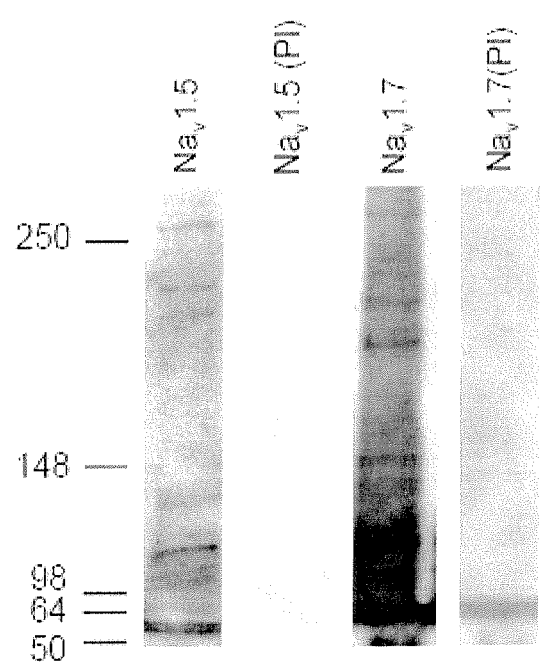

FIG. 5. Western blot analysis showing up-regulation of $Na_v1.5$ and $Na_v1.7$ in CWR22rv-1 prostate cancer cell lines.

Figure 6:
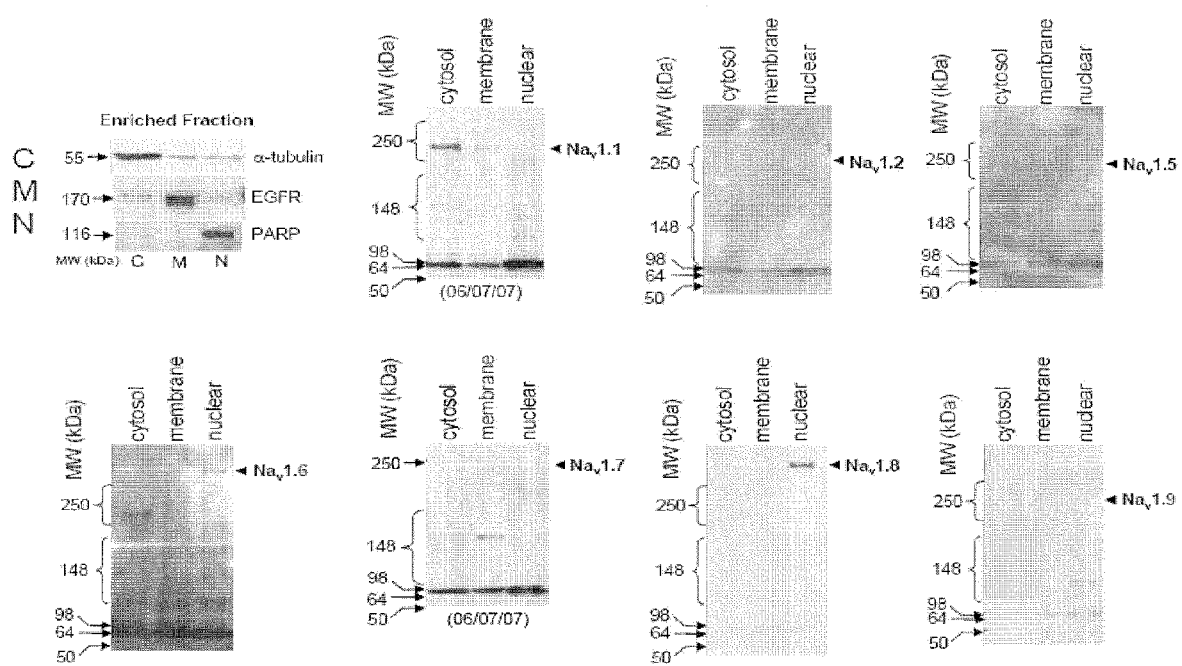

FIG. 6. Sodium Channel Localization: C4-2 Cell Fractionation

Figure 7:
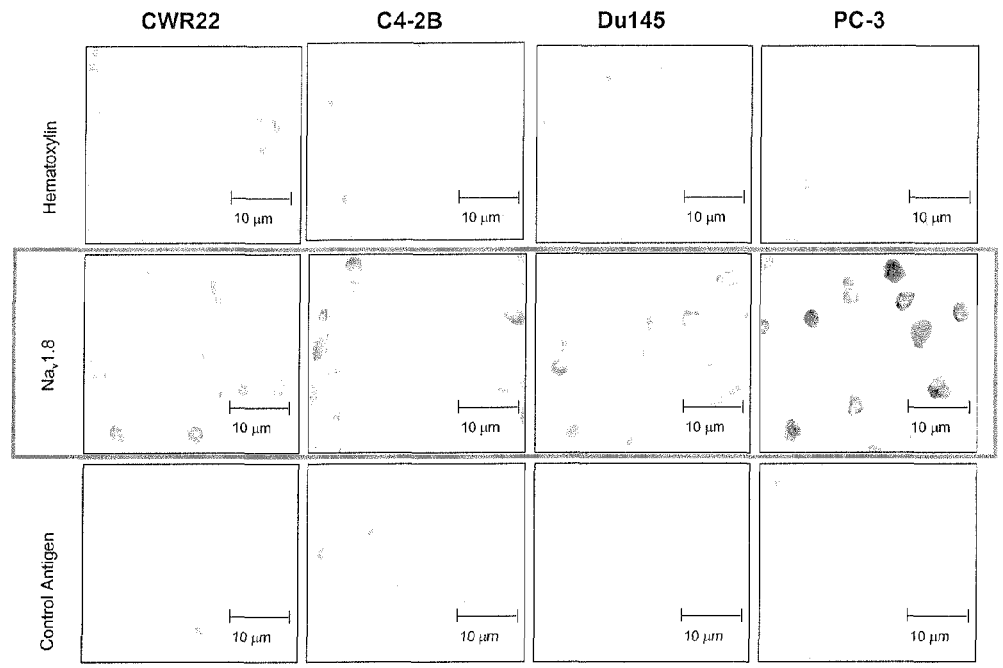

FIG. 7. Immunohistochemistry of Human Prostate Cell Lines

Figure 8:
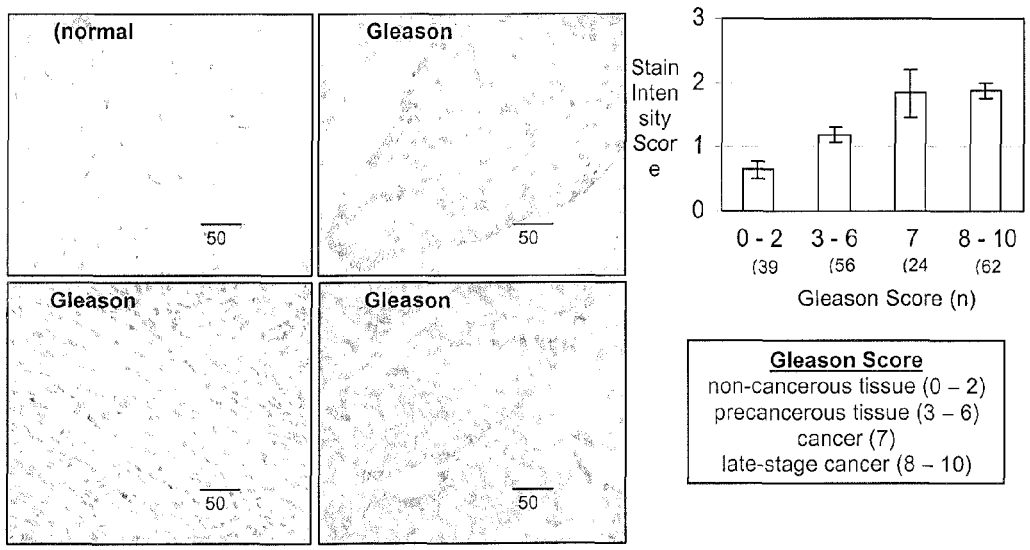

FIG. 8. Nav1.8 Expression in Human Prostate Cancer Increases with Gleason Score

Figure 9:
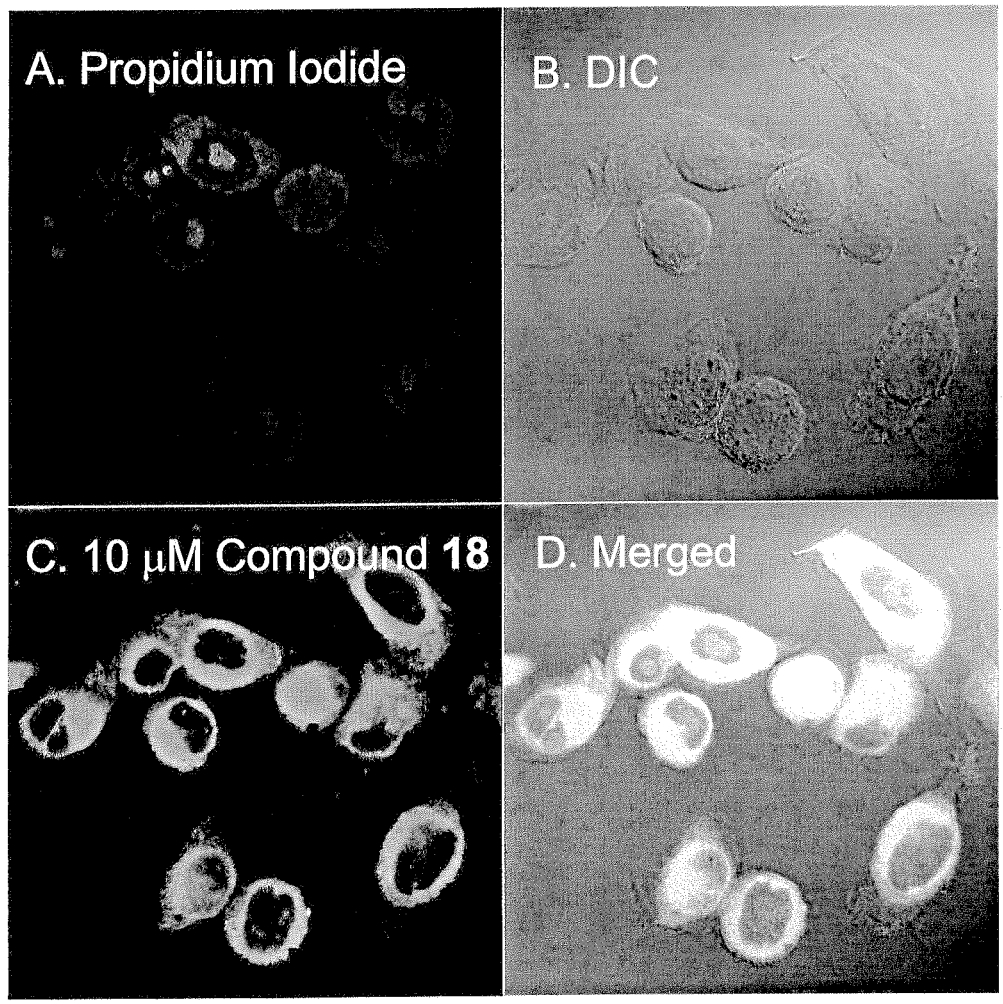

FIG. 9. PC-3 Cells were treated with CDPNS at 10 μM for 6 hours. The red staining is the result of propidium iodide and the green staining is the result of CDPNS.

Figure 10:
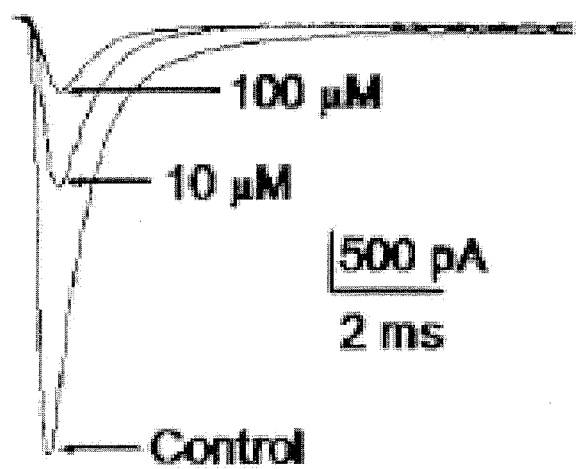

FIG. 10. CDPNS inhibition of sodium channel currents, assessed at 10 and 100 μM against human $Na_v1.2$ by patch clamp assay.

Figure 11:
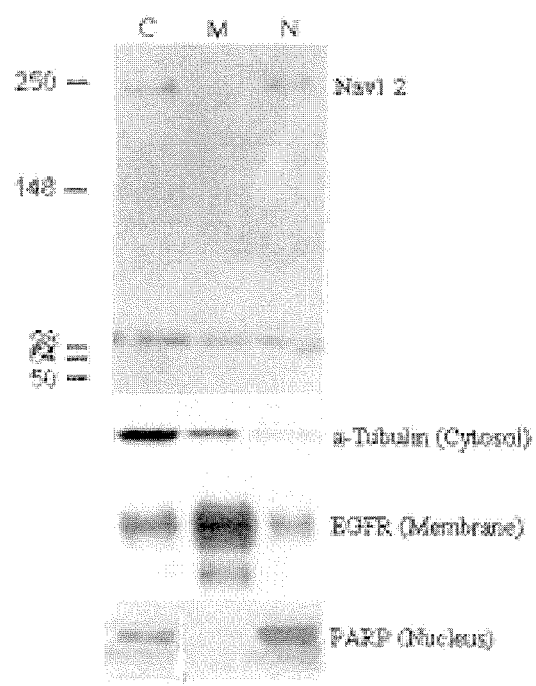

FIG. 11. Cell fraction studies of PC-3 cells. C indicates the cytoplasm, M indicates the plasma membrane, and N refers to the nuclear membrane.

Figure 12:
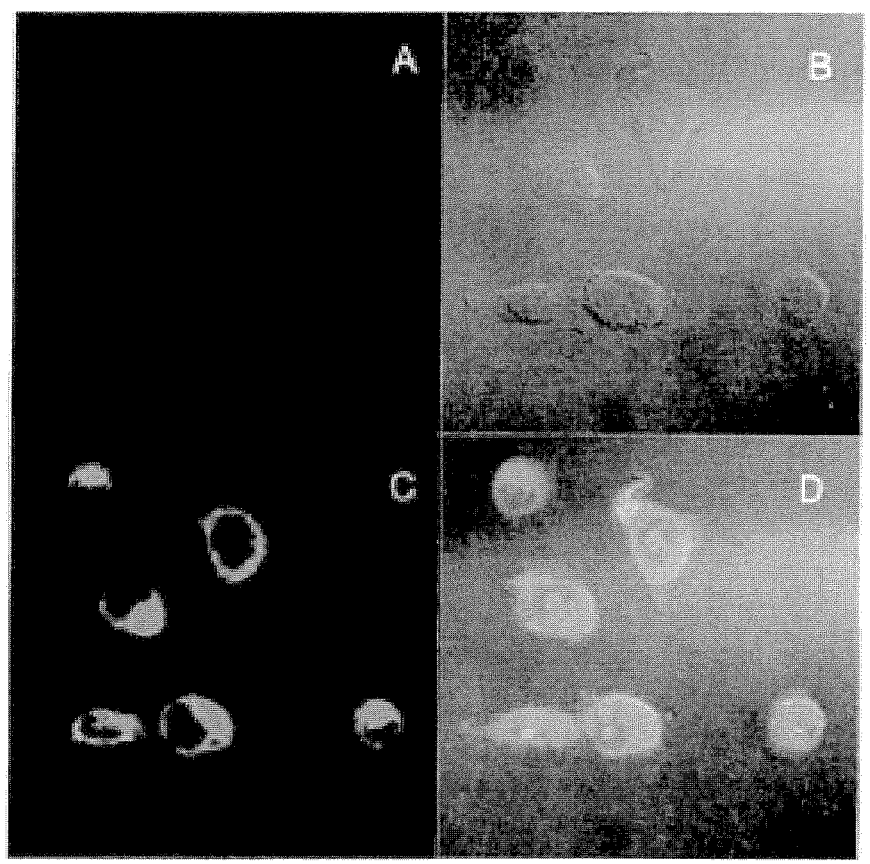

FIG. 12. Two photon confocal microscopic images for CDPNS in PC-3 cells. Stained cells were excited at 720 nm. A Propidium iodine stain. B. DCI. C. CDPNS. D. Images overlaid. PC-3 cells were treated with a 10 μM solution of CDPNS for 6 hrs.

Figure 13:
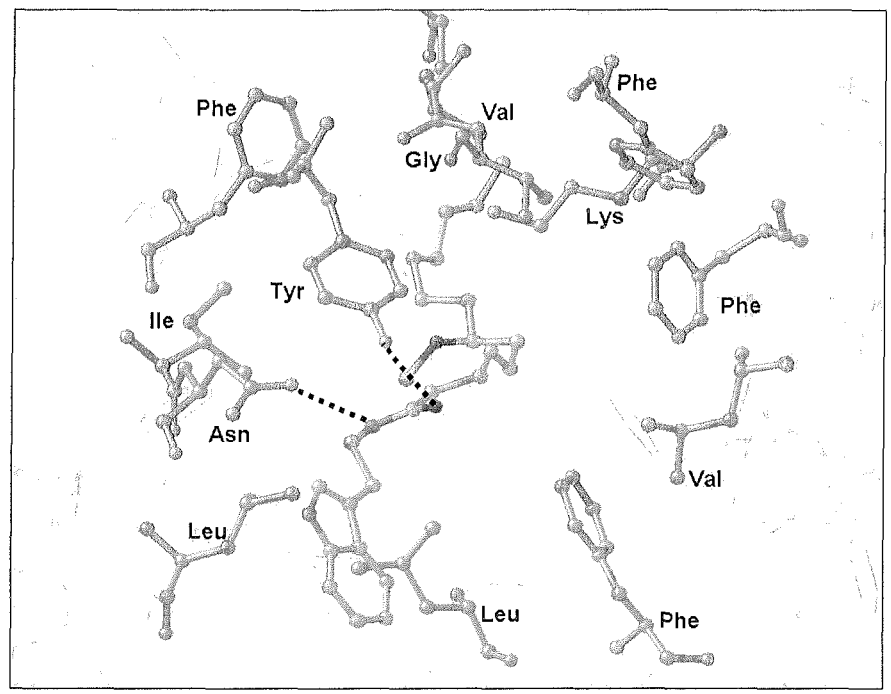

FIG. 13. Model of (S)-Hermitamide B in the BTX binding pocket of the sodium channel.

Figure 14:
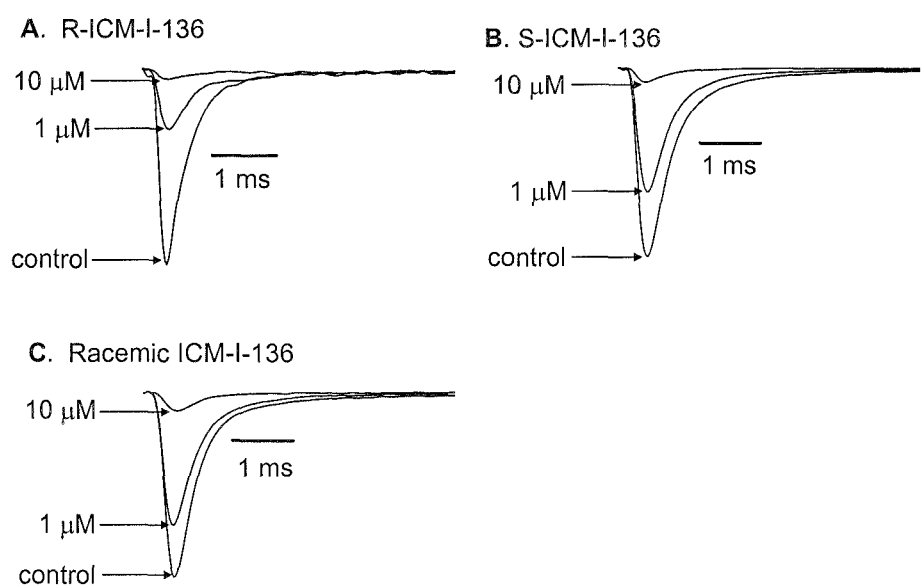

FIG. 14. Effects of racemate and enantiomers of ICM-I-136 on $hNa_v1.2$

Figure 15:
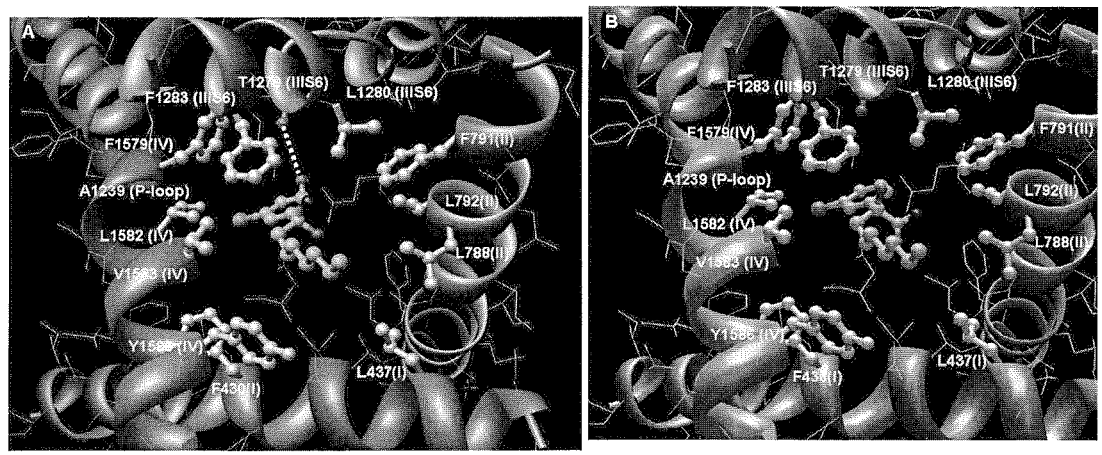

FIG. 15. Binding model of compound 1 and $Na_v1.7$ A. Proposed binding model of R-(−)-1 with $Na_v1.7$. B. Proposed binding model of S-(+)-1 with $Na_v1.7$. The sodium channel is represented as helices (cyan), ball and stick model representation for critical binding site residues (yellow), and compound 1 (atom color) with H-bond denoted by dotted lines.

Figure 16:
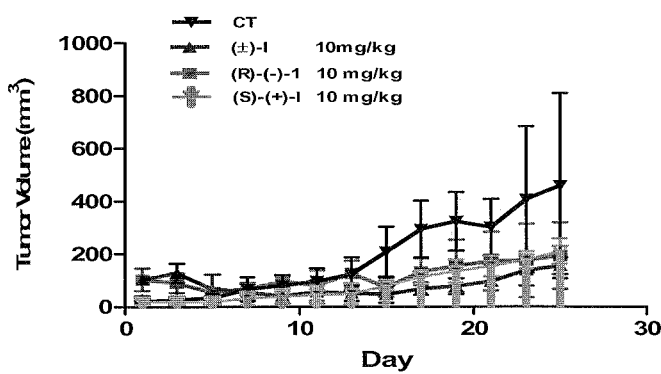

FIG. 16. Effects of (±)-1 and enantiomers of 1 on human prostate xenograft PC3.

Figure 17:
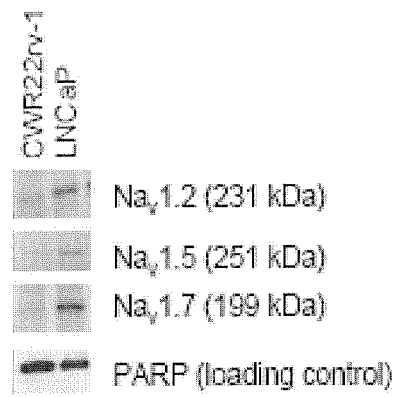

FIG. 17. Western blot analysis showing up-regulation of $Na_v$ 1.2, 1.5, 1.7, in CWR22rv-1 prostate cancer cell lines.

Figure 18:
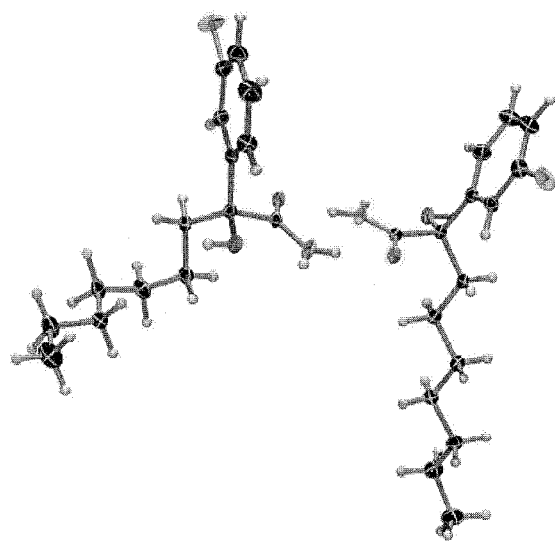

FIG. 18. An assymetric unit of (S)-(+)-2-(3-chlorophenyl-2-hydroxy-nonanoic acid amide. Displacement ellipsoids are drawn at 50% probability level, while hydrogen atoms are drawn as spheres of an arbitrary radius.

Figure 19:
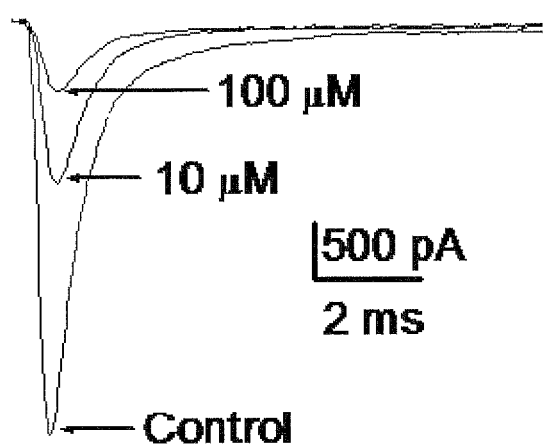

FIG. 19. Demonstration traces of $Na_v1.2$ block by compound 26. Sodium currents were elicited by a depolarizing step from a holding potential of −100 mV to +10 mV for a duration of 25 ms at 15 s intervals, after which compound 26 was applied. 10 μM and 100 μM traces are compared to the control.

Figure 20:
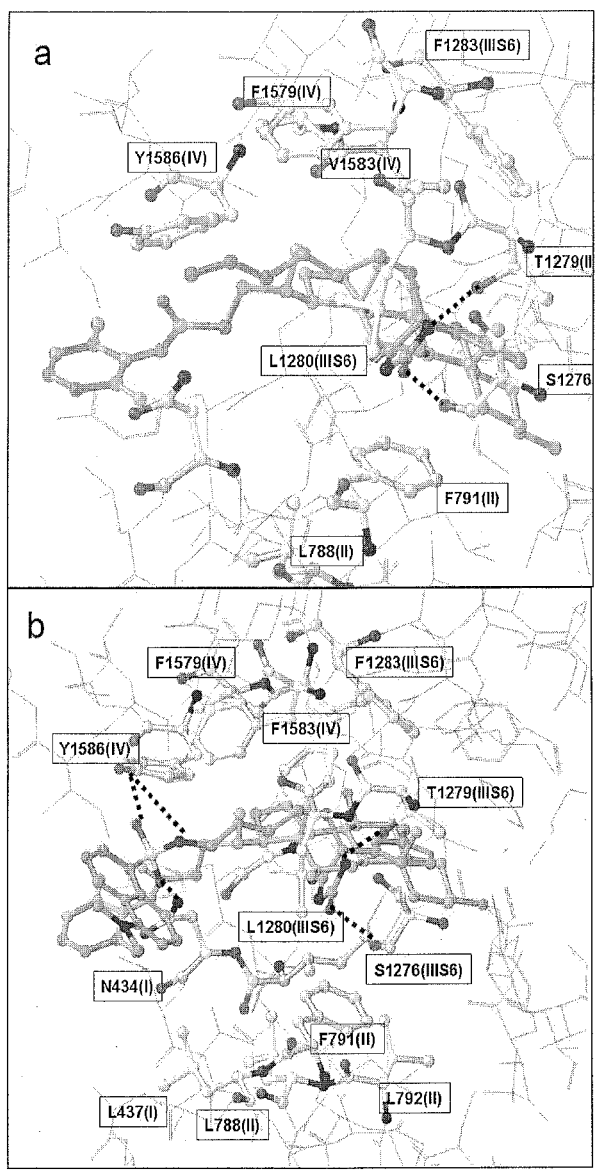

FIG. 20. (a) Proposed $Na_v$ binding model of compound 10. (b) Proposed $Na_v$ binding model of compound 26. The $Na_v$ BTX binding site is represented as a white ball and stick model. Compounds 10 and 26 are represented by a ball and stick model with carbon atoms colored green and hydrogen-bonds denoted by dotted lines. BTX, overlaid with compounds 10 and 2, is displayed by the cyan ball and stick model.

Figure 21:
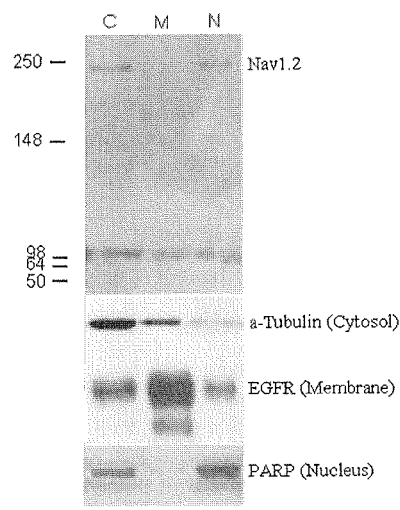
Figure 22:
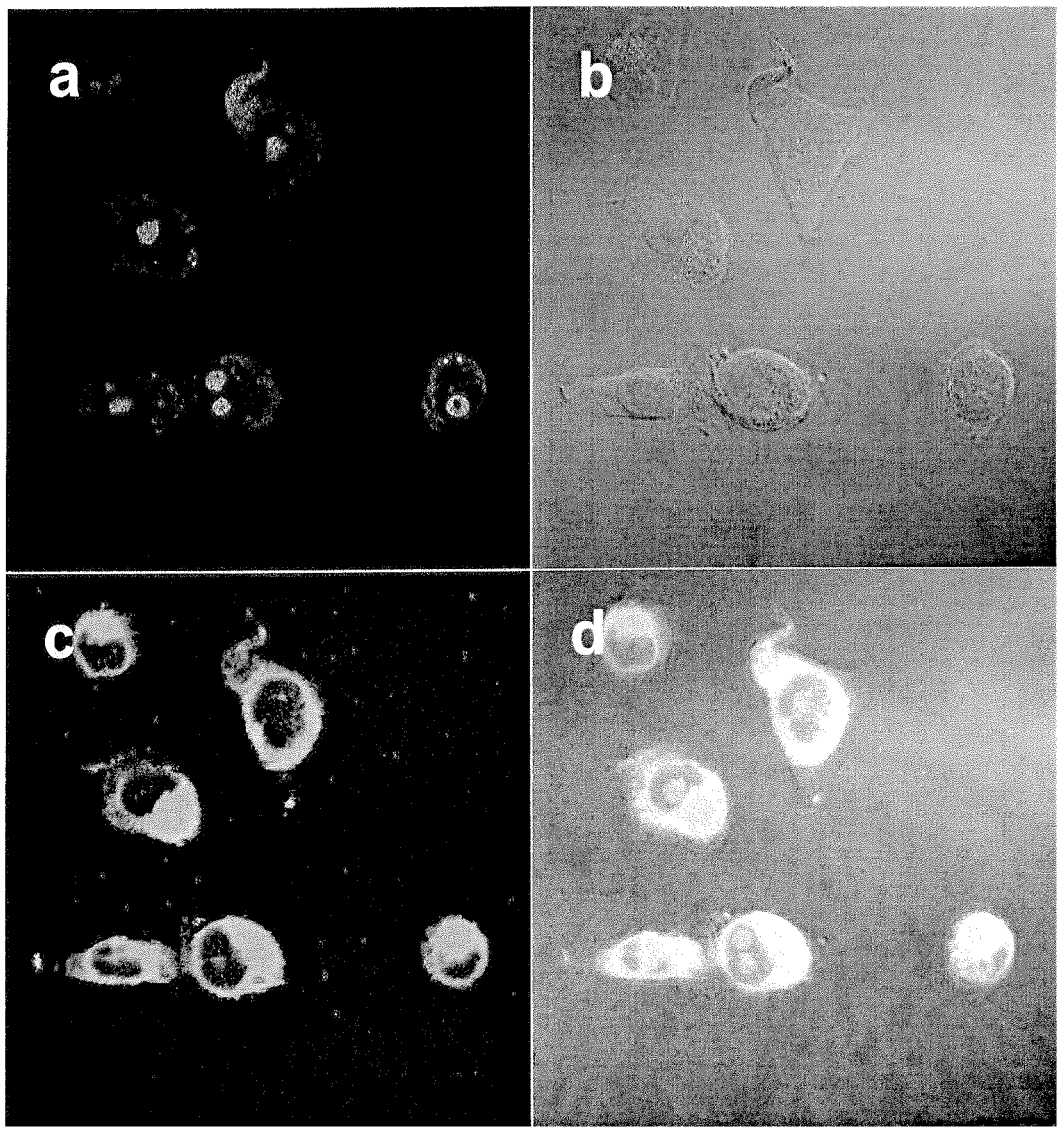

FIG. 21. Cell fractionation studies of PC-3 cells. (C) indicates the cytoplasm, (M) indicates the plasma membrane, and (N) refers to the nuclear membrane. The $Na_v1.2$ spot is referring to a 260 kDa spot which indicates the α-subunit of the $Na_v$ FIG. 22. Two-photon confocal microscopic images of compound 26 in PC-3 cells. Stained PC-3 cells were excited at 720 nm (Emission at 509 nm). (a) Propidium iodide stain, (b) DCI, (c) Compound 26, (d) Compound image. PC-3 cells were treated with a 10 μM solution of compound 26 for 6 hours.

Figure 23:
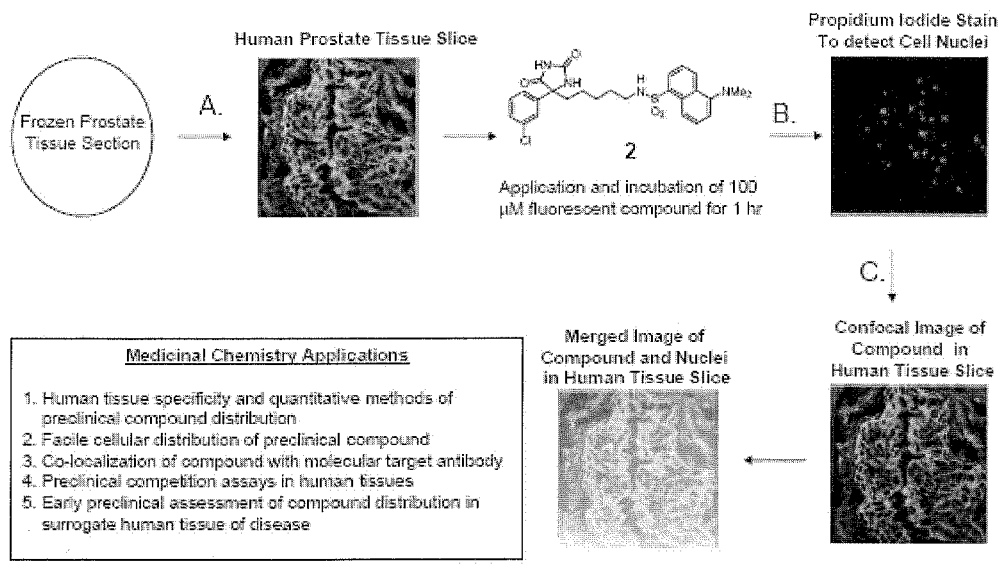

FIG. 23. Early drug discovery assay using human tissue surrogates. A: 1. Section cut at 5 nm, 2. Fixed to slide, dried and rehydrated, 3. Mock primary antibody applied for 1 hr, 4. Slide washed twice with deionized water. B: The slice was washed again twice for 5 mins. in deionized water. The sample was exposed to a 1/500 dilution of propidium iodide for 5 minutes at room temperature. The slice was mounted in Vectastain. C: Imaged at 725 nm excitation with a two photon confocal microscope.

Figure 24:
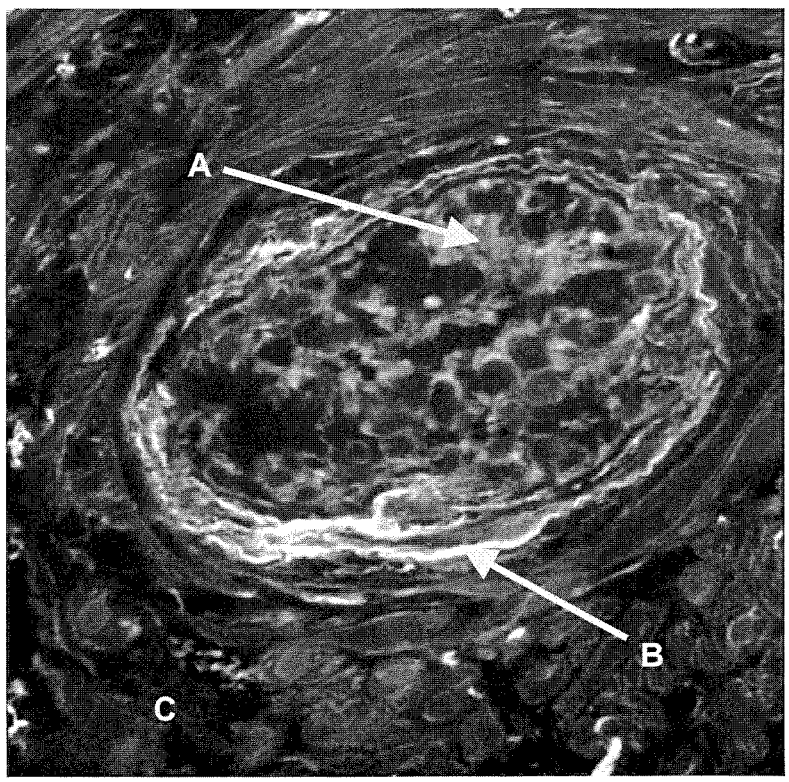

FIG. 24. A two-photon confocal microscope image of compound 26 in human prostate cancer tissue (Gleason score 7). (A) Secretory epithelial tissue, (B) Basal epithelial tissue, (C) Stromal Tissue. The regions in white indicate tissue staining by compound 26. The tissue was treated with compound 26 at 100 μM for 5 minutes.

Figure 25:
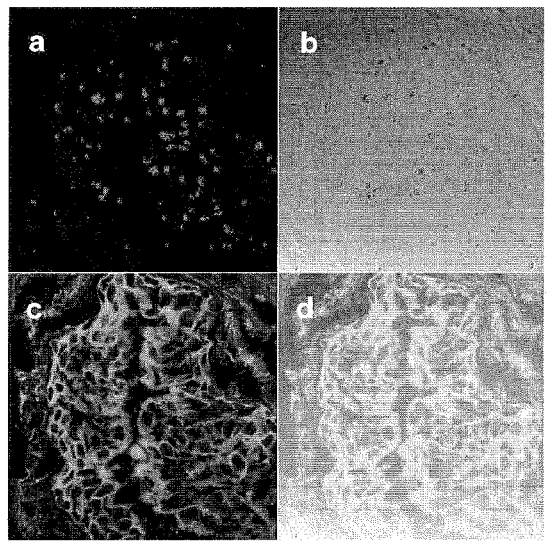

FIG. 25. A two-photon confocal microscope image of compound 26 in fresh-frozen cancerous human prostatic tissue (Gleason score 7) at 20× magnification. The tissue was treated with compound 26 at 100 μM for 5 minutes. (a) Propidium iodide stain (red), (b) DIC, (c) Compound 26 fluorescence (green) with 725 nm excitation and 510 nm emission, (d) Overlaid images of panels a, b and c.

Figure 26:
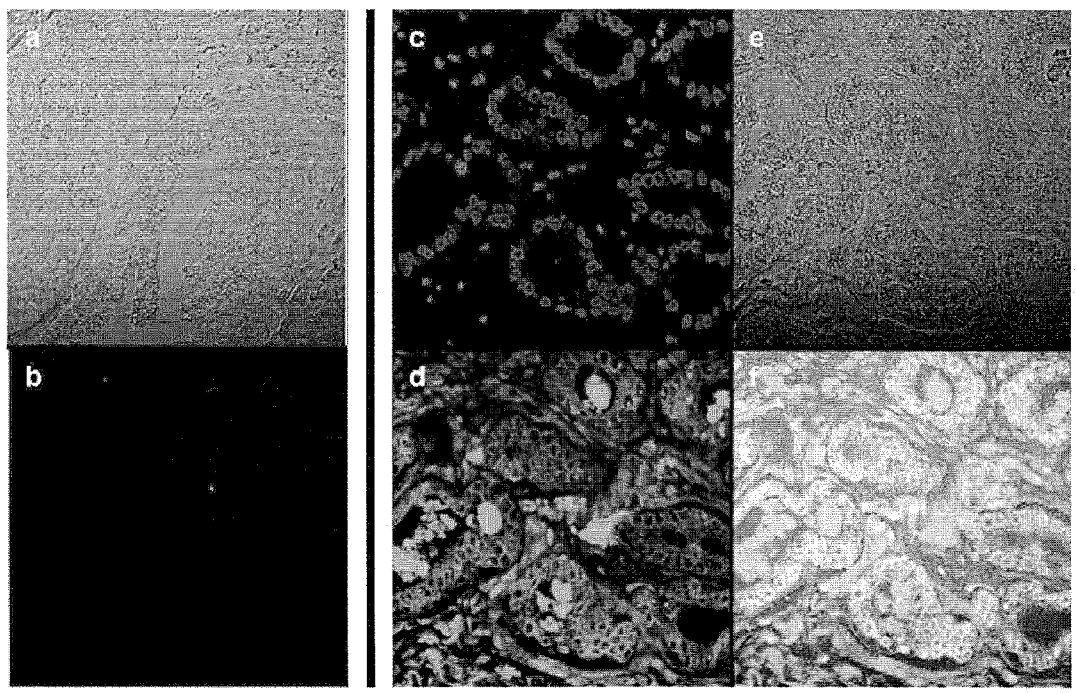

FIG. 26. Two-photon confocal microscope images of fresh diseased prostatic tissue; both untreated (a and b) and colocalized with $Na_v1.2$ antibody (labeled with Cy5) and compound 26 (c-e). (a) DIC image of blank prostate tissue. (b) Image of tissue that is excited at 725 nm (with 510 emission) demonstrating minimal autofluorescence. (c) Staining of prostate tissue with $Na_v1.2$ antibody labeled with Cy5. (d) Compound 26 fluorescence with excitation at 725 nm and emission at 510 nm. (e) DIC image of colocalized prostate tissue. (f) Mixed image (c, d, and e) demonstrating colocalization of compound 26 and $Na_v1.2$.

FIG. 27. Expression Profiles of VGSC in Human PC.

Figure 28:
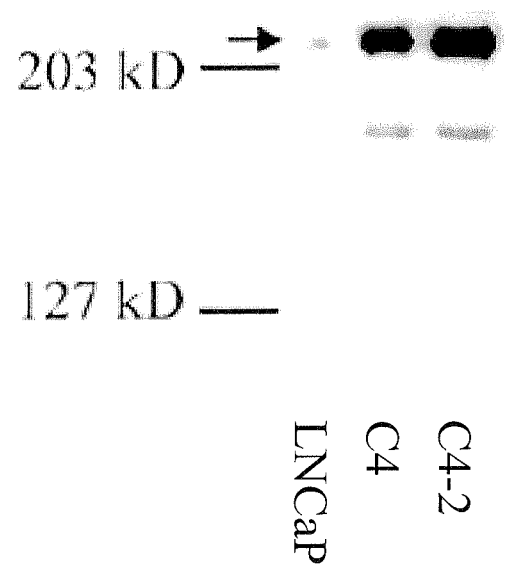

FIG. 28. VGSC Protein Expressed in Human Prostate Cancer Cells. Site-directed polyclonal antibody, α1Ab, specific for a highly conserved 19-mer in the III-IV linker region. Elevated expression with increasing metastatic potential across cell panel.

Figure 29:
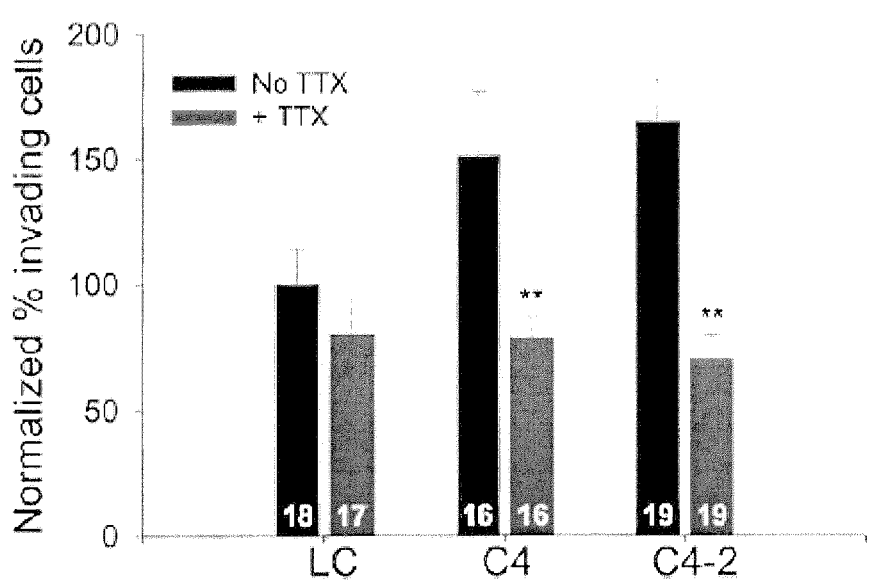

FIG. 29. Specific VGSC Blocker TTX Inhibits Human Prostate Cancer Cell Invasiveness. The VGSC function is necessary to increase metastatic potential.

FIG. 30. Probing of small molecules for the DPH binding site. Heptyl substituted, $R_1$, (7) indicates the best working functionality in this class of molecules.

Figure 31:
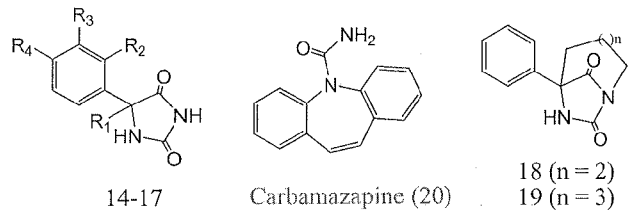

FIG. 31. Comparative Molecular Field Analysis (CoMFA) test set for determining synthetic strategies for improved properties of the drug.

Figure 32:
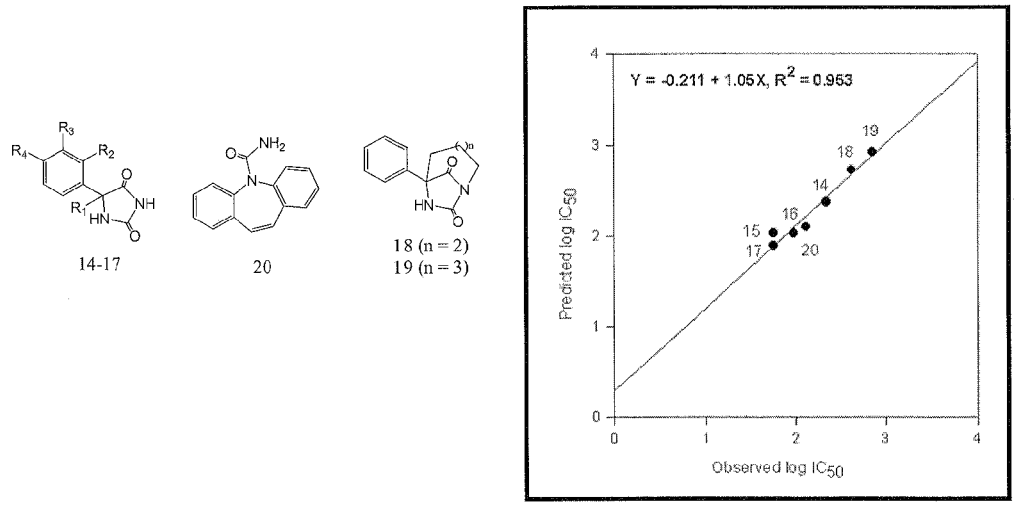

FIG. 32. Comparative Molecular Field Analysis (CoMFA) test set. The predicted data well overlays the observed data indicating a functioning CoMFA method.

Figure 33:
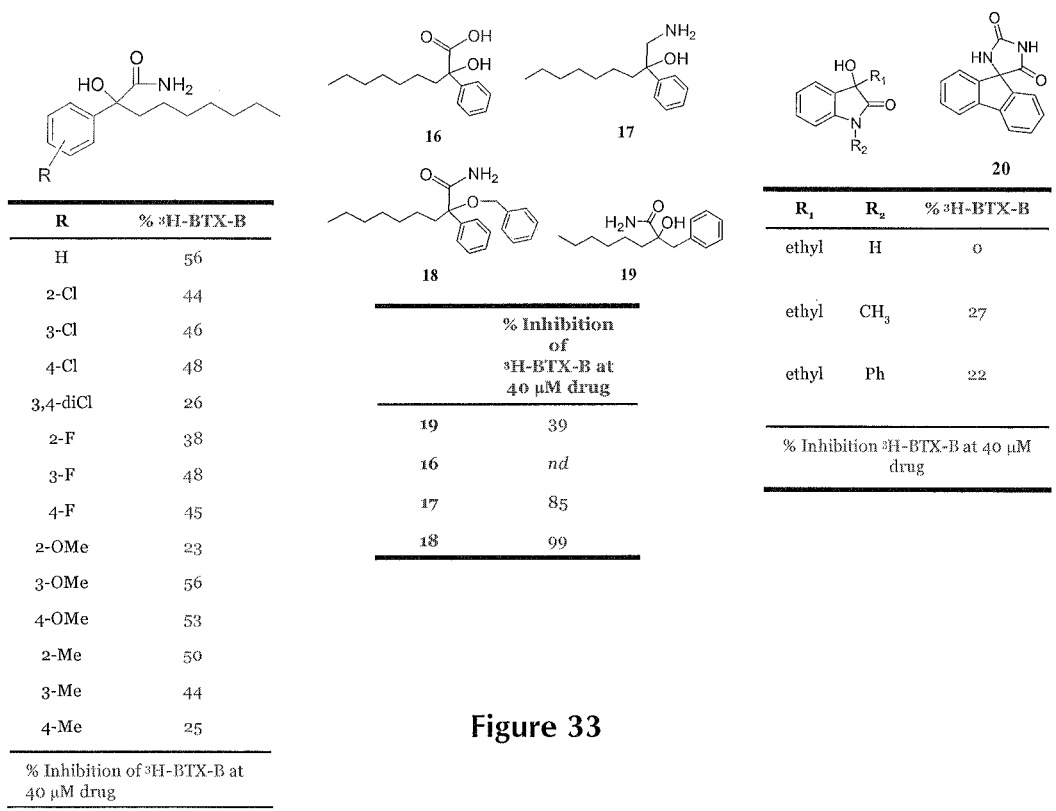

FIG. 33. Summary of percentage of inhibition of [$^3$H]-BTX-B at 40 µM with various substituent for determining the optimal functionalization of the lead compound.

Figure 34:
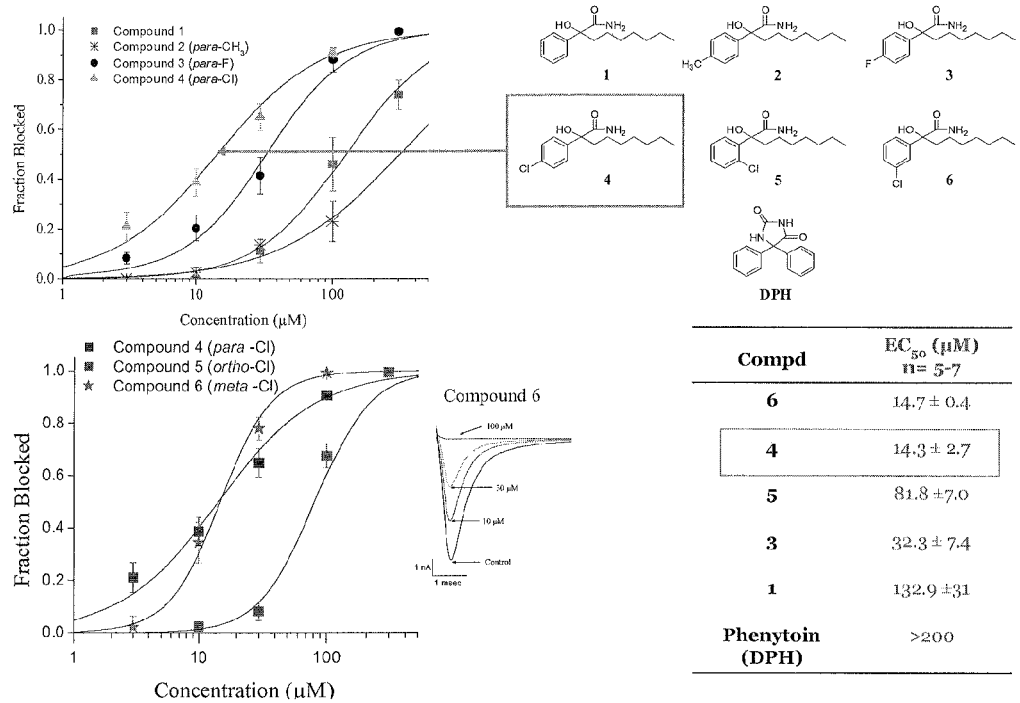

FIG. 34. Dose-Response Curves to $Na_v$ 1.5 indicating compound 4 as the best performing drug of the class of drugs showed.

Figure 35:
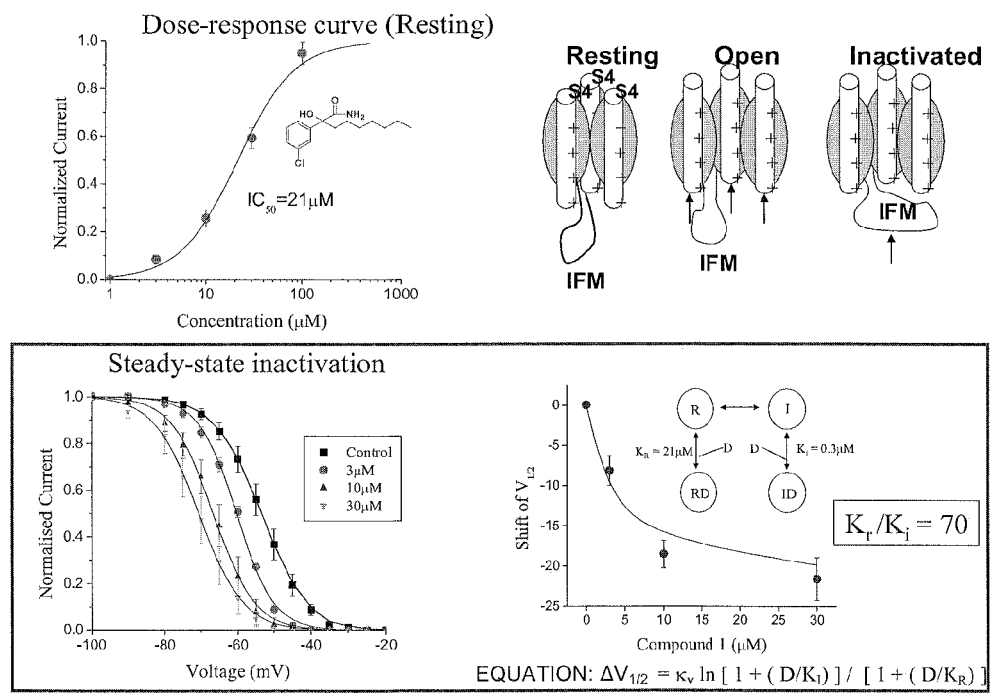

FIG. 35. Mechanism for $Na_v1.2$ inhibition of lead compound.

Figures 36, 37:
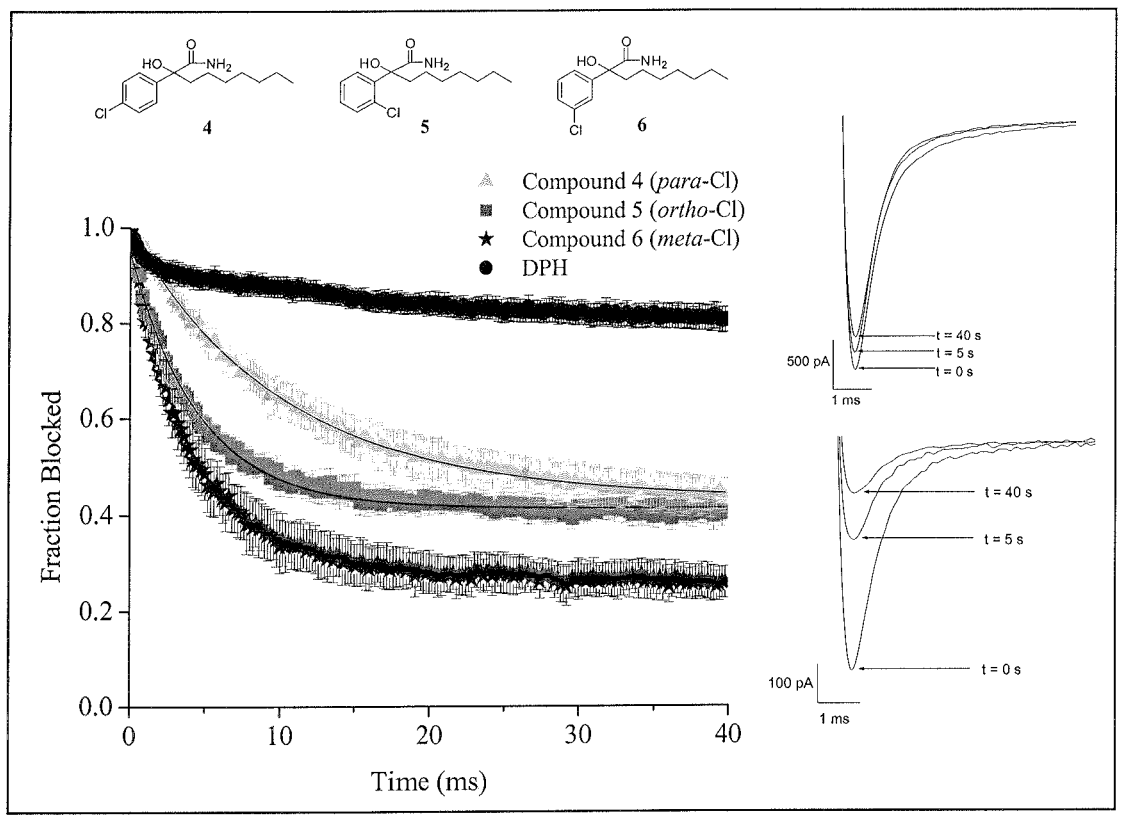

FIG. 36. Blockage of $Na_v1.2$ as a dependent of either ortho, meta, para substitution. Meta substitution with Cl showed to be most effective with in the compounds tested.

FIG. 37. Screening of compounds' $IC_{50}$ effectiveness as a function of $Na_v1.5$, 1.7, 1.8, $Ca_v2.2$, and hHerg.

Figure 38:
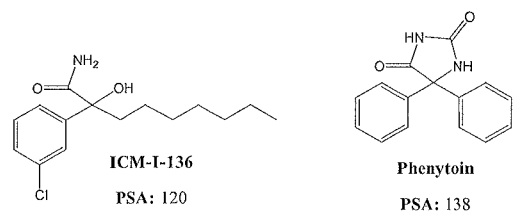

FIG. 38. Effects on various ion channels using the lead compound ICM-I-136.

Figure 39:
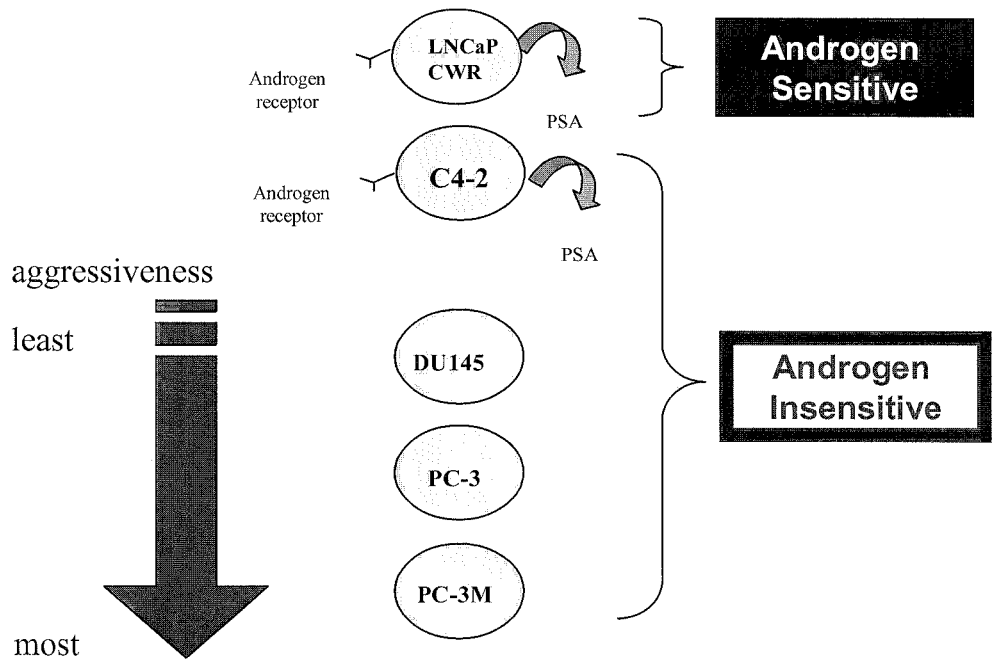

FIG. 39. Effects of sodium channel blockers on human prostate cancer cells as a function of cancer aggressiveness/cell type.

Figure 40:
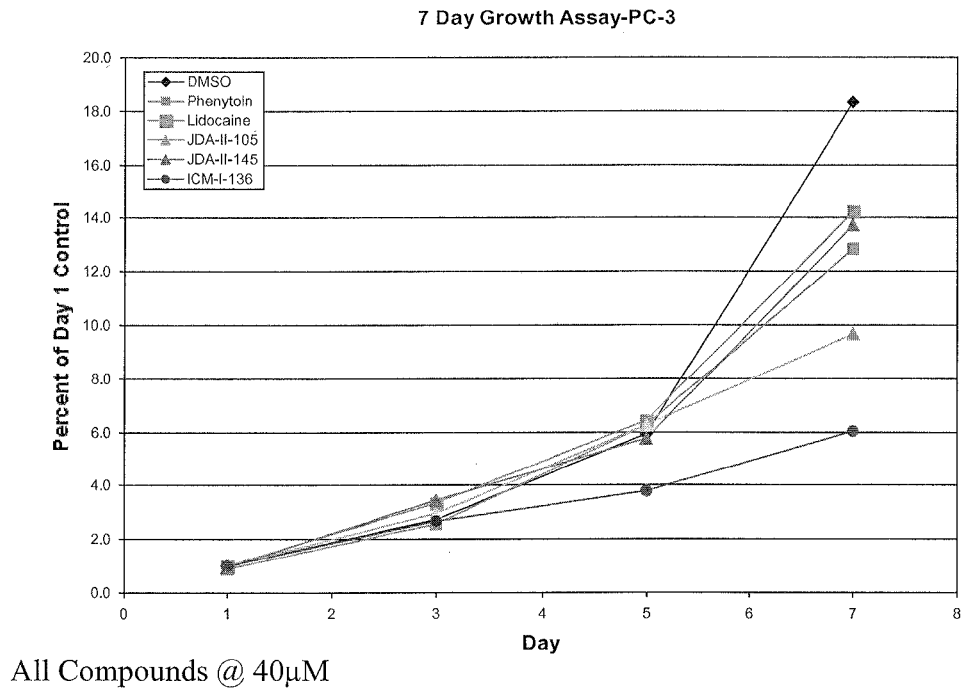

FIG. 40. Assay of PC-3 crystal violet growth as a dependence on drug.

Figure 41:
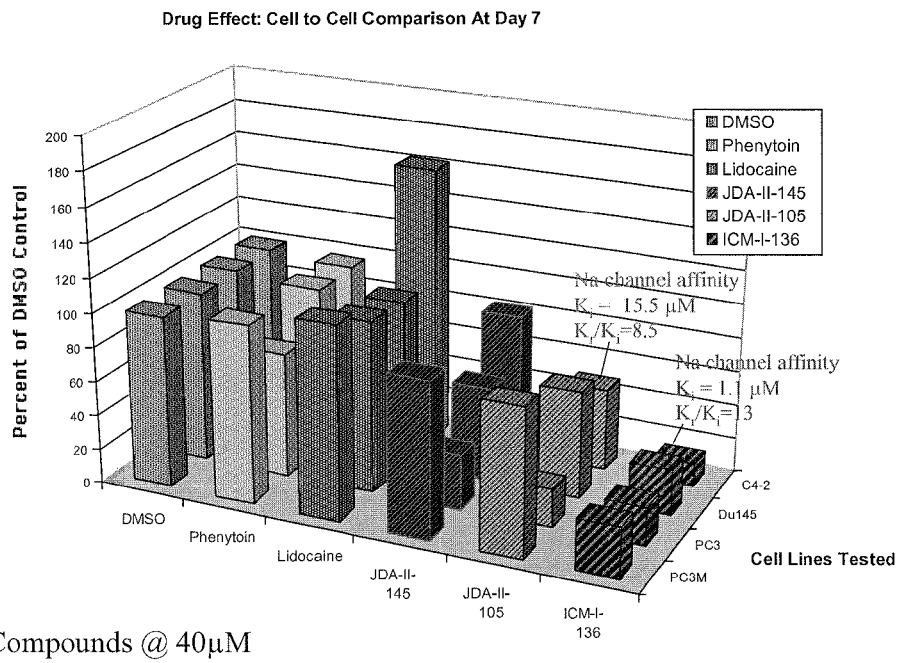

FIG. 41. Drug effect on cell to cell, from FIG. 39, comparison after 7 days of exposure to the drugs.

Figure 42:
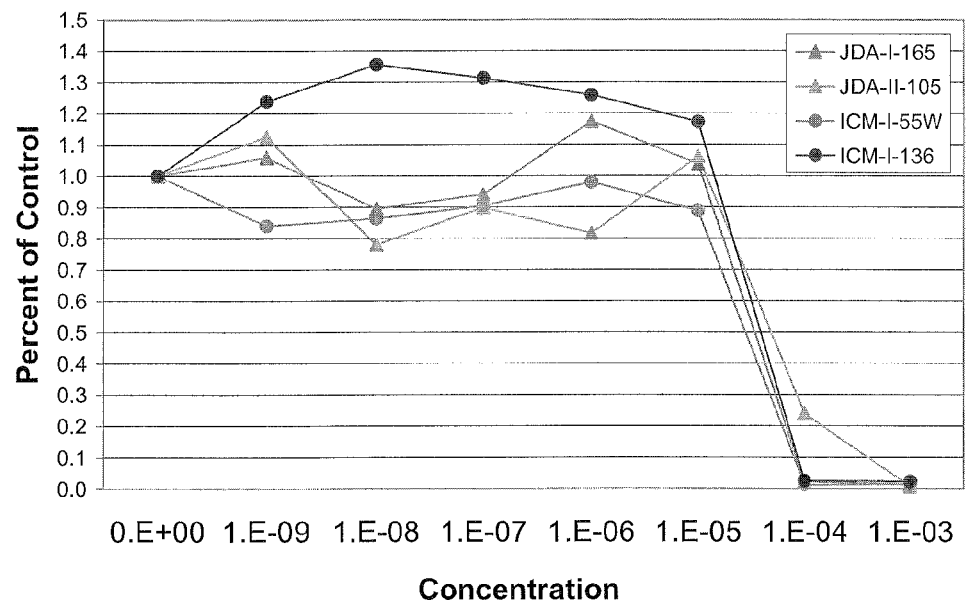

FIG. 42. $IC_{50}$ dose response curve at day 5 from PC-3 cells from FIG. 39.

Figure 43:
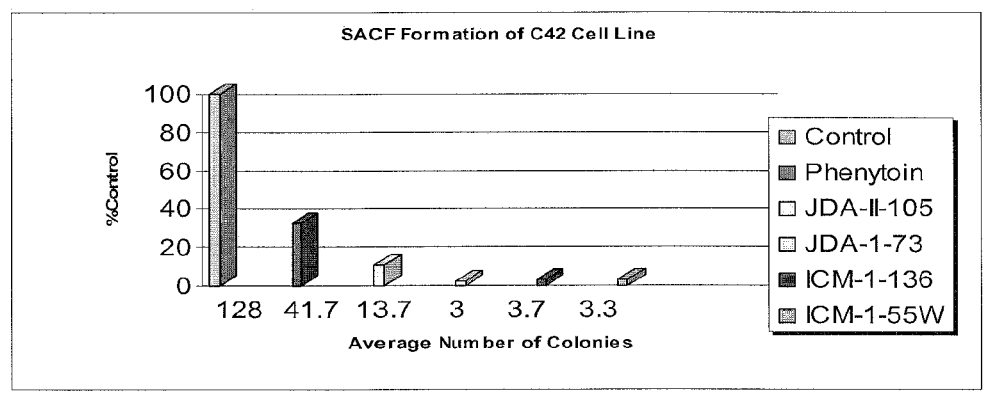
Figure 43:
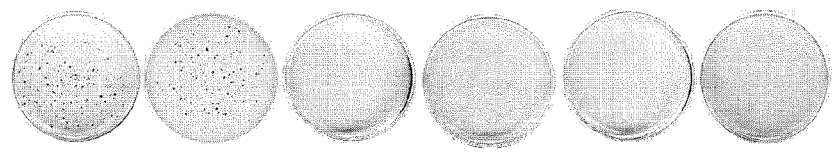

FIG. 43. Functional study: sodium channel blockers inhibition of human prostate cancer colony formation as a function of drug used.

Figure 44:
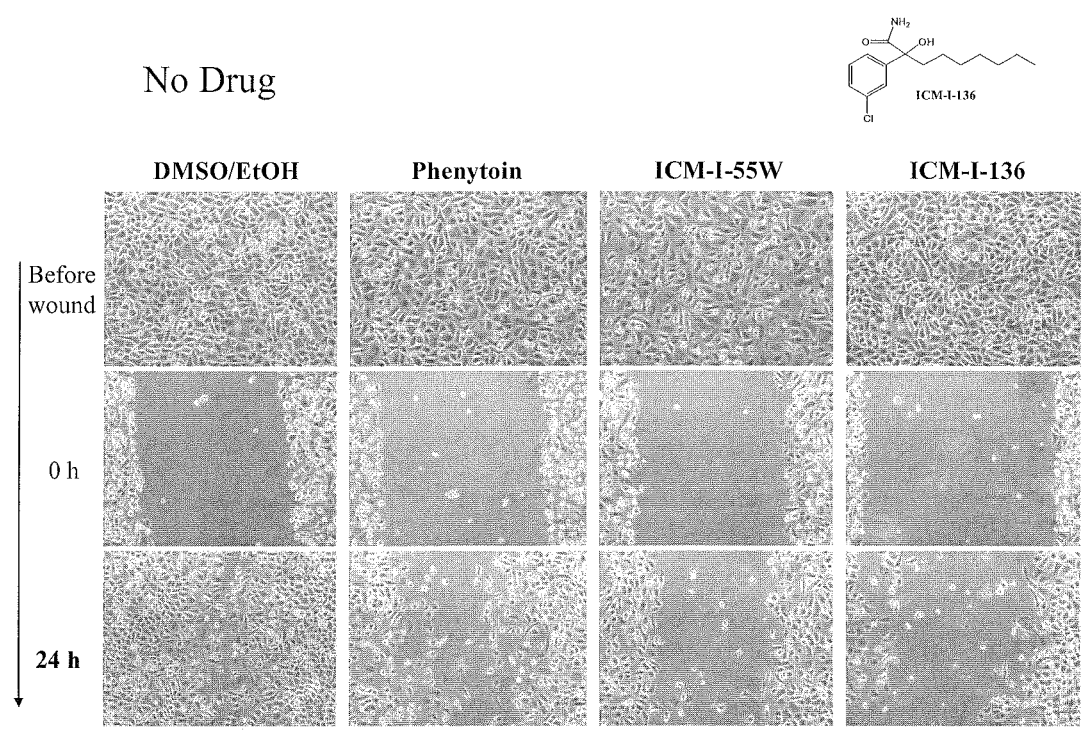

FIG. 44. Functional study: Sodium channel blockers inhibition of human prostate cancer cell migration as a function of cells used with lead compound.

Figure 45:
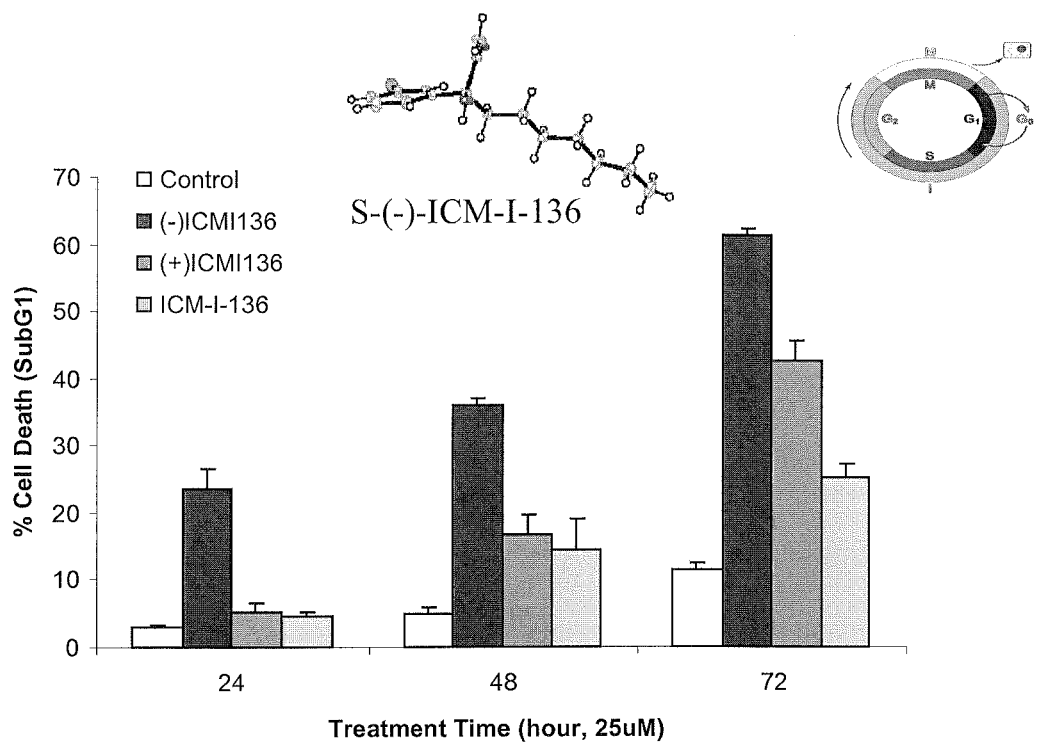

FIG. 45. Evaluation of S-(−) Enantiomer of lead to cell death in human prostate cancer cells which showed increased performance of the compound.

Figure 46:
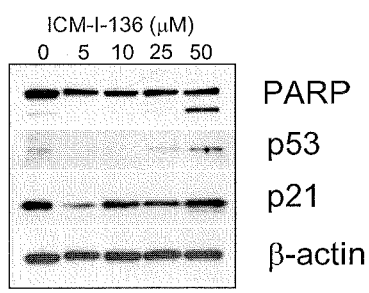
Figure 46:
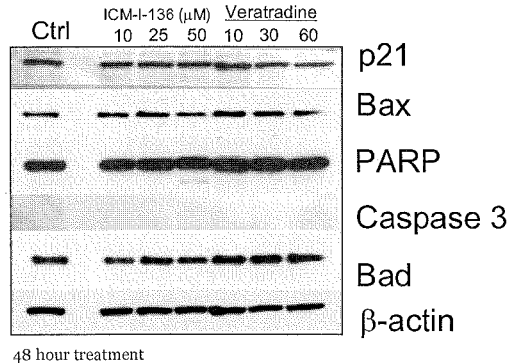

FIG. 46. Western blot mechanistic study: Sodium channel blockers showing to up-regulate tumor suppressor p53.

Figure 47:
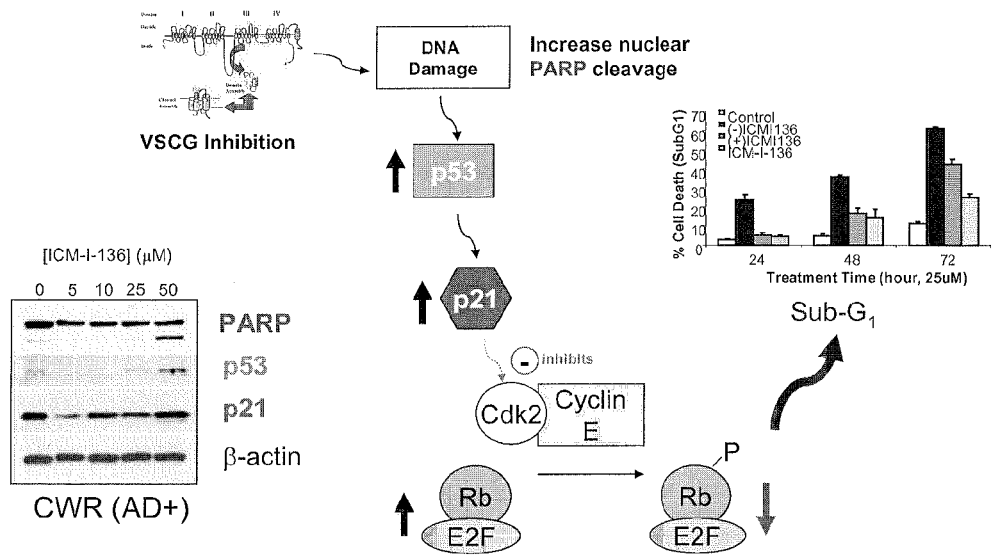

FIG. 47. Mechanism of action towards cell death as a function of sodium channel inhibition.

Figure 48:
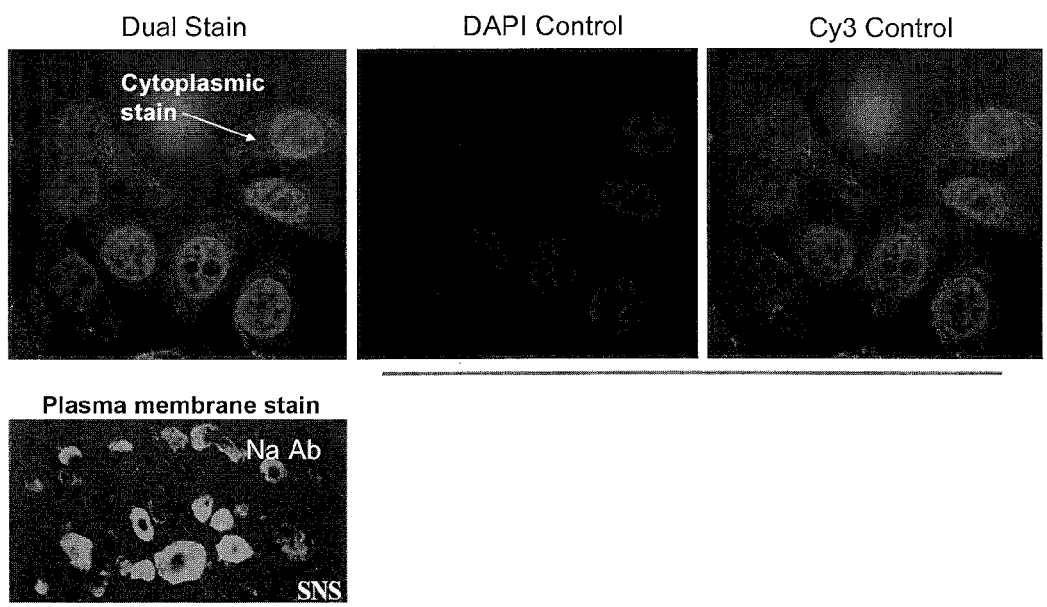

FIG. 48. Localization in human prostate cancer via $Na_v$ detection using immunofluorescence. $Na_v$ channels in prostate cancer are not localized in the plasma membrane. Cy3 was used as the fluorescent label.

Figure 49:
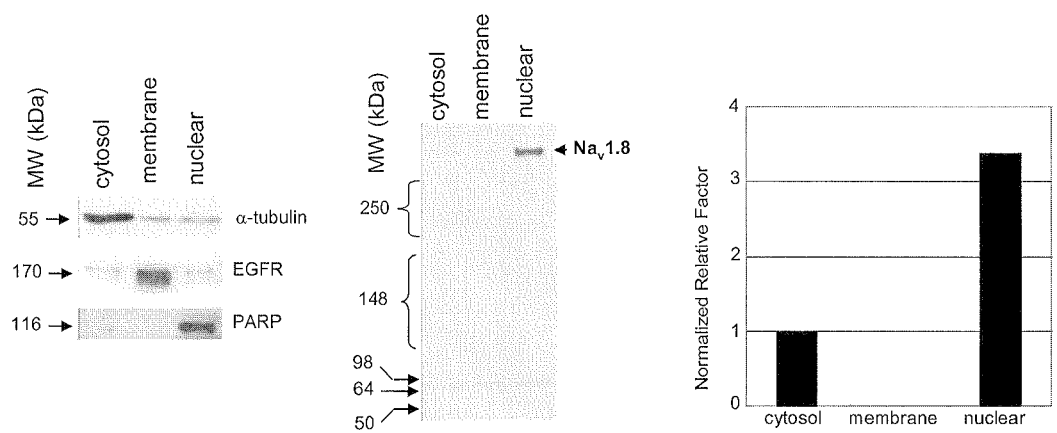

FIG. 49. Human prostate cancer cells (CWR) expression of Nav1.8 in the nuclear membrane, using western blot for detection.

Figure 50:
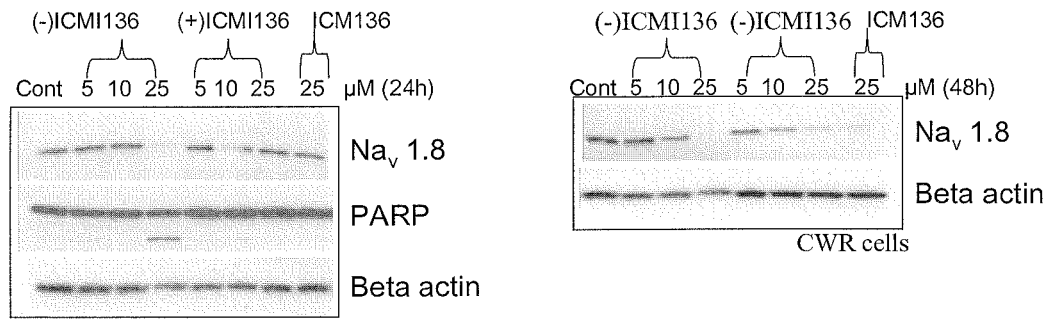
Figure 50:
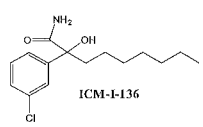

FIG. 50. Western blot of lead sodium channel blocker showing down regulated $Na_v1.8$ expression in human prostate cancer cells.

Figure 51:
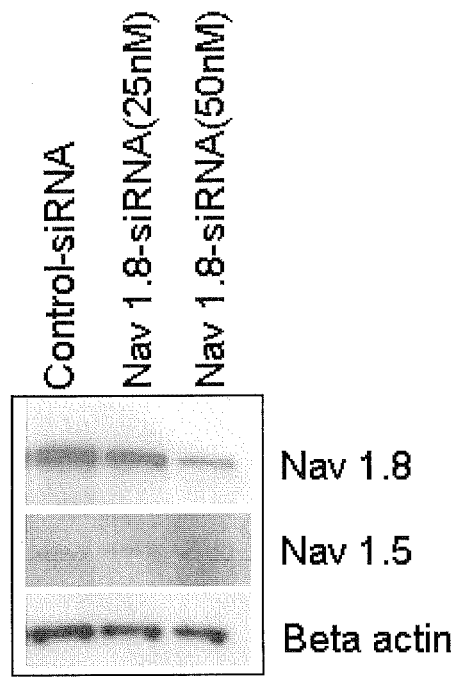

FIG. 51. Western blot of siRNA decreasing $Na_v1.8$ expression in human prostate cells.

Figure 52:

FIG. 52. Preclinical evaluation of lead compound, ICM-I-136, acute rotorod toxicity in mice. $^a$ Number of mice with impaired balance on the rotating rod/by the total number of animals tested. No deaths, spasms, respiratory disease was reported. $^b$ dose administrated i.p.

Figure 53:
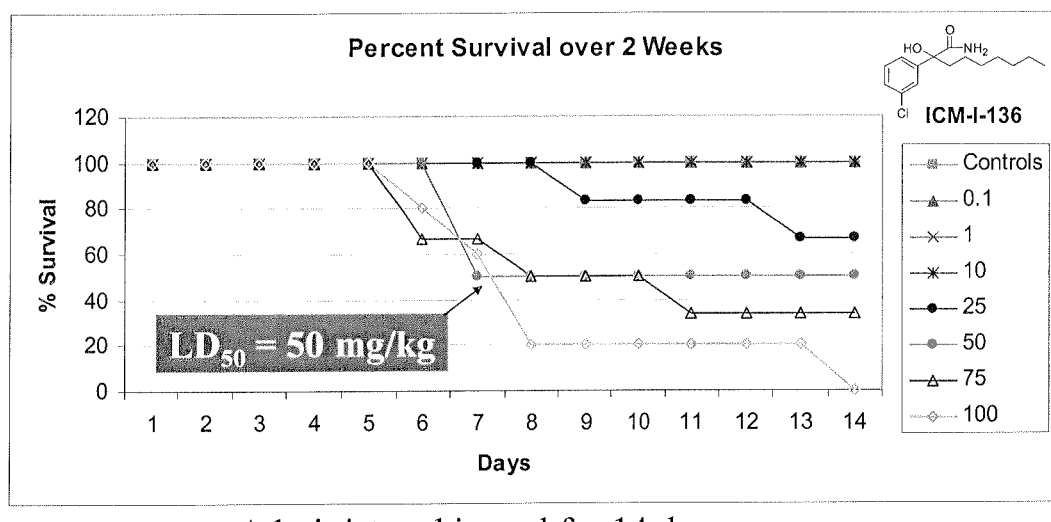

FIG. 53. Toxicity studies of lead compound using chronic dosing.

Figure 54:
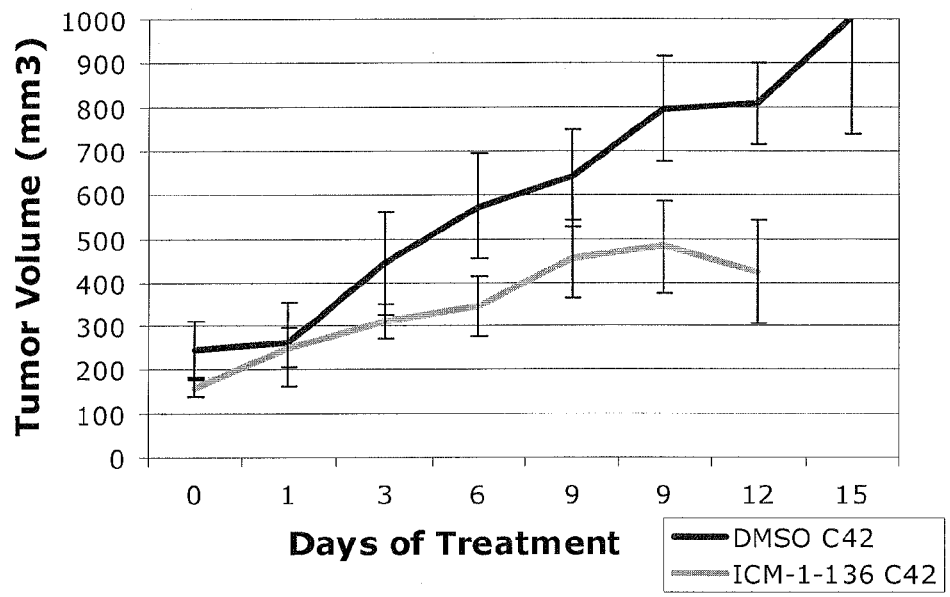

FIG. 54. Inhibition as a function of tumor volume using lead compound, ICM-I-136.

Figure 55:
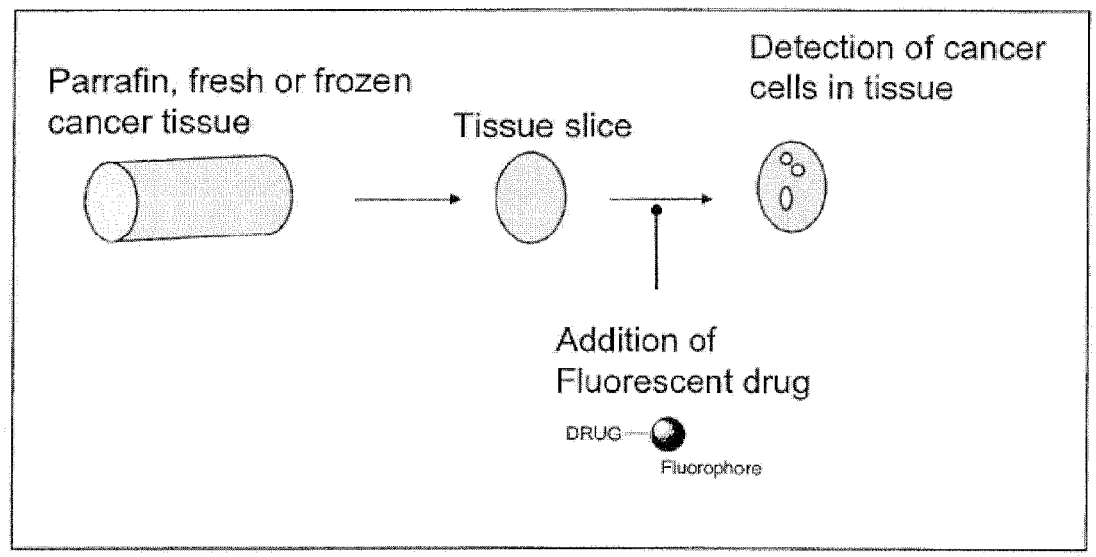

FIG. 55. Schematic of how small fluorescent molecules (drugs) directly can detect cancer. A thin slice tissue of paraffin, fresh and/or frozen cancer tissue is exposed to small fluorescent drug. The drug specifically targets Voltage-gated sodium channel 1.8 ($Na_v1.8$). Non cancer cells do not express $Na_v1.8$ which results selective attachment and rapid screening for cancer expressing $Na_v1.8$, including human prostate cancer. $Na_v1.8$ localization can clearly differentiate between normal and malignant tissue. This method can also be utilized to screen for drug performance where the delivery of the drug to a specific region, i.e. prostate cancer cells, can be monitored via fluorescence using this methodology.

V. DETAILED DESCRIPTION

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. DEFINITIONS

1. A, An The

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

2. Binding Affinity

The term binding affinity as used herein can be defined as two molecules interacting with a kd of at least $10^{-3}$, $10^{-4}$, $10^{-5}$, $10^{-6}$, $10^{-6}$, $10^{-7}$, $10^{-8}$, or $10^{-9}$ M or tighter binding.

3. Cell

The term "cell" as used herein also refers to individual cells, cell lines, or cultures derived from such cells. A "culture" refers to a composition comprising isolated cells of the same or a different type. The term co-culture is used to designate when more than one type of cell are cultured together in the same dish with either full or partial contact with each other.

4. Complex

The term complex as used herein refers to the association of a compound with an ion channel or enzyme for which the compound has a binding affinity.

5. Components

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

6. Chemistry a) Aldehyde

A reference herein to an aldehyde that has no alpha hydrogens mean an HC(=O)— group that is bonded to a carbon atom that has no covalent bond to a hydrogen atom. Non-limiting illustrative examples include alpha carbons for which each of the other three bonds is to a carbon atom, heteroatom or halogen atom; examples of such alpha carbons include that are part of aromatic, heteroaromatic, quaternary alkyl, and trihalomethyl substitutents.

b) Small Bulky Side Group

The term small bulky group as used herein with reference to an organic moiety refers to a hydrophobic substituent such as a halogen, $C_1$-$C_4$ organic, $C_1$-$C_4$ alkyl or dialkyl amino, $C_1$-$C_4$ alkoxy, $C_1$-$C_4$ sulfur moiety such as sulfyl or sulfoxyl or sulfonyl, wherein any of the organic, amino, alkoxy, or sulfur moiety may optionally be substituted with one or more halogens, methoxyl, methyl or dimethyl amino, or methyl sulfide residues.

c) $C_1$-$C_4$ Organic

The $C_1$-$C_4$ organic as used herein with respect to a substituent refers to a linear, branched or cyclical carbon residue that may be saturated or unsaturated, and may be substituted or unsubstituted as defined in this specification.

d) Close Proximity

The term close proximity as used herein with reference to a substituent relative to an aromatic or heteroaromatic ring herein refers to a location on the ring itself or on a position alpha, beta or gamma to the ring.

e) Small Bulky Group

The term small bulky group as used herein with reference to an organic moiety refers to a hydrophobic substituent such as a halogen, $C_1$-$C_4$ organic, $C_1$-$C_4$ alkyl or dialkyl amino, $C_1$-$C_4$ alkoxy, $C_1$-$C_4$ sulfur moiety such as sulfyl or sulfoxyl or sulfonyl, wherein any of the organic, amino, alkoxy, or sulfur moiety may optionally be substituted with one or more halogens, methoxyl, methyl or dimethyl amino, or methyl sulfide residues.

f) Facile Separation

The term "facile separation" as used herein with respect to stereoisomeric products refers to separation of the stereoisomers chromatographically to obtain one or both of the chiral forms in high purity in a single simple chromatographic step. For instance, obtaining by flash chromatography a stereoisomer with 90% or higher purity as determined by spectroscopic methods is a facile separation.

g) Substituted

The term "substituted" as used herein refers to an atoms or group of atoms substituted in place of a hydrogen atom on a linear, branched or cyclic organic compound or functional group. As used herein, the term substituent is employed without regard to whether the organic compound or functional group in its unsubstituted form comprises a heteroatom.

h) Lithiated Aryl

The term "lithiated" as used herein with respect to an aryl or heteroaryl group refers to an aryl or heteroaryl group having a negatively charged lone pair of electrons on the ring for which the counterion is a lithium cation.

i) Vinyl Anion

The term "vinyl anion" as used herein refers to the reactive intermediate [=C(:)—]$^-$, wherein a carbon having a double bond to a first neighboring carbon and a single bond to a second neighboring carbon furthermore has an unbonded lone pair of electrons that imparts to it a negative charge.

j) Heteroaryl Group

The term "heteroaryl group" as used herein refers to a functional group comprising at least one heteroatom in at least one aromatic ring.

k) Purine/Pyrimidine

The term "purine" or "pyrimidine" as used herein with respect to a ring system refers to a characteristic purine or pyrimidine structure, respectively, within that ring system.

l) Protected

The term "protected" as used herein has its usual and ordinary meaning in organic chemistry, and refers to a molecule or functional group that has been modified at one or more sites by reaction with a compound that may be readily removed to restore the original functional group, wherein the modified group selectively resists reaction with a chemical agent that is employed to react another site of the protected molecule. Illustrative protective groups and their chemistry are described in T. W. Green and P. G. M. Wuts, Protective Groups in Organic Synthesis, $3^{rd}$ Ed., Wiley Interscience.

m) Unprotected

The term "unprotected" as used herein has its usual and ordinary meaning in organic chemistry, and refers to a molecule or functional group that remains unmodified or has been deprotected, such that one or more unprotected sites remain susceptible to or by deprotection become susceptible to reaction with a chemical agent in a particular step to which the molecule or functional group is subjected.

n) Moiety and Functional Group

The terms "moiety" and "functional group" as used herein are synonymous. The term functional group as used herein has its usual and ordinary meaning in organic chemistry, and refers to an interconnected group of atoms that is responsible for a characteristic chemical reaction of the molecule to which the group is bonded.

o) Hydrocarbon

The term "hydrocarbon" as used herein refers to an organic substituent or compound consisting entirely of hydrogen and carbon. As used herein the term hydrocarbon may refer to a substituent or compound that is of any size; linear, branched or cyclic; achiral, prochiral, chiral or racemic, aromatic, homoaromatic or saturated or unsaturated nonaromatic; and fully bonded or having a radical, electron lone pair, or empty orbital.

p) Amine Group

The term "amine group" as used herein has its usual and ordinary meaning in organic chemistry, and refers to a functional group having a basic nitrogen atom, wherein the nitrogen atom has a lone pair and a total of three covalent bonds, being covalently bonded to one or more hydrogen atoms and or to one or more organic moieties.

q) Carboxylic Acid

The term "carboxylic acid" as used herein refers to the functional group —C(=O)—OH. The term "alpha-hydroxy carboxylic acid" as used herein to the functional group >C(—OH)—C(=O)—OH.

r) Amide

The term "amide" as used herein refers to the functional group >N—C(=O)—.

s) Sulfamide

The term "sulfamide" as used herein refers to the functional group >N—C(=S)—.

t) Phosphoamid

The term "phosph(o)amid(e)" as used herein refers to amides of phosphoric acid and of its salts and esters, such as for the functional group >N—P(=O)(—O—)$_2$.

u) Reactive Moiety

The term "reactive moiety" as used herein refers to a moiety capable of condensation with a protected or unprotected group toward which it is reactive. Examples of reactive moieties include those susceptible to nucleophilic attack, such as moieties that can lose a leaving group such as a halide, a halogenated conjugate base of an organic acid, a tosylate, or a pyridinium functional group bonded to an acid moiety. Other examples of reactive moieties include nucleophiles, for instance, amine groups. Other examples of reactive moieties include those that have a carbonyl or other site at which nucleophilic attack by a second functional group can accomplish condensation. The term reactive moiety includes but is not limited to reactive moieties that are further substituted with another moiety such as a carboxylic acid, amide, sulfamide or phosphamide.

v) Acid Moiety

The term "acid moiety" as used herein refers to an acidic functional group such as —CO$_2$H, —SO$_3$H, —O—SO$_3$H, —SO$_2$H, —O—SO$_2$H, —PO$_3$H, —O—PO$_3$H, and the like.

w) Weinreb Amide

The term "weinreb amide" as used herein refers to refers to a N,O-dimethylhydroxamic acid. An illustrative but not exclusive weinreb amide is R—C(=O)—N(—CH$_3$)—O—CH$_3$ wherein R is an alkyl group x) Grignard Reagent The term "Grignard reagent" as used herein refers to magnesium halide R$_1$—MgX, wherein X represents F, Cl, Br or I, and wherein R$_1$ represents an organic moiety such as an aryl, alkyl, alkenyl or alkynyl compound, aralkyl, alkaryl, aralkenyl, alkenyl aryl, aralkynyl, alkynyl aryl, or substituted compound of one of those types.

y) Halogen

The term halogen as used herein with respect to substitution refers to a fluoro-, chloro-, bromo-, or iodo-substituent.

z) Halogenated Conjugate

The term halogenated conjugate base of an acid as used herein refers to conjugate bases of acids—or their use as residues for leaving groups—such as mono-, di-, tri-, and poly-halo alkyl acids, such as are familiar to the person of ordinary skill in the art for application as leaving groups and anions of very weak basicity. The fluoro and chloro derivatives are particularly widely used, as are —CO2$^-$ and —SO3$^-$ conjugate acids in these applications. The alkyl portion is commonly but not exclusively short chain alkyl acids, and longer residues such as fluoropolymer-substituted conjugate bases as well as aromatic structures such as halophenoxy residues are also contemplated within the scope of the invention.

aa) Heterocyclic Group

The term heterocyclic group as used herein refers to a ring structure having 4 to 8 members including at least one heteroatom and at least one carbon atom, wherein the structure is not heteroaromatic, and wherein the ring may be saturated or unsaturated, and may optionally be substituted by one or more: C$_1$-C$_4$ organic group; =O; ether, ester, carbonate, amine, amide, or urea of a C$_1$-C$_4$ organic group; any of which may optionally be substituted by a halogen.

bb) Lipophilic Side Chain

The term lipophilic side chain or lipophilic chain or lipohilic moiety and like terms as used herein refers to a side chain having lipophilic properties. The side chain or linker may be alkyl, alkenyl, alkynyl, or may be a polyether such as a polyethylene glycol or its alkyl ether, or polypropylene glycol or its alkyl ether, or a polyalkylamine, and or may have an ester, sulfoester, phosphoester, amide, sulfamide, or phosphoamide moiety in its backbone. A lipophilic side chain as referenced herein may be substituted by a halogen, C$_1$-C$_4$ organic group, C$_1$-C$_4$ ether, C$_1$-C$_4$ ester or sulfester or phosphoester, mono- or di-C$_1$-C$_4$ alkylamine, C$_1$-C$_4$ amide or sulfamide or phosphoamide, imidazolidine-2,4-dilactone, other heterocyclic group, hydroxyl, or amino group. Exemplary lipophilic side chains or linkers have a cohesive energy density of about ≤20 (J/cm$^3$)$^{1/2}$ and relatively limited hydrogen bonding, as discussed for instance in D. W. Van Krevelen, *Properties of Polymers: Their Estimation and Correlation With Chemical Structure*, 2$^{nd}$ Ed. (1976, Elsevier), pp. 129-159. In certain embodiments the side chain can be a linker.

cc) Stable

When used with respect to pharmaceutical compositions, the term "stable" is generally understood in the art as meaning less than a certain amount, usually 10%, loss of the active ingredient under specified storage conditions for a stated period of time. The time required for a composition to be considered stable is relative to the use of each product and is dictated by the commercial practicalities of producing the product, holding it for quality control and inspection, shipping it to a wholesaler or direct to a customer where it is held again in storage before its eventual use. Including a safety factor of a few months time, the minimum product life for pharmaceuticals is usually one year, and preferably more than 18 months. As used herein, the term "stable" references these market realities and the ability to store and transport the product at readily attainable environmental conditions such as refrigerated conditions, 2° C. to 8° C.

dd) Backbone Atom

The term backbone atom when used herein with respect to a linker refers to an atom in the shortest direct path of covalent bonding between the two chief moieties that are linked by the linker.

ee) Linker

The term linker as used herein refers to a bond or organic moiety that is covalently bonded to a fluorophore moiety and to a residue that can bind to an ion channel or enzyme. A linker may have C—C bonds directly to an aromatic or heteroaromatic ring that is being linked, or may be bonded to the ring through heteroatoms in a moiety such as an amide, sulfamide, or other group. In certain embodiments the linker can be a lipophilic side chain.

ff) Small Aromatic Ring System

The term small aromatic ring system as used herein refers to a mono-, bi-, or tricyclic aromatic ring system. The term aromatic as used herein refers to a carbocyclic structure having aromatically delocalized electrons.

gg) Small Heteroaromatic Ring System

The term small heteroaromatic ring system as used herein refers to a mono-, bi-, or tricyclic heteroaromatic ring system. The term heteroaromatic as used herein refers to a cyclic structure having at least one carbon and at least one heteroatom in a ring wherein the ring has aromatically delocalized electrons.

hh) Electron Donating Group

The term electron donating group (EDG) as used herein has its usual meaning in the art, and refers to a moiety having a relatively low electronegativity and thus a relatively strong tendency to donate electron density to less electron-rich moieties.

ii) Electron Withdrawing Group

The terms electron withdrawing group (EWG) and electron accepting group (EAG) as used herein are synonymous, have their usual meaning in the art, and refer to a moiety having a relatively high electronegativity and thus a relatively strong tendency to attract or receive electron density from more electron-rich moieties.

jj) Captodative

The term captodative as used herein refers to the ability to donate electron density from one substituent to another by rearrangement or delocalization of conjugated double bonds within and or between them. The term push-pull as used herein refers to the interaction between an EDG and EWG resulting in through-bond donation of electron density between moieties, such as is found for captodative bonds. The term "in captodative electronic communication with each other" as used herein refers to connectivity of bonds and substituents such that donation of electron density may occur from one substituent to another captodatively. Illustrative examples of captodative electronic communication as the term is used herein include ortho or alternatively, para dimethyl amino phenyl nitrate, 1-methoxyphenyl-(2 or 4)-(dimethoxyboron), heteroaromatic and aromatic bicyclic analogs of those examples, and the like.

7. Coapplication

"Coapplication" is defined as the application of one or more substances simultaneously, such as in the same formulation or consecutively, within a time frame such that each substance is active during a point when the other substance or substances are active.

8. Comprise

Throughout the description and claims of this specification, the word "comprise" and variations of the word, such as "comprising" and "comprises," means "including but not limited to," and is not intended to exclude, for example, other additives, components, integers or steps.

9. Control

The terms "control" or "control levels" or "control cells" are defined as the standard by which a change is measured, for example, the controls are not subjected to the experiment; but are instead subjected to a defined set of parameters, or the controls are based on pre- or post-treatment levels. They can either be run in parallel with or before or after a test run, or they can be a pre-determined standard.

10. Different Expression

The terms different expression and like terms can include any difference including at least a 1%, 5%, 10%, 15%, 20%, 30%, 40%, 50%, 75%, 100%, 300%, 500%, 750%, 1000%, 5000%, 10,000%, or 50,000% difference.

11. Enzyme Modulator

The term enzyme modulator as used herein refers to a molecule that can bind to an ion channel or enzyme, thereby modulating its activity, and includes both reversible and irreversible modulators.

12. Fluorescent

The term fluorescent as used herein can be defined as a molecule having luminescence that is caused by the absorption of radiation at one wavelength followed by nearly immediate reradiation usually at a different wavelength and that ceases almost at once when the incident radiation stops, as understood in the art.

13. Fluorescent Labeled Molecule

A fluorescent labeled molecule or like terms is a molecule containing a fluorophore moiety.

14. Fluorophore Moiety

The term fluorophore moiety as used herein refers to a moiety that has fluorescent properties. Illustrative fluorophore moieties for the present invention include dansyl, 4-(Diethylamino)azobenzene-4'-sulfonyl, fluorescein isothiocyanate (FITC), 5,6-carboxymethyl fluorescein, Texas red, nitrobenz-2-oxa-1,3-diazol-4-yl (NBD), coumarin, dansyl chloride, rhodamine, amino-methyl coumarin (AMCA), Eosin, Erythrosin, BODIPY®, Cascade Blue®, Oregon Green®, pyrene, lissamine, xanthenes, acridines, oxazines, phycoerythrin, macrocyclic chelates of lanthanide ions such as quantum Dye™, fluorescent energy transfer dyes, such as thiazole orange-ethidium heterodimer, and the cyanine dyes Cy3, Cy3.5, Cy5, Cy5.5 and Cy7; as well as additional examples such as 3-Hydroxypyrene 5,8,10-Tri Sulfonic acid, 5-Hydroxy Tryptamine (5-HT), Acid Fuchsin, Alizarin Complexon, Alizarin Red, Allophycocyanin, Aminocoumarin, Anthroyl Stearate, Astrazon Brilliant Red 4G, Astrazon Orange R, Astrazon Red 6B, Astrazon Yellow 7 GLL, Atabrine, Auramine, Aurophosphine, Aurophosphine G, BAO 9 (Bisaminophenyloxadiazole), BCECF, Berberine Sulphate, Bisbenzamide, Blancophor FFG Solution, Blancophor SV, Bodipy F1, Brilliant Sulphoflavin FF, Calcien Blue, Calcium Green, Calcofluor RW Solution, Calcofluor White, Calcophor White ABT Solution, Calcophor White Standard Solution, Carbostyryl, Cascade Yellow, Catecholamine, Chinacrine, Coriphosphine O, Coumarin-Phalloidin, CY3.1 8, CY5.1 8, CY7, Dans (1-Dimethyl Amino Naphaline 5 Sulphonic Acid), Dansa (Diamino Naphtyl Sulphonic Acid), Dansyl NH—CH3, Diamino Phenyl Oxydiazole (DAO), Dimethylamino-5-Sulphonic acid, Dipyrromethenboron Difluoride, Diphenyl Brilliant Flavine 7GFF, Dopamine, Erythrosin ITC, Euchrysin, FIF (Formaldehyde Induced Fluorescence), Flaw Orange, Fluo 3, Fluorescamine, Fura-2, Genacryl Brilliant Red B, Genacryl Brilliant Yellow 10GF, Genacryl Pink 3G, Genacryl Yellow 5GF, Gloxalic Acid, Granular Blue, Haematoporphyrin, Indo-1, Intrawhite Cf Liquid, Leucophor PAF, Leucophor SF, Leucophor WS, Lissamine Rhodamine B200 (RD200), Lucifer Yellow CH, Lucifer Yellow VS, Magdala Red, Marina Blue, Maxilon Brilliant Flavin 10 GFF, Maxilon Brilliant Flavin 8 GFF, MPS (Methyl Green Pyronine Stilbene), Mithramycin, NBD Amine, Nitrobenzoxadidole, Noradrenaline, Nuclear Fast Red, Nuclear Yellow, Nylosan Brilliant Flavin E8G, Oxadiazole, Pacific Blue, Pararosaniline (Feulgen), Phorwite AR Solution, Phorwite BKL, Phorwite Rev, Phorwite RPA, Phosphine 3R, Phthalocyanine, Phycoerythrin R, Polyazaindacene Pontochrome Blue Black, Porphyrin, Primuline, Procion Yellow, Pyronine, Pyronine B, Pyrozal Brilliant Flavin 7GF, Quinacrine Mustard, Rhodamine 123, Rhodamine 5 GLD; Rhodamine 6G, Rhodamine B, Rhodamine B 200, Rhodamine B Extra, Rhodamine BB, Rhodamine BG, Rhodamine WT, Serotonin, Sevron Brilliant Red 2B, Sevron Brilliant Red 4G, Sevron Brilliant Red B, Sevron Orange, Sevron Yellow L, SITS (Primuline), SITS (Stilbene Isothiosulphonic acid), Stilbene, Snarf 1, sulpho Rhodamine B Can C, Sulpho Rhodamine G Extra, Tetracycline, Thiazine Red R, Thioflavin S, Thioflavin TCN, Thioflavin 5, Thiolyte, Thiozol Orange, Tinopol CBS, True Blue, Ultralite, Uranine B, Uvitex SFC, Xylene Orange, and XRITC.

15. Hybridization Assay

A hybridization assay or like terms is any assay that involves hybridization of a nucleic acid or other biomolecule. An immunohisto staining and FISH analysis are two examples of hybridization assays.

16. Higher

The terms "higher," "increases," "elevates," or "elevation" or variants of these terms, refer to increases above basal levels, e.g., as compared to a control. The terms "low," "lower," "reduces," or "reduction" or variation of these terms, refer to decreases below basal levels, e.g., as compared to a control. For example, basal levels are normal in vivo levels prior to, or in the absence of, or addition of an agent such as an agonist or antagonist to activity.

17. Ion Channel Blocker

An Ion channel blocker and like terms is a molecule or compound or composition which reduces, decreases, or inhibits the activity of an ion channel.

18. In Vitro In Vivo

The terms in vitro and in vivo as used herein have their usual and ordinary meanings in the art.

19. Inhibit

By "inhibit" or other forms of inhibit means to hinder or restrain a particular characteristic. It is understood that this is typically in relation to some standard or expected value, in other words it is relative, but that it is not always necessary for the standard or relative value to be referred to. For example, "inhibits phosphorylation" means hindering or restraining the amount of phosphorylation that takes place relative to a standard or a control.

20. Ion Channel

The term ion channel as used herein refers to any protein that bridges a cellular membrane and allows ions to flow back and forth, such as a Na or potassium ion channel.

21. Ion Channel Modulator

An ion channel modulator or like terms is a modulator that modulates an ion channel.

22. Label

The terms label and tag as used herein with reference to a fluorescent species are interchangeable and refer to its presence as a moiety covalently bound to another residue such as an antibody or a drug species, wherein the fluorescence of the label enables the location and or activity of the other residue to be monitored.

23. Modulate

The terms modulate, modulator and modulation as used herein refers to an effect that changes the rate or throughput of an enzyme or ion channel by 10% or more relative to its pre-modulation state.

24. Optionally

"Optional" or "optionally" means that the subsequently described event or circumstance may or may not occur, and that the description includes instances where said event or circumstance occurs and instances where it does not.

25. Passive

The term passive as used herein with reference to fluorescent species refers to their use for fluorescence as opposed to enhancement of binding affinity.

26. Phosphorescent

The term phosphorescent as used herein can be defined as luminescence that is caused by the absorption of radiations (as light or electrons) and continues for a noticeable time after these radiations have stopped.

27. Prevent

By "prevent" or other forms of prevent means to stop a particular characteristic or condition. Prevent does not require comparison to a control as it is typically more absolute than, for example, reduce or inhibit. As used herein, something could be reduced but not inhibited or prevented, but something that is reduced could also be inhibited or prevented. It is understood that where reduce, inhibit or prevent are used, unless specifically indicated otherwise, the use of the other two words is also expressly disclosed. Thus, if inhibits phosphorylation is disclosed, then reduces and prevents phosphorylation are also disclosed.

28. Primers

"Primers" are a subset of probes which are capable of supporting some type of enzymatic manipulation and which can hybridize with a target nucleic acid such that the enzymatic manipulation can occur. A primer can be made from any combination of nucleotides or nucleotide derivatives or analogs available in the art, which do not interfere with the enzymatic manipulation.

29. Probes

"Probes" are molecules capable of interacting with a target nucleic acid, typically in a sequence specific manner, for example through hybridization. The hybridization of nucleic acids is well understood in the art and discussed herein. Typically a probe can be made from any combination of nucleotides or nucleotide derivatives or analogs available in the art.

30. Ranges

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data are provided in a number of different formats, and that this data, represents endpoints and starting points, and ranges for any combination of the data points. For example, if a particular datum point "10" and a particular datum point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

31. Reduce

By "reduce" or other forms of reduce means lowering of an event or characteristic. It is understood that this is typically in relation to some standard or expected value, in other words it is relative, but that it is not always necessary for the standard or relative value to be referred to. For example, "reduces phosphorylation" means lowering the amount of phosphorylation that takes place relative to a standard or a control.

32. References

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

33. $Na_v$ Expression Set

A $Na_v$ expression set or like terms is more than one $Na_v$ expressions, which refers to the level of expression of a $Na_v$ channel. An expression set profile is the collection of $Na_v$ expressions within a $Na_v$ expression set.

34. Na$_v$ Signature

A Na$_v$ signature is a characteristic that a subject can have based on the expression of one or more Na$_v$ from a sample of the subject. For example, a subject can have a Na$_v$ signature where the expression of 3 Na$_v$ is obtained or received and the combination of the expression of these three channels produces a Na$_v$ signature for the subject.

35. Specifically Interacts

Specifically interacts or like terms means that the interaction is beyond a background interaction. The background interaction can be determined by for example looking at the interaction with serum albumin.

36. Subject

As used throughout, by a "subject" is meant an individual. Thus, the "subject" can include, for example, domesticated animals, such as cats, dogs, etc., livestock (e.g., cattle, horses, pigs, sheep, goats, etc.), laboratory animals (e.g., mouse, rabbit, rat, guinea pig, etc.) mammals, non-human mammals, primates, non-human primates, rodents, birds, reptiles, amphibians, fish, and any other animal. The subject can be a mammal such as a primate or a human. The subject can also be a non-human.

37. Tissue

Tissue or like terms refers to a collection of cells. Typically a tissue is obtained from a subject.

38. Treating

"Treating" or "treatment" does not mean a complete cure. It means that the symptoms of the underlying disease are reduced, and/or that one or more of the underlying cellular, physiological, or biochemical causes or mechanisms causing the symptoms are reduced. It is understood that reduced, as used in this context, means relative to the state of the disease, including the molecular state of the disease, not just the physiological state of the disease. In certain situations a treatment can inadvertently cause harm.

39. Therapeutically Effective

The term "therapeutically effective" means that the amount of the composition used is of sufficient quantity to ameliorate one or more causes or symptoms of a disease or disorder. Such amelioration only requires a reduction or alteration, not necessarily elimination. The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

40. Voltage Gated Sodium Ion Channel

The term voltage gated sodium ion channel (VGSC) as used herein refers to transmembrane proteins that allow sodium ions to permeate through the cell membrane to depolarize local electric fields.

B. COMPOSITIONS

1. Voltage Gated Ion Channels

Voltage-gated sodium channels (Na$_v$), classically associated with voltage conductance in excitable tissues, are pore forming transmembrane proteins composed of a larger 260 kDa α subunit and at least four associated β subunits (Yu F H, et al. Genome Biol 2003; 4:207-14; Yu F H, et al. J Neuro 2003; 23:7577-85). The α subunit is composed of four domains (DI-DIV), each domain containing six transmembrane α-helical segments (S1-S6). (Yu F H, Catterall W A. Overview of the voltage-gated sodium channel family. Genome Biol 2003; 4:207-14). S4 of each domain acts as the voltage sensor for the channel and the extracellular loop between S5 and S6 contains a re-entrant loop serving as an ion selectivity filter (Yu F, et al. Genome Biol 2003; 4:207-14). The intracellular DIII-DIV linker sequence is highly conserved among isoforms and functions as an inactivation gate during channel operation. (Yu F. et al. Genome Biol 2003; 4:207-14).

There are currently ten known distinct isoforms of the α subunit, Na$_v$1.1-1.9, and Na$_x$ and four known distinct isoforms of the β subunit, β1-β4. (Yu F H, et al. Genome Biol 2003; 4:207-14.) The α subunits are categorized by their sensitivity to tetrodotoxin (TTX), a highly selective Nav blocker binding to the re-entrant loop between S5 and S6 of each domain (Cestèle S, Catterall W A. Molecular mechanisms of neurotoxin action on voltage-gated sodium channels. Biochimie 2000; 82:883-92). Na$_v$1.1-1.4, 1.6, and 1.7 are TTX-sensitive displaying nanomolar IC$_{50}$ values, while Na$_v$1.5, 1.8, and 1.9 are characterized as TTX-resistant (micromolar IC$_{50}$ values) (Yu F H, Catterall W A. Overview of the voltage-gated sodium channel family. Genome Biol 2003; 4:207-14). Expression of the α subunit alone is sufficient for function and the β subunit(s) play a significant role in modifying expression levels, kinetics, and the voltage-dependence of gating (Yu F H, Catterall W A. Overview of the voltage-gated sodium channel family. Genome Biol 2003; 4:207-14).

2 Voltage Gated Ion Channels and Cancer

Recently, Na$_v$ mRNA's have been detected in a variety of cancers including prostate cancer. (Roger S, Potier M, Vandier C, Besson P, Le Guennec J Y. Voltage-gated sodium channels: new targets in cancer therapy? Curr Pharm Des 2006; 12:3681-95). Na$_v$1.1-1.4, 1.7, and 1.9 transcripts are found in human prostate cancer, with increased Na$_v$1.7 isoform mRNA expression reported. (Diss J K. J, Archer S N, Hirano J, Fraser S P, Djamgoz M B A. Expression profiles of voltage-gated Na$^+$ channel α-subunit genes in rat and human prostate cancer cell lines. Prostate 2001; 48:165-78). Evidence for functional Na$_v$ protein in prostate cancer was demonstrated in the electrophysiological characterization of TTX-sensitive cellular membrane sodium currents in the PC-3 and PC-3M cell lines. (Laniado M E, Lalani E-N, Fraser S P, et al. Expression and functional analysis of voltage-activated Na$^+$ channels in human prostate cancer cell lines and their contribution to invasion in vitro. Am J Pathol 1997; 150:1213-21; Mycielska M E, Palmer C P, Brackenbury W J, Djamgoz M B A. Expression of Na$^+$-dependent citrate transport in a strongly metastatic human prostate cancer PC-3M cell line: regulation by voltage-gated Na$^+$ channel activity. J Physiol 2005; 563:393-408). Evidence linking Na$_v$ protein expression to human prostate cancer was realized with a pan-antibody which recognizes the conserved DIII-DIV linker of all Na$_v$'s. (Laniado M E, Lalani E-N, Fraser S P, et al. Expression and functional analysis of voltage-activated Na$^+$ channels in human prostate cancer cell lines and their contribution to invasion in vitro. Am J Pathol 1997; 150:1213-21; Mycielska M E, Palmer C P, Brackenbury W J, Djamgoz M B A. Expression of Na$^+$-dependent citrate transport in a strongly metastatic human prostate cancer PC-3M cell line: regulation by voltage-gated Na$^+$ channel activity. J Physiol 2005; 563:393-408; Abdul M, Hoosein N. Voltage-gated sodium ion channels in prostate cancer: expression and activity. Anticancer Res 2002; 22:1727-30; Bennet E S, Smith B A, Harper J M. Voltage-gated Na$^+$ channels confer invasive properties on human prostate cancer cells. Pflugers Arch 2004; 447:908-14; Smith P, Rhodes N P, Shortland A P, et al. Sodium channel protein expression enhances the invasiveness of rat and human prostate cancer cells. FEBS Lett 1998;

423:19-24; Diss J K J, Stewart D, Pani F, et al. A potential novel marker for human prostate cancer: voltage-gated sodium channel expression in vivo. Prostate Cancer Prostatic Dis 2005; 8:266-73). As of yet, the expression and localization of human $Na_v$ α subunits in prostate cancer cells has not been fully characterized.

Studies support a relationship between increased expression of $Na_v$'s and in vitro metastatic potential as measured by invasion (Laniado M E, Lalani E-N, Fraser S P, et al. Expression and functional analysis of voltage-activated $Na^+$ channels in human prostate cancer cell lines and their contribution to invasion in vitro. Am J Pathol 1997; 150:1213-21; Bennet E S, Smith B A, Harper J M. Voltage-gated $Na^+$ channels confer invasive properties on human prostate cancer cells. Pflugers Arch 2004; 447:908-14; Smith P, Rhodes N P, Shortland A P, et al. Sodium channel protein expression enhances the invasiveness of rat and human prostate cancer cells. FEBS Lett 1998; 423:19-24; Diss J K J, Stewart D, Pani F, et al. A potential novel marker for human prostate cancer: voltage-gated sodium channel expression in vivo. Prostate Cancer Prostatic Dis 2005; 8:266-73; Grimes J A, Fraser S P, Stephens G J, et al. Differential expression of voltage-activated $Na^+$ currents in two prostatic tumour cell lines: contribution to invasiveness in vitro FEBS Lett 1995; 369:290-4; Sikes R A, Walls A M, Brennen W N, et al. Therapeutic approaches targeting prostate cancer progression using novel voltage-gated ion channel blockers. Clin Prostate Cancer 2003; 2:181-7), motility (Fraser S P, Salvador V, Manning E A, et al. Contribution of functional voltage-gated $Na^+$ channel expression to cell behaviors involved in the metastatic cascade in rat prostate cancer: I. lateral motility. J Cell Physiol 2003; 195:479-87), morphology (Fraser S P, Ding Y, Liu A, Foster C S, Djamgoz M B A. Tetrodotoxin suppresses morphological enhancement of the metastatic MAT-LyLu rat prostate cancer cell line. Cell Tissue Res 1999; 295:505-12), galvanotaxis (Djamgoz M B A, Mycielska M, Madeja Z, Fraser S P, Korohoda W. Directional movement of rat prostate cancer cells in direct-current electric field: involvement of voltage-gated $Na^+$ channel activity. J Cell Sci 2001; 114: 2697-705; Szatkowski M, Mycielska M, Knowles R, Kho A, Djamgoz M B A. Electrophysiological recordings from the rat prostate gland in vitro: identified single-cell and transepithelial (lumen) potentials. BJI Int 2000; 86:1068-75), and endocytosis (Mycielska M E, Fraser S P, Szatkowski M, Djamgoz M B A. Contribution of functional voltage-gated channel expression to cell behaviors involved in the metastatic cascade in rat prostate cancer: II. secretory membrane activity. J Cell Physiol 2003; 195:461-69). Indeed, human prostate cancer cells when transfected with $Na_v1.4$ had increased invasiveness (Mycielska M E, Palmer C P, Brackenbury W J, Djamgoz M B A. Expression of $Na^+$-dependent citrate transport in a strongly metastatic human prostate cancer PC-3M cell line: regulation by voltage-gated $Na^+$ channel activity. J Physiol 2005; 563:393-408).

Understanding the role of $Na_v$s in human prostate cancer cell proliferation and metastasis can provide new therapeutic targets and diagnostic markers. Small molecule $Na_v$ blockers were effective at inhibiting prostate cancer cell proliferation (Grimes J A, Fraser S P, Stephens G J, et al. Differential expression of voltage-activated $Na^+$ currents in two prostatic tumour cell lines: contribution to invasiveness in vitro FEBS Lett 1995; 369:290-4; Anderson J D, Hansen T P, Lenkowski P W, et al. Voltage-gated sodium channel blockers as cytostatic inhibitors of the androgen-independent prostate cancer cell line PC-3. Mol Cancer Ther 2003; 2:1149-54).

$Na_v$s have been identified to have increased expression in certain subpopulations of human prostate cancer tissue (Abdul M, Hoosein N. Voltage-gated sodium ion channels in prostate cancer: expression and activity. Anticancer Res 2002; 22:1727-30). In addition, a qualitative trend of increasing $Na_v$ expression and $Na_v1.7$ mRNA was correlated to prostate cancer grade and Gleason Score, respectively (Diss J K J, Stewart D, Pani F, et al. A potential novel marker for human prostate cancer: voltage-gated sodium channel expression in vivo. Prostate Cancer Prostatic Dis 2005; 8:266-73). However, neither of these studies described the distribution of $Na_v$ protein isotypes.

Prostate specific antigen (PSA) is the most widely used prostate cancer diagnostic marker. In spite of decreased mortality rates and increased screening (Hammerer P G, Kattan M W, Monet N, Prayer-Galetti T. Using prostate-specific antigen screening and nomograms to assess risk and predict outcomes in the management of prostate cancer. BJU Int 2006; 98:11-19), questions remain in regards to the diagnostic accuracy of the PSA test (especially for only slightly elevated levels of PSA) (Roddam A W, Duffy M J, Hamdy F C, et al. Use of prostate-specific antigen (PSA) isoforms for the detection of prostate cancer in men with a PSA level of 2-10 ng/ml: systematic review and meta-analysis. Eur Urol 2005; 48:386-99). Thus, the discovery of new biomarkers remains central to earlier and improved accuracy of detection and diagnosis.

The incidence of prostate cancer in epileptic men treated with sodium channel blockers was studied from 1994 to 2003. In the study, 1427 epileptic men were given phenyloin as a sodium channel blocker while 14270 epileptic men were not given a sodium channel blocker (control). It was shown that epileptic men given phenyloin were 40% less likely to be diagnosed with prostate cancer.

The binding and localization of compound 26 in prostate and prostate cancer tissue was studied. Human prostate paraffin embedded tissue slices were stained with 100 μM of compound 26 and dansyl amine. Microscopy showed that compound 26 is visible due to binding in human prostate tissue while dansyl amine does not bind to prostate tissue and, therefore, can not be visualized. The results show that the structural differences between compound 26 and dansyl amine are vital for binding human prostate tissue.

The localization of compound 26 in human prostate cancer tissue was studied. First, MYPT1 antibody was used to stain prostate cancer tissue. Propidium iodine was used to stain the tissue. Compound 26 was incubated with the tissue and the sample was analyzed using fluorescent microscopy. Merged images show the co-localization of compound 26 and MYPT1.

The localization of MYPT1 and compound 26 in normal prostate tissue was studied. First, MYPT1 antibody was used to stain prostate tissue. Propidium iodine was used to stain the tissue. Compound 26 was incubated with the tissue and the sample was analyzed using fluorescent microscopy. Merged images show the co-localization of compound 26 and MYPT1.

The difference in localization and binding of compound 26 and MYPT1 in prostate cancer tissue and normal tissue can be observed by comparing the images from the experiments discussed above.

a) Methods

Disclosed are methods of detecting prostate cancer comprising, collecting a sample from a subject, assaying the expression of a Voltage Gated Na Channel ($Na_v$) gene, comparing the expression of the $Na_v$ gene of the subject to the expression of the same $Na_v$ gene of a control subject, and detecting of prostate cancer in the subject if the expression of the $Na_v$ gene in the subject is different than the expression of the $Na_v$ gene of the control subject.

Also disclosed are methods, further comprising, assaying the expression of a second $Na_v$ gene, comparing the expression of the second $Na_v$ gene of the subject to the expression of the same $Na_v$ gene of a control subject, detecting prostate cancer in the subject if the expression of the second $Na_v$ gene in the subject is different than the expression of the second $Na_v$ gene of the control subject.

Disclosed are methods for detecting the presence of prostate cancer in a patient comprising: (a) measuring levels of a $Na_v$ in prostate tissues in a subject; and (b) comparing the measured levels of $Na_v$ with levels of $Na_v$ in prostate tissue, from a non-cancerous control, wherein a change in measured levels of $Na_v$ in the subject versus said non-cancerous control is associated with the presence of prostate cancer.

Also disclosed are methods, wherein the change is an increase.

Also disclosed are methods, wherein the change is a decrease.

Also disclosed are methods, wherein the $Na_v$ comprises SEQ ID NO:2.

Disclosed are methods of detecting a $Na_v$ comprising, Assaying a set of $Na_v$s in a tissue sample from a subject, wherein the set of $Na_v$s comprises 1.8 and another $Na_v$, wherein the tissue sample comprises prostate tissue, wherein a subject $Na_v$ signature is produced. It is understood that the $Na_v$ s and their expression or translation or function can be combined together in any combination, and for example in any combination which is predictive of cancer, such as prostate cancer or can cause detection of cancer, such as prostate cancer (for example see FIG. 1). It is understood that FIG. 1 shows increases, decreases, and amounts relative to a control.

Also disclosed are methods, further comprising the step, comparing the subject $Na_v$ signature to a Control $Na_v$ signature for the same $Na_v$ set.

Also disclosed are methods, further comprising the step, concluding the existence of a cancer cell in the prostate tissue when the subject $Na_v$ signature is different than the control $Na_v$ signature.

Also disclosed are methods, wherein the method of assaying comprises determining the expression level of a gene encoding the $Na_v$.

Also disclosed are methods, wherein determining the expression level of the gene encoding the $Na_v$ comprises performing a hybridization assay.

Also disclosed are methods, wherein determining the expression level of the gene encoding the $Na_v$ comprises performing a reverse transcription reaction producing copy DNA.

Also disclosed are methods, further comprising the step of performing polymerase chain reaction on the copy DNA producing a PCR product.

Also disclosed are methods, wherein the polymerase chain reaction is quantitative.

Also disclosed are methods, wherein the method of assaying comprises determining the expression level of the protein encoding the $Na_v$.

Also disclosed are methods, wherein determining the expression level of the protein encoding the $Na_v$ comprises contacting the $Na_v$ with an antibody, a functional nucleic acid for the $Na_v$.

Also disclosed are methods, wherein the $Na_v$ 1.2 comprises a sequence having at least 90% identity to the sequence set forth in the disclosed sequences.

Also disclosed are methods, further comprising immunohisto staining.

Also disclosed are methods, further comprising a FISH analysis.

Disclosed are methods for detecting prostate carcinoma, wherein the method comprises steps of: obtaining a prostate tissue specimen from a subject suspected of suffering from prostate cancer, and evaluating immunoreactivity between the tissue specimen and a monoclonal antibody that specifically immunoreacts with a $Na_v$ and that distinguishes prostate carcinoma cells from normal prostate cells.

Disclosed are methods of detecting prostate cancer comprising identifying from a cell from a human subject, the level of expression of $Na_v$ s, which are part of a $Na_v$ expression set, wherein the expression set comprises $Na_v$ 1.2 and 1.8, producing an expression set profile, and comparing the expression set profile to a control expression set profile of a control subject; and detecting the subject as having prostate cancer if the expression set profile of the subject is different than the control expression set profile and detecting the patient as not having prostate cancer if the expression set profile of the subject is the same as that of the control expression set profile.

Disclosed are methods of detection of prostate cancer comprising obtaining a tissue sample from a subject, determining expression of a set of $Na_v$ s in the tissue sample, producing an expression set profile, comparing the expression set profile to a control expression set profile.

Also disclosed are methods, further identifying prostate cancer in the tissue sample if the expression set profile is different than the control expression set profile.

Also disclosed are methods, wherein the $Na_v$ 1.8 is identified in the nucleus of the cell. Distribution changes to include nucleus.

Disclosed are methods of labeling a cell, comprising incubating a fluorescence labeled molecule, wherein the fluorescence labeled molecule specifically interacts with a protein present on or in the cell, wherein the incubating occurs in conditions allowing interaction of fluorescence labeled molecule with the protein.

Disclosed are methods of detecting a tumor cell comprising incubating a potential tumor cell with a compound, wherein the compound interacts with a protein on a tumor cell, where the presence or absence of the protein on the tumor indicates is related to a tumor cell, wherein the compound comprises a fluorescent moiety, identifying the association of fluorescence with the potential tumor cell.

Also disclosed are methods, comparing the fluorescence of the potential tumor cell to a control.

Also disclosed are methods, wherein the compound comprises any compound disclosed herein.

Also disclosed are methods, wherein the detection occurs in vivo.

Also disclosed are methods, wherein the detection occurs in situ.

Also disclosed are methods, wherein the potential tumor cell is a potential prostate tumor.

2. Inhibitor Identification and Optimization

As shown in SCHEME 1, optimization of the sodium channel inhibitors has employed a small aromatic or heteroaromatic ring system that bears a small bulky group, a substituted lipophilic side chain, and an amine or amide that is positioned in close

SCHEME 1.

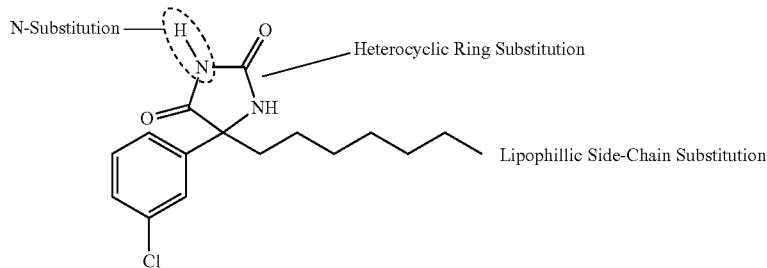

proximity to the aromatic or heteroaromatic center. Close proximity here means location on the ring itself or on a carbon position alpha, beta, or gamma to the ring.

It was previously shown that diphenylhydantoin (DPH) based molecules act as VGSC inhibitors. DHP analogs were designed and synthesized based on information arising from a QSAR model developed from [$^3$H]-BTX displacement in rat brain synaptoneurosomes. (Anderson, J. D. et al., *Mol. Cancer. Ther.* 2003, 2, 1149-1154). It was determined via comparative molecular field analysis (CoMFA) that the replacement of a DPH phenyl ring with a heptyl chain would improve the inhibitor's ability to bind/deactivate VGSC. Without being bound by theory, the length and flexibility of the heptyl chain allows the remaining parts of the DHP analog to reach and bind VGSC's hydrophobic receptive region more effectively. It has been found that the presence of a meta-chloro group on the remaining, phenyl ring further increases the binding affinity. (Lenkowski, P. W., et al., *Neuropharmacology,* 2007, 52, 1044-1054).

In a parallel approach the use of fluorescent moieties for their potential to enhance inhibition was investigated. Fluorescent molecules have been proven to be an indispensable source of information regarding drug properties in vitro and in vivo. Fluorescently labeled molecules are mostly used passively as a source for tracking a drug through biological systems while attempting to maintain a modicum of efficiency. Although a considerable number of small fluorescent moieties exist with rugged and tunable characteristics, their use in lead optimization has been entirely passive, acting only as molecular tags. It thus seemed highly desirable to have a system where the fluorescent tag not only serve as source for detection but also enhances and binds to the protein site.

Without being bound by theory, it is believed that the affinity of fluorescence-labeled drug target molecules for sodium channels is enhanced because the molecule comprises an aromatic or heteroaromatic ring system that bears an electron donating group and an electron withdrawing group in captodative electronic communication with each other. This type of push-pull arrangement on such a ring system creates a "softer", more polarizable and excitable electron cloud of aromatic delocalization, and is widely recognized to result in fluorescent properties in the push-pull moiety. The exploitation of such systems has not been employed in the prior art to improve binding affinity, or at least not as a deliberate element of the design for drug efficacy.

Appending a fluorophore on the hydrophobic tail (e.g., in the heptyl chain of JDA-3-135 below) sacrificed neither its hydrophobic character nor its fluorescence while enhancing binding to the protein. The result enables both a new form of diagnosis and increased drug performance through VGSC inhibition. In particular, the very effective fluorophore 5-(Dimethylamino)naphthalene sulfide (dansyl) can be appended to a molecule starting with commercially available dansyl chloride. Dansyl is not only inexpensive but pharmaceutically attractive due to its known bioavailability, mild reaction conditions for addition, and lack of permanent charge resulting in overall lipophilic character.

An exemplary fluorescent compound of the invention is an analog of diphenyl hydantoin covalently bonded to the 5-(dimethylamino)naphthalene sulfamide (dansyl) fluorescent moiety (SCHEME 1) resulting in N-(5-(4-(3-chlorophenyl)-2,5-dioxoimidazolidin-4-yl)pentyl)-5-dimethylamino) naphthalene-1-sulfonamide (CDPNS, shown below as THW-2-172 (1)). It was discovered that CDPNS actively interacts with the VGSC pharmacophore and allows visualization of the compound in vitro at 10 μM. Furthermore, CDPNS displayed a 58.9±4.15% functional block of the $hNa_v1.2$ isoform and a $GI_{so}$ of 36.0 μM in a PC-3 cell viability assay. CDPNS represents the first use of a fluorophore moiety to increase blocking activity toward VGSC. Remarkably the drug can fluoresce even while in the sodium ion channel, i.e., the dansyl moiety is not quenched or suppressed.

Examples of suitable fluorophore moieties for use in the invention include but are not limited to the following: dansyl, 4-(Diethylamino)azobenzene-4'-sulfonyl, fluorescein isothiocyanate (FITC), 5,6-carboxymethyl fluorescein, Texas red, nitrobenz-2-oxa-1,3-diazol-4-yl (NBD), coumarin, dansyl chloride, rhodamine, amino-methyl coumarin (AMCA), Eosin, Erythrosin, BODIPY®, Cascade Blue®, Oregon Green®, pyrene, lissamine, xanthenes, acridines, oxazines, phycoerythrin, macrocyclic chelates of lanthanide ions such as quantum Dye™, fluorescent energy transfer dyes, such as thiazole orange-ethidium heterodimer, and the cyanine dyes Cy3, Cy3.5, Cy5, Cy5.5 and Cy7. Additional suitable specific examples include 3-Hydroxypyrene 5,8,10-Tri Sulfonic acid, 5-Hydroxy Tryptamine (5-HT), Acid Fuchsin, Alizarin Complexon, Alizarin Red, Allophycocyanin, Aminocoumarin, Anthroyl Stearate, Astrazon Brilliant Red 4G, Astrazon Orange R, Astrazon Red 6B, Astrazon Yellow 7 GLL, Atabrine, Auramine, Aurophosphine, Aurophosphine G, BAO 9 (Bisaminophenyloxadiazole), BCECF, Berberine Sulphate, Bisbenzamide, Blancophor FFG Solution, Blancophor SV, Bodipy F1, Brilliant Sulphoflavin FF, Calcien Blue, Calcium Green, Calcofluor RW Solution, Calcofluor White, Calcophor White ABT Solution, Calcophor White Standard Solution, Carbostyryl, Cascade Yellow, Catecholamine, Chinacrine, Coriphosphine O, Coumarin-Phalloidin, CY3.1 8, CY5.1 8, CY7, Dans (1-Dimethyl Amino Naphaline 5 Sulphonic Acid), Dansa (Diamino Naphtyl Sulphonic Acid), Dansyl NH—CH3, Diamino Phenyl Oxydiazole (DAO), Dimethylamino-5-Sulphonic acid, Dipyrrometheneboron Difluoride, Diphenyl Brilliant Flavine 7GFF, Dopamine, Erythrosin ITC, Euchrysin, FIF (Formaldehyde Induced Fluorescence), Flazo Orange, Fluo 3, Fluorescamine, Fura-2, Genacryl Brilliant Red B, Genacryl Brilliant Yellow 10GF, Genacryl Pink 3G, Genacryl Yellow 5GF, Gloxalic Acid, Granular Blue, Haematoporphyrin, Indo-1, Intrawhite Cf Liquid, Leucophor PAF, Leucophor SF, Leucophor WS, Lissamine Rhodamine B200 (RD200), Lucifer Yellow CH, Lucifer Yellow VS, Magdala Red, Marina Blue, Maxilon Brilliant Flavin 10 GFF, Maxilon Brilliant Flavin 8 GFF, MPS (Methyl Green Pyronine Stilbene), Mithramycin, NBD Amine, Nitrobenzoxadidole, Noradrenaline, Nuclear Fast Red, Nuclear Yellow, Nylosan Brilliant Flavin EBG, Oxadiazole, Pacific Blue, Pararosaniline (Feulgen), Phorwite AR Solution, Phorwite BKL, Phorwite Rev, Phorwite RPA, Phosphine 3R, Phthalocyanine, Phycoerythrin R, Polyazaindacene Pontochrome Blue Black, Porphyrin, Primuline, Procion Yellow, Pyronine, Pyronine B, Pyrozal Brilliant Flavin 7GF, Quinacrine Mustard, Rhodamine 123, Rhodamine 5 GLD, Rhodamine 6G, Rhodamine B, Rhodamine B 200, Rhodamine B Extra, Rhodamine BB, Rhodamine BG, Rhodamine WT, Serotonin, Sevron Brilliant Red 2B, Sevron Brilliant Red 4G, Sevron Brilliant Red B, Sevron Orange, Sevron Yellow L, SITS (Primuline), SITS (Stilbene Isothiosulphonic acid), Stilbene, Snail 1, sulpho Rhodamine B Can C, Sulpho Rhodamine G Extra, Tetracycline, Thiazine Red R, Thioflavin S, Thioflavin TCN, Thioflavin 5, Thiolyte, Thiozol Orange, Tinopol CBS, True Blue, Ultralite, Uranine B, Uvitex SFC, Xylene Orange, and XRITC.

3. Diones

With the aid of ligand-based design techniques, a quantitative structure-activity relationship (QSAR) model was developed with $IC_{50}$ data recovered from whole-cell patch clamp recording in $hNa_v1.2$ expressing human embryonic kidney (HEK) cells. Further development of a CoMFA model (FIG. 2) indicated that hydrophobic bulk 6-7 carbons distal from the hydantoin ring and the addition of a m-chloro on one phenyl ring were required for optimum binding of ligand to the DPH receptor. (Lenkowski, P. W. et al. *Neuropharmacology*, 2007, 52, 1044-1054; Lenkowski, P. W. et al. *Eur. J. Pharm. Sci.*, 2004, 21, 635-644). JDA-3-135 was tested in a $hNa_v1.2$ electrophysiology study ($IC_{50}$ 13.9 µM) (Lenkowski, P. W. et al. *Neuropharmacology*, 2007, 52, 1044-1054; Lenkowski, P. W. et al. *Eur. J. Pharm. Sci.*, 2004, 21, 635-644) and was found to be a viable candidate for further lead design and development embodying the required characteristics for optimum binding. (Yu, F. H. and Catterall, W. A. *Genome Biology*, 2003, 4, 207; Brown, M. L. et al. *J. Med. Chem.* 1999, 42, 1537-1545; Scott, D. F. *J. Hist. Neurosci.*, 1992, 1, 111-118; Brown, M. L. et al. *J. Med. Chem.* 1997, 40, 602-607.).

4. Luminescence

Molecules described here with particular examples drawn to molecular conjugates having fluorescent moieties, however the invention is not so limited. The invention encompasses conjugates with other types of photoluminescence as well. These include phosphorescence.

For example, phosphorescence is a specific type of photoluminescence related to fluorescence. Unlike fluorescence, a phosphorescent material does not immediately re-emit the radiation it absorbs. The slower time scales of the re-emission are associated with "forbidden" energy state transitions in quantum mechanics. As these transitions occur less often in certain materials, absorbed radiation can be re-emitted at a lower intensity for up to several hours.

I.e., phosphorescence is a process in which energy absorbed by a substance is released relatively slowly in the form of light, in some cases providing materials with a long afterglow that can be rejuvenated by exposure to light. Most photoluminescent events, in which a chemical substrate absorbs and then re-emits a photon of light, are fast, on the order of 10 nanoseconds. However, for light to be absorbed and emitted at those time scales, the energy of the photons involved must be consistent with available quantum energy states and allowed transitions of the substrate. In the special case of phosphorescence, the absorbed photon energy undergoes intersystem crossing into an energy state of higher spin multiplicity, usually a triplet state. As a result, the energy can become trapped in the triplet state with only quantum mechanically "forbidden" transitions available to return to the lower energy state. These transitions, although "forbidden", will still occur but are kinetically unfavored and thus progress at significantly slower time scales. Most phosphorescent compounds are still relatively fast emitters, with triplet lifetimes on the order of milliseconds. However, some compounds have triplet lifetimes up to minutes or even hours, allowing these substances to effectively store light energy in the form of very slowly degrading excited electron states. If the phosphorescent quantum yield is high, these substances will release significant amounts of light over long time scales, creating so-called "glow-in-the-dark" materials.

Chemi-luminescence is a different but related phenomenon: an excited state is created via a chemical reaction; the excited state then transfers energy to a "dye" molecule (also known as a sensitizer), and subsequently fluoresce back to the ground state.

Common pigments used in phosphorescent materials include zinc sulfide and strontium aluminate. Use of zinc sulfide for safety related products dates back to the 1930s. However, the development of strontium oxide aluminate, with a luminance approximately 10 times greater than zinc sulfide, has relegated most zinc sulfide based products to the novelty category. Strontium oxide aluminate based pigments are now used in exit signs, pathway marking, and other safety related signage. Strontium aluminate based afterglow pigments are marketed under brand names like Super-Lumi-Nova™ or NoctiLumina™. In the invention case a zinc sulfide or strontium aliminate complex would be bonded to the organic modulator. The chemical equation for phosphorescence is as follows,

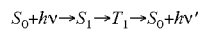

$$S_0 + h\nu \rightarrow S_1 \rightarrow T_1 \rightarrow S_0 + h\nu'$$

where S is a singlet and T a triplet for a pair of electrons; the subscripts denote states (0 is the ground state, and 1 the excited state). Transitions can also occur to higher energy levels, but the first excited state is denoted for simplicity.

5. Exemplary Inhibitor Molecules and Their Syntheses

Disclosed are compounds comprising a structure A-B—C, wherein A is a residue that can bind to one or more isoforms of an ion channel to modulate ion flow across said channel, B is a lipophilic linker or optionally a covalent bond, C comprises a fluorophore moiety, and B is covalently bonded to each of A and C.

Also disclosed are compounds, wherein the fluorophore moiety comprises an electron donating group in captodative communication with an electron withdrawing group, wherein A comprises a small aromatic or heteroaromatic ring system, wherein an amine or amide is positioned in close proximity to the aromatic or heteroaromatic center, wherein the ring system further comprises a small bulky group as a substituent, wherein the compound comprises a residue selected from the group consisting of hermitamide A, hermitamide B, an enantiomer of 2-(3-chloro-phenyl)-2-hydroxy-nonanoic acid amide, or a N-(5-(4-(3-chlorophenyl)-2,5-dioxoimidazolidin-4-yl)pentyl)-species, wherein the linker is a lipophilic side chain, wherein the lipophilic side chain has a length of from 1 to 11 atoms between A and C, and/or alone or in combination with these or any other characteristic disclosed herein.

Disclosed are compounds, wherein the lipophilic side chain is further substituted with a moiety selected from the group consisting of halogen, $C_1$-$C_4$ organic group, $C_1$-$C_4$ ether, $C_1$-$C_4$ ester or sulfester or phosphoester, mono- or di-$C_1$-$C_4$ alkylamine, $C_1$-$C_4$ amide or sulfamide or phosphoamide, imidazolidine-2,4-dilactone, other heterocyclic group, hydroxyl, or amino group, and/or alone or in combination with these or any other characteristic disclosed herein.

Disclosed are complexes comprising a compound, bound to an isoform of an ion channel.

Also disclosed are complexes, wherein the ion channel is a voltage gated sodium ion channel or a prostate sodium channel, wherein the isoform is selected from the group consisting of $hNa_v1.1$, $hNa_v1.2$, $hNa_v1.3$, $hNa_v1.4$, $hNa_v1.5$, $hNa_v1.6$, $hNa_v1.7$, $hNa_v1.8$, or $hNa_v1.9$, and/or alone or in combination with these or any other characteristic disclosed herein.

Disclosed are pharmaceutical compositions comprising any of the compounds disclosed herein, and/or alone or in combination with these or any other characteristic disclosed herein.

Also disclosed are methods of treatment comprising administering to a mammal in need thereof a pharmaceutical composition as disclosed herein.

Also disclosed are methods of treatment, wherein the medical indication being treated is epilepsy, pain, prostate cancer, or another neurological condition, and/or alone or in combination with these or any other characteristic disclosed herein.

Also disclosed are diagnostic kits comprising any of the compounds disclosed herein, and/or alone or in combination with these or any other characteristic disclosed herein.

Disclosed are methods of assessing the presence prostate cancer in a mammalian patient, wherein the method comprises a step in which an ion channel containing tissue culture from the patient is treated with a composition containing any of the disclosed compounds, and/or alone or in combination with these or any other characteristic disclosed herein.

Also disclosed are methods, further comprising identifying the stage of the prostate cancer, wherein the patient is diagnosed for prostate cancer, wherein the patient is assessed for the reduction of the prostate cancer following treatment for prostate cancer, and/or alone or in combination with these or any other characteristic disclosed herein.

Disclosed are methods for investigating cell proliferation, electrical depolarization of a tissue, or another phenomenon mediated by ion migration across an ion channel, comprising treating a cell culture, tissue culture, or other sample containing an ion channel, with a composition comprising any compound disclosed herein, and assessing the location and intensity of fluorescence in the sample.

Also disclosed are methods and compositions, wherein A-B—C manifests 10% or more of the ion channel modulation effect of A alone, wherein the linker has between 2 and 7 backbone atoms between A and C wherein the linker is a linear, branched or cyclic $C_1$-$C_{11}$ hydrocarbon residue, wherein the linker's backbone atoms are carbons, and the backbone is substituted with a moiety selected from the group consisting of halogen, $C_1$-$C_4$ organic group, $C_1$-$C_4$ ether, $C_1$-$C_4$ ester or sulfester or phosphoester, mono- or di-$C_1$-$C_4$ alkylamine, $C_1$-$C_4$ amide or sulfamide or phosphoamide, imidazolidine-2,4-dilactone, other heterocyclic group, hydroxyl, or amino group, and/or alone or in combination with these or any other characteristic disclosed herein.

Disclosed are methods for synthesizing lyngbic acid and hermitamides and their stereoisomers, wherein a BINOL-titanium complex is used to mediate asymmetric addition of allyltributylstannane into octanal to set a remote C7 stereocenter.

Also disclosed are methods, comprising the following steps: Condensing octanal with allyltributylstannane in the presence of chiral or racemic BINOL and $TiCl_2(O-i-PR)_2$; Methylating the alcohol in the product of a); Oxidizing the alpha-olefin product of b) such that the ultimate carbon is cleaved and the penultimate carbon forms an acetal; Condensing the acetal in the product of c) with a vinyl anion; Condensing the allylic alcohol in the product of d) with a protected acetic acid group, eliminating the alcohol to obtain a 4,5-didehydro-7-methoxy-tetradecanoic acid ester; Deprotecting the ester to obtain lyngbic acid; and Optionally transforming the ester from the product of e) or lyngbic acid from the product of f) to an amide, and/or alone or in combination with these or any other characteristic disclosed herein.

Also disclosed are methods, wherein the nitrogen of the optional amide is further substituted with —$CH_2CH_2Ar$, wherein Ar represent a phenyl group or indole linked at the 3-position, wherein the chiral BINOL is (R)-BINOL, wherein the chiral BINOL is (S)-BINOL, wherein the BINOL is racemic (R,S)-BINOL, wherein oxidation of the first alpha-olefin intermediate is performed by reaction with $OsO_4$ and $NaIO_4$, wherein the vinyl anion is provided as vinylmagnesium bromide, and/or alone or in combination with these or any other characteristic disclosed herein.

Also disclosed are methods, wherein the protected acetic acid is provided as the methyl orthoester of acetic acid in the presence of n-propionic acid, wherein lyngbic acid is transformed to an ester by reaction with DCC, 1-hydroxybenzotriazole and either phenethylamine or tryptamine, and/or alone or in combination with these or any other characteristic disclosed herein.

Disclosed are compositions of (S)-hermitamide A, composition of (R)-hermitamide A, composition of (S)-hermitamide B, composition of (R)-hermitamide B, composition of (S)-lyngbic acid, composition of (R)-lyngbic acid, synthesized by the methods disclosed herein, and/or alone or in combination with these or any other characteristic disclosed herein.

Disclosed are compounds having the structure and stereochemistry of (R)-hermitamide A, compound having the structure and stereochemistry of (R)-hermitamide B, compound having the structure and stereochemistry of (R)-lyngbic acid, and/or alone or in combination with these or any other characteristic disclosed herein.

Also disclosed are methods for synthesizing optically pure chiral alpha-hydroxy amides, comprising cyclic condensation of an aldehyde and chiral alpha hydroxy ester followed by facile separation of the stereoisomeric products, and/or alone or in combination with these or any other characteristic disclosed herein.

Disclosed are methods, comprising: providing a chiral alpha-hydroxy carboxylic acid, wherein the alpha position is further substituted by a small aromatic or small heteroaromatic ring system; reacting the alpha-hydroxy carboxylic acid with an aldehyde that has no alpha hydrogens, to form a substituted 4-oxo-1,3-dioxolane; separating the (R) and (S) stereoisomers of the substituted dioxolane chromatographically to obtain a chiral 4-oxo-1,3-dioxolane in high purity; functionalizing the $C_5$ position of a chiral 4-oxo-1,3-dioxolane with a lipophilic moiety having a leaving group in the presence of a base; and deconstructing the 4-oxo-1,3-dioxolane ring by reaction with a nitrogen compound, and/or alone or in combination with these or any other characteristic disclosed herein.

Also disclosed are methods, wherein the small aromatic or heteroaromatic ring system is optionally further substituted with a small bulky group.

Also disclosed are methods, wherein the small bulky group is a halogen, wherein the ring system is phenyl and the small bulky group is a 3-chloro-substituent, wherein the chiral alpha-hydroxy carboxylic acid is a pure (R) or (S) stereoisomer of 2-(3-chlorophenyl)-2-hydroxy acetic acid, wherein the aldehyde has an aromatic, heteroaromatic, quaternary alkyl, or trihalomethyl carbon alpha to the carbonyl position, wherein the aldehyde has a quaternary alkyl center alpha to the carbonyl position and/or alone or in combination with these or any other characteristic disclosed herein, wherein the aldehyde is pivaldehyde, wherein the reaction is conducted in the presence of triflic acid in pentane or under other conditions in which the acidity is as high or higher, wherein the separation of stereoisomers is performed by column chromatography, wherein a stereoisomer is obtained with at least 80% purity, wherein a stereoisomer is obtained with at least 90% purity, wherein a stereoisomer is obtained with at least 95% purity, wherein a stereoisomer is obtained with at least 98% purity, wherein the lipophilic moiety has between 1 and 11 backbone atoms, and is optionally substituted by a halogen, $C_{1-4}$ group, $C_{1-4}$ ether or ester hydroxyl group, or —$NR_1R_2$ wherein $R_1$ and $R_2$ are independently a hydrogen or unsubstituted $C_{1-4}$ group, wherein the backbone atoms consist of carbon atoms and optionally oxygen atoms, and there are 7 backbone atoms, and/or alone or in combination with these or any other characteristic disclosed herein.

Also disclosed are methods, wherein the lipophilic moiety's leaving group is a halogen, halogenated conjugate base of an acid, tosylate, or pyridinium, wherein the C5 position of the chiral 4-oxo-1,3-dioxolane is reacted with a lipophilic moiety having a leaving group in the presence of LDA and THF-HMPA at a temperature of 0° C. or less, wherein the 4-oxo-1,3-dioxolane ring is deconstructed by reaction with ammonium hydroxide, ammonia, a primary alkyl amine or a secondary alkyl amine.

a) Hermitamides

Hermitamides A and B are natural products that have been isolated from cyanobacteria, and are shown at SCHEMEs disclosed herein.

b) Asymmetric Synthesis and Evaluation of Enantiomers of 2-(3-Chloro-phenyl)-2-hydroxy-nonanoic Acid Amide α-Hydroxy-α-phenyl amides are a class of small molecules that have demonstrated potent inhibition of voltage-gated sodium channels. The hydroxyamide motif, an isostere of a hydantoin ring, provides an active scaffold from which several potent racemic sodium channel blockers have been derived. With little known about chiral preferences, the development of chiral syntheses to obtain each pure enantiomer for evaluation as sodium channel blockers is important. Using Seebach and Frater's chiral template. Cyclocondensation of (R)-3-chloromandelic acid with pivaldehyde furnished both the cis- and trans-2,5-disubstituted dioxolanones. Using this chiral template, both enantiomers of 2-(3-chloro-phenyl)-2-hydroxy-nonanoic acid amide were synthesized, and their ability was evaluated to functionally inhibit both $hNa_v1.5$ and $hNa_v1.7$. These compounds were also evaluated for antiproliferative effects against human prostate cancer cells that contain hNav1.5 and hNav1.7 isoforms. 227: Previously, Brown and co-workers (Brown, M. L. et al. *J. Med. Chem.* 1999, 42, 1537-1545) described the design and synthesis of 2-(3-chloro-phenyl)-2-hydroxy-nonanoic acid amide and its effect on sodium channels. (Ko, S. H.; et al. *Neuropharmacology.* 2006, 50, 865-873) Given the increasing focus of the effect of stereochemistry on compound efficacy and toxicity, each enantiomer of 3-chlorophenyl-α-hydroxyamide was synthesized.

The chiral template described by Seebach and Frater Seebach, et al. *Angewandte Chemie International Edition in English* 35. 1996, 23-24, 2708-2748 utilizes cis-2,5-disubstituted 1,3-dioxolan-4-ones, as scaffolds for the stereocontrol of alkylations, aldol additions, Michael additions, nucleophilic additions, and Mannich reactions. (Nagase, R.; et al. *Synthesis.* 2006, 22, 3915-3917; Misaki, T.; et al. *Org. Process Res. Dev.* 2006, 10, 500-504.; Liu, Y. M. et al. *Synth. Commun.* 2006, 36, 1815-1822.; Grover, et al. *J. Org. Chem.* 2000, 65, 6283-6287; Blay, G.; et al. *Tetrahedron.* 2006, 62, 9174-9182; et al. *Synthesis.* 2007, 1, 108-112) Cyclocondensation of a mandelic acid with pivaldehyde gives the 2,5-disubstituted dioxolanone, and alkylation is directed by the tert-butyl group. Using (R)-3-chloromandelic acid both cis- and trans-2,5-disubstituted dioxolanones was observed. The use of both isomers was employed to utilize this asymmetric strategy to synthesize each enantiomer of 3-chlorophenyl-α-hydroxyamide ((±)-1) to evaluate the chiral preference for inhibiting sodium channel isoforms.

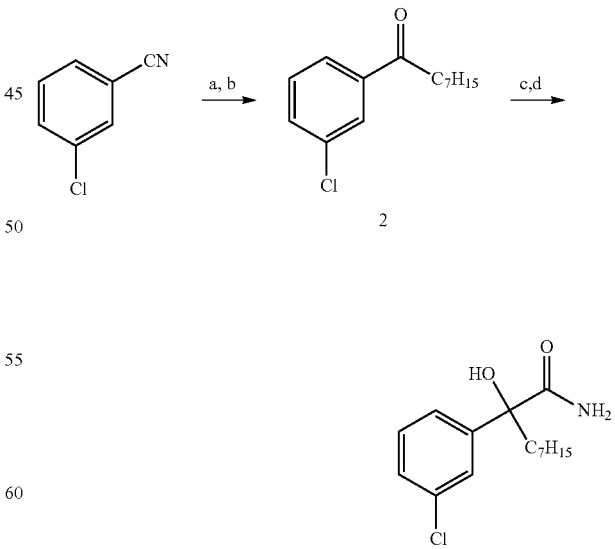

Scheme 2. Synthesis of racemic 2-(3-chloro-phenyl)-2-hydroxy-nonanoic acid amide.

Reagents and Conditions: a. (i) $C_7H_{15}MgBr$, THF, 0° to rt. overnight, (ii) 1N HCl; b. TMSCN, KCN, 18-c-6, $CH_2Cl_2$; c. conc. HCl, HCl (g), 0° C.

SCHEME 3. Synthtic method of optically pure R)- and (S)-2-(3-chloro-phenyl)-2-hydroxy-nonanoic acid amide Synthesis of optically pure (R)- & (S)-2-(3-chloro-phenyl)-2-hydroxy-nonanoic acid amide.

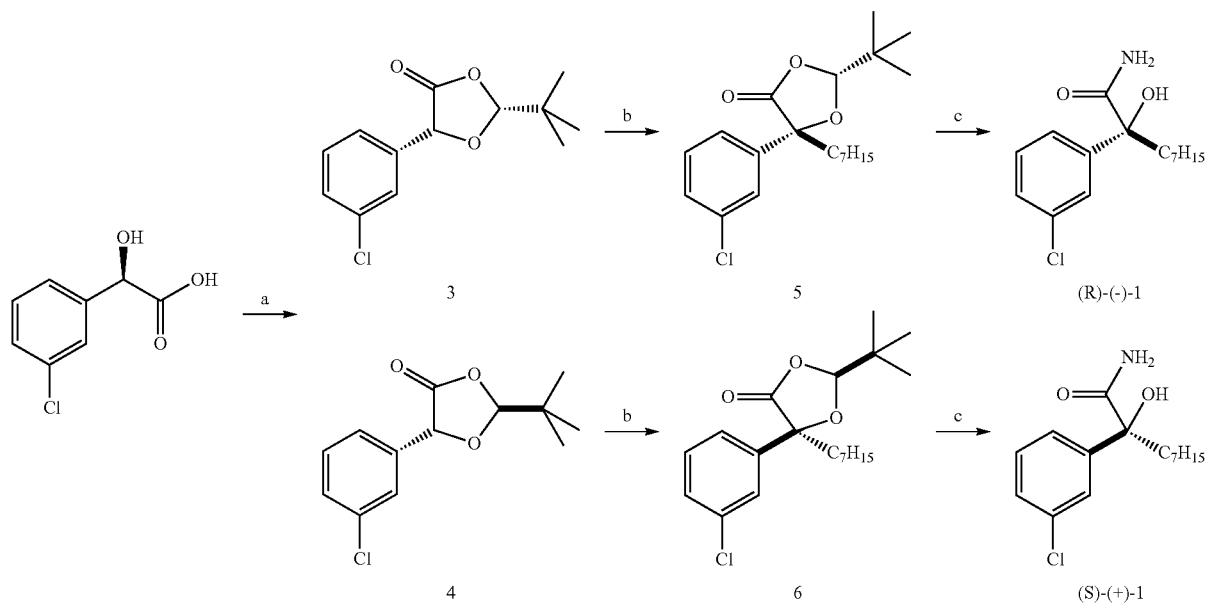

Reagents and Conditions: a. pivaldehyde, TfOH, pentane, Dean-Stark; b. LDA, $C_7H_{15}I$, THF—HMPA, -78° C., 3 hrs.; c. $NH_4OH$, EtOH, 60° C.

Synthesis of optically pure (R)- and (S)-2-(3-chloro-phenyl)-2-hydroxy-nonanoic acid amide.

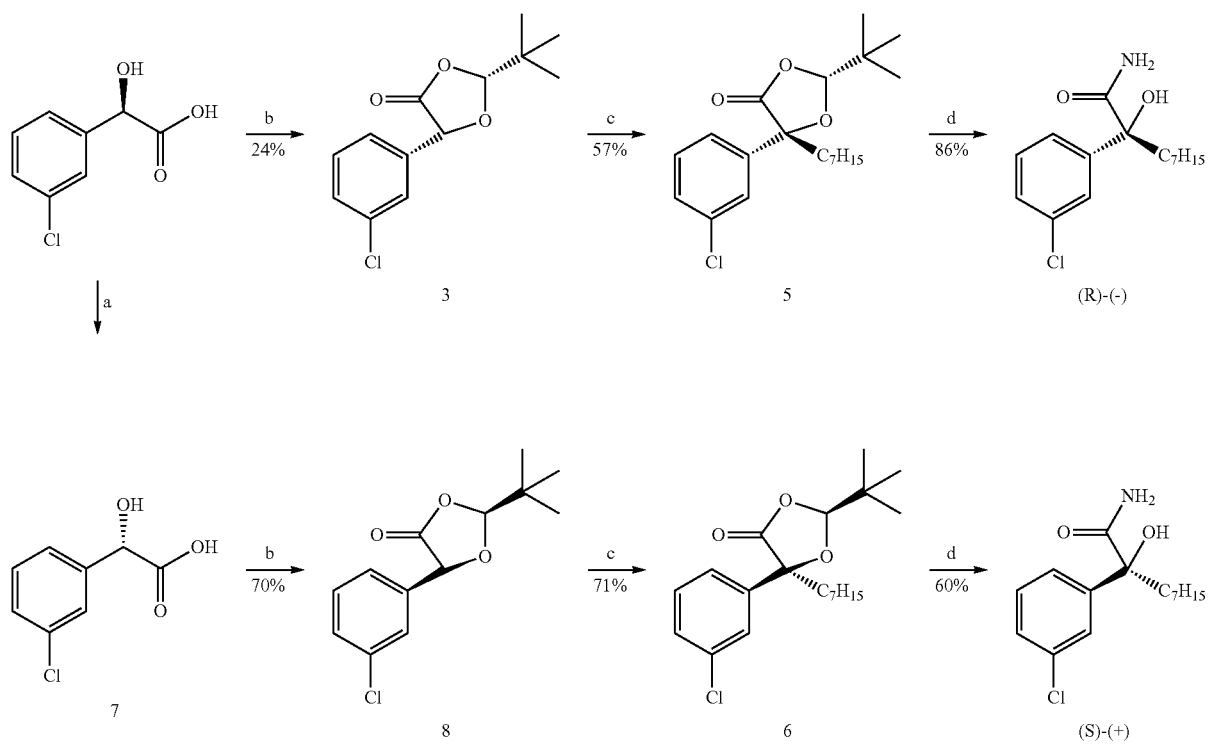

Reagents and Conditions: a. 1. AcCl, MeOH, 40° C., 87%, 2. p-nitrobenzoic acid, PPh3, DEAD, THF, 86%, 3. NaN3, MeOH, 40° C., 72%, 4. 5% NaOH, 40° C., 96%; b. Pivaldehyde, TfOH, pentane, Dean-Stark; c. LDA, $C_7H_{15}I$, THF—HMPA, -78° C., d. 7N $NH_3$, MeOH, rt.

TABLE 1

Effect of Solvent and Addition Method on Diastereoselectivity of Alkylation

| Entry | Solvent | Addition Method | dr (cis:trans) |
|---|---|---|---|
| 1 | THF | Direct | 2:1 |
| 2 | THF-$^c$Hex | Direct | NR |
| 3 | Et$_2$O | Direct | NR |
| 4 | THF-HMPA | Inverse | 1:10 |
| 5 | THF-HMPA | Inverse | 1:10 |
| 6 | THF | Inverse | NR |

Heptyl source = C$_7$H$_{15}$I

TABLE 2

Effect of Electrophile on Diastereoselectivity

| Entry | Heptyl Source | dr (cis:trans) |
|---|---|---|
| 1 | C$_7$H$_{15}$OTf | 1:4.5 |
| 2 | C$_7$H$_{15}$Br | 1:1.5 + SM |
| 3 | C$_7$H$_{15}$I | 1:10 |
| 4 | C$_7$H$_{15}$I | 6:94* |

*Reaction held at –78° C. for 3-4 h and quenched immediately

Scheme 4. Phenytoin (DPH) and 2-(3-chloro-phenyl)-2-hydroxy-nonanoic acid amide ((±)-1)

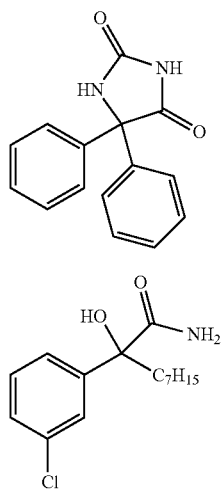

A

1

TABLE 3 hNa$_v$ 1.5 and hNa$_v$ 1.7 IC$_{50}$'s for racemic, (R)-, (S)-2-(3-chloro-phenyl)-2-hydroxy-nonanoic acid amide, and DPH.

| Compound | hNa$_v$ 1.5 IC$_{50}$ (µM) | hNa$_v$ 1.7 IC$_{50}$ (µM) |
|---|---|---|
| (±)-1 | 5.78 | 1.81 |
| R-(–)-1 | 7.43 | 1.88 |
| S-(+)-1 | 4.78 | 2.62 |
| DPH | >100 | >100 |

$^a$Fluorescent based assay

TABLE 4

% Inhibition for hERG assay.

| | % inhibition | | | | |
|---|---|---|---|---|---|
| Compound | 0.3 µM | 1 µM | 3 µM | 10 µM | 30 µM |
| (±)-1 | 15 | 17 | 15 | 51 | 78 |
| R-(–)-1 | 16 | 26 | 20 | 57 | 90 |
| S-(+)-1 | 10 | 25 | 33 | 65 | 90 |
| DPH | 9 | 20 | 28 | 17 | 40 | c) Chemistry.

Racemic (±)-1 was synthesized using the previously described procedure shown in Scheme 2. (Anderson, James D. Mol Cancer Ther. 2003 November; 2(11):1149-54) Grignard addition of heptylmagnesium bromide into 3-chlorobenzonitrile followed by acidic hydrolysis gave the desired ketone 2. Treatment of the ketone with TMSCN, followed by acidic hydrolysis furnished the racemic 2-(3-chloro-phenyl)-2-hydroxy-nonanoic acid amide ((±)-1).

In Scheme 3, commercially available (R)-(–)-3-chloromandelic acid was condensed with pivaldehyde to give both cis and trans dioxolanones 3 and 4 a 5:1 mixture, respectively. Interestingly, this same reaction using the unsubstituted mandelic acid gives almost exclusively the cis-isomer. The cis and trans isomers are easily separable by column chromatography and both were isolated with high purity. Alkylation of 3 was carried out under various conditions summarized in Table 1. Freshly prepared LDA at –78° C. in THF was used in the initial attempt to make the enlolate. After the complete addition of the dioxolanone the temperature was raised to 0° C. for 10 minutes, and then lowered back to –78° C. Heptyl iodide was then added dropwise at –78° C. This procedure is known as the direct addition method. Initial alkylation of the dioxolanone in THF using this addition method gave a 2:1 (cis:trans) mixture of the alkylated product. Paige et al. reported using 1:3 cyclohexane:ether solvent mixture to promote diastereoselectivity in Li enolate reactions. (Caine, D et al. Synlett. 1999, 9, 1391-1394) Applying these conditions to the system however, resulted in no reaction. Therefore, Et$_2$O was used as the solvent with the hypothesis that a less polar solvent would slow the reaction rate with increased selectivity. However, allowing this reaction to run overnight resulted in no conversion of the starting material. Blay et al. reported that inverse addition and the addition of 3 eq. of HMPA to these reactions resulted in an increased diastereoselectivity. (Blay, G.; et al. *Tetrahedron*. 2006, 62, 9174-9182) The inverse addition protocol calls for the addition of LDA to a premixed solution of the dioxolanone, heptyl iodide, and HMPA in THF at –78° C. Indeed, when it was treated the cis-dioxolanone 3 with LDA in THF-HMPA and heptyl iodide at –78° C. the alkylated product 5 was obtained in a 1:10 ratio of diastereomers. Under these conditions the major product had the heptyl chain trans to the tert-butyl group.

The results provided by the THF-HMPA system led to consider the effect the leaving group of the electrophile can have on this reaction. The reaction was attempted with heptyl iodide, heptyl triflate, and heptyl bromide, as summarized in Table 2. The hypothesis was that reactivity of the electrophile would strongly affect the diastereoselectivity of the alkylation product. It was predicted that using heptyl triflate would result in increased reaction rate, allowing for better selectivity. However, addition of the triflate gave a 1:4.5 mixture of isomers by $^1$H-NMR. Reaction with heptyl bromide was incomplete, and gave a 1:1.5 mixture, thus making heptyl iodide the most suitable heptyl source (1:10 mixture). A diastereoselectivity of 6:94, was obtained when using heptyl iodide at −78° C. for 3 hrs, followed by quenching the reaction at that same temperature.

Separation of the diastereomers by column chromatography was accomplished using an ether-hexanes gradient. Treatment of alkyl dioxolanone 5, with concentrated ammonium hydroxide in ethanol furnished (R)-(−)-2-(3-chlorophenyl)-2-hydroxy-nonanoic acid amide ((R)-(−)-1) directly in modest yields with 91:1 ratio of enantiomers as determined by chiral HPLC. This series of reactions proceeds by retention of stereochemistry giving the (R)-enantiomer as the main product. By utilizing the trans-dioxolanone 4, and completing the same synthetic steps as previously with the cis-isomer, (S)-(+)-2-(3-chloro-phenyl)-2-hydroxy-nonanoic acid amide ((S)-(+)-1) in 95:5 er was synthesized.

d) General Analysis

Using a FRET based assay, (±)-1, (R)-(−)-1, (S)-(+)-1 and DPH (FIG. 3) were evaluated for their isoform specific sodium channel blocking effects and the $IC_{50}$ values are shown in Table 3. Two isoforms of the channel were examined: $hNa_v1.5$, a cardiac sodium channel associated with arrhythmias, and $hNa_v1.7$, an isoform found in the peripheral nervous system. (George, A. J. Clin. Invest. 2005, 115, 1990-1999) Compound (S)-(+)-1 exhibited the greatest activity for the $hNa_v1.5$ isoform of the channel with an $IC_{50}$ of 4.78 µM. One enantiomer possessed slightly greater activity than the other, and the racemic mixture was observed in the middle. It is indicated from the proposed binding model that the (R)-enantiomer is the preferred confirmation as seen in FIG. 4. Compound (R)-(−)-1 has an $IC_{50}$=7.43 and (±)-1, the racemic mixture, has an $IC_{50}$=5.78 µM. The trend is different in the $hNa_v1.7$ data. The racemic mixture and (R)-(−)-1 had the greatest activity against this isoform of the channel with an $IC_{50}$=1.81 µM, and 1.88, respectively. The (S)-(+)-1 enantiomer was preferred by $hNa_v1.5$ and (R)-(−)-1 was more active against $hNa_v1.7$. DPH was not active on either $hNa_v1.5$ or $hNa_v1.7$ at concentrations less than 100 µM.

All four compounds were also counter-screened for human ether-a-go-go-related gene (hERG) activity against the radioligand MK-0499. Blockade of hERG $K^+$ channels is widely regarded as the predominant cause of drug-induced QT prolongation. (Aronov, A J Med Chem. 2006 Nov. 16; 49(23): 6917-21). As seen in Table 4, the racemic mixture and the enantiomers did not significantly inhibit hERG below 10 µM.

Disclosed herein several isoforms of the channel to be involved with prostate cancer cell proliferation. CWR22rv-1 whole cell lysate extracts were evaluated for expression of $hNa_v1.5$ and $hNa_v1.7$ by Western analysis. Both α-subunits were detected at 260 kDa with each antibody (FIG. 5). Specific bands were also detected at lower molecular weights and are likely degradation products. Pretreating both antibodies with their respective specific oligomer epitope control antigen eliminated the signal of both the 260 kDa band as well as the lower molecular weight bands.

With the identification of both sodium channels in human prostate cell line CWR22rv-1, (±)-1, (R)-(−)-1, and (S)-(+)-1 was evaluated for their effects on prostate cancer cell growth. Compound (R)-(−)-1 showed the greatest effect on CWR proliferation (FIG. 3). At 25 µM, approximately 25% of cells were killed after 24 hrs, while compounds (±)-1 and (S)-(+)-1 have marginal effects after 24 hrs. After 72 hrs, compound (R)-(−)-1 induced cell death in 60% of human prostate cancer cells, while compound (±)-1 and (S)-(+)-1 killed 25% and 40%, respectively.

In an effort to rationalize the differential binding of (R)-1 and (S)-1, the structure for the open and closed states of the sodium channel was predicted. For comparison, both the open and closed states of the sodium channel was modeled using the MthK and KcsA potassium channels as a template. In the closed model, F1579 and Y1586 residues in IVS6 were oriented toward the pore because of their likely interaction with local anesthetic (LA) drugs. In the open state model of the sodium channel, the S6 helical bends were produced at the serine sites which correspond to the glycine residues in the MthK open channel. Both (R)-1 and (S)-1 were docked using AutoDock 4.0. However, the docked position has a different interaction with the S6 helix residues that does not correspond to reported mutation data. (Linford, N. J. et al. Proc. Natl. Acad. Sci. U.S.A. 1998, 95, 13947-13952; Lipkind, et al. Mol. Pharmacol. 2005, 68, 1611-1622) To provide consistent results with respect to the mutation studies and previously known interactions of LA analogs, the docked positions were remodeled using step by step manual docking with MD simulations followed by minimization. Residues F1283, F1579, L1582, V1583, Y1586 in IVS6, and L1280 in IIIS6, and L788, F791, L792, in IIS6 and I433, N434, L437 in IS6, and selectivity filter residues D400, E755, K1237 in the domains of I-IV P-loops form the binding site for LA analogs. In fact some of these residues have been reported to be participating in the BTX and LA binding by mutational experiments. The (R)-1 likely interacts with N434 through H-bond interaction whereas the absence of this H-bond interaction for (S)-1 can lead to the observed loss of activity.

The effects of the racemic mixture and enantiomers of compound 1 were also examined by patch clamp electrophysiology on the human $Na_v$ channel isoform, $Na_v1.2$, stably expressed in human embryonic kidney cells (HEK 293). $Na_v$ currents were elicited by step depolarizations from a holding potential of −60 mV to +10 mV for 25 ms at 15 s intervals. Sodium currents were record during a control drug free condition, after 5 mins of drug perfusion and following washout. At 1 µM, (R)-(−)-1 inhibited the $Na_v$ channel current by 67.4±5.3% (n=4) and by 94.3±0.6% (n=3) at 10 µM. In contrast, (S)-(+)-1 and the racemic mixture were significantly less potent than the (R)-(−)-1 enantiomer at 1 µM, (P<0.05). (S)-(+)-1 inhibited the sodium channel current by 34.9±2.3% (n=3) at 1 µM and by 91.5±0.5% (n=3) at 10 µM. The racemic mixture inhibited the sodium channel current by 31.9±2.9% (n=3) at 1 µM and by 87.0±3.1% (n=3) at 10 µM (FIG. 14). All drug effects were fully reversible on washout.

In an effort to rationalize the enantioselective effects of the sodium channel blockers with the sodium channel pore, and to understand the differential activity and binding event that occurs with the drug for the R and S configuration, the structure for the open and the closed $Na_v1.7$ channel was predicted. The sodium channel pore was developed by aligning the pore-forming residues 15-101 of the x-ray structure of the open form of the KcsA potassium channel, with residues 235-410 of domain I, residues 690-799 of domain II, residues 1123-1275 of domain III, and residues 1445-1551 of domain IV of the sodium channel. KcsA potassium channel residues 22-124 were used to model the P-loop regions with the N- and C-terminal residues of these segments. The orientations of the four domains were modeled by aligning sodium channel domains I-IV with MthK channel chains A-D. The BTX binding site location, as identified by mutational studies, is on the pore-facing side of the S6 helices from domains I, III, and IV (Linford, N. et al. Proc. Natl. Acad. Sci. U.S.A. 1998, 95, 13947-13952). Upon analysis of the homology model structure, the IS6, IIIS6 and IVS6 segments, and the residues that form the drug binding site are all conserved, and are mainly hydrophobic. Both the open and the closed channel of the $Na_v$ channel was predicted based on the MthK and KcsA potassium channels as a template. In the closed channel model, F1579 and Y1586 in IVS6 were oriented toward the pore because of their possible interaction with LA drugs. In the open channel model, the bends in the S6 helices were produced at the serine sites corresponding to the glycine residues found in the MthK open channel structure. Both the R and S configuration of compound 1 were docked using AutoDock 4.0 (Morris, G. et al. *J. Computational Chemistry.* 1998, 19: 1639-1662) and FlexX incorporated in Sybyl 8.0. However, the docked poses generated by both programs show different interactions with the S6 helix residues in comparison to the mutation data. (Ragsdale, D. et al. *Science.* 1994, 265, 1724-1728; Yarov-Yarovoy, V.; et al. *J. Biol. Chem.* 2001, 276, 20-27; Yarov-Yarovoy, V et al. *J Biol Chem.* 2002, 277, 35393-35401 To be consistent with respect to the mutation studies and previous known interactions of lidocaine analogs (Lipkind, G et al. *Mol. Pharmacol.* 2005, 68, 1611-1622;), the docked positions were remodeled using step-by-step manual docking with constrained molecular dynamics (MD) simulations followed by minimization. In the restrained MD simulations, the optimum H-bond and hydrophobic distance constraints were set between the pore forming residues and the ligand. The residues such as F1283, F1579, L1582, F1283, V1583, Y1586 in IVS6, and T1279, L1280 in IIIS6, and L788, F791, L792, in IIS6 and I433, N434, L437 in IS6, and the selectivity filter residues D400, E755, K1237 in the domains of I-IV P-loops were identified as participants in the putative binding site for the compounds.

A structural model of $Na_v1.7$ predicted interaction with compounds (R)-(−)-1 and (S)-(+)-1 is shown in FIG. 15. The binding model indicates that compound 1 interacts with that residues F1283, F1579, L1582, V1583, Y1586 in IVS6, and T1279, L1280 in IIIS6, and L788, F791, L792, in IIS6 and F430, I433, L437 in IS6 and indicates amino acids that can contribute to potential binding interactions. In fact some of these residues are found to be important in alanine mutation experiments (0 (Morris, G. et al. *J. Computational Chemistry.* 1998, 19: 1639-1662; Ragsdale, D. et al. *Science.* 1994, 265, 1724-1728; Yarov-Yarovoy, V.; et al. *J. Biol. Chem.* 2001, 276, 20-27. As seen in FIG. 15, strong hydrophobic contacts were noticed between 1 and F1283, F1579, L1582, V1583, Y1586 L1280, L788, F791, L792, I433, and L437. Enantiomeric selectivity could be rationalized for the (R)-(−)-1 isomer which is driven by strong H-bonding between the amide functionality and T1279 (FIG. 15A). Modeling studies indicates that this interaction is only observed for the R enantiomer, and not present for the S enantiomer (FIG. 15B). This explains the difference in sodium channel activity observed for the R versus the S enantiomer.

Disclosed herein it was demonstrated that by using the Seebach and Frater chiral template, both enantiomers of 2-(3-chloro-phenyl)-2-hydroxy-nonanoic acid amide can be synthesized. The biological evaluation of compounds (±)-1, (R)-(−)-1, and (S)-(+)-1, shows a preference for the (R)-enantiomer over the (5) in CWR22rv-1 cells. The model of (R)-(−)-1 docked in the sodium channel shows a critical hydrogen bond interaction of the amide group with an Asn residue in the surrounding protein. This interaction is not present in the (S)-enantiomer ((S)-(+)-1), and is a possible reason for the reduced sodium channel activity.

6. General Terms and Characteristics a) Homology/Identity

It is understood that one way to define any known variants and derivatives or those that might arise, of the disclosed genes and proteins herein is through defining the variants and derivatives in terms of homology to specific known sequences. For example disclosed are human sodium channels and their protein and gene sequences. Specifically disclosed are variants of these and other genes and proteins herein disclosed which have at least, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent homology to the stated sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison can be conducted by the local homology algorithm of Smith and Waterman Adv. Appl. Math. 2: 482 (1981), by the homology alignment algorithm of Needleman and Wunsch, J. Mol. Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. Science 244:48-52, 1989, Jaeger et al. Proc. Natl. Acad. Sci. USA 86:7706-7710, 1989, Jaeger et al. Methods Enzymol. 183:281-306, 1989 which are herein incorporated by reference for at least material related to nucleic acid alignment.

It is understood that as discussed herein the use of the terms homology and identity mean the same thing as similarity. Thus, for example, if the use of the word homology is used between two non-natural sequences it is understood that this is not necessarily indicating an evolutionary relationship between these two sequences, but rather is looking at the similarity or relatedness between their nucleic acid sequences. Many of the methods for determining homology between two evolutionarily related molecules are routinely applied to any two or more nucleic acids or proteins for the purpose of measuring sequence similarity regardless of whether they are evolutionarily related or not.

b) Hybridization/Selective Hybridization

The term hybridization typically means a sequence driven interaction between at least two nucleic acid molecules, such as a primer or a probe and a gene. Sequence driven interaction means an interaction that occurs between two nucleotides or nucleotide analogs or nucleotide derivatives in a nucleotide specific manner. For example, G interacting with C or A interacting with T are sequence driven interactions. Typically sequence driven interactions occur on the Watson-Crick face or Hoogsteen face of the nucleotide. The hybridization of two nucleic acids is affected by a number of conditions and parameters known to those of skill in the art. For example, the salt concentrations, pH, and temperature of the reaction all affect whether two nucleic acid molecules will hybridize.

Parameters for selective hybridization between two nucleic acid molecules are well known to those of skill in the art. For example, in some embodiments selective hybridization conditions can be defined as stringent hybridization conditions. For example, stringency of hybridization is controlled by both temperature and salt concentration of either or both of the hybridization and washing steps. For example, the conditions of hybridization to achieve selective hybridization may involve hybridization in high ionic strength solution (6×SSC or 6×SSPE) at a temperature that is about 12-25° C. below the Tm (the melting temperature at which half of the molecules dissociate from their hybridization partners) followed by washing at a combination of temperature and salt concentration chosen so that the washing temperature is about 5° C. to 20° C. below the Tm. The temperature and salt conditions are readily determined empirically in preliminary experiments in which samples of reference DNA immobilized on filters are hybridized to a labeled nucleic acid of interest and then washed under conditions of different stringencies. Hybridization temperatures are typically higher for DNA-RNA and RNA-RNA hybridizations. The conditions can be used as described above to achieve stringency, or as is known in the art. (Sambrook et al., Molecular Cloning: A Laboratory Manual, 2nd Ed., Cold Spring Harbor Laboratory, Cold Spring Harbor, N.Y., 1989; Kunkel et al. Methods Enzymol. 1987:154:367, 1987 which is herein incorporated by reference for material at least related to hybridization of nucleic acids). A preferable stringent hybridization condition for a DNA:DNA hybridization can be at about 68° C. (in aqueous solution) in 6×SSC or 6×SSPE followed by washing at 68° C. Stringency of hybridization and washing, if desired, can be reduced accordingly as the degree of complementarity desired is decreased, and further, depending upon the G-C or A-T richness of any area wherein variability is searched for. Likewise, stringency of hybridization and washing, if desired, can be increased accordingly as homology desired is increased, and further, depending upon the G-C or A-T richness of any area wherein high homology is desired, all as known in the art.

Another way to define selective hybridization is by looking at the amount (percentage) of one of the nucleic acids bound to the other nucleic acid. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the limiting nucleic acid is bound to the non-limiting nucleic acid. Typically, the non-limiting primer is in for example, 10 or 100 or 1000 fold excess. This type of assay can be performed at under conditions where both the limiting and non-limiting primer are for example, 10 fold or 100 fold or 1000 fold below their $k_d$, or where only one of the nucleic acid molecules is 10 fold or 100 fold or 1000 fold or where one or both nucleic acid molecules are above their $k_d$.

Another way to define selective hybridization is by looking at the percentage of primer that gets enzymatically manipulated under conditions where hybridization is required to promote the desired enzymatic manipulation. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer is enzymatically manipulated under conditions which promote the enzymatic manipulation, for example if the enzymatic manipulation is DNA extension, then selective hybridization conditions would be when at least about 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer molecules are extended. Preferred conditions also include those suggested by the manufacturer or indicated in the art as being appropriate for the enzyme performing the manipulation.

Just as with homology, it is understood that there are a variety of methods herein disclosed for determining the level of hybridization between two nucleic acid molecules. It is understood that these methods and conditions may provide different percentages of hybridization between two nucleic acid molecules, but unless otherwise indicated meeting the parameters of any of the methods would be sufficient. For example if 80% hybridization was required and as long as hybridization occurs within the required parameters in any one of these methods it is considered disclosed herein.

It is understood that those of skill in the art understand that if a composition or method meets any one of these criteria for determining hybridization either collectively or singly it is a composition or method that is disclosed herein.

c) Nucleic Acids

There are a variety of molecules disclosed herein that are nucleic acid based, including for example the nucleic acids that encode, for example, the disclosed human Na channels as well as any other proteins disclosed herein, as well as various functional nucleic acids. The disclosed nucleic acids are made up of for example, nucleotides, nucleotide analogs, or nucleotide substitutes. Non-limiting examples of these and other molecules are discussed herein. It is understood that for example, when a vector is expressed in a cell, that the expressed mRNA will typically be made up of A, C, G, and U. Likewise, it is understood that if, for example, an antisense molecule is introduced into a cell or cell environment through for example exogenous delivery, it is advantageous that the antisense molecule be made up of nucleotide analogs that reduce the degradation of the antisense molecule in the cellular environment.

(1) Nucleotides and Related Molecules

A nucleotide is a molecule that contains a base moiety, a sugar moiety and a phosphate moiety. Nucleotides can be linked together through their phosphate moieties and sugar moieties creating an internucleoside linkage. The base moiety of a nucleotide can be adenin-9-yl (A), cytosin-1-yl (C), guanin-9-yl (G), uracil-1-yl (U), and thymin-1-yl (T). The sugar moiety of a nucleotide is a ribose or a deoxyribose. The phosphate moiety of a nucleotide is pentavalent phosphate. An non-limiting example of a nucleotide would be 3'-AMP (3'-adenosine monophosphate) or 5'-GMP (5'-guanosine monophosphate).

A nucleotide analog is a nucleotide which contains some type of modification to either the base, sugar, or phosphate moieties. Modifications to nucleotides are well known in the art and would include for example, 5-methylcytosine (5-me-C), 5-hydroxymethyl cytosine, xanthine, hypoxanthine, and 2-aminoadenine as well as modifications at the sugar or phosphate moieties.

Nucleotide substitutes are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety. (Letsinger et al., Proc. Natl. Acad. Sci. USA, 1989, 86, 6553-6556).

A Watson-Crick interaction is at least one interaction with the Watson-Crick face of a nucleotide, nucleotide analog, or nucleotide substitute. The Watson-Crick face of a nucleotide, nucleotide analog, or nucleotide substitute includes the C2, N1, and C6 positions of a purine based nucleotide, nucleotide analog, or nucleotide substitute and the C2, N3, C4 positions of a pyrimidine based nucleotide, nucleotide analog, or nucleotide substitute.

A Hoogsteen interaction is the interaction that takes place on the Hoogsteen face of a nucleotide or nucleotide analog, which is exposed in the major groove of duplex DNA. The Hoogsteen face includes the N7 position and reactive groups (NH2 or O) at the C6 position of purine nucleotides.

(2) Sequences

There are a variety of sequences related to, for example, the disclosed human sodium channels as well as any other protein disclosed herein that are disclosed on Genbank, and these sequences and others are herein incorporated by reference in their entireties as well as for individual subsequences contained therein.

A variety of sequences are provided herein and these and others can be found in Genbank, at www.pubmed.gov. Those of skill in the art understand how to resolve sequence discrepancies and differences and to adjust the compositions and methods relating to a particular sequence to other related sequences. Primers and/or probes can be designed for any sequence given the information disclosed herein and known in the art.

(3) Primers and Probes

Disclosed are compositions including primers and probes, which are capable of interacting with the genes disclosed herein. In certain embodiments the primers are used to support DNA amplification reactions. Typically the primers will be capable of being extended in a sequence specific manner. Extension of a primer in a sequence specific manner includes any methods wherein the sequence and/or composition of the nucleic acid molecule to which the primer is hybridized or otherwise associated directs or influences the composition or sequence of the product produced by the extension of the primer. Extension of the primer in a sequence specific manner therefore includes, but is not limited to, PCR, DNA sequencing, DNA extension, DNA polymerization, RNA transcription, or reverse transcription. Techniques and conditions that amplify the primer in a sequence specific manner are preferred. In certain embodiments the primers are used for the DNA amplification reactions, such as PCR or direct sequencing. It is understood that in certain embodiments the primers can also be extended using non-enzymatic techniques, where for example, the nucleotides or oligonucleotides used to extend the primer are modified such that they will chemically react to extend the primer in a sequence specific manner. Typically the disclosed primers hybridize with the nucleic acid or region of the nucleic acid or they hybridize with the complement of the nucleic acid or complement of a region of the nucleic acid.

(4) Functional Nucleic Acids

Functional nucleic acids are nucleic acid molecules that have a specific function, such as binding a target molecule or catalyzing a specific reaction. Functional nucleic acid molecules can be divided into the following categories, which are not meant to be limiting. For example, functional nucleic acids include antisense molecules, aptamers, ribozymes, triplex forming molecules, and external guide sequences. The functional nucleic acid molecules can act as affectors, inhibitors, modulators, and stimulators of a specific activity possessed by a target molecule, or the functional nucleic acid molecules can possess a de novo activity independent of any other molecules.

Functional nucleic acid molecules can interact with any macromolecule, such as DNA, RNA, polypeptides, or carbohydrate chains. Thus, functional nucleic acids can interact with the mRNA of the disclosed human Na channels or the genomic DNA of disclosed human Na channels or they can interact with the polypeptide of disclosed human Na channels. Often functional nucleic acids are designed to interact with other nucleic acids based on sequence homology between the target molecule and the functional nucleic acid molecule. In other situations, the specific recognition between the functional nucleic acid molecule and the target molecule is not based on sequence homology between the functional nucleic acid molecule and the target molecule, but rather is based on the formation of tertiary structure that allows specific recognition to take place.

Antisense molecules are designed to interact with a target nucleic acid molecule through either canonical or non-canonical base pairing. The interaction of the antisense molecule and the target molecule is designed to promote the destruction of the target molecule through, for example, RNAseH mediated RNA-DNA hybrid degradation. Alternatively the antisense molecule is designed to interrupt a processing function that normally would take place on the target molecule, such as transcription or replication. Antisense molecules can be designed based on the sequence of the target molecule. Numerous methods for optimization of antisense efficiency by finding the most accessible regions of the target molecule exist. Exemplary methods would be in vitro selection experiments and DNA modification studies using DMS and DEPC. It is preferred that antisense molecules bind the target molecule with a dissociation constant ($k_d$) less than or equal to $10^{-6}$, $10^{-8}$, $10^{-10}$, or $10^{-12}$. A representative sample of methods and techniques which aid in the design and use of antisense molecules can be found in the following non-limiting list of U.S. Pat. Nos. 5,135,917, 5,294,533, 5,627,158, 5,641,754, 5,691,317, 5,780,607, 5,786,138, 5,849,903, 5,856,103, 5,919,772, 5,955,590, 5,990,088, 5,994,320, 5,998,602, 6,005,095, 6,007,995, 6,013,522, 6,017,898, 6,018,042, 6,025,198, 6,033,910, 6,040,296, 6,046,004, 6,046,319, and 6,057,437.

Aptamers are molecules that interact with a target molecule, preferably in a specific way. Typically aptamers are small nucleic acids ranging from 15-50 bases in length that fold into defined secondary and tertiary structures, such as stem-loops or G-quartets. Aptamers can bind small molecules, such as ATP (U.S. Pat. No. 5,631,146) and theophiline (U.S. Pat. No. 5,580,737), as well as large molecules, such as reverse transcriptase (U.S. Pat. No. 5,786,462) and thrombin (U.S. Pat. No. 5,543,293). Aptamers can bind very tightly with $k_d$s from the target molecule of less than $10^{-12}$ M. It is preferred that the aptamers bind the target molecule with a $k_d$ less than $10^{-6}$, $10^{-8}$, $10^{-10}$, or $10^{-12}$. Aptamers can bind the target molecule with a very high degree of specificity. For example, aptamers have been isolated that have greater than a 10000 fold difference in binding affinities between the target molecule and another molecule that differ at only a single position on the molecule (U.S. Pat. No. 5,543,293). It is preferred that the aptamer have a $k_d$ with the target molecule at least 10, 100, 1000, 10,000, or 100,000 fold lower than the $k_d$ with a background binding molecule. It is preferred when doing the comparison for a polypeptide for example, that the background molecule be a different polypeptide. For example, when determining the specificity of disclosed human Na channels aptamers, the background protein could be serum albumin. Representative examples of how to make and use aptamers to bind a variety of different target molecules can be found in the following non-limiting list of U.S. Pat. Nos. 5,476,766, 5,503,978, 5,631,146, 5,731,424, 5,780, 228, 5,792,613, 5,795,721, 5,846,713, 5,858,660, 5,861,254, 5,864,026, 5,869,641, 5,958,691, 6,001,988, 6,011,020, 6,013,443, 6,020,130, 6,028,186, 6,030,776, and 6,051,698.

Ribozymes are nucleic acid molecules that are capable of catalyzing a chemical reaction, either intramolecularly or intermolecularly. Ribozymes are thus catalytic nucleic acid. It is preferred that the ribozymes catalyze intermolecular reactions. There are a number of different types of ribozymes that catalyze nuclease or nucleic acid polymerase type reactions which are based on ribozymes found in natural systems; such as hammerhead ribozymes, (for example, but not limited to the following U.S. Pat. Nos. 5,334,711, 5,436,330, 5,616,466, 5,633,133, 5,646,020, 5,652,094, 5,712,384, 5,770,715, 5,856,463, 5,861,288, 5,891,683, 5,891,684, 5,985,621, 5,989,908, 5,998,193, 5,998,203, WO 9858058 by Ludwig and Spioat, WO 9858057 by Ludwig and Sproat, and WO 9718312 by Ludwig and Sproat) hairpin ribozymes (for example, but not limited to the following U.S. Pat. Nos. 5,631,115, 5,646,031, 5,683,902, 5,712,384, 5,856,188, 5,866,701, 5,869,339, and 6,022,962), and tetrahymena ribozymes (for example, but not limited to the following U.S. Pat. Nos. 5,595,873 and 5,652,107). There are also a number of ribozymes that are not found in natural systems, but which have been engineered to catalyze specific reactions de novo (for example, but not limited to the following U.S. Pat. Nos. 5,580,967, 5,688,670, 5,807,718, and 5,910,408). Preferred ribozymes cleave RNA or DNA substrates, and more preferably cleave RNA substrates. Ribozymes typically cleave nucleic acid substrates through recognition and binding of the target substrate with subsequent cleavage. This recognition is often based mostly on canonical or non-canonical base pair interactions. This property makes ribozymes particularly good candidates for target specific cleavage of nucleic acids because recognition of the target substrate is based on the target substrates sequence. Representative examples of how to make and use ribozymes to catalyze a variety of different reactions can be found in the following non-limiting list of U.S. Pat. Nos. 5,646,042, 5,693,535, 5,731,295, 5,811,300, 5,837,855, 5,869,253, 5,877,021, 5,877,022, 5,972,699, 5,972,704, 5,989,906, and 6,017,756.

Triplex forming functional nucleic acid molecules are molecules that can interact with either double-stranded or single-stranded nucleic acid. When triplex molecules interact with a target region, a structure called a triplex is formed, in which there are three strands of DNA forming a complex dependant on both Watson-Crick and Hoogsteen base-pairing. Triplex molecules are preferred because they can bind target regions with high affinity and specificity. It is preferred that the triplex forming molecules bind the target molecule with a $k_d$ less than $10^{-6}$, $10^{-8}$, $10^{-10}$, or $10^{-12}$. Representative examples of how to make and use triplex forming molecules to bind a variety of different target molecules can be found in the following non-limiting list of U.S. Pat. Nos. 5,176,996, 5,645,985, 5,650,316, 5,683,874, 5,693,773, 5,834,185, 5,869,246, 5,874,566, and 5,962,426.

External guide sequences (EGSs) are molecules that bind a target nucleic acid molecule forming a complex, and this complex is recognized by RNase P, which cleaves the target molecule. EGSs can be designed to specifically target a RNA molecule of choice. RNAse P aids in processing transfer RNA (tRNA) within a cell. Bacterial RNAse P can be recruited to cleave virtually any RNA sequence by using an EGS that causes the target RNA:EGS complex to mimic the natural tRNA substrate. (WO 92/03566 by Yale, and Forster and Altman, *Science* 238:407-409 (1990)).

Similarly, eukaryotic EGS/RNAse P-directed cleavage of RNA can be utilized to cleave desired targets within eukarotic cells. (Yuan et al., *Proc. Natl. Acad. Sci. USA* 89:8006-8010 (1992); WO 93/22434 by Yale; WO 95/24489 by Yale; Yuan and Altman, *EMBO J* 14:159-168 (1995), and Carrara et al., *Proc. Natl. Acad. Sci.* (USA) 92:2627-2631 (1995)). Representative examples of how to make and use EGS molecules to facilitate cleavage of a variety of different target molecules be found in the following non-limiting list of U.S. Pat. Nos. 5,168,053, 5,624,824, 5,683,873, 5,728,521, 5,869,248, and 5,877,162.

d) Nucleic Acid Delivery

In the methods described above which include the administration and uptake of exogenous DNA into the cells of a subject (i.e., gene transduction or transfection), the disclosed nucleic acids can be in the form of naked DNA or RNA, or the nucleic acids can be in a vector for delivering the nucleic acids to the cells, whereby the antibody-encoding DNA fragment is under the transcriptional regulation of a promoter, as would be well understood by one of ordinary skill in the art. The vector can be a commercially available preparation, such as an adenovirus vector (Quantum Biotechnologies, Inc. (Laval, Quebec, Canada). Delivery of the nucleic acid or vector to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the disclosed nucleic acid or vector can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

As one example, vector delivery can be via a viral system, such as a retroviral vector system which can package a recombinant retroviral genome (see e.g., Pastan et al., *Proc. Natl. Acad. Sci. U.S.A.* 85:4486, 1988; Miller et al., *Mol. Cell. Biol.* 6:2895, 1986). The recombinant retrovirus can then be used to infect and thereby deliver to the infected cells nucleic acid encoding a broadly neutralizing antibody (or active fragment thereof). The exact method of introducing the altered nucleic acid into mammalian cells is, of course, not limited to the use of retroviral vectors. Other techniques are widely available for this procedure including the use of adenoviral vectors (Mitani et al., *Hum. Gene Ther.* 5:941-948, 1994), adeno-associated viral (AAV) vectors (Goodman et al., *Blood* 84:1492-1500, 1994), lentiviral vectors (Naidini et al., *Science* 272:263-267, 1996), pseudotyped retroviral vectors (Agrawal et al., *Exper. Hematol.* 24:738-747, 1996). Physical transduction techniques can also be used, such as liposome delivery and receptor-mediated and other endocytosis mechanisms (see, for example, Schwartzenberger et al., *Blood* 87:472-478, 1996). This disclosed compositions and methods can be used in conjunction with any of these or other commonly used gene transfer methods.

As one example, if the antibody-encoding nucleic acid is delivered to the cells of a subject in an adenovirus vector, the dosage for administration of adenovirus to humans can range from about $10^7$ to $10^9$ plaque forming units (pfu) per injection but can be as high as $10^{12}$ pfu per injection. (Crystal, *Hum. Gene Ther.* 8:985-1001, 1997; Alvarez and Curiel, *Hum. Gene Ther.* 8:597-613, 1997). A subject can receive a single injection, or, if additional injections are necessary, they can be repeated at six month intervals (or other appropriate time intervals, as determined by the skilled practitioner) for an indefinite period and/or until the efficacy of the treatment has been established.

Parenteral administration of the nucleic acid or vector, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein. For additional discussion of suitable formulations and various routes of administration of therapeutic compounds, see, e.g., Remington: The Science and Practice of Pharmacy (19th ed.) ed. A. R. Gennaro, Mack Publishing Company, Easton, Pa. 1995.

e) Peptides (1) Protein Variants

As discussed herein there are numerous variants of the disclosed human Na channel proteins that are known and herein contemplated. In addition, to the known functional disclosed human Na channels strain variants there are derivatives of the disclosed human Na channel proteins which also function in the disclosed methods and compositions. Protein variants and derivatives are well understood to those of skill in the art and in can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Immunogenic fusion protein derivatives, such as those described in the examples, are made by fusing a polypeptide sufficiently large to confer immunogenicity to the target sequence by cross-linking in vitro or by recombinant cell culture transformed with DNA encoding the fusion. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof can be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with the following Tables 5 and 6 and are referred to as conservative substitutions.

TABLE 5

Amino Acid Abbreviations

| Amino Acid | Abbreviations |
| --- | --- |
| alanine | AlaA |
| allosoleucine | AIle |
| arginine | ArgR |
| asparagine | AsnN |
| aspartic acid | AspD |
| cysteine | CysC |
| glutamic acid | GluE |
| glutamine | GlnK |

TABLE 5-continued

Amino Acid Abbreviations

| Amino Acid | Abbreviations |
| --- | --- |
| glycine | GlyG |
| histidine | HisH |
| isolelucine | IleI |
| leucine | LeuL |
| lysine | LysK |
| phenylalanine | PheF |
| proline | ProP |
| pyroglutamic acidp | Glu |
| serine | SerS |
| threonine | ThrT |
| tyrosine | TyrY |
| tryptophan | TrpW |
| valine | ValV |

TABLE 6

Amino Acid Substitutions
Original Residue Exemplary Conservative Substitutions, others are known in the art.

Alaser
Arglys, gln
Asngln; his
Aspglu
Cysser
Glnasn, lys
Gluasp
Glypro
Hisasn; gln
Ileleu; val
Leuile; val
Lysarg; gln;
MetLeu; ile
Phemet; leu; tyr
Serthr
Thrser
Trptyr
Tyrtrp; phe
Valile; leu Substantial changes in function or immunological identity are made by selecting substitutions that are less conservative than those in Table 6, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr;

Lys, Arg; and Phe, Tyr. Such conservatively substituted variations of each explicitly disclosed sequence are included within the mosaic polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also can be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W. H. Freeman & Co., San Francisco pp 79-86 [1983]), acetylation of the N-terminal amine and, in some instances, amidation of the C-terminal carboxyl.

It is understood that one way to define the variants and derivatives of the disclosed proteins herein is through defining the variants and derivatives in terms of homology/identity to specific known sequences. Those of skill in the art readily understand how to determine the homology of two proteins. For example, the homology can be calculated after aligning the two sequences so that the homology is at its highest level.

Another way of calculating homology can be performed by published algorithms. Optimal alignment of sequences for comparison can be conducted by the local homology algorithm of Smith and Waterman Adv. Appl. Math. 2: 482 (1981), by the homology alignment algorithm of Needleman and Wunsch, J. Mol. Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. Science 244:48-52, 1989, Jaeger et al. *Proc. Natl. Acad. Sci. USA* 86:7706-7710, 1989, Jaeger et al. *Methods Enzymol.* 183:281-306, 1989 which are herein incorporated by reference for at least material related to nucleic acid alignment.

It is understood that the description of conservative mutations and homology can be combined together in any combination, such as embodiments that have at least 70% homology to a particular sequence wherein the variants are conservative mutations.

As this specification discusses various proteins and protein sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence. It is also understood that while no amino acid sequence indicates what particular DNA sequence encodes that protein within an organism, where particular variants of a disclosed protein are disclosed herein, the known nucleic acid sequence that encodes that protein in the particular strain or species from which that protein arises is also known and herein disclosed and described.

It is understood that there are numerous amino acid and peptide analogs which can be incorporated into the disclosed compositions. For example, there are numerous D amino acids or amino acids which have a different functional substituent then the amino acids shown in Table 5 and Table 6. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way (Thorson et al., Methods in Molec. Biol. 77:43-73 (1991), Zoller, Current Opinion in Biotechnology, 3:348-354 (1992); Ibba, Biotechnology & Genetic Enginerring Reviews 13:197-216 (1995), Cahill et al., TIBS, 14(10):400-403 (1989); Benner, TIB Tech, 12:158-163 (1994); Ibba and Hennecke, Bio/technology, 12:678-682 (1994) all of which are herein incorporated by reference at least for material related to amino acid analogs).

Molecules can be produced that resemble peptides, but which are not connected via a natural peptide linkage. For example, linkages for amino acids or amino acid analogs can include $CH_2NH$—, —$CH_2S$—, —$CH_2$—$CH_2$—$CH=CH$— (cis and trans), —$COCH_2$—, —$CH(OH)CH_2$—, and —$CHH_2SO$— (These and others can be found in Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm Sci (1980) pp. 463-468; Hudson, D. et al., Int J Pept Prot Res 14:177-185 (1979) (—$CH_2NH$—, $CH_2CH_2$—); Spatola et al. Life Sci 38:1243-1249 (1986) (—$CHH_2$—S); Hann J. Chem. Soc Perkin Trans. 1307-314 (1982) (—CH—CH—, cis and trans); Almquist et al. J. Med. Chem. 23:1392-1398 (1980) (—$COCH_2$—); Jennings-White et al. Tetrahedron Lett 23:2533 (1982) (—$COCH_2$—); Szelke et al. European Appln, EP 45665 CA (1982): 97:39405 (1982) (—$CH(OH)CH_2$—); Holladay et al. Tetrahedron. Lett 24:4401-4404 (1983) (—$C(OH)CH_2$—); and Hruby Life Sci 31:189-199 (1982) (—$CH_2$—S—); each of which is incorporated herein by reference. A particularly preferred non-peptide linkage is —$CH_2NH$—. It is understood that peptide analogs can have more than one atom between the bond atoms, such as b-alanine, g-aminobutyric acid, and the like.

Amino acid analogs and analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations. (Rizo and Gierasch Ann. Rev. Biochem. 61:387 (1992), incorporated herein by reference).

f) Antibodies
(a) Antibodies Generally

The term "antibodies" is used herein in a broad sense and includes both polyclonal and monoclonal antibodies. In addition to intact immunoglobulin molecules, also included in the term "antibodies" are fragments or polymers of those immunoglobulin molecules, and human or humanized versions of immunoglobulin molecules or fragments thereof, as long as they are chosen for their ability to interact with disclosed human Na channels such that cancer, such as prostate cancer, is inhibited. Antibodies that bind the disclosed regions of disclosed human Na channel are also disclosed. The antibodies can be tested for their desired activity using the in vitro assays described herein, or by analogous methods, after which their in vivo therapeutic and/or prophylactic activities are tested according to known clinical testing methods.

The term "monoclonal antibody" as used herein refers to an antibody obtained from a substantially homogeneous population of antibodies, i.e., the individual antibodies within the population are identical except for possible naturally occurring mutations that may be present in a small subset of the antibody molecules. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or, belonging to another antibody class or subclass, as well as fragments of such antibodies, as long as they exhibit the desired antagonistic activity. (U.S. Pat. No. 4,816,567 and Morrison et al., *Proc. Natl. Acad. Sci. USA*, 81:6851-6855 (1984).

The disclosed monoclonal antibodies can be made using any procedure which produces mono clonal antibodies. For example, disclosed monoclonal antibodies can be prepared using hybridoma methods, such as those described by Kohler and Milstein, *Nature,* 256:495 (1975). In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro, e.g., using the HIV Env-CD4-co-receptor complexes described herein.

The monoclonal antibodies may also be made by recombinant DNA methods, such as those described in U.S. Pat. No. 4,816,567 (Cabilly et al.). DNA encoding the disclosed monoclonal antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques, e.g., as described in U.S. Pat. No. 5,804,440 to Burton et al. and U.S. Pat. No. 6,096,441 to Barbas et al.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fc fragment. Pepsin treatment yields a fragment that has two antigen combining sites and is still capable of cross-linking antigen.

The fragments, whether attached to other sequences or not, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment. (Zoller, M. J. *Curr. Opin. Biotechnol.* 3:348-354, 1992).

As used herein, the term "antibody" or "antibodies" can also refer to a human antibody and/or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

(b) Human Antibodies

The disclosed human antibodies can be prepared using any technique. Examples of techniques for human monoclonal antibody production include those described by Cole et al. (*Monoclonal Antibodies and Cancer Therapy*, Alan R. Liss, p. 77, 1985) and by Boerner et al. (*J. Immunol.,* 147(1):86-95, 1991). Human antibodies (and fragments thereof) can also be produced using phage display libraries (Hoogenboom et al., *J. Mol. Biol.,* 227:381, 1991; Marks et al., *J. Mol. Biol.,* 222:581, 1991).

The disclosed human antibodies can also be obtained from transgenic animals. For example, transgenic, mutant mice that are capable of producing a full repertoire of human antibodies, in response to immunization, have been described. (Jakobovits et al., *Proc. Natl. Acad. Sci. USA,* 90:2551-255 (1993); Jakobovits et al., *Nature,* 362:255-258 (1993); Bruggermann et al., *Year in Immunol.,* 7:33 (1993)). Specifically, the homozygous deletion of the antibody heavy chain joining region (J(H)) gene in these chimeric and germ-line mutant mice results in complete inhibition of endogenous antibody production, and the successful transfer of the human germ-line antibody gene array into such germ-line mutant mice results in the production of human antibodies upon antigen challenge. Antibodies having the desired activity are selected using Env-CD4-co-receptor complexes as described herein.

(c) Humanized Antibodies

Antibody humanization techniques generally involve the use of recombinant DNA technology to manipulate the DNA sequence encoding one or more polypeptide chains of an antibody molecule. Accordingly, a humanized form of a non-human antibody (or a fragment thereof) is a chimeric antibody or antibody chain (or a fragment thereof, such as an Fv, Fab, Fab', or other antigen-binding portion of an antibody) which contains a portion of an antigen binding site from a non-human (donor) antibody integrated into the framework of a human (recipient) antibody.

To generate a humanized antibody, residues from one or more complementarity determining regions (CDRs) of a recipient (human) antibody molecule are replaced by residues from one or more CDRs of a donor (non-human) antibody molecule that is known to have desired antigen binding characteristics (e.g., a certain level of specificity and affinity for the target antigen). In some instances, Fv framework (FR) residues of the human antibody are replaced by corresponding non-human residues. Humanized antibodies may also contain residues which are found neither in the recipient antibody nor in the imported CDR or framework sequences. Generally, a humanized antibody has one or more amino acid residues introduced into it from a source which is non-human. In practice, humanized antibodies are typically human antibodies in which some CDR residues and possibly some FR residues are substituted by residues from analogous sites in rodent antibodies. Humanized antibodies generally contain at least a portion of an antibody constant region (Fc), typically that of a human antibody. (Jones et al., *Nature*, 321:522-525 (1986), Reichmann et al., *Nature*, 332:323-327 (1988), and Presta, *Curr. Opin. Struct. Biol.*, 2:593-596 (1992)).

Methods for humanizing non-human antibodies are well known in the art. For example, humanized antibodies can be generated according to the methods of Winter and co-workers (Jones et al., *Nature*, 321:522-525 (1986), Riechmann et al., *Nature*, 332:323-327 (1988), Verhoeyen et al., *Science*, 239: 1534-1536 (1988)), by substituting rodent CDRs or CDR sequences for the corresponding sequences of a human antibody. Methods that can be used to produce humanized antibodies are also described in U.S. Pat. No. 4,816,567 (Cabilly et al.), U.S. Pat. No. 5,565,332 (Hoogenboom et al.), U.S. Pat. No. 5,721,367 (Kay et al.), U.S. Pat. No. 5,837,243 (Deo et al.), U.S. Pat. No. 5,939,598 (Kucherlapati et al.), U.S. Pat. No. 6,130,364 (Jakobovits et al.), and U.S. Pat. No. 6,180,377 (Morgan et al.).

(d) Administration of Antibodies

Administration of the antibodies can be done as disclosed herein. Nucleic acid approaches for antibody delivery also exist. The broadly neutralizing anti disclosed human Na channel antibodies and antibody fragments can also be administered to patients or subjects as a nucleic acid preparation (e.g., DNA or RNA) that encodes the antibody or antibody fragment, such that the patient's or subject's own cells take up the nucleic acid and produce and secrete the encoded antibody or antibody fragment. The delivery of the nucleic acid can be by any means, as disclosed herein, for example.

g) Pharmaceutical Carriers/Delivery of Pharmaceutical Products

As described above, the compositions can also be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein. Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials can be in solution, suspension (for example, incorporated into microparticles, liposomes, or cells). These can be targeted to a particular cell type via antibodies, receptors, or receptor ligands. The following references are examples of the use of this technology to target specific proteins to tumor tissue. (Senter, et al., *Bioconjugate Chem.*, 2:447-451, (1991); Bagshawe, K. D., *Br. J. Cancer*, 60:275-281, (1989); Bagshawe, et al., *Br. J. Cancer*, 58:700-703, (1988); Senter, et al., *Bioconjugate Chem.*, 4:3-9, (1993); Battelli, et al., *Cancer Immunol. Immunother.*, 35:421-425, (1992); Pietersz and McKenzie, *Immunolog. Reviews*, 129: 57-80, (1992); and Roffler, et al., *Biochem. Pharmacol*, 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue. (Hughes et al., *Cancer Research*, 49:6214-6220, (1989); and Litzinger and Huang, *Biochimica et Biophysica Acta*, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis have been reviewed. (Brown and Greene, *DNA and Cell Biology* 10:6, 399-409 (1991)).

(1) Pharmaceutically Acceptable Carriers

The compositions, including antibodies, can be used therapeutically in combination with a pharmaceutically acceptable carrier.

Suitable carriers and their formulations are described in *Remington: The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions can include carriers, thickeners, diluents, buffers, preservatives, surface active agents and the like in addition to the molecule of choice. Pharmaceutical compositions can also include one or more active ingredients such as antimicrobial agents, antiinflammatory agents, anesthetics, and the like.

The pharmaceutical composition can be administered in a number of ways depending on whether local or systemic treatment is desired, and on the area to be treated. Administration can be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives can also be present such as, for example, antimicrobials, antioxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

(2) Therapeutic Uses

Effective dosages and schedules for administering the compositions may be determined empirically, and making such determinations is within the skill in the art. The dosage ranges for the administration of the compositions are those large enough to produce the desired effect in which the symptoms disorder is effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counter indications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., Handbook of Monoclonal Antibodies, Ferrone et al., eds., Noges Publications, Park Ridge, N.J., (1985) ch. 22 and pp. 303-357; Smith et al., Antibodies in Human Diagnosis and Therapy, Haber et al., eds., Raven Press, New York (1977) pp. 365-389. A typical daily dosage of the antibody used alone might range from about 1 µg/kg to up to 100 mg/kg of body weight or more per day, depending on the factors mentioned above.

Following administration of a disclosed composition, such as an antibody, for treating, inhibiting, or preventing a cancer, such as prostate cancer, the efficacy of the therapeutic antibody can be assessed in various ways well known to the skilled practitioner The compositions that inhibit disclosed human Na channel and cancer, such as prostate cancer, interactions disclosed herein may be administered as a therapy or prophylactically to patients or subjects who are at risk for the cancer or prostate cancer.

h) Chips and Micro Arrays

Disclosed are chips where at least one address is the sequences or part of the sequences set forth in any of the nucleic acid sequences disclosed herein. Also disclosed are chips where at least one address is the sequences or portion of sequences set forth in any of the peptide sequences disclosed herein.

Also disclosed are chips where at least one address is a variant of the sequences or part of the sequences set forth in any of the nucleic acid sequences disclosed herein. Also disclosed are chips where at least one address is a variant of the sequences or portion of sequences set forth in any of the peptide sequences disclosed herein.

i) Compositions Identified by Screening with Disclosed Compositions/Combinatorial Chemistry (1) Combinatorial Chemistry The disclosed compositions can be used as targets for any combinatorial technique to identify molecules or macromolecular molecules that interact with the disclosed compositions in a desired way. The nucleic acids, peptides, and related molecules disclosed herein can be used as targets for the combinatorial approaches. Also disclosed are the compositions that are identified through combinatorial techniques or screening techniques in which the compositions disclosed herein, or portions thereof, are used as the target in a combinatorial or screening protocol.

It is understood that when using the disclosed compositions in combinatorial techniques or screening methods, molecules, such as macromolecular molecules, will be identified that have particular desired properties such as inhibition or stimulation or the target molecule's function. The molecules identified and isolated when using the disclosed compositions, such as, disclosed human Na channels, are also disclosed. Thus, the products produced using the combinatorial or screening approaches that involve the disclosed compositions, such as, disclosed human Na channels, are also considered herein disclosed.

It is understood that the disclosed methods for identifying molecules that inhibit the interactions between, for example, disclosed human Na channel can be performed using high through put means. For example, putative inhibitors can be identified using Fluorescence Resonance Energy Transfer (FRET) to quickly identify interactions. The underlying theory of the techniques is that when two molecules are close in space, ie, interacting at a level beyond background, a signal is produced or a signal can be quenched. Then, a variety of experiments can be performed, including, for example, adding in a putative inhibitor. If the inhibitor competes with the interaction between the two signaling molecules, the signals will be removed from each other in space, and this will cause a decrease or an increase in the signal, depending on the type of signal used. This decrease or increasing signal can be correlated to the presence or absence of the putative inhibitor. Any signaling means can be used. For example, disclosed are methods of identifying an inhibitor of the interaction between any two of the disclosed molecules comprising, contacting a first molecule and a second molecule together in the presence of a putative inhibitor, wherein the first molecule or second molecule comprises a fluorescence donor, wherein the first or second molecule, typically the molecule not comprising the donor, comprises a fluorescence acceptor; and measuring Fluorescence Resonance Energy Transfer (FRET), in the presence of the putative inhibitor and the in absence of the putative inhibitor, wherein a decrease in FRET in the presence of the putative inhibitor as compared to FRET measurement in its absence indicates the putative inhibitor inhibits binding between the two molecules. This type of method can be performed with a cell system as well.

Combinatorial chemistry includes but is not limited to all methods for isolating small molecules or macromolecules that are capable of binding either a small molecule or another macromolecule, typically in an iterative process. Proteins, oligonucleotides, and sugars are examples of macromolecules. For example, oligonucleotide molecules with a given function, catalytic or ligand-binding, can be isolated from a complex mixture of random oligonucleotides in what has been referred to as "in vitro genetics" (Szostak, *TIBS* 19:89, 1992). One synthesizes a large pool of molecules bearing random and defined sequences and subjects that complex mixture, for example, approximately $10^{15}$ individual sequences in 100 µg of a 100 nucleotide RNA, to some selection and enrichment process. Through repeated cycles of affinity chromatography and PCR amplification of the molecules bound to the ligand on the column, Ellington and Szostak (1990) estimated that 1 in $10^{10}$ RNA molecules folded in such a way as to bind a small molecule dyes. DNA molecules with such ligand-binding behavior have been isolated as well (Ellington and Szostak, 1992; Bock et al, 1992). Techniques aimed at similar goals exist for small organic molecules, proteins, antibodies and other macromolecules known to those of skill in the art. Screening sets of molecules for a desired activity whether based on small organic libraries, oligonucleotides, or antibodies is broadly referred to as combinatorial chemistry. Combinatorial techniques are particularly suited for defining binding interactions between molecules and for isolating molecules that have a specific binding activity, often called aptamers when the macromolecules are nucleic acids.

There are a number of methods for isolating proteins which either have de novo activity or a modified activity. For example, phage display libraries have been used to isolate numerous peptides that interact with a specific target. (See for example, U.S. Pat. Nos. 6,031,071; 5,824,520; 5,596,079; and 5,565,332 which are herein incorporated by reference at least for their material related to phage display and methods relate to combinatorial chemistry)

A preferred method for isolating proteins that have a given function is described by Roberts and Szostak (Roberts R. W. and Szostak J. W. Proc. Natl. Acad. Sci. USA, 94(23)12997-302 (1997). This combinatorial chemistry method couples the functional power of proteins and the genetic power of nucleic acids. An RNA molecule is generated in which a puromycin molecule is covalently attached to the 3'-end of the RNA molecule. An in vitro translation of this modified RNA molecule causes the correct protein, encoded by the RNA to be translated. In addition, because of the attachment of the puromycin, a peptidyl acceptor which cannot be extended, the growing peptide chain is attached to the puromycin which is attached to the RNA. Thus, the protein molecule is attached to the genetic material that encodes it. Normal in vitro selection procedures can now be done to isolate functional peptides. Once the selection procedure for peptide function is complete traditional nucleic acid manipulation procedures are performed to amplify the nucleic acid that codes for the selected functional peptides. After amplification of the genetic material, new RNA is transcribed with puromycin at the 3'-end, new peptide is translated and another functional round of selection is performed. Thus, protein selection can be performed in an iterative manner just like nucleic acid selection techniques. The peptide which is translated is controlled by the sequence of the RNA attached to the puromycin. This sequence can be anything from a random sequence engineered for optimum translation (i.e. no stop codons etc.) or it can be a degenerate sequence of a known RNA molecule to look for improved or altered function of a known peptide. The conditions for nucleic acid amplification and in vitro translation are well known to those of ordinary skill in the art and are preferably performed as in Roberts and Szostak (Roberts R. W. and Szostak J. W. Proc. Natl. Acad. Sci. USA, 94(23) 12997-302 (1997)).[110]

Another preferred method for combinatorial methods designed to isolate peptides is described in Cohen et al. (Cohen B. A., et al., Proc. Natl. Acad. Sci. USA 95(24):14272-7 (1998)). This method utilizes and modifies two-hybrid technology. Yeast two-hybrid systems are useful for the detection and analysis of protein:protein interactions. The two-hybrid system, initially described in the yeast *Saccharomyces cerevisiae*, is a powerful molecular genetic technique for identifying new regulatory molecules, specific to the protein of interest. (Fields and Song, *Nature* 340:245-6 (1989)). Cohen et al., modified this technology so that novel interactions between synthetic or engineered peptide sequences could be identified which bind a molecule of choice. The benefit of this type of technology is that the selection is done in an intracellular environment. The method utilizes a library of peptide molecules that attached to an acidic activation domain. A peptide of choice, for example an extracellular portion of disclosed human Na channel is attached to a DNA binding domain of a transcriptional activation protein, such as Gal 4. By performing the Two-hybrid technique on this type of system, molecules that bind the extracellular portion of disclosed human Na channel can be identified.

Using methodology well known to those of skill in the art, in combination with various combinatorial libraries, one can isolate and characterize those small molecules or macromolecules, which bind to or interact with the desired target. The relative binding affinity of these compounds can be compared and optimum compounds identified using competitive binding studies, which are well known to those of skill in the art.

Techniques for making combinatorial libraries and screening combinatorial libraries to isolate molecules which bind a desired target are well known to those of skill in the art. Representative techniques and methods can be found in but are not limited to U.S. Pat. Nos. 5,084,824, 5,288,514, 5,449, 754, 5,506,337, 5,539,083, 5,545,568, 5,556,762, 5,565,324, 5,565,332, 5,573,905, 5,618,825, 5,619,680, 5,627,210, 5,646,285, 5,663,046, 5,670,326, 5,677,195, 5,683,899, 5,688,696, 5,688,997, 5,698,685, 5,712,146, 5,721,099, 5,723,598, 5,741,713, 5,792,431, 5,807,683, 5,807,754, 5,821,130, 5,831,014, 5,834,195, 5,834,318, 5,834,588, 5,840,500, 5,847,150, 5,856,107, 5,856,496, 5,859,190, 5,864,010, 5,874,443, 5,877,214, 5,880,972, 5,886,126, 5,886,127, 5,891,737, 5,916,899, 5,919,955, 5,925,527, 5,939,268, 5,942,387, 5,945,070, 5,948,696, 5,958,702, 5,958,792, 5,962,337, 5,965,719, 5,972,719, 5,976,894, 5,980,704, 5,985,356, 5,999,086, 6,001,579, 6,004,617, 6,008,321, 6,017,768, 6,025,371, 6,030,917, 6,040,193, 6,045,671, 6,045,755, 6,060,596, and 6,061,636.

Combinatorial libraries can be made from a wide array of molecules using a number of different synthetic techniques. For example, libraries containing fused 2,4-pyrimidinediones (U.S. Pat. No. 6,025,371) dihydrobenzopyrans (U.S. Pat. Nos. 6,017,768 and 5,821,130), amide alcohols (U.S. Pat. No. 5,976,894), hydroxy-amino acid amides (U.S. Pat. No. 5,972, 719) carbohydrates (U.S. Pat. No. 5,965,719), 1,4-benzodiazepin-2,5-diones (U.S. Pat. No. 5,962,337), cyclics (U.S. Pat. No. 5,958,792), biaryl amino acid amides (U.S. Pat. No. 5,948,696), thiophenes (U.S. Pat. No. 5,942,387), tricyclic Tetrahydroquinolines (U.S. Pat. No. 5,925,527), benzofurans (U.S. Pat. No. 5,919,955), isoquinolines (U.S. Pat. No. 5,916, 899), hydantoin and thiohydantoin (U.S. Pat. No. 5,859,190), indoles (U.S. Pat. No. 5,856,496), imidazol-pyrido-indole and imidazol-pyrido-benzothiophenes (U.S. Pat. No. 5,856, 107) substituted 2-methylene-2,3-dihydrothiazoles (U.S. Pat. No. 5,847,150), quinolines (U.S. Pat. No. 5,840,500), PNA (U.S. Pat. No. 5,831,014), containing tags (U.S. Pat. No. 5,721,099), polyketides (U.S. Pat. No. 5,712,146), morpholino-subunits (U.S. Pat. Nos. 5,698,685 and 5,506,337), sulfamides (U.S. Pat. No. 5,618,825), and benzodiazepines (U.S. Pat. No. 5,288,514).

As used herein combinatorial methods and libraries included traditional screening methods and libraries as well as methods and libraries used in interactive processes.

(2) Computer Assisted Drug Design

The disclosed compositions can be used as targets for any molecular modeling technique to identify either the structure of the disclosed compositions or to identify potential or actual molecules, such as small molecules, which interact in a desired way with the disclosed compositions. The nucleic acids, peptides, and related molecules disclosed herein can be used as targets in any molecular modeling program or approach.

It is understood that when using the disclosed compositions in modeling techniques, molecules, such as macromolecular molecules, will be identified that have particular desired properties such as inhibition or stimulation or the target molecule's function. The molecules identified and isolated when using the disclosed compositions, such as, disclosed human Na channel, are also disclosed. Thus, the products produced using the molecular modeling approaches that involve the disclosed compositions, such as, disclosed human Na channels, are also considered herein disclosed.

Thus, one way to isolate molecules that bind a molecule of choice is through rational design. This is achieved through structural information and computer modeling. Computer modeling technology allows visualization of the three-dimensional atomic structure of a selected molecule and the rational design of new compounds that will interact with the molecule. The three-dimensional construct typically depends on data from x-ray crystallographic analyses or NMR imaging of the selected molecule. The molecular dynamics require force field data. The computer graphics systems enable prediction of how a new compound will link to the target molecule and allow experimental manipulation of the structures of the compound and target molecule to perfect binding specificity. Prediction of what the molecule-compound interaction will be when small changes are made in one or both requires molecular mechanics software and computationally intensive computers, usually coupled with user-friendly, menu-driven interfaces between the molecular design program and the user.

Examples of molecular modeling systems are the CHARMm and QUANTA programs, Polygen Corporation, Waltham, Mass. CHARMm performs the energy minimization and molecular dynamics functions. QUANTA performs the construction, graphic modeling and analysis of molecular structure. QUANTA allows interactive construction, modification, visualization, and analysis of the behavior of molecules with each other.

A number of articles review computer modeling of drugs interactive with specific proteins, such as Rotivinen, et al., 1988 *Acta Pharmaceutica Fennica* 97, 159-166; Ripka, *New Scientist* 54-57 (Jun. 16, 1988); McKinaly and Rossmann, 1989 *Annu. Rev. Pharmacol. Toxiciol.* 29, 111-122; Perry and Davies, *QSAR: Quantitative Structure-Activity Relationships in Drug Design* pp. 189-193 (Alan R. Liss, Inc. 1989); Lewis and Dean, 1989 *Proc. R. Soc. Lond.* 236, 125-140 and 141- 162; and, with respect to a model enzyme for nucleic acid components, Askew, et al., 1989 *J. Am. Chem. Soc.* 111, 1082-1090. Other computer programs that screen and graphically depict chemicals are available from companies such as BioDesign, Inc., Pasadena, Calif., Allelix, Inc, Mississauga, Ontario, Canada, and Hypercube, Inc., Cambridge, Ontario. Although these are primarily designed for application to drugs specific to particular proteins, they can be adapted to design of molecules specifically interacting with specific regions of DNA or RNA, once that region is identified.

Although described above with reference to design and generation of compounds which could alter binding, one could also screen libraries of known compounds, including natural products or synthetic chemicals, and biologically active materials, including proteins, for compounds which alter substrate binding or enzymatic activity.

Kits

Disclosed herein are kits that are drawn to reagents that can be used in practicing the methods disclosed herein. The kits can include any reagent or combination of reagent discussed herein or that would be understood to be required or beneficial in the practice of the disclosed methods. For example, the kits could include primers to perform the amplification reactions discussed in certain embodiments of the methods, as well as the buffers and enzymes required to use the primers as intended. For example, disclosed is a kit for assessing a subject's risk for acquiring prostate cancer, comprising one or more of the molecules disclosed herein.

C. METHODS OF MAKING THE COMPOSITIONS

The compositions disclosed herein and the compositions necessary to perform the disclosed methods can be made using any method known to those of skill in the art for that particular reagent or compound unless otherwise specifically noted.

1. Nucleic Acid Synthesis

For example, the nucleic acids, such as, the oligonucleotides to be used as primers can be made using standard chemical synthesis methods or can be produced using enzymatic methods or any other known method. Such methods can range from standard enzymatic digestion followed by nucleotide fragment isolation. (Sambrook et al., *Molecular Cloning: A Laboratory Manual*, 2nd Edition (Cold Spring Harbor Laboratory Press, Cold Spring Harbor, N.Y., 1989) Chapters 5, 6) to purely synthetic methods, for example, by the cyanoethyl phosphoramidite method using a Milligen or Beckman System 1Plus DNA synthesizer (for example, Model 8700 automated synthesizer of Milligen-Biosearch, Burlington, Mass. or ABI Model 380B). Synthetic methods useful for making oligonucleotides are also described by Ikuta et al., *Ann. Rev. Biochem.* 53:323-356 (1984), (phosphotriester and phosphite-triester methods), and Narang et al., *Methods Enzymol.*, 65:610-620 (1980), (phosphotriester method). Protein nucleic acid molecules can be made using known methods such as those described by Nielsen et al., *Bioconjug. Chem.* 5:3-7 (1994)).

2. Peptide Synthesis

One method of producing the disclosed proteins, is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. (Grant G A (1992) Synthetic Peptides: A User Guide. W.H. Freeman and Co., N.Y. (1992); Bodansky M and Trost B., Ed. (1993) Principles of Peptide Synthesis. Springer-Verlag Inc., NY (which is herein incorporated by reference at least for material related to peptide synthesis). Alternatively, the peptide or polypeptide is independently synthesized in vivo as described herein. Once isolated, these independent peptides or polypeptides may be linked to form a peptide or fragment thereof via similar peptide condensation reactions.

For example, enzymatic ligation of cloned or synthetic peptide segments allow relatively short peptide fragments to be joined to produce larger peptide fragments, polypeptides or whole protein domains. (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two step chemical reaction. (Dawson et al. Synthesis of Proteins by Native Chemical Ligation. Science, 266:776-779 (1994)). The first step is the chemoselective reaction of an unprotected synthetic peptide—thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site. (Baggiolini M et al. (1992) FEBS Lett. 307:97-101; Clark-Lewis I et al., J. Biol. Chem., 269:16075 (1994); Clark-Lewis I et al., Biochemistry, 30:3128 (1991); Rajarathnam K et al., Biochemistry 33:6623-30 (1994)).

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with full biological activity. (deLisle Milton R C et al., Techniques in Protein Chemistry IV. Academic Press, New York, pp. 257-267 (1992)).

3. Process Claims for Making the Compositions

Disclosed are processes for making the compositions as well as making the intermediates leading to the compositions. There are a variety of methods that can be used for making these compositions, such as synthetic chemical methods and standard molecular biology methods. It is understood that the methods of making these and the other disclosed compositions are specifically disclosed.

Disclosed are nucleic acid molecules produced by the process comprising linking in an operative way a nucleic acid comprising the sequences set forth in herein and a sequence controlling the expression of the nucleic acid.

Also disclosed are nucleic acid molecules produced by the process comprising linking in an operative way a nucleic acid molecule comprising a sequence having 80% identity to a sequence set forth herein, and a sequence controlling the expression of the nucleic acid.

Disclosed are nucleic acid molecules produced by the process comprising linking in an operative way a nucleic acid molecule comprising a sequence that hybridizes under stringent hybridization conditions to a sequence set forth herein and a sequence controlling the expression of the nucleic acid.

Disclosed are nucleic acid molecules produced by the process comprising linking in an operative way a nucleic acid molecule comprising a sequence encoding a peptide set forth herein and a sequence controlling an expression of the nucleic acid molecule.

Disclosed are nucleic acid molecules produced by the process comprising linking in an operative way a nucleic acid molecule comprising a sequence encoding a peptide having 80% identity to a peptide set forth herein and a sequence controlling an expression of the nucleic acid molecule.

Disclosed are nucleic acids produced by the process comprising linking in an operative way a nucleic acid molecule comprising a sequence encoding a peptide having 80% identity to a peptide set forth herein, wherein any change from the a sequence set forth herein are conservative changes and a sequence controlling an expression of the nucleic acid molecule.

Disclosed are cells produced by the process of transforming the cell with any of the disclosed nucleic acids. Disclosed are cells produced by the process of transforming the cell with any of the non-naturally occurring disclosed nucleic acids.

Disclosed are any of the disclosed peptides produced by the process of expressing any of the disclosed nucleic acids. Disclosed are any of the non-naturally occurring disclosed peptides produced by the process of expressing any of the disclosed nucleic acids. Disclosed are any of the disclosed peptides produced by the process of expressing any of the non-naturally disclosed nucleic acids.

Disclosed are animals produced by the process of transfecting a cell within the animal with any of the nucleic acid molecules disclosed herein. Disclosed are animals produced by the process of transfecting a cell within the animal any of the nucleic acid molecules' disclosed herein, wherein the animal is a mammal. Also disclosed are animals produced by the process of transfecting a cell within the animal any of the nucleic acid molecules disclosed herein, wherein the mammal is mouse, rat, rabbit, cow, sheep, pig, or primate.

Also disclose are animals produced by the process of adding to the animal any of the cells disclosed herein.

D. METHODS OF USING THE COMPOSITIONS

The disclosed compositions can be used as discussed herein as either reagents in micro arrays or as reagents to probe or analyze existing microarrays. The disclosed compositions can be used in any known method for isolating or identifying single nucleotide polymorphisms. The compositions can also be used in any known method of screening assays, related to chip/micro arrays. The compositions can also be used in any known way of using the computer readable embodiments of the disclosed compositions, for example, to study relatedness or to perform molecular modeling analysis related to the disclosed compositions.

E. EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts; temperature, etc.), but some errors and deviations should be accounted for. Unless indicated otherwise, parts are parts by weight, temperature is in ° C. or is at ambient temperature, and pressure is at or near atmospheric.

1. Example 1

Na Channel Isoforms and Prostate Cancer

Voltage-gated sodium channels ($Na_v$), commonly associated with impulse conductance in excitable tissues, have been found in prostate cancer. Disclosed herein is the expression and localization of $Na_v$ isoforms in human prostate cancer and evaluate $Na_v1.8$ as a prostate cancer biomarker in prostate specimens.

Human prostate cell lines were investigated by Western blot analysis for the expression of $Na_v$ protein. Prostate cancer cells were then fractionated into sub-cellular compartments to identify $Na_v$ sub-cellular localization. Tissue microarrays (TMA) were employed to compare $Na_v1.8$ expression and localization between normal prostate tissue and malignant prostate cancer tissue of varying histopathological grade.

Using western blot, the expression of $Na_v1.1$, $Na_v1.2$, and $Na_v1.5$-$Na_v1.9$ in the human prostate cancer cells, CWR22rv-1, LNCaP, C4-2, C4-2B, Du145, PC-3, and PC-3M.s was identified. An isoform-specific correlation was found between $Na_v$ expression and prostate cancer cell metastatic potential. $Na_v$ isoforms were differentially localized to specific cellular compartments in fractionated prostate cancer cells and nuclear localization was observed. Analyses of TMAs by immunohistochemistry revealed $Na_v1.8$ expression exclusively localized to basal cell layer nuclei in non-cancerous prostate tissues. In malignant prostate cancer tissues, increasing $Na_v1.8$ expression levels and cytoplasmic localization correlated with more advanced pathologic stage and higher Gleason score.

Voltage gated sodium channels normally found in the plasma membrane of excitable tissue like neurons are expressed in human prostate cancer.

a) Materials & Methods (1) Cell Culture and Reagents

The LNCaP, C4-2, and C4-2B (gift from Dr. Robert Sikes, University of Delaware, Department of Biological Sciences, Newark, Del.) and the CWR22rv-1, Du145, PC-3, and PC-3M cell lines (ATCC, Manassas, Va.) were cultured in RPMI-1640 with L-glutamine (CellGro, Lawrence, Kans.) containing 5% fetal bovine serum, 2.5 mM L-glutamine at 37° C. with 5% $CO_2$. LNCaP cells were cultured in the presence of 0:5 nM dihydrotestosterone (5α-androstan-17β-ol-3-one) (Sigma-Aldrich, St. Louis, Mo.).

(2) Western Blot Analysis

Western protocols were adapted from Collins et. Al. (Collins S P, Reoma J L, Gamm D M, Uhler M D. LKB1, a novel serine/threonine protein kinase and potential tumour suppressor, is phosphorylated by cAMP-dependent protein kinase (PKA) and prenylated in vivo. Biochem J 2000; 345:673-80) Briefly, prostate cancer cells were lysed in the radioimmunoprecipitation (RIPA) buffer (Sigma, St. Louis, Mo.) plus 50 mM Tris-HCl, pH 7.6, 5 mM EDTA, 150 mM NaCl, 30 mM sodium pyrophosphate, 50 mM sodium fluoride, 1 mM sodium orthovanadate, 1% Triton X-100, 0.01% SDS, 0.5% sodium deoxycholate and 1× protease inhibitor cocktail (Sigma-Aldrich). The protein samples were separated by SDS-PAGE and transferred onto immun-Blot PVDF membranes (Biorad Laboratories, Hercules, Calif.). The membranes were blocked with blocking buffer [50 mM Tris-Cl, 150 mM NaCl, 10 g/L BSA, and 500 mg/L sodium azide in $diH_2O$] and probed with the following antibodies: anti-$Na_v1.1$, anti-$Na_v1.2$, anti-$Na_v1.3$, anti-$Na_v1.5$, anti-$Na_v1.6$, anti-$Na_v1.7$, anti-$Na_v1.8$, anti-$Na_v1.9$ (Upstate/Millipore, Billerica, Mass.), and anti-PARP (Cell Signaling Technology, Danvers, Mass.) Chemiluminescent detection was performed using ECL reagents according to the vendor's instructions (Pierce, Rockford, Ill.).

(3) Membrane Fractionation

Fractionation of the C4-2 and PC-3 cells was accomplished by using the FractionPREP Cell Fractionation system (Biovision, Mountain View, Calif.). Briefly, $10^7$ cells were treated with a series of extraction buffers, each followed by centrifugation to segregate first cytoplasmic, then membrane, and finally nuclear fractions. Fractions were stored at −80° C. prior to use. Westerns of fractionated C4-2 and PC-3 cells were performed using anti-PARP, anti-EGFR and anti-α-tubulin antibody (Cell Signaling Technology, Danvers, Mass.) as reference controls.

(4) Immunohistochemical Detection of $Na_v1.8$ in Human Prostate Specimens

Paraffin-embedded cells or arrayed prostate cancer specimens (US Biomax, Inc, Rockville, Va.) containing normal (17) and malignant (160) prostate tissues were deparaffinized, rehydrated, boiled with citrate buffer (pH 6), treated with 0.3% $H_2O_2$, and preincubated in blocking solution (10% normal goat serum). The primary antibody, anti-$Na_v1.8$, was incubated with the specimens at a concentration of 1:50 for one hour at room temperature. Antigen-antibody complexes were detected using a horseradish-peroxidase complexed anti-rabbit secondary antibody (Dako Envision-Plus) (Dako North America, Inc., Carpinteria, Calif.). 3,3'-diaminobenzidine (Dako) was used as chromogen and hematoxylin as counterstain. A subtype-specific IgG was used as a negative control. Samples were imaged with an Olympus (Center Valley, Pa.) DP-70 camera/BX 61 inverted microscope using provided DP Controller software with a ×20 objective for cells and a ×40 objective for tissues.

Sprague-Dawley rat sciatic nerve dorsal root ganglia was used as a positive control tissue. Individual prostate cancer samples were scored (n=3) for their staining intensity as previously described (Li H, Ahonen T J, Alanen K, et al. Activation of signal transducer and activator of transcription 5 in human prostate cancer is associated with high histological grade. Cancer Res 2004; 64:4774-82). Semi-quantitative ranking of staining intensity were as follows: 0 (undetectable), 1+ (low immunostaining), 2+ (intermediate immunostaining), and 3+ (high immunostaining). Clinical features were only considered among the malignant samples for analysis. Fisher's exact test was used to compare presence of staining (negative stain vs. positive stain) and localization in each site among the clinical features. The exact Jonckheere-Terpstra test was used to determine if staining intensity was associated with the clinical features. The association between two sites of localization controlling for clinical factors were compared using the exact Cochran-Mantel-Haenszel test. Statistical analyses were performed using SAS software (SAS Institute Inc., Cary, N.C.).

b) Results (1) Voltage-Gated Sodium Channel Isoforms are Differentially Expressed in Human Prostate Cancer Cell Lines.

$Na_v$ expression in seven human prostate cancer cells was examined, including androgen-sensitive (LNCaP), and the androgen insensitive (C4-2, C4-2B, CWR22rv-1, Du145, PC-3, and PC-3M) cells (FIG. 1). Antibodies against unique epitopes of the α-subunit of sodium channel isoforms were used to detect the neuronal ($Na_v1.1$-$Na_v1.2$, $Na_v1.6$), cardiac ($Na_v1.5$), and peripheral ($Na_v1.7$-$Na_v1.9$) isoforms. Except for anti-$Na_v1.7$, antibodies detected bands of appropriate molecular weight. The anti-$Na_v1.7$ antibody detected prominent bands ~30 kDa below the predicted theoretical molecular weight of $Na_v1.7$ as previously reported (Toledo-Aral J J, Moss B L, He Z-J, et al. Identification of PN1, a predominant voltage-dependent sodium channel expressed principally in peripheral neurons. Proc. Natl. Acad. Sci. 1997; 94:1527-32). The specificity of all bands was verified by peptide inhibition studies (see supplemental data).

The neuronal $Na_v$ isoforms, 1.1 and 1.2, were both ubiquitously expressed across the human prostate cancer cells and had elevated expression levels in the highly metastatic Du145, PC-3, and PC-3M cell lines. $Na_v1.8$ and $Na_v1.9$ were also ubiquitously expressed among the prostate cell types. $Na_v1.8$ was highly expressed in the LNCaP cells and its two lineage cell lines, C4-2 and C4-2B, while $Na_v1.9$ was more highly expressed in Du145, PC-3, and PC-3M cells. Corresponding to its mRNA levels, $Na_v1.6$ was more highly expressed in the LNCaP, C4-2, and C4-2B cell lines (Diss J K. J, Archer S N, Hirano J, Fraser S P, Djamgoz M B A. Expression profiles of voltage-gated $Na^+$ channel α-subunit genes in rat and human prostate cancer cell lines. Prostate 2001; 48:165-78). However, $Na_v1.7$ expression levels did not reflect previously reported mRNA levels (Diss J K. J, Archer S N, Hirano J, Fraser S P, Djamgoz M B A. Expression profiles of voltage-gated $Na^+$ channel α-subunit genes in rat and human prostate cancer cell lines. Prostate 2001; 48:165-78). Instead, $Na_v1.7$ expression was higher in LNCaP cells than in C4-2 or C4-2B cells and linearly decreased from Du145, PC-3, and PC-3M cells. $Na_v1.5$ displayed low levels of expression across the entire panel of prostate cancer cells. Plasma membranes challenged with anti-$Na_v1.3$ provided no detectable signal. This could be due to the quality of the antibodies and/or the lack of expression of these isoforms.

Analysis of $Na_v1.7$ western blot data has special significance because of the correlation between its expression level and the relationships between cell lines. The LNCaP and C4-2 cell lines model progression towards androgen-independence and the C4-2 and C4-2B cell lines model progression towards metastasis. The decrease in expression levels of $Na_v1.7$ in this LNCaP progression model indicate that $Na_v1.7$ protein levels decrease with progression towards androgen independence and metastasis. Such a conclusion is further supported by $Na_v1.7$'s decreasing expression levels in the Du145, PC-3, and PC-3M cell lines. The Du145, PC-3, and PC-3M cell lines model increasing metastatic potential in that order. Thus, $Na_v1.7$ demonstrated decreased expression with metastasis and the degree of metastatic potential.

(2) Voltage-Gated Sodium Channel α-Subunit Isoforms Display Distinct Patterns of Localization While the function of $Na_v$s in excitable cells require expression in the plasma membrane, localization of these transmembrane proteins in cancer cells has not been established. Examination of the sub-cellular localization of $Na_v$ isoforms 1.1, 1.7, and 1.8 in fractionated C4-2 and PC-3 cell lines provided insights into their distribution (FIG. 6). To demonstrate fraction purity, α-Tubulin, EGFR, and PARP, specific to the cytoplasmic, membrane, and nuclear fractions, respectively, were used as benchmarks. Although western blots of fractionated cells afforded less intense staining as compared to whole cell lysates, clear expression profiles were determined (FIG. 6).

Interestingly, $Na_v1.8$ segregated to the nuclear fraction in both the C4-2 and PC-3 cells. $Na_v1.1$, whose expression levels increased with metastatic potential (FIG. 1), also did not localize to the plasma membrane. The two bands detected in C4-2 cell whole cell lysates (FIG. 1) were localized to separate cellular compartments upon C4-2 fractionation (FIG. 6). The higher molecular weight band was isolated to the cytoplasmic fraction while the 10 kDa lower molecular weight band was isolated to the nuclear fraction. $Na_v1.7$ localized to the plasma membrane of C4-2 and PC-3 cells. These results demonstrate that voltage-gated sodium channel isoforms are expressed differently in cancer cells as compared to neurons. Furthermore, localization of $Na_v$ transmembrane proteins appears to be isoform-dependent. This can be related to aberrant trafficking and/or alternative function in regards to cellular signaling (3) $Na_v1.8$ Expression in Prostate Cancer Tissue Before moving to tissues, $Na_v1.8$ immunocytochemical expression was examined in CWR22rv-1, C4-2B, Du145, and PC-3 cells (FIG. 7). Immunocytochemical analysis showed $Na_v1.8$ expression in all four cell lines. Specificity was confirmed by peptide competition as a negative control and in dorsal root ganglia staining as a positive control (Amaya F, Decosterd I, Samad T A, et al. Diversity of expression of the sensory neuron-specific TTX-resistant voltage-gated sodium ion channels SNS and SNS2. Mol Cell Neurosci 2000; 15:331-42).

Human prostate tissue specimens consisting of normal to high Gleason grade were obtained. FIG. 8 provides a history of the patient specimens. The specimens obtained were analyzed for $Na_v1.8$ expression and localization by immunohistochemistry.

$Na_v1.8$ immunostaining was either absent or weak in normal prostate epithelia (n=17). However, over 50% of malignant prostate tissues showed moderate or strong $Na_v1.8$ immunostaining. The observed difference in staining intensity between normal and malignant tissues was statistically significant (P<0.0001). Therefore, $Na_v1.8$ can be weakly expressed in healthy prostate tissue but its expression levels significantly increase in prostate cancer.

$Na_v1.8$ expression was compared with PSA secretion, pathologic stage, pathologic Gleason score, and pathologic lymph node stage in malignant prostate cancer tissues (FIG. 8). Statistically significant correlations were observed for comparisons of all clinical features except for a correlation between PSA secretion and $Na_v1.8$ staining. $Na_v1.8$ expression levels increased with both pathologic stage (P=0.04) and Gleason score (P=0.01). Representative prostate cancer tissue specimens of various Gleason scores increasing in $Na_v1.8$ staining intensity are depicted in FIG. 4. The relationship between $Na_v1.8$ intensity and the distribution of prostate tissue specimens segregated by Gleason Score is represented in FIG. 8.

Several patterns of Nav1.8 localization were observed in prostate tissues. In normal prostate tissues, distinct nuclear Nav1.8 immunostaining was found in the basal layer of prostate acini. Such nuclear staining was absent in normal prostate secretory cells. When present, Nav1.8 localized exclusively to the cytoplasm of normal prostate secretory cells. However, 66% of malignant prostate tissues expressed Nav1.8 in the nucleus (P<0.0001). This data indicates that malignant prostate epithelia adopt aspects of a basal phenotype.

It was also observed that a significant difference between normal and malignant prostate tissues in $Na_v1.8$ plasma membrane localization. $Na_v1.8$ was completely absent in normal prostate epithelia—for both basal and secretory cells. A significant sub-population of malignant prostate tissue specimens (19%) expressing $Na_v1.8$ was identified in the plasma membrane.

While $Na_v1.8$ localized to the cytoplasm in normal prostate secretory cells, cytoplasmic localization increased in malignant prostate tissues (P=0.0037). Two phenotypes were evident from $Na_v1.8$ cytoplasmic staining: 36% without and 64% with nuclear staining. Of note, $Na_v1.8$ nuclear localization was not dependent on cytoplasmic localization. However, a staining pattern of exclusive nuclear localization was rare (n=8/160).

$Na_v1.8$ cytoplasmic and nuclear staining correlated with prostate cancer clinical characteristics. $Na_v1.8$ cytoplasmic localization increased with both pathologic stage (P=0.04) and pathologic Gleason score (P=0.01) (FIG. 8). $Na_v1.8$ nuclear immunostaining decreased in tissues metastatic to local lymph node(s). Thus, despite the neoplastic localization of $Na_v1.8$ to the nucleus, that basal phenotype is lost in tumors that have metastasized to local lymph node(s).

Nuclear localization of a voltage regulated ion channel in both prostate cells and specimens. Membrane fractionation and IHC confirmed that $Na_v1.8$ localizes to the nucleus of prostate cancer cells and prostate specimen.

Finding of $Na_v1.8$ expression in human prostate cancer specimens led to several important clinical correlations with pathologic stage, Gleason score, and nodal involvement. $Na_v1.8$ localization could clearly differentiate between normal and malignant tissues. It was found that $Na_v1.8$ primarily in the nuclei of the basal cell layer but not secretory cells of normal prostate acini making it a potential biomarker for distinguishing between benign and malignant prostate cancer.

2. Example 2

Dansyl 2.4 Diones

A synthetic plan was developed to: analyze the region around the imide nitrogen of the hydantoin, provide hydrophobic/hydrophillic bulk at aliphatic chain terminus, and determine possible hydantoin isosteric replacements. Following the proposed synthetic plan, analogs were synthesized and tested by [$^3$H]-BTX-B displacement assay at site 2 (Table 7) in neuronal VGSCs.

The BTX binding site (site 2) of the VGSC was evaluated by molecular docking software with a cholic acid analog of BTX, for which the following residues of the ion channel appeared to interact with and represent the binding site for the guest molecule: helix I residues I433, N434, L437; helix II residues L788, F791, L792; p-loop residues D400, E755, K1237; helix IIIS6 residues T1279, L1280, F1283; and helix IV residues F1579, L1582, Y1583, Y1588. A three-dimensional QSAR model for interaction with hydantoin accounts for spatial regions that do and do not accommodate steric bulk, and also models the positive and negative (charge) regions of the channel.

SCHEME 5.

-continued
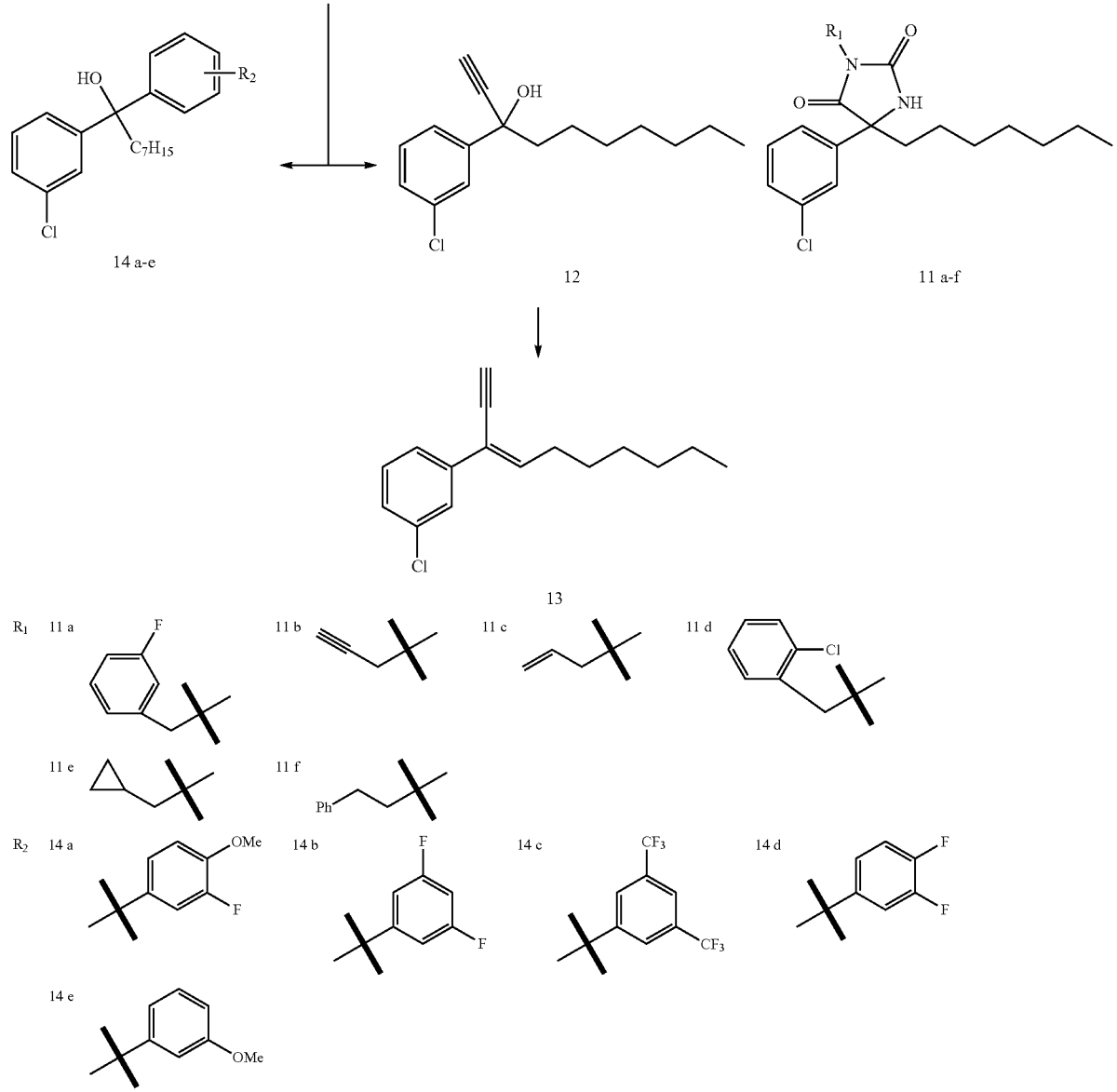
a. 1) BrMgC7H15, Et2O, rt, 16 h, 2) 1 N HCl, 89% b. (NH4)2CO3, KCN, 50% EtOH, 55-60° C., 69%. c. R1Br, K2CO3, Acetone, rt, 16
d. 1) Acetylene, BuLi, THF, -78° C., 2 h, 2) H2O, 56%. e. MsCl, TEA, DCM, 0-23° C., 14 h, 24%. f. R2MgBr, THF, 0-23° C., 6-59%.
SCHEME 6
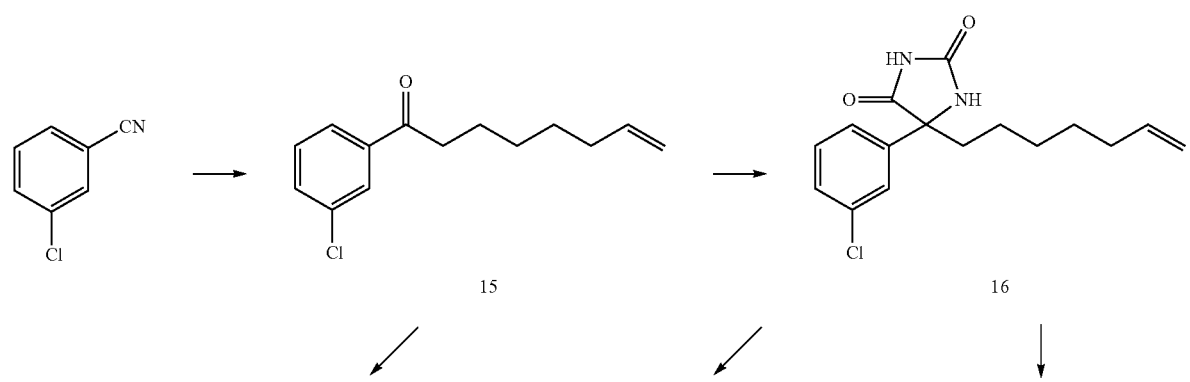

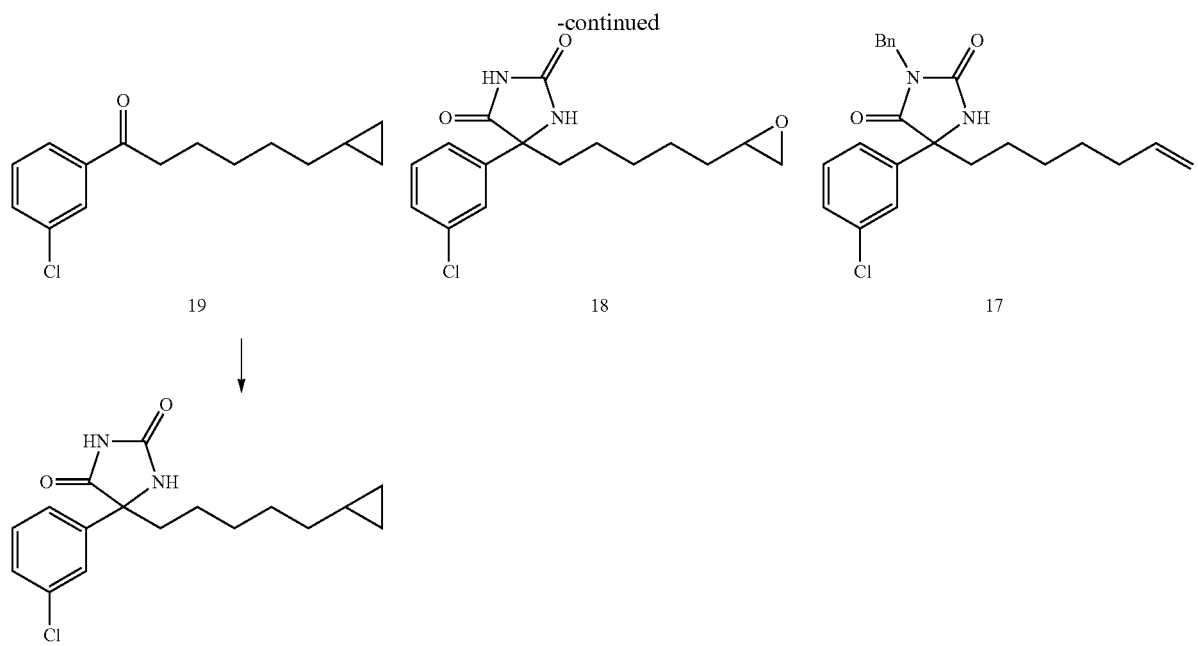
a. 1) BrMgC$_7$H$_{15}$, Et$_2$O, rt, 16 h, 2) 1 N HCl, 37%. b. (NH$_4$)$_2$CO$_3$, KCN, 50% EtOH, 55-60° C., 26%. c. BnBr, K$_2$CO$_3$, Acetone, rt, 16 h, 82%.
d. mCPBA, NaHCO$_3$, DCM, rt, 14 h, 33%. e. TFA, Et$_2$Zn, CH$_2$I$_2$, DCM, 0-23 C, 14 h, 54%. f. (NH$_4$)$_2$CO$_3$, KCN, 50%, EtOH, 55-60 C, 43%.
SCHEME 7
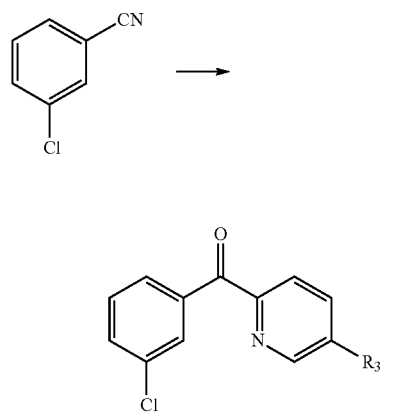
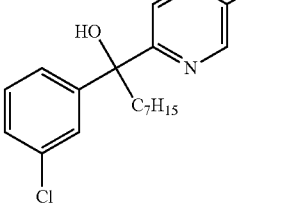
R$_3$ 21 a and 22 a = H,
21 a and 22 b = OMe
a. 1) Pyridinyl Bromide, BuLi, -78° C., Et$_2$O. 2) 3 M HCl, 85-100%.
b. 1) BrMgC$_7$H$_{15}$, Et$_2$O, rt, 16 h, 2) 1 N HCl, 51-57%.
Scheme 8
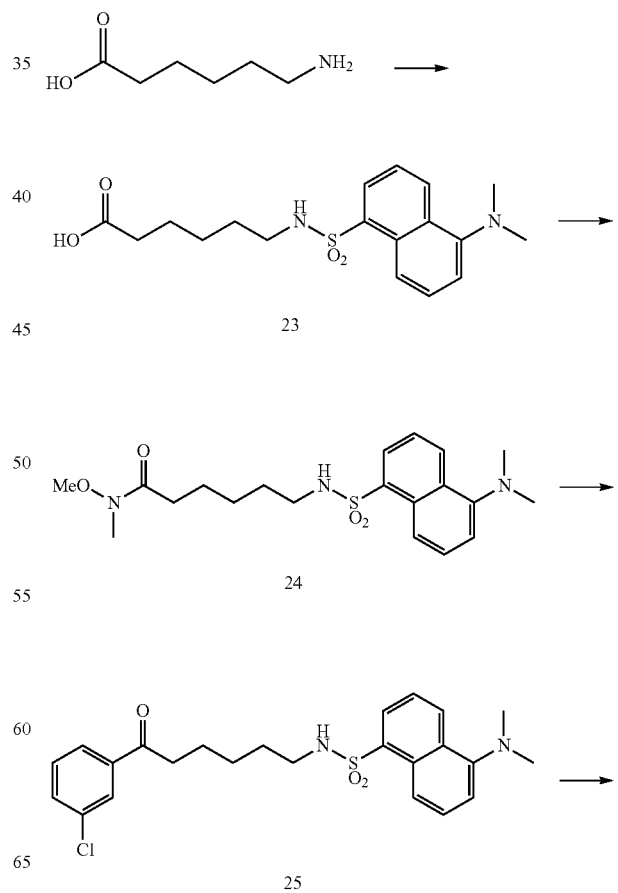

-continued

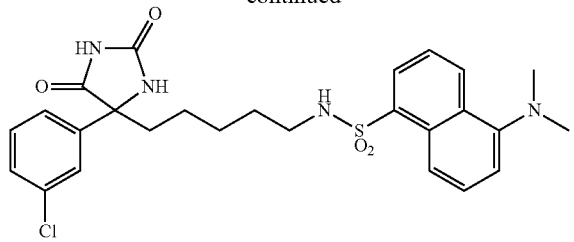

26 a. TBSCl, Imid. DCM, rt, 12 h, b. 1) Dansyl Chloride, TEA, DCM, rt, 24 h, 53%.
2) AcOH, H$_2$O, THF, 76% c. 1) (COCl)$_2$, DMSO, TEA, DCM, -78° C., 65%.
2) BrMgC$_6$H$_4$Cl, THF, rt, 12 h, 59%. 3) (COCl)$_2$, DMSO, TEA, DCM, -78° C., 81%.
d. (NH$_4$)$_2$CO$_3$, KCN, 50% EtOH, 55-60° C., 19d, 8%.

Of the 20 analogs tested, six had [$^3$H]-BTX displacement characteristics much greater then that of phenyloin (Table 7), see Schemes 5, 6, 7 and 8 for the chemical synthesis and structure of the tested compounds. Compound 26, having the greatest [$^3$H]-BTX displacement at 86% (40 μM), was further tested for VGSC functional blocking ability in HEK cells stably expressing Na$_v$1.2 (Table 8). PC-3 cells, known to express VGSCs, were also treated with 26 over six hours and demonstrated the ability to penetrate cell membranes and reside in the cytosol (see FIG. 9).

TABLE 7

[$^3$H]-BTX-B$^a$ Binding Data

| Compound | Displacement % |
|---|---|
| DPH | 50 |
| 11a | 71 |
| 11b | 57 |
| 11c | 83 |
| 11d | 19 |
| 11e | 78 |
| 11f | 17 |
| 12 | 78 |
| 13 | 32 |
| 14a | 56 |
| 14b | 35 |
| 14c | 8 |
| 14d | 48 |
| 14e | 51 |
| 16 | 79 |
| 17 | 23 |
| 18 | 28 |
| 20 | 8 |
| 21a | 28 |
| 21b | 41 |
| 26 | 86 |

Screen performed at 40 μM, with 2 replicates, referenced to Aconitine.
($^a$ [$^3$H]-Batrachotoxin-B ([$^3$H]-BTX-B) is a radioligand that binds to site 2 of the VGSC.)

TABLE 8

VGSC Functional Blocking Data

| Compound | % hNaV 1.2 Functional Block (10 μM) |
|---|---|
| DPH | 10.9 ± 4.2 |
| JDA-3-135 | 30.5 ± 5.1 |
| 26 | 58.9 ± 4.1 |

The hydrophobic carbon (2-10 carbon long) chain of DHP was modified with dansyl. The flexibility of the chain combined with its hydrophobicity, of the side chain and the dansyl group, allows for the side chain to efficiently bind to the hydrophobic region of the VGSC. The dansyl group not only increases the efficiency of binding and therefore improves the inhibition in the VGSC but also simultaneously provides a method to fluorescently image where binding occurs. Since PCs uniquely express a hyperactivity of VGSC in contrast to normal prostate cells the drug can selectively bind to its target. The hyperactive VGSC are thought to promote several stages of mitosis in PCs. As N-(5-(4-(3-chlorophenyl)-2,5-dioxoimidazolidin-4-yl)pentyl)-5-dimethylamino)naphthalene-1-sulfonamide (CDPNS) binds to VGSC it blocks the channel which depresses the hyperactivity of VGSC leading to limited or stopped growth of human prostate cancer cells. By the incorporation of the dansyl group to the drug it would be possible to monitor the growth and progress of treatment of prostate cancer tumors. The dansyl group in CDPNS is also shown to increase binding compared to its heptyl analog, instead of the side chain being terminated with dansyl it is terminated with CH$_3$. The dansyl group creates bulk hydrophobicity several carbons from the hydantoin core. The addition of the hydrophobic fluorescent dansyl group not only provides visual capabilities but also increased the efficiency in binding (86.4% at 40 μM) and also functional blocking (58.9±4.1%) in Na$_v$1.2 VGSCs. With a GI$_{50}$ of 36.0 μM in PC-3 cells. CDPNS is therefore an efficient PCs inhibitor, fluorescent lead compound where all functionalities can promote binding and the dansyl group provides fluorescent capabilities in vitro. The disclosed material and process was designed for the direct purpose of enhancing activity/binding with a designated pharmacophore, therefore, giving multiple advantages in treatment and diagnosis human PCs the single addition of a dansyl group.

a) Organic Synthesis of the Proposed Compounds.

The synthesis of N-(5-(4-(3-chlorophenyl)-2,5-dioxoimidazolidin-4-yl)pentyl)-5-dimethylamino)naphthalene-1-sulfonamide (CDPNS) begins with the addition of dansyl chloride to 6-aminohexanoic acid under basic conditions to yield the sulfamide 2 (Scheme 8). An acid-amine coupling was performed under the presence of EDCI to afford the Weinreb amide 3 in moderate yield. The commercially available Grignard reagent 3-chlorophenyl magnesium bromide was then added directly to a solution containing amide 3 resulting in the aryl ketone 4. The hydantoin (N-(5-(4-(3-chlorophenyl)-2,5-dioxoimidazolidin-4-yl)pentyl)-5-dimethylamino)naphthalene-1-sulfonamide (CDPNS)) 1 was then synthesized in a one step Bucherer-Berg reaction.

(1) Chemical Synthesis.

Chemicals were purchased from Aldrich Chemical Company, and were used without any further purification unless mentioned otherwise in the procedure. Dry solvents were dried over 4 Å molecular sieves prior to use. Air sensitive reactions were carried out in flame-dried glassware under an N2 atmosphere unless otherwise noted. Flash Column Chromatography (FC) separations were done on a Biotage SP1 system monitoring at 254 nm. All NMR spectra were recorded on a Varian 400 spectrometer, operating at 400 MHz for 1H and 100 MHz for $^{13}$C NMR. Melting points were recorded on a Meltemp instrument and are uncorrected.

(a) 6-(5-(dimethylamino)naphthalene-1-sulonamido)hexanoic acid

In a round-bottom flask (RBF) 6-heanoic acid (3.70 g, 27.8 mmol) was added to a 1 M solution of NaHCO$_3$ (45 mL). To this was added dansyl chloride (5.05 g, 18.5 mmol) in acetone (20 ml) and TEA (16.0 mL, 111 mmol). The solution was stirred for 3 hours, 2 M Hcl 2 as then added to the solution until the pH reached ~3. The product was then extracted with EtOAc (3×25 mL) and washed successively with H$_2$O (25 mL) and brine (25 mL). The organic fraction was then dried over Na$_2$SO$_4$, concentrated, then purified by FCC (1:10

MeOH/DCM) to yield a sticky, yellow oil (5.80 g, 85%). $^1$H-NMR (400 MHz, CDCl$_3$) ppm 1.13 (m, 2H), 1.35 (tt, 4H, J=7.2 Hz, J=14.1 Hz).

b) Determination of CDPNS Binding Efficiency

To determine the effects of CDPNS on the hydantoin binding site, a direct displacement assay was carried out with [$^3$H]-BTX-A-20-α-benzoate ([$^3$H]-BTX-B) binding to VGSC's in rat brain synaptoneurosomes. CDPNS was more than two and half times more effective at displacing [$^3$H]-BTX-B binding. This indicated that CDPNS does bind to the hydantoin binding site (Table 9).

TABLE 9

| Compound | % [$^3$H]-BTX Inhibition (40 µM) | % hNaV 1.2 Functional Block (10 µM) |
|---|---|---|
| DPH | 30.4 ± 3.3 | 10.9 ± 4.2 |
| JDA-3-135 | 69.6 | 30.5 ± 5.1 |
| 26 | 86.4 | 58.9 ± 4.1 |

In addition the functional blocking ability of 9 was tested after site two affinities was confirmed. The potential reason for this increased blocking ability stems from the dansyl addition in a hydrophobically receptive region of the binding site in the VGSC (Anderson, J. D., et al. Mol. Cancer. Ther. 2003, 2, 1149-1154; Lenkowski, P et al. Neuropharmacology, 2007, 52, 1044-1054). This enhanced potency could be due to the dansyl substituent interacting with L1465 and 11469, located in S6 of domain III in the binding site, which are believed to be the source of hydrophobic receptivity 17. The ability to inhibit VGSC currents is an important property and represents functional blocking. The ability of CDPNS to inhibit sodium channel currents was assessed at 10 and 100 µM against human Na$_v$1.2 by patch clamp assay (FIG. 10).

The intracellular localization of VGSC in human prostate cells presented an optimal situation to evaluate the distribution of CDPNS, the fluorescent VGSC inhibitor. CDPNS appeared to gain access to the cell and reside in the cytoplasm where Na$_v$1.2 is expressed in PC-3 cells. In addition, there is no apparent nuclear staining which indicates that CDPNS is prohibited from crossing the nuclear membrane. Unfortunately, the resolution of the image did not allow for a closer examination of the membrane-cytoplasm or cytoplasm-nuclear membrane interfaces.

TABLE 10

| (FIG. 16) | |
|---|---|
| Compound | GI$_{50}$ ± SEM (10 µM) |
| DPH | >100 |
| JDA-3-135 | 18.6 ± 1.5 |
| 26 | 36.0 |

Following the determination that compound CDPNS inhibits the VGSCs that are present in androgen independent PC-3 cells, a 3-(4,5-Dimethylthiazol-2-yl)-2,5-diphenyltetrazolium bromide (MTT) cell viability assay was utilized to measure the ability of compound CDPNS to inhibit PC-3 cell growth via VGSC blockade. In this experiment data yielded from CDPNS was compared to previously determined DPH and JDA-3-135 antiproliferation data (Table 10).

Surprisingly, while CDPNS displayed enhanced binding a functional blocking characteristic, it was a lesser inhibitor of PC-3 cell growth when compared to JDA-3-135. This discrepancy could possibly be explained by JDA-3-135 being an inhibitor of another VGSC isoform present in the PC-3 cell. Nevertheless, it still appears that the addition of the dansyl fluorophore, in the hydrophobically receptive region of the BTX binding site, greatly enhanced the binding and functional blockade of Na$_v$1.2 VGSCs.

FIG. 10 shows demonstration traces of hNav1.2 block by CDPNS. Sodium currents were elicited by a depolarizing step from a holding potential of −100 mV to +10 mV for a duration of 25 ms at 15 s intervals, after which compound 1 was applied. 10 µM and 100 µM traces are compared to the control. The androgen independent PC-3 cells express several VGSC isoforms including Nav1.2.14, 24, 31 (Yu, F. H. and Catterall, W. A. Genome Biology, 2003, 4, 207; Roger, S., Potier, M., Vandier, C., Besson, P., Le Guennec, J. Y. Voltage-Gated Sodium Channels: New Targets in Cancer Therapy? Curro Pharm. Des., 2006, J2, 3681-3695; Diss, J. K. J., Archer, S. N., Hirano, J., Fraser, S. P., Djamgoz, M. B. A Expression Profiles of Voltage-Gated Sodium Channel α-Subunit Genes in Rat and Human Prostate Cancer Cell Lines. Prostate, 2001, 48, 165-178.) However, unlike neurons, prostate cancer cell fractionation experiments (FIG. 11) reveal the expression of Nav1.2 in nuclear and cytoplasmic fractions and not in the plasma membrane.

FIG. 11 shows the cell fractionation studies of PC-3 cells. C indicates the cytoplasm, M indicates the plasma membrane, and N refers to the nuclear membrane. The Na$_v$1.2 spot is referring to a 260 kDa spot which indicates the α-subunit of the VGSC. PC-3 Cells were treated with CDPNS at 10 µM and fixed with paraformaldehyde for imaging by two-photon confocal microscopy (FIG. 12).

Twenty compounds were designed and synthesized utilizing ligand-based and rational drug design methods. Of the twenty compounds synthesized and tested, [$^3$H]-BTX-B displacement results revealed compound 26 as having the greatest binding site affinity with 86% displacement at 40 µM. This compound was further tested for functional blocking ability in hNa$_v$1.2 cells with an IC$_{50}$ of 58.9±4.1 at 10 µM. In agreement with the CoMFA predictions the increased bulk of the dansyl moiety promoted a positive interaction with the VGSC pharmacophore while adding a fluorescent component for in vitro and in vivo characterization.

Hyper-excited neuronal voltage-gated sodium channels (VGSCs) play an integral role in seizure activity, a characteristic symptom of epilepsy. The state dependent inhibition of hyper-excited VGSCs is feasible with phenyloin (IC$_{50}$ 40 µM) and other imidazolidine-2,4-dione analogs. Implementation of ligand-based drug design techniques predicted that selected changes to the structure of the lead compounds, including phenyloin, would provide for increased inhibition of hyper-excited neuronal VGSCs. Three molecular regions of a current phenyloin analog were identified for modification and analogous design to probe the binding pocket located at Site 2 in the VGSC. Promising molecular entities predicted by the conformational molecular field analysis (CoMFA) were synthesized. These synthesized entities were summarily tested by [$^3$H]-BTX-B displacement assay (40 µM Site 2). Six of the developed compounds demonstrated displacement, greater than that of phenyloin, with compound 26 displaying a displacement of 86%. This compound also demonstrated functional blocking ability in hNa$_v$1.2 VGSCs with an inhibition of 58.9±4.1% at 10 µM.

Due to the relationship between VGSC expression and invasiveness in the metastatic, androgen-independent PC-3 cell line, the use of VGSC inhibitors is attractive as a potential therapy. Although the exact role of VGSC in prostate cancer growth is not clear it is speculated that a hyperactive VGSC influences the capacity of the cell to alter its morphology and migrate which is inherent to different stages of cancer cell metathesis. These include proliferation, migration, and adhesion/interaction with the cellular matrix. The role of VGSC in shaping the cellular morphology has been described for neurons. (Mattei et al., *J. Neurosci. Res.*, 1999, 55: 666-673).

3. Example 3

Hermitamides A and B Synthesis and Evaluation of Hermitamides A and B as Human Voltage-Gated Sodium Channel Blockers The hermitamides A and B are lipopeptides isolated from a Papau, New Guinea collection of the marine cyanobacterium *Lyngbya majuscula*. *L. majuscula* is a rich source of structurally diverse compounds, many of which were found to be ligands for the voltage-gated sodium channel ($Na_v$). Described herein is the nonracemic total synthesis of hermitamides A and B and their epimers. These compounds were then shown to displace [$^3$H]BTX at 10 μM more potently than phenyloin, a clinically used sodium channel blocker. A potential binding mode is given for (S)-hermitamide B in the BTX-binding pocket as seen in FIG. 13. Finally, patch-clamp experiments showed that these compounds are potent blockers of the human voltage-gated sodium channels.

The sodium channel is an important target in medicine. Blockers of the human voltage-gated sodium channel ($Na_v$) have proven to be effective anticonvulsants, anesthetics, and antiarrhythmics. Despite the success of these agents in the clinic, the sodium channel remains a complex target for drug discovery. Sodium channel selectivity over potassium and calcium channels remains a challenge. And, subtype selectivity of the sodium channel has only recently been addressed with moderate success. (Anger, T.; Madge, D. J.; Mulla, M.; Riddall, D. Medicinal Chemistry of Neuronal Voltage-Gated Sodium Channel Blockers. *J. Med. Chem.* 2001, 44, 115-137.) In an effort to discover novel ligands for the sodium channel, natural products of marine cyanobacteria have been synthesized and evaluated for their ability to inhibit the sodium channel.

Several lipopeptidic secondary metabolites from the marine cyanobacterium *Lyngbya majuscula* were found to be ligands for the voltage-gated sodium channel. The *L. majuscula* metabolites antillatoxin and antillatoxin-B are sodium channel activators with potencies that compare with the brevetoxins. These cyclic lipopeptides have a novel binding site that can serve as a new target for inhibiting sodium channel activity. (Li, W. 1.; Berma, F. W.; Okino, T.; Yokokawa, F.; Shiori, T.; Gerwick, W. H.; Murray, T. F. Antillatoxin is a marine cyanobacterial toxin that potently activates voltage-gated sodium channels. *Proc. Natl. Acad. USA*, 2003, 98, 7599-7604.) Kalkatoxin is a potent sodium channel blocker also isolated from *L. majuscula*. This metabolite is a thiazoline-containing lipopeptide that has been shown to interact with site 7 of the sodium channel. (LePage, K. T.; Goeger, D.; Yokokawa, F.; Asano, T.; Shiori, T.; Gerwick, W. H.; Murray, T. F.; The neurotoxic lipopeptide kalkitoxin interacts with voltage-sensitive sodium channels in cerebellar granule neurons. *Toxicol. Lett.* 2005, 158, 133-139.) Recently, jamaicamides A, B, and C were isolated from the dark green strain of *L. majuscula* collected at Hector's Bay, Jamaica. These lipopeptides were shown to block the sodium channel at 5 μM, producing half the response of saxitoxin applied at 0.15 μM. (Edwards, D. J.; Marquez, B. L.; Nogle, L. M.; McPhail, K.; Goeger, D. E.; Roberts, M. A.; Gerwick, W. H. Structure and Biosynthesis of the Jamaicamides, New Mixed Polyketide-Peptide Neurotoxins from the Marine Cyanobacterium *Lyngbya majuscula*. *Chem. and Biol.* 2004, 11, 817-833.)

The hermitamides A and B, Scheme 1, are lipopeptides isolated from a Papau, New Guinea collection of marine *L. majuscula*. (Tan, L. T.; Okino, T.; Gerwick, W. H. Hermitamides A and B, Toxic Malyngamide-Type Natural Products from the Marine Cyanobacterium *Lyngbya majuscula*. *J. Nat. Prod* 2000, 63, 952-955.) *L. majuscula* has already proven to be a rich source of sodium channel ligands. However, the effect of the hermitamides on sodium channel activity has not been reported in the literature. The hermitamides resemble the jamaicamides as well as the potent sodium channel blocker kalkatoxin, albeit with a much simpler structure. Therefore, it was hypothesized that the hermitamides are also sodium channel blockers, and can serve as a synthetically accessible structure for further development of lipopeptides as a new class of sodium channel blockers.

The hermitamides can be divided into the following three regions: the lipophilic chain, the peptide linkage, and the aromatic moiety (Scheme 9). The lipophilic

SCHEME 9 chain contains one methoxy stereocenter with the S configuration for the natural product and an E double bond. The aromatic moiety is a phenethylamine for hermitamide A, or a tryptamine group for hermitamide B. The carboxylic acid of the lipophilic chain alone is a known natural product named lyngbic acid, which is the precursor for the total synthesis of the hermitamides.

The configuration of the remote stereocenter was confirmed by semisynthesis of the hermitamides from (S)-lyngbic acid that was isolated with the hermitamides. The preparation of enantiopure lyngbic acid has been accomplished by ring-opening of a chiral epoxide (Mueller, C.; Voss, G.; Gerlach, H. Synthesis of (4E,7S)-(−)-methoxy-4-tetradecenoic acid, a major constituent of the marine cyanophyte *Lyngbya majuscula*. *Liebigs Ann. Chem.* 1995, 4, 673-676.), lipase resolution (Sankaranarayanan, S.; Sharma, A.; Chattopadhyay, S. Convenient synthesis of (±)- and (S)-antipode of (4E,7S)-7-methoxytetradec-4-enoic acid, the antimicrobial principle of marine cyanophyte. *Tetrahedron Asymm.* 1996, 7, 2639-2643.), and asymmetric allylation of the requisite aldehyde (Li, Y.; Chen, 1.; Cao, X.-P. A Stereoselective Synthesis of (4E,7S)-(−)-7-Methoxydodec-4-enoic Acid. *Synlett* 2006, 320-324.). A racemic total synthesis of hermitamides A and B and a formal synthesis of the nonracemic compounds are reported. (Virolleaud, M.-A.; Menant, C.; Fenet, B.; Piva, O. Total and formal enantioselective synthesis of lyngbic acid and hermitamides A and B. *Tetrahedron Lett.* 2006, 47, 5127-5130.) Herein, is reported a facile enantioselective total synthesis of the hermitamides for each enantiomer, their ability to displace [$^3$H]BTX from sodium channels, and their ability to functionally block the sodium channels as measured by patch-clamping experiments.

a) Results and Discussion

The synthesis of nonracemic lyngbic acid commenced with the asymmetric allylation of octyl aldehyde with allyltributylstannane mediated by a titanium-binol complex to give alcohol 3 in 40% yield and greater than 95:5 er as previously reported. (Costa, A. L.; Piazza, M. G.; Tagliavini, E.; Trombini, c.; Umani-Ronchi, A. Catalytic Asymmetric Synthesis of Homoallylic Alcohols. *J. Am. Chem. Soc.* 1993, 115, 7001-7002.) Treatment with sodium hydride in DMF followed by methyl iodide then gave methyl ether 28 in 92% yield. Dihydroxylation and in situ oxidative cleavage with sodium periodate under Johnson-Lemieux conditions then gave aldehyde 29, which was used in the next step without further purification. Addition of vinylmagnesium bromide in tetrahydrofuran gave the corresponding allylic alcohol 30 as a mixture of diastereomers in 51% yield. The Johnson-Claisen rearrangement was then effected by treatment with trimethylorthoacetate with catalytic propionic acid followed by distillation of the methanol generated during the reaction to give the methyl ester of lyngbic acid 31 in 63% yield.

Saponification of the methyl ester with lithium hydroxide in a tetrahydrofuran-water solvent system gave nonracemic lyngbic acid 32 in 41% yield. Total synthesis of the hermitamides was accomplished in excellent yield by diisopropylcarbodiimide-mediated amide coupling in the presence of 1-hydroxybenzotriazole with phenethylamine or tryptamine in good yield to give hermitamide A and B, respectively, see scheme 10 for the complete synthesis of Hermitamide A and B.

SCHEME 10. Synthesis of hermitamides A and B

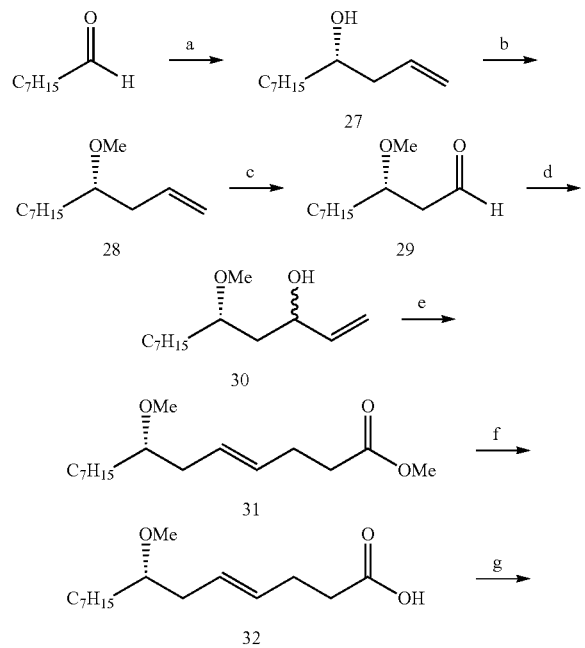

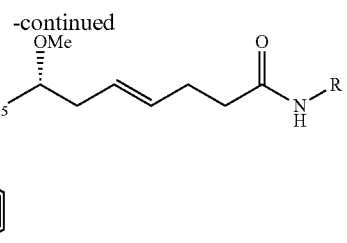

33 R = CH$_2$CH$_2$Ph
34 R = CH$_2$CH$_2$-

(a) allyltributylstannane, (R)-BINOL (20 mol %), TiCl$^2$(O—i-Pr)$_2$ (20 mol %), CH$_2$Cl$_2$, 4 Å MS, -20° C. (40%); (b) i. NaH, DMF; ii. MeI (92%); (c) OSO$_4$, NaIO$_4$, (d) vinylmagnesium bromide, THF (51%, 2 steps); (e) CH$_3$C(OCH$_3$)$_3$, n-PrCO$_2$H, Δ (63%); (f) LiOH, H$_2$O—THF (41%); (g) DCC, 1-hydroxybenzotriazole, R—NH$_2$ (R—NH$_2$ =phenethylamine (77%) or tryptamine (88%)).

The jamaicamide structure resembles the hermitamides in that it is a lipopeptide with a lipophilic chain, peptide linkage, and aromatic moiety. However, the carbon skeletal arrangement of the jamaicamides is much more complicated for both the aliphatic chain and the aromatic moiety, which is actually a highly unsaturated alkaloid with one stereocenter. The hermitamides are simplified analogs of the jamaicamides and the hypothesis is that these compounds are likely to also be sodium channel blockers.

In order to determine if the hermitamides bind to the sodium channel, the natural products, their enantiomers, and the racemic mixture were tested for their ability to displace [$^3$H]-batrachatoxin. Batrachatoxin is a lipid-soluble neurotoxin that binds to site 2 of the sodium channel. This site is known to overlap with the local anesthetic binding site 9. Ligands known to bind to site 9 of the sodium channel include anesthetics, anticonvulsants and antiarrthymics. As a control, phenyloin, a clinically-used sodium channel blocker that is known to displace [$^3$H]BTX was also included.

The disclosed compounds were ligands for the sodium channel. The assays were run at 10 μM and recorded as percent displacement of BTX. As shown in Table 11, hermitamide B was the most active compound, followed by hermitamide A, and then lyngbic acid. The remote methoxy stereocenter does not appear to have much effect on the activity of these compounds.

TABLE 11

Percent Displacement of [$^3$H]-BTX at 10 Ó μM.

| | Compounds | % [$^3$H]-BTX Displacement At 10 μM |
|---|---|---|
| 1 | rac-lyngbic acid | 7.35 ± 2.88 (2) |
| 2 | (S)-lyngbic acid | 7.77 ± 2.20 (2) |
| 3 | (R)-lyngbic acid | 11.91 ± 0.16 (2) |
| 4 | rac-hermitamide A | 15.71 ± 0.14 (2) |
| 5 | (S)-hermitamide A | 15.89 ± 3.06 (2) |
| 6 | (R)-hermitamide A | 13.79 ± 1.28 (2) |
| 7 | rac-hermitamide B | 36.05 ± 0.77 (2) |
| 8 | (S)-hermitamide B | 29.02 ± 0.29 (2) |
| 9 | (R)-hermitamide B | 20.31 ± 5.82 (2) |
| 10 | phenytoin | 19.78 ± 1.21 (2) |

Values represent percentage block (%) ± S.E.M.
Values in brackets ( ) represents n numbers The ability of the hermitamides to displace [$^3$H]BTX indicates that these lipopeptides bind to the sodium channel at site 2 of the sodium channel, or at site 9 which overlaps with site 2. However, binding to either site does not necessary mean that these compounds can block sodium channel current. To test whether these compounds were functionally active as sodium channel blockers, the effects of the hermitamides were tested on human embryonic kidney cells (HEK) cells stably expressing human $Na_v1.2$ using the two-microelectrode voltage clamp technique.

As shown in Table 12, the hermitamides indeed act as sodium channel blockers. Hermitamide A blocks ~50% sodium channel current at 1 μM. Hermitamide B is a more potent blocker of sodium channel current, eliciting ~80% block at 1 μM. Apparently, the aromatic region of these compounds are important for activity, with the indole group of hermitamide B being advantageous over the simple phenyl ring of hermitamide A. Interestingly, the remote methoxy stereocenter does not appear to have much influence on the ability of these compounds to inhibit channel current. A similar trend is also seen in the electrophysiology data Table 12.

TABLE 12

Patch-clamp experiments

| Compound | 100 μM | 10 μM | 1 μM | 100 nM |
|---|---|---|---|---|
| rac-lyngbic acid | 55.6 ± 5.9 (4) | | | |
| (S)-lyngbic acid | | 44.4 ± 0.3 (4) | | |
| (R)-lyngbic acid | | | 52.5 ± 3.9 (4) | 11.9 ± 1.0 (4) |
| rac-hermitamide A | | 90.2 ± 2.5 (3) | 49.7 ± 3.8 (4) | |
| (S)-hermitamide A | | 94.4 ± 1.3 (4) | Need to test | |
| (R)-hermitamide A | | | 58.7 ± 1.3 (4) | |
| rac-hermitamide B | | 100 (1) | 88.4 ± 2.9 (40 | 24.3 ± 2.9 (4) |
| (S)-hermitamide B | | 100 (3) | 80 | |
| (R)-hermitamide B | | | 93.6 (1) | 28.8 ± 3.0 (4) |

Values represent percentage block (%) ± SE.M
Values in brackets( ) represent n numbers.

(S)-Hermitamide B was shown to displace [$^3$H]BTX, which indicates that the drug binds to the open state of the sodium channel. The structure of the open channel of the human voltage-gated sodium channel was predicted by homology, and is the subject of another paper that is currently being prepared as a separate communication. (S)-Hermitamide B was docked into the homology model using the program FlexX incorporated in Sybyl 8.0. Comparison with a BTX binding model that was initially predicted with this homology model indicates that binding mode of hermitamide B differs from BTX at its interactions with the S6 helix residues. In order to provide consistent results, the docked position of hermitamide B was remodeled using a step-by-step manual docking methodology with restrained MD simulations followed by minimization. In the restrained MD simulations, the optimum van der Waals and H-bond distance constraints was set between the ligand and the pore forming residues.

The following residues were identified as important residues for the binding for hermitamide B to the sodium channel: F1283, F1579, L1582, V1583, Y1586 in IVS6; T1279, L1280 in IIIS6; L788, F791, L792, in IIS6; I433, N434, L437 in IS6; and selectivity filter residues D400, E755, K1237 in the domains of I-IV P-loops. Mutation experiments and computational modeling studies further support that several of these residues participate in the BTX, LTG and LA binding (Ragsdale, D. et al *Science* 1994, 265, 1724-1728; Yarov-Yarovoy, V. et al. *J. Biol. Chem.* 2001, 276, 20-27; Yarov-Yarovoy, V et al. *J. Biol. Chem.* 2002, 277, 35393-35401). As shown in FIG. 13, binding is driven mainly by a hydrophobic interaction with residue K1237, and H-bonds between the amide group of hermitamide B with N434 and Y1586. Strong hydrophobic contacts were also predicted between hermitamide B and F1283, F1579, L1582, V1583, Y1586 L1280, L788, F791, L792, I433, and L437. The affinity of hermitamide B for the sodium channel over hermitamide A can be due to putative stacking interaction of the indole moiety with F791, and favorable van der Waals contact with L437 and L788. In addition, the predicted model shows no interactions between the sodium channel and the methoxy group. This is in agreement with biological evaluations showing that the stereochemistry of the methoxy group did not significantly contribute to the activity of the compounds.

As shown in the molecular model, no interactions were predicted between the sodium channel and the methoxy group. This is in agreement with the biological evaluations showing that the stereochemistry of the methoxy group did not contribute to the activity of the compounds. Two putative hydrogen bonds are shown between the carbonyl of the amide with the phenolic group of the a Tyr residue and the proton of the amide nitrogen with the amide side chain of an Asn group.

b) Conclusion

For the first time it has been demonstrated that the hermitamides are inhibitors of the human voltage-gated sodium channel. The hypothesis that these compounds would be ligands for the sodium channel was derived from a common pharmacophore that the hermitamides share with other known sodium channel blockers. The pharmacophore contains an aromatic region that is connected to a lipophilic chain via a carbonyl moiety. The results show that these compounds are more potent at displacing [$^3$H]BTX from the sodium channel than the clinical agent phenyloin. And, the hermitamides block sodium channel current more effectively than the jamaicamides, a related set of natural products that have a much more complicated structure. Further investigations utilizing this pharmacophore are underway for the development of novel sodium channel blockers.

c) Materials and Methods (1) Modeling of the Sodium Channel with Hermitamide B

Complete description of the Na channel prediction will be reported in a separate communication. Initial docking studies between the ligand and the sodium channel were carried out using the program FlexX. After consistent manual intervention, a final model was arrived. The structure of the $Na_v$-hermitamide B complex was then refined by molecular dynamics simulation using the Amber 9 program suite (Case, D. et al. (2006). AMBER 9, University of California, San Francisco.) with the PARM98 force-field parameter. The charge and force field parameters of hermitamide B was obtained using the most recent Antechamber module in the Amber 9 program, where hermitamide B was minimized at the MP2/6-31G* level. The SHAKE algorithm (Hanson, R. et al. J. Med. Chem. 2003, 46, 2865-2876) was used to keep all bonds involving hydrogen atoms rigid. Weak coupling temperature and pressure coupling algorithms (Berendsen, H. et al. J. Chem. Phys. 1984, 81, 3684-3690) were used to maintain constant temperature and pressure, respectively. Electrostatic interactions were calculated with the Ewald particle mesh method (Berendsen, H. et al. J. Chem. Phys. 1984, 81, 3684-3690.) with a dielectric constant at $1R_{ij}$ and a non-bonded cutoff of 12 Å for the real part of electrostatic interactions and for van der Waals' interactions. The total charge of the system was neutralized by addition of a chloride ion. The system was solvated in a 14 Å cubic box of water where the TIP3P model8 was used. 3000 steps of minimization of the system were performed in which the sodium channel was constrained by a force constant of 100 kcal/mol/Å$^2$. After minimization, a 10 ps simulation was used to gradually raise the temperature of the system to 298 K while the complex was constrained by a force constant of 20 kcal/mol/Å. Another 20 ps equilibration run was used where only the backbone atoms of the complex were constrained by a force constant of 5 kcal/mol/Å. Final production run of 100 ps was performed with no constraints. When applying constraints, the initial complex structure was used as a reference structure. The PME method10 was used and the time step was 5 fs, and a neighboring pairs list was updated in every 30 steps.

(2) [$^3$H]-BTX Assay

Briefly, rat forebrain membranes (10 mg tissue/well) were incubated with [$^3$H]-BTX (30-60 Ci/mmol). Reactions are carried out in 50 mM HEPES (pH 7.4) containing 130 mM choline chloride at 37° C. for 60 min. The reaction was terminated by rapid vacuum filtration of the reaction contents onto glass fiber filters. Radioactivity trapped onto the filters was determined and compared with control values to ascertain any interactions of the test compound with the Na$^+$ channel site 2 binding site. Aconitine (1 μM) was used as a positive control (Sigma Aldrich, Inc., St. Louis, Mo.).

(3) Sodium Channel Electrophysiology.

Human embryonic kidney cells (HEK) cells stably expressing human Na$_v$1.2 were a kind gift from Dr. H. A. Hartmann (University of Baltimore, Md., USA) and were grown in DMEM/F12 media (Invitrogen, Corp, CA, USA) supplemented with 10% fetal bovine serum, penicillin (100 U/ml), streptomycin (100 μg/ml) and G418 (500 μg/ml; Sigma, Mo., USA). Cells were grown in a humidified atmosphere of 5% $CO_2$ and 95% air at 37° C.

Sodium currents were recorded using the whole-cell configuration of the patch clamp recording technique with an Axopatch 200 amplifier (Axon Instruments, Foster City, Calif.). All voltage protocols were applied using pCLAMP 9 software (Axon, USA) and a Digidata 1322A (Axon, USA). Currents were amplified and low pass filtered (2 kHz) and sampled at 33 kHz. Borosilicate glass pipettes were pulled using a Brown-Flaming puller (model P87, Sutter Instruments Co, Novato, Calif.) and heat polished to produce electrode resistances of 0.5-1.5 MW when filled with the following electrode solution (in mM); CsCl 130, $MgCl_2$ 1, MgATP 5, BAPTA 10, HEPES 5 (pH adjusted to 7.4 with CsOH). Cells were plated on glass coverslips and superfused with solution containing the following composition; (in mM) NaCl 130, KCl 4, $CaCl_2$ 1, $MgCl_2$ 5, HEPES 5, and glucose 5 (pH adjusted to 7.4 with NaOH).

(S)-Hermitamide B was prepared as 100 mM stock solutions in DMSO and diluted to the desired concentration in perfusion solution. The maximum DMSO concentration used was 0.1% and had no effect on current amplitude. All experiments were performed at room temperature (20-22° C.). After establishing whole-cell, a minimum series resistance compensation of 75% was applied. Sodium currents were elicited by a depolarizing step from a holding potential of −100 mV to +10 mV for a duration of 25 ms at 15 s intervals. (S)-Hermitamide B was applied after a 3 min control period and continued until a steady state current amplitude was observed. All data represent percentage mean block±standard error of the mean (S.E.M.).

d) Experimentals (1) Racemic Synthesis:

(a) rac-Undec-1-en-4-ol (rac-3)

To a solution of 1.2 mL (7.8 mmol) of octanal in 30 mL of ether was added 15.6 mL of a 1.0 M solution of allylmagnesium bromide in ether. The reaction was allowed to stir at room temperature for 18 h and then quenched with saturated $NH_4Cl$. The product was extracted with ether (2×20 mL), dried over $Na_2SO_4$ and filtered. The solvent was removed under reduced pressure and the remaining residue was purified by flash chromatography to give 0.79 g (60%) of the allylic alcohol. $^1$H NMR (400 MHz, $CDCl_3$) δ 5.80-5.70 (m, 1H), 5.04-4.99 (m, 2H), 3.53 (m, 1H), 2.52 (br s, 1H), 2.20-2.05 (m, 2H), 1.381-34 (m, 2H), 1.25-1.15 (m, 10H), 0.80 (t, J=7.1 Hz, 3H); $^{13}$C NMR (400 MHz, $CDCl_3$) δ 133.6, 116.3, 70.6, 42.5, 37.5, 32.7, 30.6, 30.2, 26.7, 23.7, 15.2.

(2) (S) Enantiomer Synthesis:

(a) (S)-1-Undecen-4-ol (27)

To a flame dried flask under a $N_2$ atmosphere was added 5.0 g of 4 Å molecular sieves and 100 mL of anhydrous $CH_2Cl_2$, followed by 1.9 g (7.8 mmol) of $TiCl_2(i-PrO)_2$ and 2.2 g (7.8 mmol) of (R)-(+)-1,1'-bi-2-naphthol. The solution immediately turned red and was stirred at room temperature for 2 h. To this solution was added 17.9 mL (58.3 mmol) of allyltributyltin. The reaction was cooled to −20° C. and 5.0 g (39.0 mmol) of octanal was added. The solution was allowed to stir for 48 h at −20° C. The solution was filtered through a plug of Celite and the solvent was removed under reduced pressure. The remaining residue was purified by flash chromatography eluting with 1:9 EtOAc-hexanes to give 2.5 g (38%) of allylic alcohol 27. $^1$H NMR (400 MHz, $CDCl_3$) δ 5.85-5.75 (m, 1H), 5.11-5.07 (m, 2H), 3.60 (m, 1H), 2.29-2.22 (m, 1H), 2.14-2.07 (m, 1H), 1.91 (br s, 1H), 1.44-1.41 (m, 2H), 1.32-1.22 (m, 10H), 0.85 (t, J=6.5 Hz, 3H); $^{13}$C NMR (400 MHz, $CDCl_3$) δ 133.6, 116.8, 70.8, 42.6, 37.6, 32.8, 30.6, 30.3, 26.7, 23.8, 15.4. [α]$^{23}$ (c 1.04, $CHCl_3$)=−7.7; lit. [α]$^{25}$ (c 1.04, $CHCl_3$)=−6.5.

(b) (4S)-Methoxy-undec-1-ene (28)

To a solution of 2.5 g (14.7 mmol) of alcohol 27 in 50 mL of DMF was added 0.90 g (22.0 mmol) of NaH (60% dispersion in mineral oil) and 1.4 mL (22.0 mmol) of $CH_3I$. The reaction was refluxed for 10 h. The solution was cooled to room temperature, taken up in EtOAc, and washed with saturated LiCl (3×). The organic phase was dried over $Na_2SO_4$, filtered, and the solvent was removed under reduced pressure. The resulting residue was purified by flash chromatography eluting with 1:9 EtOAc-hexanes to give 2.5 g (92%) of the desired compound. $^1$H NMR (400 MHz, $CDCl_3$) δ 5.85-5.75 (m, 1H), 5.08-5.01 (m, 2H), 3.32 (s, 3H), 3.18 (quin, J=5.8 Hz, 1H), 2.24 (m, 2H), 1.46-1.40 (m, 2H), 1.30-1.20 (m, 10H), 0.86 (t, J=6.9 Hz, 3H); $^{13}$C NMR (400 MHz, $CDCl_3$) δ 133.6, 115.7, 80.4, 56.9, 38.6, 34.3, 32.8, 30.8, 30.3, 26.4, 23.8, 15.4. [α]$^{22}$ (c 2.00, $CHCl_3$)=−4.0.

(c) Methyl (4E,7S)-Methoxy-tetradecenoate (31)

To a biphasic solution of 2.5 g (13.5 mmol) of alkene 28 in 30 mL of 1:1 $Et_2O$—$H_2O$ was added 2.2 mL (5 mol %) of $O_5O_4$ (2.5 wt % solution in t-BuOH). At room temperature, 6.4 g (29.7 mmol) of $NaIO_4$ was added dropwise over 30 min. The solution was stirred for an additional 18 h. The reaction was taken up in EtOAc and the aqueous phase was removed. The organic phase was dried over $Na_2SO_4$, filtered, and the solvent was removed under reduced pressure to give (3S)-methoxydecanal (29) as a yellow oil. No further purification was performed.

To a solution of aldehyde 29 in 50 mL of THF was added 27 mL of a 1.0 M solution of vinylmagnesium bromide. The reaction was stirred at room temperature for 3 h and then quenched with saturated $NH_4Cl$. The product was extracted with EtOAc (3×30 mL), dried over $Na_2SO_4$, filtered, and the solvent was removed under reduced pressure. The resulting residue was purified by flash chromatography eluting with 1:5 EtOAc-hexanes to give 1.5 g (51% over two steps) of 3-hydroxy-5-methoxydodec-1-ene (30) as a mixture of diastereomers.

To vinyl alcohol 30 in 6 mL of trimethyl orthoacetate was added one drop of propionic acid. The flask was fitted with a distillation head, the solution was heated to 100° C. for 1.5 hours, and the resulting evolution of MeOH was removed by distillation. The solvent was then removed under reduced pressure and the remaining residue was purified by flash chromatography eluting with 1:5 EtOAc-hexanes to give 1.2 g (63%) of methyl ester 31. $^1$H NMR (400 MHz, CDCl$_3$) δ 5.47 (m, 2H), 3.66 (s, 3H), 3.32 (s, 3H), 3.12 (quin, J=5.8 Hz, 1H), 2.24-2.16 (m, 4H), 2.18 (m, 2H), 1.30-1.23 (m, 2H), 1.19-1.09 (m, 10H), 0.87 (t, J=6.9 Hz, 3H); $^{13}$C NMR (400 MHz, CDCl$_3$) δ 172.5, 130.2, 127.5, 81.6, 58.0, 53.1, 38.2, 36.0, 35.3, 33.8, 31.8, 31.3, 30.0, 27.4, 24.9, 16.5.

(d) (7S,4E)-Methoxytetradecenoic Acid (32)

To a solution of 1.1 g (4.1 mmol) of methyl ester 31 in 20 mL of 1:1 THF—H$_2$O was added 0.49 g (20.3 mmol) of LiOH. The solution was allowed to stir at room temperature for 18 h. The solution was then acidified with 1 N HCl and the product was extracted with EtOAc (2×30 mL). The organic phase was dried over Na$_2$SO$_4$, filtered, and the solvent was removed under reduced pressure. The remaining residue was purified by flash chromatography eluting with 1:1. EtOAc-hexanes to give 0.43 g (41%) of carboxylic acid 32. $^1$H NMR (400 MHz, CDCl$_3$) δ 11.04 (br s, 1H), 5.44 (m, 2H), 3.29 (s, 3H), 3.12 (quin, J=5.8 Hz, 1H), 2.39-2.29 (m, 4H), 2.15 (m, 2H), 1.42-1.37 (m, 2H), 1.28-1.19 (m, 10H), 0.83 (t, J=6.9 Hz, 3H); $^{13}$C NMR (400 MHz, CDCl$_3$) δ 176.5, 129.0, 126.4, 80.7, 56.7, 37.1, 34.8, 34.1, 32.7, 30.7, 30.2, 28.7, 26.3, 23.8, 15.4. Anal. (C$_{15}$H$_{28}$O$_3$) C, H, N. C: calcd, 70.27; found, 69.98. H: calcd, 11.01; found, 11.12. [α]$^{23}$ (c 1.91, CHCl$_3$)=−4.2.

(e) Phenethyl (7S,4E)-methoxytetradecenamide (33)

To a solution of 0.18 g (0.68 mmol) of carboxylic acid 32 in 10 mL of CH$_2$Cl$_2$ was added 0.12 mL (0.75 mmol) of diisopropylcarbodiimide and 0.10 g (0.75 mmol) of 1-hydroxybenzotriazole. After stirring at room temperature for 10 min, 0.090 mL (0.68 mmol) of phenethylamine was added. The reaction was stirred at room temperature for 15 h, during which a white precipitate formed. The solvent was then removed under reduced pressure and the residue was taken up in EtOAc. The solution was washed with 1 N HCl (3×20 mL) followed by saturated NaHCO$_3$ (1×20 mL). The organic phase was dried over Na$_2$SO$_4$, filtered, and the solvent was removed under reduced pressure. The remaining residue was purified by flash chromatography eluting with 1:3 EtOAc-hexanes to give 0.19 g (77%) of (S)-hermitamide A. $^1$H NMR (400 MHz, CDCl$_3$) δ 7.27-7.13 (m, 5H), 5.82 (br s, 1H), 5.40 (m, 2H), 3.45 (q, J=6.9 Hz, 2H), 3.26 (s, 3H), 3.09 (quin, J=5.7 Hz, 1H), 2.76 (t, J=7.1 Hz, 2H), 2.29-2.25 (m, 2H), 2.17-2.11 (m, 4H), 1.40-1.33 (m, 2H), 1.30-1.22 (m, 10H), 0.83 (t, J=6.8 Hz, 3H); $^{13}$C NMR (400 MHz, CDCl$_3$) δ 170.2, 137.4, 129.6, 127.4, 127.3, 126.2, 125.2, 80.4, 56.7, 41.3, 37.2, 37.1, 36.5, 34.1, 32.7, 30.7, 30.2, 29.6, 26.3, 23.7, 15.4. [α]$^{23}$ (c 0.45, CHCl$_3$)=−8.9; lit. [c]$^{26}$ (c 0.45, CHCl$_3$)=−9.3. (*J. Nat. Prod* 2000, 63, 952-955).

(f) 2-(1H-indol-3-yl)-ethyl (7S,4E)-Methoxytetradecenamide (34)

To a solution of 0.18 g (0.68 mmol) of carboxylic acid 32 in 10 mL of CH$_2$Cl$_2$ was added 0.12 mL (0.75 mmol) of diisopropylcarbodiimide and 0.10 g (0.75 mmol) of 1-hydroxybenzotriazole. After stirring at room temperature for 10 min, 0.11 g (0.68 mmol) of tryptamine was added. The reaction was stirred at room temperature for 15 h. The solvent was then removed under reduced pressure and the residue was taken up in EtOAc. The solution was washed with 1 N HCl (5×20 mL) followed by saturated NaHCO$_3$ (1×20 mL). The organic phase was dried over Na$_2$SO$_4$, filtered, and the solvent was removed under reduced pressure. The resulting residue was purified by flash chromatography eluting with 1:3 EtOAc-hexanes to give 0.24 g (88%) of (S)-Hermitamide B. $^1$H NMR (400 MHz, CDCl$_3$) δ 8.89 (br s, 1H), 7.58 (d, J=7.8 Hz, 1H), 7.35 (d, J=8.1 Hz, 1H), 7.19 (t, J=8.1 Hz, 1H), 7.10 (t, J=7.9 Hz, 1H), 6.97 (s, 1H), 5.80 (br s, 1H), 5.44 (m, 2H), 3.57 (q, J'=6.6 Hz, 2H), 3.32 (s, 3H), 3.15 (quin, J=5.7 Hz, 1H), 2.95 (t, J=6.8 Hz, 2H), 2.33-2.28 (m, 2H), 2.18-2.14 (m, 4H), 1.45-1.41 (m, 2H), 1.32-1.22 (m, 10H), 0.89 (t, J=6.8 Hz, 3H); $^{13}$C NMR (400 MHz, CDCl$_3$) δ 170.4, 135.0, 129.5, 126.2, 126.1, 121.1, 120.8, 118.1, 117.5, 111.6, 110.5, 80.5, 56.7, 40.5, 37.2, 37.1, 34.1, 32.7, 30.7, 30.2, 29.6, 26.3, 26.2, 23.7, 15.4. Anal. (C$_{25}$H$_{38}$N$_2$O$_2$) C, H, N. C: calcd, 75.33; found, 74.86. H: calcd, 9.61; found, 9.67. N: calcd, 7.03; found, 6.92. [α]$^{24}$ (c 2.00, CHCl$_3$)=−2.

(3) (R) Enantiomer:

(a) (R)-1-Undecen-4-ol (27)

Yield=33%. $^1$H NMR (400 MHz, CDCl$_3$) δ 5.81-5.70 (m, 1H), 5.05-5.00 (m, 2H), 3.55 (m, 1H), 2.54 (br s, 1H), 2.22-2.04 (m, 1H), 2.07 (m, 1H), 1.39-1.35 (m, 2H), 1.27-1.17 (m, 10H), 0.80 (t, J=6.9 Hz, 3H); $^{13}$C NMR (400 MHz, CDCl$_3$) δ 133.6, 116.4, 70.7, 42.5, 37.5, 32.7, 30.5, 30.2, 26.7, 23.7, 15.3. [α]$^{23}$ (1.04, CHCl$_3$)=+7.7, lit. [α]$^{25}$ (1.04, CHCl$_3$)=+6.5.

(b) (4S)-Methoxy-undec-1-ene (28)

Yield=80%. $^1$H NMR (400 MHz, CDCl$_3$) δ 5.71-5.61 (m, 1H), 4.93-4.86 (m, 2H), 3.17 (s, 3H), 3.02 (quin, J=5.8 Hz, 1H), 2.10 (m, 2H), 1.34-1.30 (m, 2H), 1.19-1.09 (m, 10H), 0.75 (t, J=6.9 Hz, 3H); $^{13}$C NMR (400 MHz, CDCl$_3$) δ 133.3, 115.3, 80.1, 56.4, 38.4, 34.1, 32.6, 30.6, 30.1, 26.1, 23.6, 15.1.

(c) Methyl (4E,7R)-Methoxy-tetradecenoate (31)

Yield=51%. $^1$H NMR (400 MHz, CDCl$_3$) δ 5.33 (m, 2H), 3.51 (s, 3H), 3.17 (s, 3H), 2.99 (quin, J=5.8 Hz, 1H), 2.25-2.18 (m, 4H), 2.04 (m, 2H), 1.30-1.26 (m, 2H), 1.18-1.09 (m, 10H), 0.74 (t, J=6.9 Hz, 3H); $^{13}$C NMR (400 MHz, CDCl$_3$) δ 173.0, 130.1, 127.3, 80.4, 56.1, 51.0, 36.0, 33.6, 33.0, 31.5, 31.8, 29.4, 29.0, 27.6, 24.9, 22.3, 13.7.

(d) (7R,4E)-Methoxytetradecenoic Acid (32)

Yield=65%. $^1$H NMR (400 MHz, CDCl$_3$) δ 10.23 (br s, 1H), 5.48 (m, 2H), 3.32 (s, 3H), 3.15 (quin, J=5.8 Hz, 1H), 2.44-2.31 (m, 4H), 2.18 (m, 2H), 1.44-1.38 (m, 2H), 1.31-1.20 (m, 10H), 0.87 (t, J=6.8 Hz, 3H); $^{13}$C NMR (400 MHz, CDCl$_3$) δ 176.8 128.9, 126.6, 80.7, 56.9, 37.2, 34.9, 34.3, 32.8, 30.8, 30.3, 28.7, 26.4, 23.9, 15.5. Anal. (C$_{15}$H$_{28}$O$_3$) C, H, N. C: calcd, 70.27; found, 70.13. H: calcd, 11.01; found, 11.21. [α]$^{23}$ (c 1.91, CHCl$_3$)=+4.2.

(e) Phenethyl (7R,4E)-methoxytetradecenamide (33)

Yield=74% for (R)-hermitamide A. $^1$H NMR (400 MHz, CDCl$_3$) δ 7.26-7.12 (m, 5H), 5.93 (br s, 1H), 5.40 (m, 2H), 3.42 (q, J=6.9 Hz, 2H), 3.25 (s, 3H), 3.09 (quin, J=5.8 Hz, 1H), 2.75 (t, J=7.1 Hz, 2H), 2.28-2.24 (m, 2H), 2.16-2.10 (m, 4H), 1.43-1.35 (m, 2H), 1.28-1.18 (m, 10H), 0.83 (t, J=6.8 Hz, 3H); $^{13}$C NMR (400 MHz, CDCl$_3$) δ 170.2, 137.4, 129.5, 127.4, 127.2, 126.1, 125.1, 80.4, 56.7, 41.2, 37.1, 37.0, 36.4, 34.1, 32.6, 30.6, 30.2, 29.6, 26.3, 23.7, 15.3. [α]$^{23}$ (c 0.45, CHCl$_3$)=+8.9.

(f) 2-(1H-indol-3-yl)-ethyl (7R,4E)-Methoxytetradecenamide (34)

Yield=96% for (R)-hermitamide B. $^1$H NMR (400 MHz, CDCl$_3$) 8.97 (br s, 1H), 7.58 (d, J=7.9 Hz, 1H), 7.35 (d, J=8.1 Hz, 1H), 7.18 (t, J=7.9 Hz, 1H), 7.10 (t, J=7.7 Hz, 1H), 6.97 (s, 1H), 5.84 (br s, 1H), 5.44 (m, 2H), 3.57 (q, J=6.6 Hz, 2H), 3.33 (s, 3H), 3.16 (quin, J=5.7 Hz, 1H), 2.95 (t, J=6.8 Hz, 2H), 2.33-2.29 (m, 2H), 2.18-2.14 (m, 4H), 1.45-1.39 (m, 2H), 1.37-1.29 (m, 10H), 0.90 (t, J=6.8 Hz, 3H); $^{13}$C NMR (400 MHz, CDCl$_3$) δ 170.4, 135.0, 129.5, 126.1, 126.0, 121.1, 120.7, 118.1, 117.5, 111.6, 110.5, 80.5, 56.7, 40.5, 37.2, 37.1, 34.1, 32.7, 30.6, 30.2, 29.6, 26.3, 26.2, 23.7, 15.4. Anal. (C$_{25}$H$_{38}$N$_2$O$_2$) C, H, N. C: calcd, 75.33; found, 74.80. H: calcd, 9.61; found, 9.65. N: calcd, 7.03; found, 7.02. [α]$^{24}$ (c 2.00, CHCl$_3$)=+2.0.

4. Example 4

Asymmetric Synthesis and Evaluation of Enantiomers of 2-(3-chloro-phenyl)-2-hydroxy-nonanoic Acid Amide for Inhibitory Effects on Voltage Gated Sodium Channels and Human Prostate Cancer Cell Proliferation Voltage-gated sodium channels are known to be expressed in neurons and other excitable cells. Recently, voltage-gated sodium channels have been found to be expressed in human prostate cancer cells. α-Hydroxy-α-phenyl amides are a new class of small molecules that have demonstrated potent inhibition of voltage-gated sodium channels. The hydroxyamide motif, an isostere of a hydantoin ring, provides an active scaffold from which several potent racemic sodium channel blockers have been derived. With little known about chiral preferences, the development of chiral syntheses to obtain each pure enantiomer for evaluation as sodium channel blockers is important. Using Seebach and Frater's chiral template, cyclocondensation of (R)-3-chloromandelic acid with pivaldehyde furnished both the cis- and trans-2,5-disubstituted dioxolanones. Using this chiral template, both enantiomers of 2-(3-chloro-phenyl)-2-hydroxy-nonanoic acid amide were synthesized, and evaluated their ability to functionally inhibit both hNa$_v$1.5 and hNa$_v$1.7. Finally, these compounds were evaluated for antiproliferative effects against human prostate cancer cells that contain hNav1.5 and hNav1.7 isoforms The role of the Na$_v$ channels in prostate cancer was studied. It was previously shown that sodium channel blockers have marked effects on prostate cancer cell proliferation (Anderson, J et al. *Mol. Cancer Ther.* 2003, 2, 1149-1154). It is shown herein that several isoforms of the channel are involved with prostate cancer cell proliferation. CWR22rv-1 whole cell lysate extracts were evaluated for expression of hNa$_v$1.5 and hNa$_v$1.7 by Western blot analysis. Both α-subunits were detected at 260 kDa with each antibody (see FIG. 17). Specific bands were also detected at lower molecular weights and are likely degradation products. Pretreating with their respective specific oligomer epitope control antigen before antibody addition eliminated the signal of both the 260 kDa band as well as the lower molecular weight bands.

With the identification of both sodium channels in human prostate cancer cell line CWR22rv-1, both the (±)-1, (R)-(−)-1, and (S)-(+)-1 were evaluated for their effects on prostate cancer cell growth. Compound (R)-(−)-1 showed the greatest effect on CWR proliferation (FIG. 3). A concentration of 25 µM induced approximately 25% cell death after 24 h, while compounds (±)-1 and (S)-(+)-1 showed marginal effects after 24 h. After 72 h, compound (R)-(−)-1 induced cell death in 60% of the human prostate cancer cells, while compounds (±)-1 and (S)-(+)-1 induced 25% and 40% cell death, respectively.

Intraperitoneally (ip) 10 mg/kg of racemic (±)-1 and each enantiomer was administered in mice bearing PC3 xenografts (FIG. 16). This dose was administered qd every other day for 24 days and effects on reducing the tumor volume were measured. A statistical reduction was observed in the prostate tumor volume after day 15. Treatment with the racemic and both enantiomers resulted in a 62% decrease in tumor volume at a 10 mg/kg dose and a qd dosing schedule. This demonstrates for the first time that Na$_v$ blockers (such as (±)-1 or its enantiomers) can significantly reduce the size of prostate tumors in vivo and tumors that are androgen insensitive.

a) Discussion and Conclusions

The relationship between voltage-gated ion channels and cancer represents an exciting new area of investigation, and the synthesis of active chiral inhibitors for selected isoforms can provide potential therapeutic opportunities. Using the Seebach and Frater chiral template, both enantiomers of 2-(3-chlorophenyl)-2-hydroxynonanamide can be synthesized. The biological evaluation of compounds (±)-1, (R)-(−)-1, and (S)-(+)-1, shows a preference for the R enantiomer over the S enantiomer in CWR22rv-1 cells. The model of (R)-(−)-1 docked in the sodium channel shows a critical hydrogen bond interaction of the amide group with the T1279 residue in the surrounding protein. This interaction is not present with (S)-(+)-1, and is a potential reason for its reduced sodium channel activity.

Xenograft studies showed that treatment with Na$_v$ blockers (such as (±)-1 or its enantiomers) can significantly reduce the size of prostate tumors in vivo including tumors that are androgen insensitive. Since 80-90% of prostate cancer patients develop androgen-independent tumors 12-33 months after androgen ablation, these findings can have significant clinical potential for this phenotype (Hellerstedt, B. A.; et al. *CA Cancer J Clin.* 2002, 52, 154-179).

b) Experimental Section (1) General

Chemicals were purchased from Aldrich Chemical Company, and were used without any further purification. Dry solvents were dried over 4 Å molecular sieves prior to use. Air-sensitive reactions were carried out in oven-dried glassware under an N$_2$ atmosphere. Flash column chromatography separations were done on a Biotage SP1 systems monitoring at 254 nm. All NMR spectra were recorded on a Varian 400 spectrometer, operating at 400 MHz for $^1$H and 100 MHz for $^{13}$C NMR. Optical rotations were taken on a Bellingham & Stanley ADP220 polarimeter using a 25 mm cell. Chiral HPLC analysis was carried out on a Shimadzu LCMS-2010EV using a ChiralPak AS column monitoring at 254 nm.

(2) Computational Chemistry.

Multiple sequence alignment of the S6 transmembrane residues from domains I, III, and IV was carried out using PSI-BLAST and CLUSTALW (Thompson, J. et al. *Nucleic Acids Research.* 1994, 22, 4673-4680). Homology modeling of the S5, the P-loops, and S6 from all four domains was accomplished using open MthK channel X-ray structure (PDB: 1lnq) as a template. Non-homologous regions in the longer P-loops of domains I and III, which correspond to putative glycosylation sites, were deleted. The P-loops and the N and C termini were modeled based on homologous segments of the KcsA channel structure (PDB: 1bl8). Sodium channel sequences were aligned versus the MthK channel using ClustalW, and the structure was modeled employing the program Modeler 8.1. To avoid close contacts of the side chain atoms with each other, different rotamer states of the residues were considered to find the state with minimal clashes but favorable interactions. Local minimization of side chain atoms was also performed. Docking studies between the ligand and the sodium channel were carried out using the program AUTODOCK 4.0 ((Morris, G. et al. *J. Computational Chemistry.* 1998, 19: 1639-1662) with all the parameters set to default. Molecular dynamics simulations were carried out using AMBER 8.0 (Case, D. et al. 2004 AMBER 8. San Francisco: University of California) with default parameters.

(a) (2R,5R)-2-(tert-Butyl)-5-(3-chlorophenyl)-1,3-dioxolan-4-one.

To a suspension of R-(−)-3-chloromandelic acid (6.0 g, 32.15 mmol) in dry pentane was added pivaldehyde (4.2 mL, 38.59 mmol), followed by the addition of triflic acid (0.11 mL, 1.29 mmol) at r.t. A Dean-Stark trap was then added to the flask, and the reaction mixture warmed to 36° C. and allowed to reflux for 6 hrs. The mixture was cooled to r.t. and 8% wt. aq. NaHCO$_3$ was added and the reaction was concentrated to remove pentane. The slurry was filtered and dried to the product as a 5:1 mixture of diastereomers. The diastereomers were separated by flash column chromatography eluting with 1:5 EtOAc/hexanes to give 4.26 g of pure product as a fluffy white solid. mp 84-86° C.; $^1$H NMR (400 MHz, CDCl$_3$, δ): 1.06 (s, 9H), 5.19 (s, 1H), 5.30 (d, J=1 Hz, 1H), 7.33-7.34 (m, 3H), 7.44 (m, 1H). $^{13}$C NMR (100 MHz, CDCl$_3$, δ): 20.1, 34.2, 91.1, 121.6, 127.3, 128.1, 134.2, 136.1, 173.5. $[\alpha]^{25}_D$ −72.0° (c 1.00, CHCl$_3$).

(b) S-(+)-3-chloromandelic Acid.

To a round bottom flask was added 50 mL of MeOH and 3 drops of AcCl, 1.61 g (8.60 mmol) of (R)-3-chloromandelic acid was then added in one portion. The mixture was allowed to stir at rt. overnight. The reaction was then poured in to 150 mL of H$_2$O containing 10 mL of saturated NaHCO$_3$ and extracted with CH$_2$Cl$_2$ (3×30 mL). The combined organic fractions were washed with brine, dried (Na$_2$SO$_4$), filtered and concentrated to give 1.53 g (87%) of the product as a thick viscous oil which was sufficiently pure for the next step. $^1$H NMR (400 MHz, CDCl$_3$, δ): 3.73 (s, 3H), 3.78 (d, J=6 Hz, 1H), 5.13 (d, J=5 Hz, 1H), 7.26-7.28 (m, 3H), 7.40-7.41 (m, 1H). $^{13}$C NMR (100 MHz, CDCl$_3$, δ): 53.4, 72.4, 125.0, 127.0, 128.8, 130.1, 134.7, 140.3, 173.7. $[\alpha]^{23}_D$ −168° (c 1.00, CHCl$_3$).

To a stirred solution of 0.350 g (1.74 mmol) of (R)-3-chloromandelic acid methyl ester in dry THF was added 0.913 g (3.48 mmol) of PPh$_3$ and 0.582 g (3.48 mmol) of p-nitrobenzoic acid. The solution was cooled to 0° C. and 1.31 mL (3.48 mmol) of a 40% wt. solution of DEAD was slowly added. The reaction mixture was allowed to stir at rt. for 6 hrs. under N$_2$. THF was then removed in vacuo and the crude product partitioned between H$_2$O and EtOAc. The combined organic layers were washed with brine, dried (Na$_2$SO$_4$), filtered and concentrated. The residue was purified by flash column chromatography eluting with 1:19 EtOAc/hexanes then 1:9 EtOAc/hexanes to give 0.523 g (86%) of the product as a sticky yellow oil. $^1$H NMR (400 MHz, CDCl$_3$, δ): 3.74 (s, 3H), 6.14 (s, 1H), 7.34-7.36 (m, 2H), 7.42-7.45 (m, 1H), 7.53-7.54 (m, 1H), 8.25 (s, 4H). $^{13}$C NMR (100 MHz, CDCl$_3$, δ): 53.2, 74.8, 123.9, 126.1, 127.9, 130.0, 130.5, 131.3, 134.5, 135.1, 135.4, 151.1, 164.0, 168.5.

The prepared nitroester (4.58 g, 22.85 mmol) was added to 7.43 g (114.23 mmol) of NaN$_3$ and the mixture was heated for 1 hr. at 40° C. The solvent was then removed and the residue purified by flash column chromatography eluting with 1:5 EtOAc/hexanes to give 3.291 g (72%) of a white solid. $^1$H NMR (400 MHz, CDCl$_3$, δ): 3.53 (d, J=6 Hz, 1H), 3.76 (s, 3H), 5.13 (d, J=5 Hz, 1H), 7.28-7.30 (m, 3H), 7.40-7.41 (m, 1H). $^{13}$C NMR (100 MHz, CDCl$_3$, δ): 53.4, 72.3, 125.0, 126.9, 128.9, 130.1, 134.7, 140.3, 173.8.

To a 3.091 g (15.41 mmol) of (S)-3-chloromandelic acid methyl ester was added 100 mL of 5% NaOH. The reaction mixture was heated to 40° C. for one and then allowed to cool to rt. The reaction was then acidified with 1N and extracted with EtOAc (3×20 mL). The combined organic fractions were dried (Na$_2$SO$_4$), filtered and concentrated in vacuo. The solid residue was recrystallized from hot toluene to give 2.768 g (96%) of a white crystalline solid 5. $^1$H NMR (400 MHz, DMSO-d$_6$, δ): 5.05 (s, 1H), 7.32-7.36 (m, 3H). $^{13}$C NMR (100 MHz, DMSO-d$_6$, δ): 72.4, 126.0, 127.0, 128.2, 130.7, 133.5, 143.3, 174.2. $[\alpha]^{23}_D$ +123° (c 3.00, H$_2$O).

(c) (2R,5S)-2-(tert-Butyl)-5-(3-chlorophenyl)-1,3-dioxolan-4-one mp 40-42° C.; $^1$H NMR (400 MHz, CDCl$_3$, δ): 1.06 (s, 9H), 5.24 (s, 1H), 5.30 (d, J=1 Hz, 1H), 7.33-7.34 (m, 3H), 7.44 (m, 1H). $^{13}$C NMR (100 MHz, CDCl$_3$, δ): 21.1, 35.2, 91.6, 122.9, 127.3, 128.1, 133.5, 137.1, 173.5. $[\alpha]^{25}_D$ −4.0° (c 1.00, CHCl$_3$).

(d) (2R,5R)-2-(tert-Butyl)-5-(3-chlorophenyl)-5-heptyl-1,3-dioxolan-4-one

To a flame dried round bottom flask equipped with a magnetic stir bar was added diisopropylamine in THF under N$_2$. The flask was cooled to −78° C. and ° BuLi was added in one portion. The cooling bath was removed and replaced with an ice-water bath. Meanwhile, (2R,5R)-2-(tert-Butyl)-5-(3-chlorophenyl)-1,3-dioxolan-4-one, heptyl iodide, and HMPA were dissolved in THF and place in a separate flame dried round bottom under an N$_2$ atmosphere. The flask was cooled to −78° C. and the previously prepared LDA was added dropwise over 15 minutes. The reaction mixture was maintained at a constant temperature of −78° C. for 3 hrs at which time it was quenched with saturated NH$_4$Cl solution. The product was then extracted with Et$_2$O, the organic layers combined, dried (Na$_2$SO$_4$), filtered and concentrated in vacuo. The crude 96:4 mixture of diastereomers was separated by flash column chromatography carefully eluting with 1% Et$_2$O in hexanes. $^1$H NMR (400 MHz, CDCl$_3$, δ): 0.84 (t, J=7 Hz, 3H), 0.96 (s, 9H), 1.16-1.35 (m, 10H), 1.88-2.06 (m, 2H), 5.35 (s, 1H), 7.26-7.30 (m, 2H), 7.50-7.54 (m, 1H), 7.62-7.63 (m, 1H). $^{13}$C NMR (100 MHz, CDCl$_3$, δ): 14.3, 22.8, 23.7, 23.8, 29.2, 29.5, 31.9, 35.2, 38.9, 82.3, 109.1, 123.4, 125.4, 128.3, 129.7, 134.5, 140.5, 173.5. $[\alpha]^{22.4}_D$ −40° (c 1.00, CH$_2$Cl$_2$).

(e) R-(−)-2-(3-Chlorophenyl)-2-hydroxy-nonanoic acid amide ((R)-(−)-1)

Concentrated NH$_4$OH was added to (2R,5R)-2-(tert-Butyl)-5-(3-chlorophenyl)-5-heptyl-1,3-dioxolan-4-one in EtOH, and the mixture was stirred for 2 hrs. monitoring by TLC (1:1 hexanes/EtOAc). The reaction mixture was then poured into water and extracted with CH$_2$Cl$_2$ (4×10 mL). The combined organic layers were then washed with brine, dried (Na$_2$SO$_4$), filtered and concentrated. The residue was purified by flash column chromatography eluting with 1:1 hexanes/EtOAc. mp 78-79° C.; $^1$H NMR (400 MHz, CDCl$_3$, δ): 0.85 (t, J=7 Hz, 3H), 1.23-1.29 (m, 10H), 1.94-2.01 (m, 1H), 2.16-2.22 (m, 1H), 3.19 (s, 1H), 5.65 (bs, 1H), 6.47 (bs, 1H), 7.23-7.28 (m, 2H), 7.44-7.47 (m, 1H), 7.58-7.59 (m, 1H). $^{13}$C NMR (100 MHz, CDCl$_3$, δ): 14.3, 22.8, 23.5, 29.3, 29.8, 32.0, 39.6, 78.8, 123.9, 125.9, 128.1, 129.9, 134.6, 144.6, 176.3. $[\alpha]^{23.1}_D$ −24° (c 0.50, CHCl$_3$).

(f) (2S,5S)-2-(tert-Butyl)-5-(3-chlorophenyl)-5-heptyl-1,3-dioxolan-4-one

Prepared in the same manner as (2R,5R)-2-(tert-Butyl)-5-(3-chlorophenyl)-5-heptyl-1,3-dioxolan-4-one using (2S,5R)-2-(tert-Butyl)-5-(3-chlorophenyl)-1,3-dioxolan-4-one. $^1$H NMR (400 MHz, CDCl$_3$, δ): 0.84 (t, J=7 Hz, 3H), 0.96 (s, 9H), 1.16-1.35 (m, 10H), 1.88-2.06 (m, 2H), 5.35 (s, 1H), 7.26-7.30 (m, 2H), 7.50-7.54 (m, 1H), 7.62-7.63 (m, 1H). $^{13}$C NMR (100 MHz, CDCl$_3$, δ): 14.3, 22.8, 23.7, 23.8, 29.2, 29.5, 31.9, 35.2, 38.9, 82.3, 109.1, 123.4, 125.4, 128.3, 129.7, 134.5, 140.5, 173.5.

(g) S-(+)-2-(3-Chlorophenyl)-2-hydroxy-nonanoic acid amide ((S)-(+)-1)

Prepared in the same manner as (−)-2-(3-Chlorophenyl)-2-hydroxy-nonanoic acid amide using (2S,5S)-2-(tert-Butyl)-5-(3-chlorophenyl)-5-heptyl-1,3-dioxolan-4-one. mp 78-79° C.; $^1$H NMR (400 MHz, CDCl$_3$, δ): 0.85 (t, J=7 Hz, 3H), 1.23-1.29 (m, 10H), 1.94-2.01 (m, 1H), 2.16-2.22 (m, 1H), 3.19 (s, 1H), 5.65 (bs, 1H), 6.47 (bs, 1H), 7.23-7.28 (m, 2H), 7.44-7.47 (m, 1H), 7.58-7.59 (m, 1H). $^{13}$C NMR (100 MHz, CDCl$_3$, δ): 14.3, 22.8, 23.5, 29.3, 29.8, 32.0, 39.6, 78.8, 123.9, 125.9, 128.1, 129.9, 134.6, 144.6, 176.3. $[\alpha]^{23.1}_D$ +24° (c 0.50, CHCl$_3$).

(3) X-Ray Crystallography.

Both (ICM-2-136-1) (S)-2-(3-Chloro-phenyl)-2-hydroxy-nonanoic acid amide and (ICM-1-136-2) (R)-2-(3-Chloro-phenyl)-2-hydroxy-nonanoic acid amide were crystallized from 70% ethanol using slow evaporation method at room temperature. The diffraction data were collected at 100K using a Rigaku R-axis Rapid diffractometer, equipped with a Mo Kα radiation source (60 kV, 40 mA). The radiation was monochromatized with graphite monochromator. HKL-2000 (Otwinowski, Z. et al. *Macromolecular Crystallography, part A*, C. W. Carter, Jr. & R. M. Sweet, Eds.; Academic Press.: New York, pp. 307-326, 1997; Otwinowski, Z.; et al. *Acta Cryst.* 2003, A59, 228-234) was used for control of the data collection as well as for data reduction. The structure was solved and refined by the HKL-3000SM system (Minor, W.; et al. *Acta Cryst.* 2006, D62, 859-866) which is integrated with SHELXS, SHELXL (Sheldrick, G. M. A short history of SHELX. *Acta Cryst.* 2008, A64, 112-122) and O (Jones, T. et al. *Acta Cryst.* 1991, A47, 110-119). Absolute configurations of both compounds were determined using anomalous dispersion. Details of data collection, processing and refinement (See FIG. 18). Interestingly both compounds crystallized with two molecules in asymmetric unit (See FIG. 18). The molecules of the (+)-2-(3-Chloro-phenyl)-2-hydroxy-nonanoic acid amide forming crystals have two different conformations of the aliphatic chains.

c) Biological Methods (1) Cell Culture for Western Blots

The CWR22rv-1 cell line was obtained from the American Tissue Culture Collection (Manassas, Va.). All cell lines were maintained in RPMI-1640 with L-glutamine (CellGro, Lawrence, Kans.) supplemented with 5% heat-inactivated fetal bovine serum (Sigma, St. Louis, Mo.). LNCaP media was additionally supplemented with 0.1 nM DHT (Sigma, St. Louis, Mo.). Cells were seeded into Corning T-75 flasks (Fisher, Pittsburgh, Pa.) and incubated at 37° C., 5% CO$_2$, and 100% relative humidity. Cultures were subcultured once per week via trypsinization.

Western protocols were adapted from Collins et. al. (*Biochem J.* 2000, 345, 673-80). Cells were trypsin-harvested, washed and flash frozen prior to lysis. Lysates were prepared in modified radioimmunoprecipitation (RIPA) buffer (Sigma, St. Louis, Mo.) plus 50 mM Tris-HCl, 5 mM EDTA, 150 mM NaCl, 30 mM NaPP$_i$, 50 mM NaF, 1 mM Na orthovamatate, 1% Triton-X 100, 0.01% SDS, 0.5% Na deoxycholate, 1 mM phenylmethylsulphonyl fluoride (SIGMA, St. Louis, Mo.) and 1% protease inhibitor cocktail (SIGMA, St. Louis, Mo.) for 2 h. Insoluble debris was removed by centrifugation at 15000 g for 45 min. Total protein was determined using the Bradford Method (Bio-Rad, Hercules, Calif.). Equivalent amounts of protein from different lysate samples (30 µg/well) were denatured by boiling for 5 min and were resolved against Seeblue2 (Invitrogen, Carlsbad, Calif.) by SDS-PAGE using 4% tris-glycine gels (Invitrogen, Carlsbad, Calif.) in Tris-Gly SDS buffer (Biorad) at 85 V for 30 min and then 125 V for 2 h. Protein was transferred to methanol-pretreated PVDF membranes at 4° C. in Tris-glycine transfer buffer (Bio-Rad, Hercules, Calif.) at 30 V for 16 h. Membranes were washed in 0.1% PBS-Tween, blocked for 1 h in blocking buffer (50 mM Tris-Cl, 150 mM NaCl, and 10 g/L BSA in diH$_2$0), and subsequently incubated with either 625 ng/ml (1:2000) human Na$_v$1.5 antibody pretreated with 1:10 blocking peptide in blocking buffer with 500 mg/L NaN$_3$ at 4° C. for 16 h or 7 µg/ml (1:1000) rat Na$_v$1.7 (13/15 sequence homology to human) pretreated with 1:1 blocking peptide under similar conditions. Membranes were washed four times for 15 minutes in 0.1% PBS-Tween, blocked for 30 min in blocking buffer, and incubated in 75 ng/ml (3:40000) horse radish peroxidase-conjugated goat anti-rabbit secondary antibody in blocking buffer for 1 h. Membranes were washed in dH$_2$O. After the last of four washes for 15 minutes with 0.1% PBS-Tween, the blots were developed using the ECL chemiluminescence system (Amersham, Piscataway, N.J.) and visualized by exposure to Biomax MR Film (Kodak, Rochester, N.Y.). Membranes were washed in dH$_2$O and then washed twice for 5 minutes with 0.1% PBS-Tween. Blots were then stripped with stripping buffer (0.375 M Tris HCl, 12% SDS, 60 mM HCl, pH 6.8) for 1 hr at 56° C. and again washed in dH$_2$O and then washed twice for 5 minutes with 0.1% PBS-Tween. Membranes were blocked for 1 hr in blocking buffer and subsequently incubated with either 625 ng/ml (1:2000) human Na$_v$1.5 antibody without blocking peptide pretreatment in blocking buffer with 500 mg/L NaN$_3$ at 4° C. for 16 h or 7 µg/ml (1:1000) rat Na$_v$1.7 without blocking peptide pretreatment in blocking buffer with 500 mg/L NaN$_3$ at 4° C. for 16 h. The western procedure was repeated as described above.

(2) Cell Culture and Treatment

CWR22Rv1 cells (ATCC, Manassas, Va.) were seeded in 6 well tissue culture plate at density of 300,000 cells/well and maintained in RPMI 1640 (Mediatech, Herndon, Va.) containing 10% fetal bovine serum, 2.5 mM L-glutamine, and penicillin-streptomycin (100 IU/ml and 100 µg/ml, respectively) at 37° C. with 5% CO2. Cells were then switched to serum free RPMI media overnight prior to drug treatment. Compounds were dissolved in 100% dimethylsulfoxide (DMSO) and diluted to the desired concentrations in serum free RPMI. Cells were treated with indicated drug concentrations (in triplicate per treatment point) for 24, 48, 72 hour. After treatment, cells were harvested by trypsinization and fixed in 70% ethanol. The fixed cells were then stained with propidium iodide (50 µg/ml) after treatment with RNase (5 µg/ml). The stained cells were analyzed for DNA content using FACSsort (Becton Dickinson). Cell cycle fractions were quantified with Cell Quest (Becton Dickinson) or Mod-Fit LT (Verity Software House).

(a) Fluorescent Based Sodium Channel Assay.

A functional fluorescent assay for Na$_v$1.5 and Na$_v$1.7 channel activity was performed as previously described (Felix, J. P.; et al. *Assay and Drug Development Technologies.* 2004, 2, 260-268).[1] Tissue culture media and CC2-DMPE and DiSBAC$_2$ were purchased from Invitrogen Corporation, Carlsbad Calif., and pluronic acid from Molecular Probes, Eugene, Oreg. HEK293 cells stably transfected with either hNa$_v$1.5 or hNav1.7 were plated at approximately 11,000-20,000 cells/well in flat bottom, poly-D-lysine coated black-wall, clear-bottom, 384-well plates (Becton Dickinson, Bedford, Mass.), and incubated overnight at 37° C. in a 10% CO$_2$ atmosphere in growth medium. Cells were washed with 0.03 mL of Dulbecco's phosphate buffered saline (D-PBS) containing calcium and magnesium. Cells were then incubated with 0.025 mL of a solution containing 10 µM CC2-DMPE and 0.02% pluronic acid in D-PBS with calcium and magnesium; supplemented with 10 mM glucose, and 10 mM Hepes-NaOH, pH 7.4. After incubation in the dark for 45 min at 25° C., cells were washed twice with 0.03 mL of (in mM): 165 NaCl, 4.5 KCl, 2 CaCl$_2$, 1 MgCl$_2$, 10 glucose, 10 Hepes-NaOH, pH 7.4 (VIPR-S). Afterwards, cells were incubated in the dark at 25° C. for 45 min with 0.025 mL of a solution containing 5 µM DiSBAC$_2$(3) in VIPR-S, in the absence or presence of test compound. At the end of the incubation period, the plate was placed in a FLIPR TETRA instrument (MDS Analytical Technologies, Sunnyvale Calif.), illuminated at 390-420 nm, and fluorescence emissions were recorded at approximately 1 Hz at 460 and 580 nm. Following a 7 second baseline reading, 0.025 mL of VIPR-S containing 10 μM veratridine for Nav1.5 or 20 μM veratridine for Nav1.7 was added to each well, and the emissions of both dyes were recorded for an additional 33 seconds. The change in fluorescence resonance energy transfer (FRET) ratio ($F/F_0$) was calculated as:

$$F/F_0 = ((A_{460}/A_{580})/(I_{460}/I_{580})$$

where A and I represent the readings after or before addition of veratridine, respectively, at the indicated wavelengths. For I, the readings from 2-5 seconds were averaged, and for A, readings from 3 seconds after the signal had reached a plateau level (usually within 30-40 s) were also averaged. Triplicate measurements were performed for each experimental condition and the data were averaged.

(b) HERG Binding Assay.

MK-499, a potent hERG blocker, was used in a ligand binding assay to evaluate the binding of test compounds to hERG potassium channels as previously described (Wang, J et al. Am J Physiol Heart Circ Physiol, 2003, 284: H256-H267).[2] Test compounds were incubated with 0.05 nM of radiolabeled MK-499 ([35S]MK-499; specific Activity=1,279,010 μCi/μmol) in an assay buffer solution (70 mM NaCl, 60 mM KCl, 10 mM HEPES/NaOH (pH 7.4), 2 mM $MgCl_2$, 1 mM $CaCl_2$) also containing membranes isolated from HEK-293 cells stably expressing hERG channels in 96 well polypropylene deep-well assay plates at room temperature (25° C.) for >90 min. Assay plates were rinsed three time with buffer (130 mM NaCl, 10 mM HEPES/NaOH (pH 7.4), 2 mM $MgCl_2$, 1 mM $CaCl_2$) and the solution transferred to a Packard FilterMate Universal Harvester apparatus and filtered using PerkinElmer UniFilter-96 GF/C 96-well white microplates pre-soaked with 0.3% BSA (10 mL/L of 30% BSA). Plates were dried overnight at 37° C., or for 2 hrs at 56° C. The bottom of the plates were sealed and 0.025 mL of Microscint 0 was added to each well. The plates were top sealed and counted for 2 min/well in a Packard TopCount Scintillation counter. Test compounds were evaluated in a five point titration format using half-log steps from 0.3 μM to 30 μM. Percent inhibition of [35S]MK-499 was calculated relative to high control values (no unlabeled MK-499 added) and values obtained in the presence of 1 μM unlabeled MK-499. Less than 5% of the added radioactivity was retained on the filters. Assays were performed in triplicate.

(c) $Na_v$ Electrophysiology Studies.

Sodium currents were recorded using the whole-cell configuration of the patch clamp recording technique with an Axopatch 200 amplifier (Axon Instruments, Foster City, Calif.). All voltage protocols were applied using pCLAMP 9 software (Axon, USA) and a Digidata 1322A (Axon, USA). Currents were amplified and low pass filtered (2 kHz) and sampled at 33 kHz. Borosilicate glass pipettes were pulled using a Brown-Flaming puller (model P87, Sutter Instruments Co, Novato, Calif.) and heat polished to produce electrode resistances of 1.5-3.0 MΩ when filled with the following electrode solution (in mM); CsCl 130, $MgCl_2$ 1, MgATP 5, BAPTA 10, HEPES 5 (pH adjusted to 7.4 with CsOH). Cells were plated on glass coverslips and superfused with solution containing the following composition; (in mM) NaCl 130, KCl 4, $CaCl_2$ 1, $MgCl_2$ 5, HEPES 5, and glucose 5 (pH adjusted to 7.4 with NaOH). Compounds were prepared as 100 mM stock solutions in dimethyl sulfoxide (DMSO) and diluted to desired concentration (1 μM or 10 μM) in perfusion solution. All experiments were performed at room temperature (20-22° C.). After establishing whole-cell, a minimum series resistance compensation of 75% was applied and cells were held at −100 mV for 5 minutes to account for equilibrium gating shifts. Sodium currents were evoked by stepping to +10 mV from a holding potential of −60 mV for 25 ms at 15 s intervals. After control recordings, test compounds were applied for five minutes to allow for bath equilibration. Tonic block was assessed by comparing peak sodium current in drug free conditions to peak current when drug was present. Data analysis was performed using Clampfit software (v9, Axon Instruments, CA, USA) and Origin (v6, Microcal Software, MA, USA).

(d) Animals.

Balb/c mice and Athymic Balb/c Nude mice were purchased from the National Cancer Institute (NCl). Animals were housed 4-6 per cage with microisolater tops and provided food (Furina mice chow) and water ad libitum. The light cycle was regulated automatically (12 hours light/dark cycle) and temperature was maintained at 23±1° C. All animals were allowed to acclimate to this environment for one week prior to experimental manipulations. The Georgetown University Animal Care and Use Committee approved all animal studies in accordance with the guideline adopted by the National Institute of Health.

(e) Cell Culture for Xenograft.

PC-3 cell line (ATCC, Manassas, Va.) was cultured in RPMI-1640 with L-glutamine (Mediatech Inc., Herdon, Va.) containing 5% fetal bovine serum (FBS), 2.5 mM L-glutamine at 37° C. with 5% CO2.

(f) Xenograft Study.

Male athymic balbc/nude mice (18-22 g) were injected with 3×106 (0.3 mL) of the human prostate cancer cells (PC3). The human prostate cancer cells were injected in the subcutaneous tissue of the right axillary region of the mice. One week after the injection, the mice were randomly sorted into four groups with 6 mice per group. Stock solutions of compounds (±)-1, (R)-(−)-1 and (S)-(+)-1 were obtained by dissolving 1 mg of compound in 1 μl DMSO. The stock of each compound was added to polyethylene glycol 400 (PEG) (Hampton) and PBS in a 1:1 ratio. The test concentrations were obtained by diluting with PEG/PBS. The tumor-bearing mice received an intraperitoneal injection (IP) with either 10 mg/kg of (±)-1, R-(−)-1 or S-(+)-1 or vehicle control respectively once every other day for 4 weeks. At the same time, the tumor size of each mouse was measured by caliper and calculated by the formula: Length×width×height/2.

(g) Data Analysis

Statistical analyses were performed using the standard one-way ANOVA or ANOVA on ranks followed by a Tukey or Dunn's post hoc test. Data is reported as mean±S.E.M.

(3) Voltage Gated Sodium Channel Assay.

(4) Computer Modeling.

Modeling of the Sodium Channel—Multiple sequence alignment of the S6 transmembrane residues from domains I, III, and IV was carried out using PSI-BLAST and CLUSTALW. Homology modeling of S5, the P-loops, and S6 from all four domains used the open MthK channel x-ray structure (PDB: 1lnq) as a template. Since LAs bind to the inactivated form of domains the potassium channel were aligned, i.e. S5 and S6 transmembrane segments based on both homology and secondary structure prediction. Non-homologous regions in the longer P-loops of domains I and III, which correspond to putative glycosylation sites, were deleted. The P-loops, N and C termini were modeled based on homologous segments of the KcsA channel structure (PDB: 1bl8). Sodium channel sequences were aligned versus the MthK channel using ClustalW, and the structure was modeled employing the program Modeler 8.1. To avoid side chain atom contacts, different rotamer states of the residue were considered and the one with minimal contacts, but a favorable interaction was chosen. Local side chain atom minimization was also performed. Docking studies between ligand and the sodium channel were carried out using the program AUTODOCK 4.0 using default parameters. (Morris, G. et al. *J. Computational Chemistry.* 1998, 19: 1639-1662) Molecular dynamics simulations were carried out using AMBER 8.0 with default parameters.

5. Example 5

Evaluation of a Novel Fluorescent Sodium Channel Blocker in Human Prostate Cells and Tissues The distribution of a novel, fluorescent antagonist of voltage-gated sodium channels ($Na_v$) was evaluated in human prostate cells and intact prostatic tissues. Intact human tissue assays represent a rich untapped ex vivo resource between in vitro and in vivo models, capable of preclinical compound evaluation in non-invasive human systems. The rationally designed, fluorescent ligand 26 was evaluated by [$^1$H]-batrachotoxin (BTX) displacement in $Na_v$ protein and $Na_v1.2$ functional blockade by whole-cell patch clamp electrophysiology. Compound 26 displayed a 58.9±4.2% functional block of the $Na_v1.2$ isoform at 10 μM and a $GI_{50}$ in PC3 prostate cancer cells of 9.95±0.07 μM. The $Na_v$ blocker 26 was visualized by two-photon confocal microscopy in immortalized human prostate cells and human prostatic tissue to determine distribution and tissue specificity. In prostatic tissue the antagonist 26 deposited in glandular tissue as opposed to stroma and distributed within the cytosol of PC-3 cells. When combined with an active, fluorescent ligand this methodology provides a simple, quantitative experiment amenable to high-throughput screening. This methodology can provide new insights in drug discovery on a preclinical compound in regards to human tissue specificity, cellular distribution, and molecular target co-localization.

Non-invasive human tissue models that can consistently and accurately predict in vivo activity represent the 'holy grail' of pre-clinical drug discovery. In the mid-1950's the NCI promoted the initial use of mouse solid tumor tissue models followed thereafter by human tumor xenograft models in immunodeficient mice (Johnson, J. et al. *British Journal of Cancer* 2001, 84, 1424-1431; Sausville, E. et al. *Cancer Res* 2006, 66, 3351-3354). While mouse xenograft assays address the need for expedient drug analysis and anti-tumorgenic growth in vivo approximately 90% of potential drugs that show promise in these models subsequently fail clinical trials (The End of the Beginning? *Nat. Rev. Drug. Discov.* 2006, 5, 705; Sharpless, N. et al. *Nat. Rev. Drug. Discov.* 2006, 5, 741-754. Undeniably, every clinically approved anti-cancer drug has first demonstrated activity in mouse xenograft assays—yet these models remain far from ideal (Sausville, E. et al. *Cancer Res* 2006, 66, 3351-3354). Xenograft models utilize a limited collection of human tumor cells grown on plastic that potentially have been passaged in vitro hundreds of times prior to injection into the orthotopic site of an immunodeficient mouse (Sharpless, N. et al. *Nat. Rev. Drug. Discov.* 2006, 5, 741-754; Haddad, T. et al. *J. Clin. Oncol.* 2008, 26, 830-832). Unfortunately these systems, while cheap and traditional, model cancer as if it was a disease comprised of homogeneous rogue cells (Sharpless, N. et al. *Nat. Rev. Drug. Discov.* 2006, 5, 741-754. There is a considerable need to develop translational ex vivo human tissue assays, in addition to mouse in vivo models, to properly understand and predict future drug activity or distribution in a pre-clinical setting (Sharpless, N. et al. *Nat. Rev. Drug. Discov.* 2006, 5, 741-754: Haddad, T. et al. *J. Clin. Oncol.* 2008, 26, 830-832; Becher, O. et al. *Cancer Res* 2006, 66, 3355-3359; Zheng, S et al. *Oncogene* 2007, 26, 6896-6904).

An important addition to current xenograft methodologies could include the use of fresh, diseased and normal tissue acquired from available biopsied material. Using a fluorescent, or fluorescently labeled, candidate molecule a slice of fresh-frozen diseased prostatic tissue could be 'treated', washed and then examined by two-photon confocal microscopy ex vivo. Such a model would aid in delineating a drugs cellular distribution, tissue specificity, and target localization in human cancer tissue. This intact human tissue model would act in tandem with known mouse xenograft models for the prediction of clinical drug activity.

As a whole, fluorescent molecules in drug discovery and development have proven to be an indispensable source of information in understanding drug properties in vitro as well as in vivo (Lavis, L. et al. *ACS Chem. Biol.* 2008, 3, 142-155; McGrath, J. et al. *Br. J. Pharmacol.* 2003, 139, 187-189; Baindur, N., et al. *Drug. Dev. Res.* 1994, 33, 373-398). Owing to this interest, there exists an enumerable assortment of both tunable and rugged fluorescent moieties to suit most synthetic systems with many of them being commercially available. While the use of fluorescent ligands in drug discovery is extensive, there are few cases where a fluorescent moiety was implemented into the synthetic design for the purpose of predictably interacting with a protein binding site (Crane, C. et al. *Angew. Chem. Int. Ed.* 2006, 45, 1069-1074; Hermetter, A., et al. *Bioorg. Med. Chem. Lett.* 2001, 11, 1339-1342; Lansdell, M. et al. *Bioorg. Med. Chem. Lett.* 2008, 18, 4944-4947). In most cases, the development of fluorescently labeled drugs is solely for passive purposes where a fluorescent moiety acts literally as a label used to follow the drug through biological studies while attempting to maintain a modicum of efficacy (McGrath, J. et al. *Br. J. Pharmacol.* 2003, 139, 187-189; Baindur, N., et al. *Drug. Dev. Res.* 1994, 33, 373-398; Crane, C. et al. *Angew. Chem. Int. Ed.* 2006, 45, 1069-1074).

Considering that there are 55 known drugs in the FDA database (U.S. Food and Drug Administration, Center for Drug Evaluation and Research. http://www.accessdata.fda.gov/scripts/cder/drugsatfda/. November 2008) that contain the sulfonamide moiety, sulfonamides have a significant place in drug discovery. Sulfonamides exhibit diverse biological activity and are well known for a variety of pharmacological effects including antibiotic, hypoglycemic, diuretic, and anti-hypertensive activities (Banerjee, M., et al. *J. Med. Chem.* 2005, 48, 547-555; Drews, J. *Science* 2000, 287, 1960-1964). The use of unsubstituted sulfonamides has presented predominantly in the development of carbonic anhydrase inhibitors as diuretic, anti-convulsant, and anti-cancer agents for hypoxic tumors and imaging agents (Gruzel, O et al. *Bioorg. Med. Chem. Lett.* 2008, 18, 152-158; Biton, V. *Clin. Neuropharmacol.* 2007, 30, 230; Simone, G et al. *Bioorg. Med. Chem. Lett.* 2005, 15, 2315-2320; Holmes, C., et al. *Bioorg. Med. Chem. Lett.* 2005, 15, 4336-4341). The 5-(dimethylamino)naphthalene sulfide (dansyl) fluorophore, prepared from commercially available dansyl chloride, has proven to be a cheap and effective fluorescent sulfonamide moiety due to its known bioavailability, mild preparation, and lack of permanent charge resulting in overall hydrophobicity (Biton, V. *Clin. Neuropharmacol.* 2007, 30, 230; Luo, N. et al. *Colloids Surf. B.* 2006, 50, 89-96; Janout, V., et al. *J. Am. Chem. Soc.* 1996, 118, 1573-1574; Weber, G., et al. *Biochem-* istry 1979, 18, 3075-3078). The dansyl polycyclic aromatic fluorophore was chosen for the combined purpose of inhibition at the voltage-gated sodium channel ($Na_v$) hydantoin binding site as well as providing a sulfonamide fluorescent tag.

Medicinal chemistry of compounds targeting $Na_v$s are of great interest. (Anderson, J. et al. *Mol. Cancer Ther.* 2003, 2, 1149-1154; Sikes, R. et al. *Clinical Prostate Cancer* 2003, 2, 181-187; Grimm, et al. *Bioorg. Med. Chem.* 2003, 11, 4133-4141; Schenck, H. et al. *Bioorg. Med. Chem.* 2004, 12, 979-993; Lenkowski, P. et al. *Neuropharmacology* 2007, 52, 1044-1054). $Na_v$s are heterotrimeric transmembrane proteins composed of a large α-subunit (260 kDa) that serves as the gated ion pore and two or more β-subunits (33-36 kDa) that modulate channel gating and participate in cell-cell interactions. The α-subunit is further divided into four homologous domains (I to IV) each containing six transmembrane α-helices (S1-S6) with the S4 segments serving as the voltage sensors which move outward in the form of a sliding helix to initiate activation of the channel (Catterall, W. *Novartis Foundation Symposium* 2002, 241, 206-225; Cestele, S., et al. *Biochimie* 2000, 82, 883-892; Yu, F. H., et al. *Genome Biology* 2003, 4, 207; Nau, C., et al. *J. Membrane Biol.* 2004, 201, 1-8; Catterall, W. *Physiol. Rev.* 1992, 72, S15-S48. Local anesthetics, antiarrhythmics, and anticonvulsants are known to act at the batrachotoxin (BTX) binding site (site 2) located in S6 of domains I, III and IV (Correa, F. et al. *Neurosci. Lett.* 1980, 16, 47-53). Compounds known to bind to site 2 cause persistent inactivation of the $Na_v$, which has been measured by voltage (patch) clamp assays. $Na_v$s are found most prominently in excitable tissues such as brain, heart, and skeletal muscle but have also been found in non-excitable prostate cancer (PCa) epithelial tissue (Sikes, R. et al. *Clinical Prostate Cancer* 2003, 2, 181-187; Fraser, S et al. *The Prostate* 2000, 44, 61-76; Shao, B., et al. *J. Med. Chem.* 2004, 47, 4277-4285; Poupaert, J. et al. *J. Med. Chem.* 1989, 27, 76-78; Grimes, J. et al. *J. Cell. Physiol.* 1998, 175, 50-58).

Prostate cancer is the most commonly diagnosed cancer in men and is the second leading cause of male, cancer-related mortality (Singer, E. et al. *Expert Opin. Pharmacother.* 2008, 9, 211-228. In 2008, 186,320 men were diagnosed with prostate cancer in the United States with 28,660 patients succumbing to the disease (ACS; www.cancer.org). Although gland localized, androgen-dependent prostate cancer is readily treatable with surgery and radiation therapies, advanced prostate cancer is invariably more difficult to treat. Advanced prostate cancer can be characterized by growth of the cancer beyond the gland with 8-14% of patients presenting with some form of metastasis (Sikes, R. et al. *Clinical Prostate Cancer* 2003, 2, 181-187). The mainstay of advanced prostate cancer treatment is androgen ablation therapy due to the androgen dependence of prostate adenocarcinomas. With androgen deprivation by orchiectomy or chemical castration, remission is induced in 80-90% of patients. Unfortunately in most cases an androgen-independent phenotype eventually emerges of which there is still no effective treatment. Furthermore, once the cancer metastasizes from prostate to bone, despite androgen deprivation therapy, the median survival time is 2.5 years from the initiation of treatment (Robinson, D., et al. *J. Urol.* 2008, 179, 117-123.

Although the exact purpose of $Na_v$ expression in prostate epithelial tissue is not fully understood, $Na_v$ upregulation has been linked to prostate adenocarcinoma invasiveness and metastatic potential (Anderson, J. et al. *Mol. Cancer Ther.* 2003, 2, 1149-1154; Brackenbury, W., et al. *J. Physiol.* 2006, 573, 343-356; Brackenbury, W. et al. *J. Cell. Physiol.* 2007, 210, 602-608; Brackenbury, W. et al. *The Neuroscientist* 2008, 14, 571-583; Fraser, S. et al. *EMBO Reports* 2008, 9, 512-515; Uysal-Onganer, P., et al. *Molecular Cancer* 2007, 6, 76; Roger, S., et al. *The International Journal of Biochemistry & Cell Biology* 2007, 39, 774-786; Palmer, C. et al. *Eur. Biophys. J.* 2008, 37, 359-368). The highly metastatic, androgen independent PC-3 (human) and Mat-Lys-Lu (Rat) prostate cancer cell lines have shown $Na_v$ upregulation, specifically $Na_v$ 1.7 of the nine known $Na_v$ isoforms. When compared to highly metastatic cell lines, the weakly metastatic cell lines AT-2 and LnCaP cells show little $Na_v$ expression (Grimes, J. et al. *J. Cell. Physiol.* 1998, 175, 50-58; Roger, S. et al. *Curr. Pharm. Des.* 2006, 12, 3681-3695). Furthermore, non-metastatic LnCaP cells can be made metastatic (C4 and C4-2 cells) after electroporation of the adult skeletal-muscular $Na_v$ isoform $Na_v$ 1.4 (Bennett, E. et al. *Eur. J. Physiol.* 2004, 447, 908-914). Due to the connection between $Na_v$ expression and invasiveness in the metastatic, androgen independent, PC-3 cell line the use of $Na_v$ inhibitors can provide new therapeutic options.

Diphenylhydantoin (DPH) (Scheme 11), a clinical $Na_v$ inhibitor used to treat epilepsy and chronic pain, has served as the initial lead compound in the discovery of novel $Na_v$ inhibitors (Grimm, et al. *Bioorg. Med. Chem.* 2003, 11, 4133-4141; Schenck, H. et al. *Bioorg. Med. Chem.* 2004, 12, 979-993; Brown, M et al. *J. Med. Chem.* 1999, 42, 1537-1545; Choudhury-Mukherjee, I., et al. *J. Med. Chem.* 2003, 46, 2494-2501). DPH analogs were designed based on information utilized from the QSAR model developed from [$^3$H]-BTX displacement in rat brain synaptoneurosomes (Anderson, J. et al. *Mol. Cancer Ther.* 2003, 2, 1149-1154). The resulting comparative molecular field analysis (CoMFA) model demonstrated that replacing one of the phenyl rings of DPH with a heptyl side chain, which reached a hydrophobically receptive region of the binding site, was preferred. This finding agrees with prior studies concerning the affect of increased chain length, in n-alcohols, on $Na_v$ inhibition (Horishita, T. et al. *Xenopus Oocytes. JPET* 2008, 326, 270-277; Haydon, D. et al. *J. Physiol.* 1983, 341, 411-427. Furthermore, the addition of a meta-chloro group on the remaining phenyl ring was optimal to binding (Lenkowski, P. et al. *Neuropharmacology* 2007, 52, 1044-1054). One of the active analogs from this study was compound 10, which represents the highlighted additions predicted by the model. In an effort to design a more efficacious analog, a pentyl tethered dansyl sulfonamide group was positioned in the region of the binding site in place of the heptyl side chain, resulting in the synthesis of compound 26. The addition of this tethered dansyl sulfonamide provides two important advantages: 1) the dansyl addition allows for the monitoring of intracellular deliveries with in vitro and in vivo studies, and 2) the placement of hydrophobic bulk in a lipophilic region of the site 2 binding site increases $Na_v$ inhibition.

Scheme 11. Evolution of DPH deriviatives.

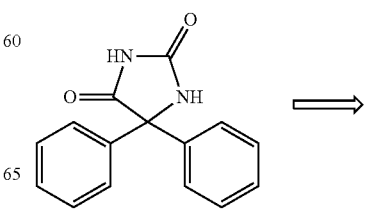

Scheme 11. DHP, compound 10 and compound 26 a) Results

The synthesis of compound 26 commenced with the addition of dansyl chloride to 6-aminohexanoic acid under basic conditions to yield the sulfonamide 35 (Scheme 12).

An acid-amine coupling was performed under the presence of EDCI to afford the Weinreb amide 36. The commercially available Grignard reagent 3-chlorophenyl magnesium bromide (Sigma Aldrich) was added directly to a solution of amide 36 resulting in the aryl ketone 36. The hydantoin 26 was procured via a one-step Bucherer-Berg reaction (Zha, C., et al. *J. Med. Chem.* 2004, 47, 6519-6528).

Scheme 12. Syntheic strategy for making compound 26

To determine the effects of 26 on the BTX binding site (site 2), a direct displacement assay was carried out with [$^3$H]-BTX-A-20-α-benzoate ([$^3$H]-BTX-B) binding to Na$_v$s in rat brain synaptoneurosomes. The [$^3$H]-BTX-B displacement data (Table 1) indicated that compound 26 binds to the Na$_v$ channel protein and is more effective at displacing [$^3$H]-BTX-B binding when compared to compound 10.

TABLE 13

| Compound | % [$^3$H]-BTX Displacement (40 μm) | % Na$_v$ 1.2 Functional Block (10 μm) | PC3 GI$_{50}$ (μg) |
| --- | --- | --- | --- |
| DPH | 27.7 | 10.9 ± 4.2 | >100 |
| 10 | 69.6 | 30.5 ± 5.1 | 18.97 ± 0.04 |
| 26 | 86.4 | 58.9 ± 4.1 | 9.95 ± 0.07 |

The ability of a ligand to inhibit Na$_v$ currents is an important property and represents functional Na$_v$ blockade. A comparison of functional blocking data indicated that compound 26 is almost twice as potent in relation to lead compound 10. The ability of 26 to inhibit sodium channel currents was assessed at 10 and 100 μM against human Na$_v$1.2 by patch clamp assay (FIG. 19 and Table 13). Compound 26 blocked greater than 50% of the Na$_v$ current at 10 μM. The addition of the dansyl moiety resulted in increased functional block as compared to DPH and compound 10.

Several studies provide support for engaging the hydrophobic region in the hydantoin binding site of the Na$_v$ (Anderson, J. et al. *Mol. Cancer Ther.* 2003, 2, 1149-1154; Lenkowski, P. et al. *Neuropharmacology* 2007, 52, 1044-1054). Using the potassium ion channel, a homology model of the BTX binding site was developed. The compounds in this study were docked in the model using FlexX (Sybyl8.0, Tripos Inc.) and AutoDock 4.0 (Morris, G. et al. *J. Comput. Chem.* 1998, 19, 1639-1662). Upon analysis of the docked poses, compounds 10 and 26 possessed different interactions with the S6 helix residues in comparison to mutation data (Ragsdale, D., et al. *Science* 1994, 265, 1724-1728; Yarov-Yarovoy, V., et al. *J. Biol. Chem.* 2001, 276, 20-27; Yarov-Yarovoy, V., et al. *J. Biol. Chem.* 2002, 277, 35393-35401). To be consistent with the mutation studies (Ragsdale, D., et al. *Science* 1994, 265, 1724-1728; Yarov-Yarovoy, V., et al. *J. Biol. Chem.* 2001, 276, 20-27; Yarov-Yarovoy, V., et al. *J. Biol. Chem.* 2002, 277, 35393-35401) and previous known interactions of BTX analogs, the docked positions were remodeled using step by step manual docking with constrained Molecular Dynamics (MD) simulations followed by minimization. In the restrained MD simulations, the optimal hydrogen-bond and hydrophobic distance constraints were set between the Na$_v$ pore-forming residues and the compounds.

The structural model of compounds 10 and 26 are shown in (FIGS. 20*a-b*). Although some uncertainty remains for several residues, the binding model predicts that the residues F1283, F1579, L1582, V1583, Y1586 in IVS6, and T1279, L1280 in IIIS6, and L788, F791, L792, in IIS6 and F430, I433, L437 in IS6 contributed to the tight binding interaction of compound 26. Notably, the predicted interaction of the aromatic ring, of compounds 10 and 26, with F1579 and Y1586 agrees with the position that for optimal binding to occur at the local anesthetic (Site 2) target an aromatic moiety is required to necessitate the cation-π interaction (Ahern, C. et al. *Circ. Res.* 2008, 102, 86-94). As confirmation, some of these residues are important in alanine mutation experiments (Lenkowski, P. et al. *Neuropharmacology* 2007, 52, 1044-1054; Zha, C., et al. *J. Med. Chem.* 2004, 47, 6519-6528; Morris, G. et al. *J. Comput. Chem.* 1998, 19, 1639-1662).

The shape and size of compounds 10 and 26 are complimentary to the model of the binding site in the open pore similar to BTX, and the hydantoin moiety fits into the subcavity region formed by the side chains of T1279 (IIIS6), L1280 (IIIS6), F791(II), and L792 (II). The potential reason for the increased displacement ability of 26 over 10 is predicted to stem from the following favorable interactions: 1) The amide functionality of the hydantoin forms hydrogen bond interactions with 1279(IIIS6) and 1279(IIIS6) 2) Hydrogen bond interactions between the dansyl sulfonamide, N434(I), and Y1586(IV) 3) The favorable hydrophobic contact of the dansyl group with F1283 (IIIS6), L437(I), L788 (II), L1280(IIIS6) in a hydrophobically receptive region of the binding site.

$Na_v$ channels are expressed in human prostate cancer cells (Anderson, J. et al. *Mol. Cancer Ther.* 2003, 2, 1149-1154; Sikes, R. et al. *Clinical Prostate Cancer* 2003, 2, 181-187). The androgen independent PC-3 cells express several $Na_v$ isoforms including $Na_v1.2$ (Anderson, J. et al. *Mol. Cancer Ther.* 2003, 2, 1149-1154; Lenkowski, P. et al. *Neuropharmacology* 2007, 52, 1044-1054; Diss, J., et al. *Prostate Cancer and Prostatic Diseases* 2005, 8, 266-273; Diss, J. et al. *Prostate* 2001, 48, 165-178. Unlike neurons, prostate cancer cell fractionation experiments (FIGS. 21 and 22) reveal the expression of $Na_v1.2$ in nuclear and cytoplasmic fractions and not in the plasma membrane.

The effect of compound 2 was studied on the proliferation of human androgen independent prostate cancer (PC-3) cells, using a cell viability assay with WST-8. Diphenylhydantoin was considered to be ineffective with a $GI_{50}$ in excess of 100 μM and compounds 10 and 26 displayed $GI_{50}$ values of 18.97±0.04 and 9.95±0.07 μM respectively. Human prostate cancer $GI_{50}$ values for compounds 10 and 26 followed the same trend as the $Na_v1.2$ functional blocking data (Table 13), with compound exhibiting the most effective antiproliferative effects.

The intracellular localization of $Na_vs$ in human prostate cells presents an optimal situation to evaluate the distribution of 26, the fluorescent $Na_v$ inhibitor. Compound 26 appears to gain access to the cell and reside in the cytoplasm where $Na_v1.2$ is expressed in PC-3 cells. In addition, there is no apparent nuclear staining which indicates that 26 is prohibited from crossing the nuclear membrane. Unfortunately, the resolution of the image did not allow for a closer examination of the membrane-cytoplasm or cytoplasm-nuclear membrane interfaces.

The distribution of compound 26 was studied in human prostate cancer tissues. Frozen human prostate sections were fixed to the slide in acetone for 30 seconds at −20° C., then dried and rehydrated. Human prostate tissue slices were prepared and incubated for 1 hour with a solution of compound 26 (100 μM). Upon washing, the tissue was examined by two-photon confocal microscopy to determine the presence and distribution of compound 26 (FIG. 23). The results are provided in FIGS. 24 and 25.

In FIG. 24 the cancerous glandular tissue in the prostate slice can be identified in the middle of the image which is stained heavily by compound 26. There is also little staining of the stroma tissue surrounding the glandular tissue indicating a selective uptake of compound 26 in prostate epithelial cells. Under magnification (FIG. 25) the deposition of compound 26 in the cytosol of the prostate tissue is apparent and agrees with earlier PC-3 cell staining.

While the use of fresh frozen tissue in the ex vivo assay demonstrates a preliminary model, it can not be regarded as optimal. Initially paraffin embedded tissue was used but later discarded due to the lack of differentiation between drug staining and auto-fluorescence due to the increased laser powered required. At the time it was believed that the paraffin in some way hindered the drugs path to the binding site limiting drug fluorescence at the target and reducing the image clarity. The use of fresh frozen tissue allowed for the passage of drug to target and the fluorescence could be visualized and separated from auto-fluorescence. The cutting of the fresh frozen slices though warped the morphology of the tissue and made recognition difficult while not altogether impossible.

To configure a better protocol, fresh tissue was immediately paraffin embedded, sliced, and treated with drug directly. The imaged slides displayed intact morphology, enhanced fluorescence, and improved clarity with the reduction in laser power (FIG. 8). By using fresh tissue and treating the paraffin embedded slice directly it is believed that there was less time for the surface of the tissue to oxidize and thus alter the binding site.

Demonstrated in FIG. 26 is the presence of the $Na_v1.2$ isoform in prostatic glandular tissue (pictured in red). In addition, the tissue was treated with drug colocalizing with $Na_v1.2$ in the glandular tissue. The stromal tissue surrounding the gland in this image is predominantly smooth muscle tissue and, being an excitable cell type known to contain sodium channels, it is not surprising that there is drug uptake.

This study supports the use of fluorescent ligands in human tissues (paraffin embedded and fresh frozen), as a relevant surrogate for measuring tissue specificity, distribution, and cellular localization early in the drug discovery process. Further, the selective distribution in invading prostate epithelial cells provides in vivo potential translational utility of the $Na_v$ ligand in clinical situations where confocal imaging is appropriate.

(1) Conclusion

While small fluorescent moieties are utilized extensively in drug discovery, they predominantly serve in a spectatorial capacity. Traditionally the inclusion of fluorescent analogs in lead development and medicinal chemistry arises from the necessity for monitoring pharmacological drug action in biological assays while attempting to maintain efficacy. Described herein is an example where the addition of the dansyl group predictably enhanced activity at the protein target. The addition of the hydrophobic, and fluorescent, dansyl moiety not only increased the efficacy of compound 26 in site 2 binding (86.4% at 40 μM) but also functional blocking (58.9±4.2% at 10 μM) of $Na_v1.2$ current. This compound was also screened for its ability to inhibit PC3 prostate cancer cell growth and displayed a $GI_{50}$ of 9.95±0.07 μM which was almost a two-fold improvement over the lead compound 10. This represents one of the first reported instances of a fluorescent moiety designed into rational lead optimization for the direct purpose of enhancing activity within a designated binding site.

Cellular imaging studies revealed a cytoplasmic localization of compound 26 in immortalized human prostate cells. In human prostate tissues compound 26 localized in the cytoplasm of cancerous prostate glands (Gleason score of 7) and colocalized with the Na$_v$1.2 isoform. Disclosed herein is the first example of the use of human tissue slices as a human surrogate early in the drug discovery process to ascertain a compounds distribution in human tissue. Human prostate ex vivo tissue studies also confirmed an intracellular distribution of compound 2 consistent with the in vitro results.

The use of human tissues as presented in this study has not previously been advanced. Advantages include a) new methods for early identification and quantification of a preclinical compound's distribution in intact normal and diseased human tissues, b) the requirement of minimal amounts of compound, c) facile and reproducible evaluation of cellular distribution within human tissue, d) an opportunity to co-localize the preclinical compound with the antibody of the molecular target, e) developing new types of preclinical competition assays in human tissues, and f) advancement of these types of compounds with diagnostic and therapeutic activity could provide for a new class of "theranostic" agents.

The present study points to a new and exciting shift in medicinal chemistry towards evaluating the use of human tissue slices to model a compound's tissue specificity and distribution. The use of human tissue early in the drug discovery and preclinical process addresses a current drug development need to create more relevant surrogates of human disease models.

b) Materials and Methods (1) Chemical Synthesis.

Chemicals were purchased from Aldrich Chemical Company and were used without any further purification unless mentioned otherwise in the procedure. Dry solvents were dried over 4 Å molecular sieves prior to use. Air-sensitive reactions were carried out in flame-dried glassware under an N$_2$ atmosphere unless otherwise noted. Flash Column Chromatography (FCC) separations were done on a Biotage SP1 system monitoring at 254 nm. All NMR spectra were recorded on a Varian 400 spectrometer, operating at 400 MHz for $^1$H and 100 MHz for $^{13}$C NMR. Meting points were recorded on a Meltemp instrument and are uncorrected.

(a) 6-(5-(dimethylamino)naphthalene-1-sulfonamido)hexanoic acid (35).

In a round-bottom flask (RBF) 6-hexanoic acid (3.70 g, 27.8 mmol) was added to a 1 M solution of NaHCO$_3$ (45 mL). To this was added dansyl chloride (5.05 g, 18.5 mmol) in acetone (20 mL) and TEA (16.0 mL, 111 mmol). The solution was stirred for 3 hours, then 2 M HCl was then added to the solution until the pH reached ~3. The product was then extracted with EtOAc (3×25 mL) and washed successively with H$_2$O (25 mL) and brine (25 mL). The organic fraction was then dried over Na$_2$SO$_4$, concentrated, then purified by FCC (1:10 MeOH/DCM) to yield a sticky, yellow oil (5.80 g, 85%). $^1$H-NMR (400 MHz, CDCl$_3$) δ 1.13 (m, 2H), 1.35 (tt, 4H, J=7.2 Hz, J=14.1 Hz), 2.11 (t, 2H, J=7.4 Hz), 2.837-2.883 (m, 8H), 5.53 (t, 1H, J=6.1 Hz), 7.14 (d, 1H, J=7.3 Hz), 7.49 (dt, 2H, J=7.5 Hz, J=8.8 Hz), 8.22 (dd, 1H, J=1.2 Hz, J=7.3 Hz), 8.34 (d, 1H, J=8.7 Hz), 8.50 (d, 1H, J=8.5 Hz), 11.14 (s, 1H). $^{13}$C-NMR δ 179.0, 151.4, 134.6, 130.0, 129.5, 129.3, 129.1, 128.0, 122.9, 118.7, 115.0, 53.3, 45.1, 42.6, 33.4, 28.8, 25.5, 23.6.

(b) 6-(5-(dimethylamino)naphthalene-1-sulfonamido)-N-methoxy-N-methylhexanamide (36).

In a flame dried RBF, EDCI (2.93 g, 20.6 mmol), N,O-dimethylhydroxylamine HCl (2.02 g, 20.6 mmol), and DMAP (2.54 g, 20.6 mmol) were added to a solution of acid 35 (3.02 g, 8.23 mmol) in DCM. The resultant mixture was stirred for 2.5 hours before being quenched with brine (20 mL). The phases were separated and the organic phase was washed with 2 M HCl (10 mL) and brine (10 mL) before being dried over Na$_2$SO$_4$. The solution was then concentrated and purified by FCC (1:20 MeOH/DCM) to yield a yellow oil (2.54 g, 75%). $^1$H-NMR (400 MHz, CDCl$_3$) δ 1.21 (m, 2H), 1.42 (tdd, 4H, J=7.2 Hz, J=14.5 Hz, J=21.9 Hz), 2.27 (t, 2H, J=7.3 Hz), 2.87 (m, 8H), 3.12 (s, 3H), 3.61 (s, 3H), 5.17 (t, 1H, J=6.1 Hz), 7.16 (d, 1H, J=7.5 Hz), 7.51 (ddd, 1H, J=7.5 Hz, J=8.5 Hz, J=10.5 Hz), 8.21 (dd, 1H, J=1.2 Hz, J=7.3 Hz), 8.31 (d, 1H, J=8.7 Hz), 8.52 (d, 1H, J=8.5 Hz). $^{13}$C-NMR δ 134.9, 130.1, 129.7, 129.5, 129.3, 128.1, 123.1, 118.8, 115.0, 61.0, 45.3, 42.9, 31.3, 29.1, 25.9, 23.6.

(c) N-(6-(3-chlorophenyl)-6-oxohexyl)-5-(dimethylamino)naphthalene-1-sulfonamide (37).

A flame dried RBF was charged with amide 36 (1.56 g, 3.82 mmol) which was dissolved in THF (30 mL). The flask was then cooled to 0° C. and 3-chlorophenylmagnesium bromide solution was added dropwise (0.50 M, 39.0 mL, 19.1 mmol). This was allowed warm to room temperature and stir overnight. The reaction was then quenched with saturated ammonium chloride solution (20 mL). The organic phase was extracted with EtOAc (3×25 mL), washed with brine (25 mL), and dried under Na$_2$SO$_4$. It was then concentrated to dryness and purified by FCC (1:1 EtOAc/hex) to yield a yellow oil (1.04 g, 60%). $^1$H-NMR (400 MHz, CHCl$_3$) δ 1.21 (m, 2H), 1.43 (tdd, 4H, J=7.1 Hz, J=14.7 Hz, J=35.3 Hz), 2.71 (t, 2H, J=7.2 Hz), 2.83 (s, 6H), 2.91 (dd, 2H, J=6.8 Hz, J=13.2 Hz), 5.30 (t, 1H, J=6.2 Hz), 7.12 (d, 1H, J=7.0 Hz), 7.34 (t, 1H, J=7.9 Hz), 7.49 (m, 3H), 7.72 (d, 1H, J=7.8 Hz), 7.83 (s, 1H), 8.23 (d, 1H, J=6.1 Hz), 8.34 (d, 1H, J=8.7 Hz), 8.50 (d, 1H, J=8.5 Hz). $^{13}$C-NMR δ 198.6, 151.7, 138.1, 134.7, 134.6, 132.7, 130.1, 129.7, 129.6, 129.4, 129.3, 128.1, 127.8, 125.9, 123.0, 118.6, 114.9, 45.2, 45.2, 42.8, 38.0, 29.0, 25.7, 22.9.

(d) N-(5-(4-(3-chlorophenyl)-2,5-dioxoimidazolidin-4-yl)pentyl)-5-(dimethylamino)naphthalene-1-sulfonamide (26).

In an RBF a 50% EtOH/H$_2$O solution (50 mL) was prepared to which was added KCN (709 mg, 10.9 mmol), ammonium carbonate (2.09 g, 21.8 mmol), and ketone 36 (1.00 g, 2.18 mmol) in 1-2 mL of THF. This mixture was allowed to stir at 65° C. for 1 week. The product was then extracted with DCM (3×25 mL), washed with brine (3×35 mL) and the organic layer was dried over Na$_2$SO$_4$ and evaporated to dryness. It was then purified by FCC (1:1 EtOAc/Hex) to yield a light green crystalline solid (265 mg, 22%). $^1$H-NMR (400 MHz) δ 1.12 (m, 4H), 1.25 (m, 2H) 1.96 (m, 2H), 2.86 (m, 8H), 5.72 (t, 1H, J=6.0 Hz), 7.13 (d, 1H, J=7.5 Hz), 7.28 (m, 2H), 7.38 (m, 1H), 7.49 (dd, 3H, J=8.6 Hz, J=17.0 Hz), 7.85 (s, 1H), 8.19 (d, 1H, J=7.3 Hz), 8.29 (d, 1H, J=8.6 Hz), 8.51 (d, 1H, J=8.4 Hz), 9.21 (s, 1H). $^{13}$C-NMR δ 175.0, 157.9, 139.8, 139.4, 134.7, 134.6, 130.3, 130.0, 129.5, 129.4, 128.7, 128.4, 128.2, 125.6, 125.2, 123.6, 123.2, 115.1, 68.4, 45.3, 42.5, 38.3, 28.8, 25.7, 22.9, 14.1. LC-MS (ESI): m/z 530 (M+H)$^+$; HRMS (TOF): C$_{26}$H$_{29}$ClN$_4$O$_4$S. Calculated (M+1) 529.16. Found 529.18.

(2) Sodium Channel Electrophysiology.

Human embryonic kidney cells (HEK) cells stably expressing human Na$_v$1.2 were a kind gift from Dr. H. A. Hartmann (University of Baltimore, Md., USA) and were grown in DMEM/F12 media (Invitrogen, Corp, CA, USA) supplemented with 10% fetal bovine serum, penicillin (100 U/ml), streptomycin (100 µg/ml) and G418 (500 µg/ml; Sigma, Mo., USA). Cells were grown in a humidified atmosphere of 5% CO$_2$ and 95% air at 37° C.

Sodium currents were recorded using the whole-cell configuration of the patch clamp recording technique with an Axopatch 200 amplifier (Axon Instruments, Foster City, Calif.). All voltage protocols were applied using pCLAMP 9 software (Axon, USA) and a Digidata 1322A (Axon, USA). Currents were amplified and low pass filtered (2 kHz) and sampled at 33 kHz. Borosilicate glass pipettes were pulled using a Brown-Flaming puller (model P87, Sutter Instruments Co, Novato, Calif.) and heat polished to produce electrode resistances of 0.5-1.5 MΩ when filled with the following electrode solution (in mM); CsCl 130, $MgCl_2$ 1, MgATP 5, BAPTA 10, HEPES 5 (pH adjusted to 7.4 with CsOH). Cells were plated on glass coverslips and superfused with solution containing the following composition; (in mM) NaCl 130, KCl 4, $CaCl_2$ 1, $MgCl_2$ 5, HEPES 5, and glucose 5 (pH adjusted to 7.4 with NaOH).

Compound 26 was prepared as 100 mM stock solutions in dimethyl sulfoxide (DMSO) and diluted to desired concentration in perfusion solution. The maximum DMSO concentration used was 0.1% and had no effect on current amplitude. All experiments were performed at room temperature (20-22° C.). After establishing whole-cell, a minimum series resistance compensation of 75% was applied. Sodium currents were elicited by a depolarizing step from a holding potential of −100 mV to +10 mV for a duration of 25 ms at 15 s intervals. Compound 26 was applied after a 3 min control period and continued until a steady state current amplitude was observed. All data represent percentage mean block±standard error of the mean (S.E.M.).

(a) PC-3 Cell Growth Inhibition Assay.

PC-3 cells were added to the wells of a 96 well plate at 7500 cells per well in 100 uL of RPMI medium with 10% serum and allowed to plate down overnight. The medium was then removed and replaced with serum free medium containing the appropriate concentration of drug. DMSO concentration was kept below 1%. At this time WST-8 cell counting reagent was added to the control (T=0) wells and allowed to incubate for 2 hours and the absorbance was read at 450 nm to determine the starting number of cells per well. The plates were incubated for 48 hours, the medium was removed and the wells were washed with 100 uL of PBS. The PBS was removed that the wells were filled with 110 uL of serum free RPMI media containing the WST-8 reagent. After two hours of incubation, the plates absorbance was read at 450 nm and normalized to the control value.

(b) Immunofluorescence.

PC-3 cells were plated onto glass slides at a density of 500,000 cells per slide in RPMI media with 10% serum and allowed to plate down overnight. The media was removed and replaced with media with 10% serum and 10 µM compound 26 and allowed to incubate for 6 hours. The slides were then washed three times with 1×PBS and fixed with 4% paraformaldehyde for 10 minutes followed by four washings with 1×PBS. Cells were then treated with a 50 µg/mL (1:500 dilution) solution of propidium iodide for 4 minutes followed by three washings with 1×PBS. Slides were then mounted and imaged on Zeiss 510LSM/META/NLO using a 63× objective. Compound 26 was excited with a multiphoton laser at a wavelength of 720 nm and the emission was detected using a 488-500 nm band pass filter.

(c) Tissue Immunofluorescence.

The control tissue was prostate cancer block RTB637-AT provided by the Georgetown University Hospital Department of Pathology. Compound 26 was provided as a 100 mM stock solution in DMSO and was diluted to 100 µM with deionized water as a starting point. The frozen tissue sections were cut at 5 µm. The frozen sections where fixed to the slide in Acetone for 30 secs. at −20° C. then dried and rehydrated in TBST. Mock the primary antibody in −5% goat serum in TBST for 1 hour at RT. This was then washed twice for 5 mins. in deionized water. The tissue was then exposed to 100 µM of compound 26 for 60 mins. at RT. The slice was then washed again twice for 5 mins. in deionized water. The sample was exposed to a 1/500 dilution of propidium iodide for 5 mins. at RT. The slice was then mounted in Vectastain. Four slides were prepared: −ve Control, −ve Control+PI, Compound 26 (60 mins.), and Compound 2 (60 mins.)+PI.

(d) Molecular Modeling.

Docking studies between ligands and the sodium channel were carried out using the program AUTODOCK 4.0 with all the parameters were set to default. Molecular dynamics simulations were carried out using AMBER 8.0 with default parameters.

(e) Molecular Dynamics.

The structure models of the sodium channel were refined by molecular dynamics simulation using the Amber 8.0 program suite. The charge and force field parameters of compounds were obtained using the most recent Antechamber module in Amber 9 program, where the compounds are minimized at the MP2/6-31G* level using Gaussian 03. The protocols for the MD simulation are briefly. The total charge of the system was neutralized by first adding one chloride ion. The system was solvated in a 12 Å cubic box of water where the TIP3P model8 was used. Two thousand steps of minimization of the system were performed in which sodium channel were constrained by a force constant of 75 kcal/mol/Å². After minimization, a 10 ps simulation was used to gradually raise the temperature of the system to 298 K while the complex was constrained by a force constant of 15 kcal/mol/Å. Another 25 ps of equilibrium run was used where only the backbone atoms of the complex were constrained by a force constant of 5 kcal/mol/Å. A final production run of 200 ps was performed with no constraints on any atoms of the complex structure. When applying constraints, the initial complex structure was used as a reference structure. All the MD simulations were at NTP. The SHAKE algorithm was used to fix the bonds involving hydrogen. The PME method10 was used and the non-bonded cutoff distance was set at 12 Å. The time step was 5 fs, and neighboring pairs list was updated in every 25 steps.

6. Example 7

Design, Synthesis, and Biological Evaluation of a Novel, α-Hydroxy Amide Sodium Channel Ligand Integrating a BODIPY Moiety into the Pharmacore Fluorescent α-hydroxy amide analogs that target voltage-gated sodium channels (Nav) as 'theranostic' treatments for metastatic prostate cancer are of great interest. For example, as disclosed elsewhere herein, a dansyl modified α-hydroxy amide displays both enhanced [³H]-batrachotoxin (BTX) displacement, $Na_v1.2$ functional blockade, and human PC-3 cell growth inhibition in relation to diphenylhydantoin. This enhancement was, in part, due to the addition of a hydrophobic side chain extending into a lipophilic region of the anesthetic binding site. The binding site was studied to gain structural information to optimize drug design to further increase the potency of fluorescent α-hydroxy amide analogs. The structural features and chemical properties within the anesthetic binding site indicated that hydrophobic, tunable fluorophores such as 4,4-difluoro-4-bora-3a,4α-diaza-s-indacene (BODIPY) would bind strongly. To study the potency of such compound BODIPY was chemically bonded to a potent α-hydroxy amide analog, (Scheme 13).

The fluorescent product was used to treat PC-3 cells, cancerous prostatic tissues, and PC-3 xenograft mouse models. Fluorescent imaging of the system was carried out by confocal microscopy.

SCHEME 13

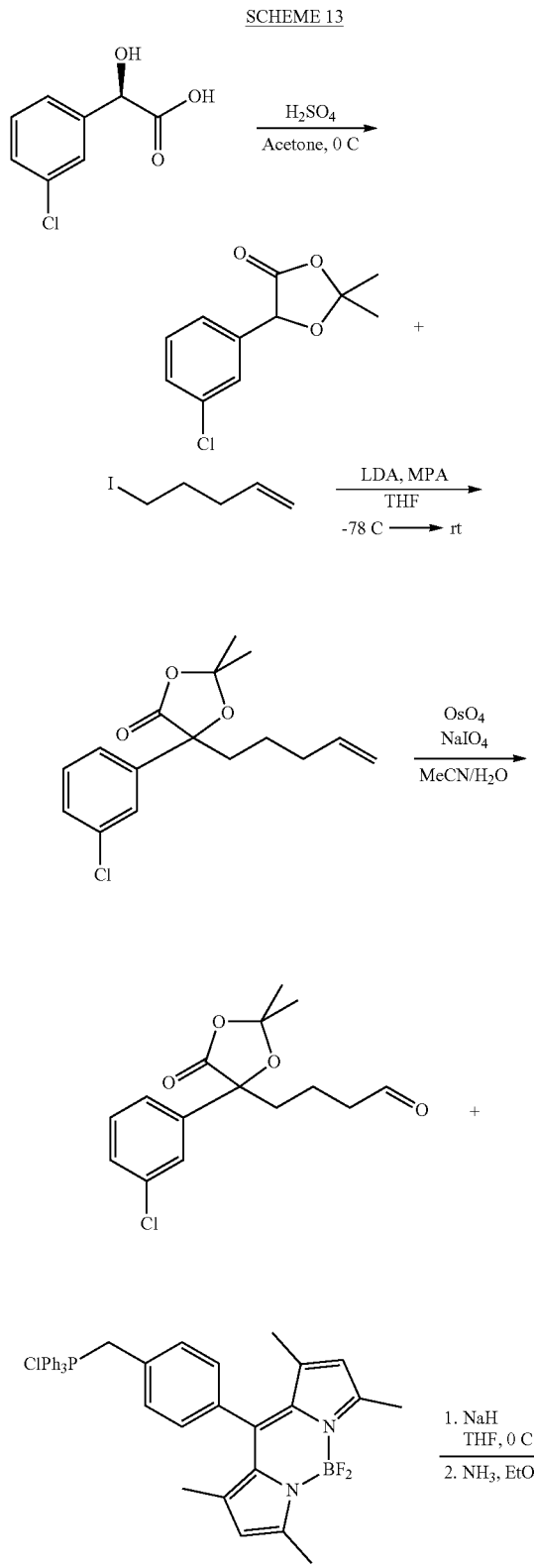

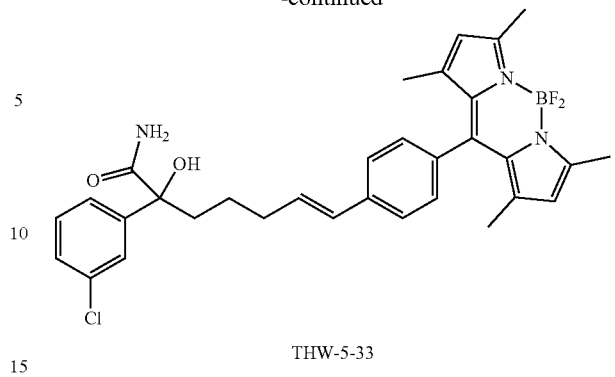

THW-5-33

Tunable fluorophores can have many advantages in early drug discovery. The ability to tune both chemical and physical properties of a moiety while maintaining fluorescence can be extremely useful. For example, optimization of the potency can be achieved while maintaining the diagnostic ability that fluorescence achieves.

The integration of tunable fluorophores designed within the active pharmacophore represents a new paradigm in early drug discovery. Such active theranostics will not only treat but aid in the visualization of disease in vivo as well as ex vivo.

a) Materials and Methods

Chemicals were purchased from Aldrich Chemical Company, and were used without any further purification. Dry solvents were dried over 4 Å molecular sieves prior to use. Air-sensitive reactions were carried out in oven-dried glassware under an $N_2$ atmosphere. Flash column chromatography separations were done on a Biotage SP1 system monitoring at 254 nm. All NMR spectra were recorded on a Varian 400 spectrometer, operating at 400 MHz for $^1$H and 100 MHz for $^{13}$C NMR. Optical rotations were taken on a Bellingham & Stanley ADP220 polarimeter using a 25 mm cell. Chiral HPLC analysis was carried out on a Shimadzu LCMS-2010EV using a ChiralPak AS column monitoring at 254 nm.

(1) Chemistry

2-[(3,5-Dimethyl-2H-pyrrol-2-ylidene)methyl]-3,5-dimethyl-1H-pyrrole monohydrochloride (4 g, 16.89 mmol) was dissolved into 125 ml of dry dichloromethane to which triethylamine (17.09 g, 168.9 mmol) was added and allowed to stir for 15 minutes. The solution was then cooled with an ice bath to control the temperature during the slow addition of boron trifluoride etherate (2185 g, 168.9 mmol). Once the addition was complete, the ice bath was removed and the reaction was allowed to stir at room temperature for 2 hours. The reaction was then quenched with water and extracted three times with dichloromethane. The organic layer was then washed with saturated sodium carbonate. The organic layer was impregnated onto silica gel and then purified via column chromatography (10% dichloromethane in hexanes) to yield 3.44 g of Bodipy (82% yield).

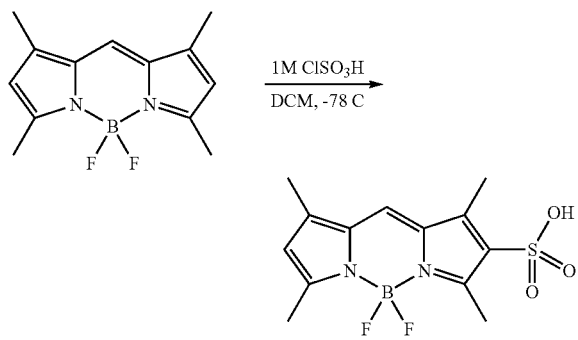

Bodipy (2 g, 8.06 mmol) was dissolved into dichloromethane and cooled to −78 deg. 1M chlorosulfonic acid in acetonitrile (7.9 ml) was added dropwise to the stirred solution. Once the addition was complete, the reaction was allowed to warm to room temperature and stir for 2 hours. The bodipy sulfonic acid precipitate was filtered from the solution and purified via column chromatography (15% methanol in dichloromethane) to yield 741.7 mg (26% yield) of a bright orange solid. The filtrate was then impregnated onto silica gel and purified via column chromatography (10% dichloromethane in hexanes) to recover the starting material Bodipy.

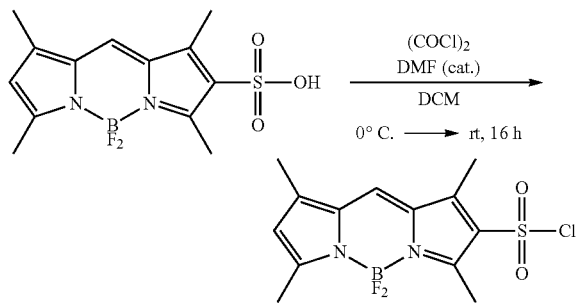

To a stirred solution of the sulfonic acid (0.100 g, 0.28 mmol, 1.0 Eq.) in DCM, at 0 C was added sequentially oxalyl chloride (0.12 mL, 1.42 mmol, 5.0 Eq.) and DMF (0.05 mL). The resulting mixture was stirred up to rt over 16 h. The reaction was washed with water and extracted with DCM. It was washed with a saturated LiCl solution and the organic fraction was dried over sodium sulfate. The product was then concentrated and purified via FCC (1:1 EtOAc/Hex) to yield the sulfonyl chloride (76 mg, 74%).

7. Example 8

Additional Figures

FIGS. 24-60

F. SEQUENCES

Sequences for the disclosed Na channels can be found in for example Genbank, published references, or in for example the publication Yu and Catterall, Overview of the Voltage-gated sodium channel family, Genomoe Biology 2003, 4:207 (2003) and U.S. patent application Ser. No. 11/707,882, filed Feb. 20, 2007 for Human Sodium Channel Isoforms, which are specifically incorporated by reference at least for material related to the sequence of any human Na Channel Isoform.

G. REFERENCES

Abdul M, Hoosein N. Voltage-gated sodium ion channels in prostate cancer: expression and activity. Anticancer Res 2002; 22:1727-30.
Abrahmsen L et al., Biochemistry, 30:4151 (1991)
Agbottah E, de La Fuente C, Nekhai S, Barnett A, Gianella-Borradori A, Pumfery A, Kashanchi F (28 Jan. 2005). "Antiviral activity of CYC202 in HIV-1-infected cells". *J. Biol. Chem.* 280 (4): 3029-42.
Agrawal et al., *Exper. Hematol.* 24:738-747, 1996
Ahern, C. A., Eastwood, A. L., Dougherty, D. A., and Horn, R. Electrostatic Contributions of Aromatic Residues in the Local Anesthetic Receptor of Voltage-Gated Sodium Channels. *Circ. Res.* 2008, 102, 86-94.
Almquist et al. J. Med. Chem. 23:1392-1398 (1980)
Alvarez and Curiel, *Hum. Gene Ther.* 8:597-613, 1997
Amaya F, Decosterd I, Samad T A, et al. Diversity of expression of the sensory neuron-specific TTX-resistant voltage-gated sodium ion channels SNS and SNS2. Mol Cell Neurosci 2000; 15:331-42.
Anderson, J. D., Hansen, T. P., Lenkowski, P. W., Walls, A. M., Choudhury, I. M., Schenck, H. A., Friehling, M., Holl, G. M., Patel, M. K., Sikes, R. A., and Brown, M. L. Voltage-Gated Sodium Channel Blockers as Cytostatic Inhibitors of the Androgen-Independent Prostate Cancer Cell Line PC-3. *Mol. Cancer Ther.* 2003, 2, 1149-1154.
Anger, T.; Madge, D. J.; Mulla, M.; Riddall, D. Medicinal Chemistry of Neuronal Voltage-Gated Sodium Channel Blockers. *J. Med. Chem.* 2001, 44, 115-137.
Aronov, A. M., Common Pharmacophores for Uncharged Human Ether-a-go-go-Related Gene (hERG) Blockers. *J. Med. Chem.* 2006, 49, 6917-6921.
Baggiolini M et al. (1992) FEBS Lett. 307:97-101; Clark-Lewis I et al., J. Biol. Chem., 269:16075 (1994); Clark-Lewis I et al., Biochemistry, 30:3128 (1991); Rajarathnam K et al., Biochemistry 33:6623-30 (1994)
Baindur, N., and Triggle, D. J. Selective Fluorescent Ligands for Pharmacological Receptors. *Drug. Dev. Res.* 1994, 33, 373-398.
Baker, M. D.; Wood, J. N. Involvement of Na+ channels in pain pathways. *Trends Pharmacol. Sci.* 2001, 22, 27-31.
Banerjee, M., Poddar, A., Mitra, G., Surolia, A., Owa, T. and Bhattacharyya, B. Sulfonamide Drugs Binding to the Colchicine Site of Tubulin: Thermodynamic Analysis of the Drug-Tubulin Interactions by Isothermal Titration calorimetry. *J. Med. Chem.* 2005, 48, 547-555.
Becher, O. J., and Holland, E. C. Genetically Engineered Models Have Advantages over Xenografts for Preclinical Studies. *Cancer Res* 2006, 66, 3355-3359.
Becker F, Murthi K, Smith C, Come J, Costa-Roldan N, Kaufmann C et al. A three-hybrid approach to scanning the proteome for targets of small molecule kinase inhibitors. Chem Biol 2004; 11:211-223.
Bennett, E. S., Smith, B. A., and Harper, J. M. Voltage-Gated $Na^+$ Channels Confer Invasive Properties on Human Prostate Cancer Cells. *Eur. J. Physiol.* 2004, 447, 908-914.
Berendsen, H. J. C.; Postma, J. P. M.; Vangunsteren, W. F.; Dinola, A.; Haak, J. R. Molecular-dynamics with coupling to an external bath. *J. Chem. Phys.* 1984, 81, 3684-3690.

Biton, V. Clinical Pharmacology and Mechanism of Action of Zonisamide. *Clin. Neuropharmacol.* 2007, 30, 230.

Blay, G.; Cardona, L.; Torres, L.; Pedro, J. R., Enantioselective synthesis of (S)-3-hydroxy-3-phenyl-3,4-dihydroquinolin-2(1H)-one ring system. *Synthesis.* 2007, 1, 108-112.

Blay, G.; Fernandez, I.; Monje, B.; Munoz, M. C.; Pedro, J. R.; Vila, C., Enantioselective synthesis of 2-substituted-1, 4-diketones from (S)-mandelic acid enolate and alpha, beta-enones. *Tetrahedron.* 2006, 62, 9174-9182.

Boerner et al. (*J. Immunol.,* 147(1):86-95, 1991)

Brackenbury, W. J., and Djamgoz, M. B. A. Activity-Dependent Regulation of Voltage-Gated $Na^+$ Channel Expression in Mat-LyLu Rat Prostate Cancer Cell Line. *J. Physiol.* 2006, 573, 343-356.

Brackenbury, W. J., and Djamgoz, M. B. A. Nerve Growth Factor Enhances Voltage-Gated $Na^+$ Channel Activity and Transwell Migration in Mat-LyLu Rat Prostate Cancer Cell Line. *J. Cell. Physiol.* 2007, 210, 602-608.

Brackenbury, W. J., Djamgoz, M. B. A., and Isom, L. L. An Emerging Role for Voltage-Gated $Na^+$ Channels in Cellular Migration: Regulation of Central Nervous System Development and Potentiation of Invasive Cancers. *The Neuroscientist* 2008, 14, 571-583.

Brown and Greene, *DNA and Cell Biology* 10:6, 399-409 (1991)

Brown, M. L. et al. *J. Med. Chem.* 1997, 40, 602-607

Brown, M. L., Zha, C. C., Van Dyke, C. C., Brown, G. B., and Brouillette, W. J. Comparative Molecular Field Analysis of Hydantoin Binding to the Neuronal Voltage-Dependent Sodium Channel. *J. Med. Chem.* 1999, 42, 1537-1545.

Bruggermann et al., *Year in Immunol.,* 7:33 (1993)

Cahill et al., TIBS, 14(10):400-403 (1989); Benner, TIB Tech, 12:158-163 (1994)

Caine, D. S.; Paige, M. A., Reactions of a 3(2H)-furanone lithium enolate with 4-halocrotonates. *Synlett.* 1999, 9, 1391-1394.

Carrara et al., Proc. Natl. Acad. Sci. (USA) 92:2627-2631 (1995)

Case, D. A.; Darden, T. A.; Cheatham, T. E.; Simmerling, C. L.; Wang, J.; Duke, R. E.; Luo, R.; Merz, K. M.; Pearlman, D. A.; Crowley, M.; Walker, R. C.; Zhang, W.; Wang, B.; Hayik, S.; Roitberg, A.; Seabra, G.; Wong, K. F.; Paesani, F.; Wu, X.; Brozell, S.; Tsui, V.; Gohlke, H.; Yang, L.; Tan, C.; Mongan, J.; Hornak, V.; Cui, G.; Beroza, P.; Mathews, D. H.; Schafmeister, C.; Ross, W. S.; Kollman, P. A. (2006). AMBER 9, University of California, San Francisco.

Case, D. A.; Darden, T. A.; Cheatham, T. E.; Simmerling, C. L.; Wang, J.; Duke, R. E.; Luo, R.; Merz, K. M.; Wang, B.; Pearlman, D. A.; Crowley, M.; Brozell, S.; Tsui, V.; Gohlke, H.; Mongan, J.; Hornak, V.; Cui, G.; Beroza, P.; Schafmeister, C.; Caldwell, J. W.; Ross, W. S.; Kollman, P. A. 2004 AMBER 8. San Francisco: University of California.

Catterall, W. A. Cellular and Molecular Biology of Voltage-Gated Sodium Channels. *Physiol. Rev.* 1992, 72, S15-S48.

Catterall, W. A. Molecular Mechanisms of Gating and Drug Block of Sodium Channels. *Novartis Foundation Symposium* 2002, 241, 206-225.

Catterall, W. A., From ionic currents to molecular mechanisms: the structure and function of voltage-gated sodium channels. *Neuron.* 2000, 26, 13-25.

Cestèle S, Catterall W A. Molecular mechanisms of neurotoxin action on voltage-gated sodium channels. Biochimie 2000; 82:883-92.

Chang Y T, Gray N S, Rosania G R, Sutherlin D P, Kwon S, Norman T C et al. Synthesis and application of functionally diverse 2,6,9-trisubstituted purine libraries as CDK inhibitors. Chem Biol 1999; 6:361-375.

Choudhury-Mukherjee, I., Schenck, H. A., Cechova, S., Pajewski, T. N., Kapur, J., Ellena, J., Cafiso, D. S., and Brown, M. L. Design, Synthesis, and Evaluation of Analogues of 3,3,3-Trifluoro-2-Hydroxy-2-Phenyl-Propionamide as Orally Available General Anesthetics. *J. Med. Chem.* 2003, 46, 2494-2501.

Chu X J, DePinto W, Bartkovitz D, So S S, Vu B T, Packman K et al. Discovery of [4-Amino-2-(1-methanesulfonylpiperidin-4-ylamino)pyrimidin-5-yl](2,3-difluoro-6-methoxyphenyl)methanone (R547), a potent and selective cyclin-dependent kinase inhibitor with significant in vivo antitumor activity. J Med Chem 2006; 49:6549-6560.

Cohen A, Ziv I, Aloya T, Levin G, Kidron D, Grimberg H et al. Monitoring of chemotherapy-induced cell death in melanoma tumors by N,N'-Didansyl-L-cystine. Technol Cancer Res Treat 2007; 6:221-234.

Cohen B. A., et al., Proc. Natl. Acad. Sci. USA 95(24):14272-7 (1998)

Cole et al. (Monoclonal Antibodies and Cancer Therapy, Alan R. Liss, p. 77, 1985)

Collins I, Garrett M D. Targeting the cell division cycle in cancer: CDK and cell cycle checkpoint kinase inhibitors. Curr Opin Pharmacol 2005; 5:366-373.

Collins, S. P.; Reoma, J. L.; Gamm, D. M.; Uhler, M. D. LKB1, a novel serine/threonine protein kinase and potential tumour suppressor, is phosphorylated by cAMP-dependent protein kinase (PKA) and prenylated in vivo. *Biochem J.* 2000, 345, 673-80.

Correa, F. M. A., Innis, R. B., Rouot, B., Pasternak, G. W., and Snyder, S. H. Fluorescent Probes of α- and β-Biochemical and Histochemical Evaluation. *Neurosci. Lett.* 1980, 16, 47-53.

Costa, A. L.; Piazza, M. G.; Tagliavini, E.; Trombini, c.; Umani-Ronchi, A. Catalytic Asymmetric Synthesis of Homoallylic Alcohols. *J. Am. Chem. Soc.* 1993, 115, 7001-7002.

Crane, C. M., Kaiser, J., Ramsden, N. L., Lauw, S., Rohdich, F., Eisenreich, W., Hunter, W. N., Bacher, A., and Diederich, F. Fluorescent Inhibitors for IspF, an Enzyme in the Non-Mevalonate Pathway for Isoprenoid Biosynthesis and a Potential Target for Antimalarial Therapy. *Angew. Chem. Int. Ed.* 2006, 45, 1069-1074.

Creighton, T. E., Proteins: Structure and Molecular Properties, W. H. Freeman & Co., San Francisco pp 79-86 [1983]

Crystal, *Hum. Gene Ther.* 8:985-1001, 1997

Leonard G. Presta, *Curr. Opin. Struct. Biol.,* 2:593-596 (1992)

Cyclacel Begins a Phase IIb Randomized Trial of Seliciclib for Previously Treated Non-Small Cell Lung Cancer". BIOWIRE (Jun. 29, 2006).

Cyclacel Pharmaceuticals Reports Second Quarter 2006 Financial Results". Business Wire (Aug. 14, 2006).

Cyclacel Reports Interim Seliciclib Phase IIa Data at 2005 ASCO". Business Wire (May 15, 2005).

D. W. Van Krevelen, Properties of Polymers: Their Estimation and Correlation With Chemical Structure, $2^{nd}$ Ed. (1976, Elsevier), pp. 129-159

Damianovich M, Ziv I, Heyman S N, Rosen S, Shina A, Kidron D et al. ApoSense: a novel technology for functional molecular imaging of cell death in models of acute renal tubular necrosis. Eur J Nucl Med Mol Imaging 2006; 33:281-291.

Darden, T.; York, D.; Pedersen, L. Particle mesh Ewald: an N-Log(N) method for Ewald sums in large systems. *J. Chem. Phys.* 1993, 98, 10089-10092

Davies T. G.; Pratt, D. J.; Endicott, J. A.; Johnson, L. N.; Noble, M. E. M. (2002). Structure-based design of cyclin-dependent kinase inhibitors. *Pharmacology & Therapeutics.* 93, 125-133.

Davies T G, Bentley J, Arris C E, Boyle F T, Curtin N J, Endicott J A et al. Structure-based design of a potent purine-based cyclin-dependent kinase inhibitor. Nat Struct Biol 2002; 9:745-749.

Dawson et al. Synthesis of Proteins by Native Chemical Ligation. Science, 266:776-779 (1994)

De Azevedo W F, Leclerc S, Meijer L, Havlicek L, Strnad M, Kim S H (1997). "Inhibition of cyclin-dependent kinases by purine analogues: crystal structure of human cdk2 complexed with roscovitine". *Eur J Biochem* 243 (1-2): 518-526.

Deb T B, Coticchia C M, Dickson R B. Calmodulin-mediated activation of Akt regulates survival of c-Myc-overexpressing mouse mammary carcinoma cells. J Biol Chem 2004; 279:38903-38911.

deLisle Milton R C et al., Techniques in Protein Chemistry IV. Academic Press, New York, pp. 257-267 (1992)

Diss J K. J, Archer S N, Hirano J, Fraser S P, Djamgoz M B A. Expression profiles of voltage-gated $Na^+$ channel α-subunit genes in rat and human prostate cancer cell lines. Prostate 2001; 48:165-78.

Diss, J. K. J., Stewart, D., Poni, F., Foster, C. S., Walker, M. M., Patel, A., and Djamgoz, M. B. A. A Potential Novel Marker for Human Prostate Cancer: Voltage-Gated Sodium Channel Expression in vitro. *Prostate Cancer and Prostatic Diseases* 2005, 8, 266-273.

Djamgoz M B A, Mycielska M, Madeja Z, Fraser S P, Korohoda W. Directional movement of rat prostate cancer cells in direct-current electric field: involvement of voltage-gated $Na^+$ channel activity. J Cell Sci 2001; 114:2697-705.

Doyle E L, Hunter C A, Phillips H C, Webb S J, Williams N H. Cooperative binding at lipid bilayer membrane surfaces. J Am Chem Soc 2003; 125:4593-4599.

Drews, J. Drug Discovery: A Historical Perspective. *Science* 2000, 287, 1960-1964.

Edwards, D. J.; Marquez, B. L.; Nogle, L. M.; McPhail, K.; Goeger, D. E.; Roberts, M. A.; Gerwick, W. H. Structure and Biosynthesis of the Jamaicamides, New Mixed Polyketide-Peptide Neurotoxins from the Marine Cyanobacterium *Lyngbya majuscula. Chem. and Biol.* 2004, 11, 817-833.

Ellington and Szostak, 1992; Bock et al, 1992

Fadok V A, Voelker D R, Campbell P A, Cohen J J, Bratton D L, Henson P M. Exposure of phosphatidylserine on the surface of apoptotic lymphocytes triggers specific recognition and removal by macrophages. J Immunol 1992; 148:2207-2216.

Felix, J. P.; Williams, B. S.; Priest, B. T.; Brochu, R. M.; Dick, I. E.; Warren, V. A.; Yan, L.; Slaughter, R. S.; Kaczorowski, G. J.; Smith, M. M.; Garcia, M. L. Functional Assay of Voltage-Gated Sodium Channels Using Membrane Potential-Sensitive Dyes. *Assay and Drug Development Technologies.* 2004, 2, 260-268.

Ferrone et al., eds., Handbook of Monoclonal Antibodies, Noges Publications, Park Ridge, N.J., (1985) ch. 22 and pp. 303-357; Smith et al., Antibodies in Human Diagnosis and Therapy, Haber et al., eds., Raven Press, New York (1977) pp. 365-389.

Fields and Song, *Nature* 340:245-6 (1989)

Fiske, J. L.; Fomin, V. P.; Brown, M. L.; Duncan, R. L.; Sikes, R. A. Voltage-sensitive ion channels and cancer. *Cancer Metastasis Rev.* 2006, 25, 493-500.

Fraser S P, Ding Y, Liu A, Foster C S, Djamgoz M B A. Tetrodotoxin suppresses morphological enhancement of the metastatic MAT-LyLu rat prostate cancer cell line. Cell Tissue Res 1999; 295:505-12.

Fraser S P, Salvador V, Manning E A, et al. Contribution of functional voltage-gated $Na^+$ channel expression to cell behaviors involved in the metastatic cascade in rat prostate cancer: I. lateral motility. J Cell Physiol 2003; 195:479-87.

Fraser, S. P., and Pardo, L. A. Ion Channels: Functional Expression and Therapeutic Potential in Cancer. *EMBO Reports* 2008, 9, 512-515.

Fraser, S. P., Grimes, J. A., and Djamgos, M. B. A. Effects of Voltage-Gated Ion Channel Modulators on Rat Prostatic Cancer Cell Proliferation: Comparison of Strongly and Weakly Metastatic Cell Lines. *The Prostate* 2000, 44, 61-76.

George, A. L., Jr., Inherited disorders of voltage-gated sodium channels. *J. Clin. Invest.* 2005, 115, 1990-1999.

Goldin, A. L., Resurgence of sodium channel research. *Annu. Rev. Physiol.* 2001, 63, 871-894.

Goodman et al., *Blood* 84:1492-1500, 1994

Grant G A (1992) Synthetic Peptides: A User Guide. W.H. Freeman and Co., N.Y. (1992); Bodansky M and Trost B., Ed. (1993) Principles of Peptide Synthesis. Springer-Verlag Inc., NY Gray N S, Wodicka L, Thunnissen A M, Norman T C, Kwon S, Espinoza F H et al. Exploiting chemical libraries, structure, and genomics in the search for kinase inhibitors. Science 1998; 281:533-538.

Grimes J A, Fraser S P, Stephens G J, et al. Differential expression of voltage-activated $Na^+$ currents in two prostatic tumour cell lines: contribution to invasiveness in vitro FEBS Lett 1995; 369:290-4.

Grimes, J. A., and Djamgoz, M. B. A. Electrophysiological Characterization of Voltage-Gated Na Current Expressed in the Highly Metastatic Mat-LyLu Cell Line of Rat Prostate Cancer. *J. Cell. Physiol.* 1998, 175, 50-58.

Grimm, J. B., Stables, J. P., and Brown, M. L. Design, Synthesis, and Development of Novel Caprolactam Anticonvulsants. *Bioorg. Med. Chem.* 2003, 11, 4133-4141.

Grover, P. T.; Bhongle, N. N.; Wald, S. A.; Senanayake, C. H., Chiral mandelic acid template provides a highly practical solution for (S)-oxybutynin synthesis. *J. Org. Chem.* 2000, 65, 6283-6287.

Gruzel, O., Temperini, C., Innocenti, A., Scozzafava, A., Salmon, A., and Supuran, C. Carbonic Anhydrase Inhibitors. Interaction of 2-(hydrazinocarbonyl)-3-phenyl-1H-indole-5-sulfonamide with 12 Mammalian Isoforms Kinetic and X-Ray Crystallographic Studies. *Bioorg. Med. Chem. Lett.* 2008, 18, 152-158.

Haddad, T. C., and Yee, D. Of Mice and (Wo)Men: Is This Any Way to Test a New Drug. *J. Clin. Oncol.* 2008, 26, 830-832.

Hammerer P G, Kattan M W, Mottet N, Prayer-Galetti T. Using prostate-specific antigen screening and nomograms to assess risk and predict outcomes in the management of prostate cancer. BJU Int 2006; 98:11-19.

Handbook of Monoclonal Antibodies, Ferrone et al., eds., Noges Publications, Park Ridge, N.J., (1985) ch. 22 and pp. 303-357; Smith et al., Antibodies in Human Diagnosis and Therapy, Haber et al., eds., Raven Press, New York (1977) pp. 365-389.

Hann J. Chem. Soc Perkin Trans. I 307-314 (1982)

Hanson, R. N.; Lee, C. Y.; Friel, C. J.; Dilis, R.; Hughes, A.; DeSombre, E. R. Synthesis and evaluation of 17α-20E-21-(4-Substituted phenyl)-19-norpregna-1,3,5(10),20-tetraene-3,17β-diols as probes for the estrogen receptor αα hormone binding domain. *J. Med. Chem.* 2003, 46, 2865-2876

Harper J W, Elledge S J. Cdk inhibitors in development and cancer. Curr Opin Genet Dev 1996; 6:56-64.

Haydon, D. A., and Urban, B. W. The Action of Alcohols and Other Non-Ionic Surface Active Substances on the Sodium Current of the Squid Giant Axon. *J. Physiol.* 1983, 341, 411-427.

Hellerstedt, B. A.; Pienta, K. J. The current state of hormonal therapy for prostate cancer. *CA Cancer J Clin.* 2002, 52, 154-179.

Hermetter, A., Schoize, H., Stutz, A. E., Withers, S. G., and Wrodnigg, T. M. Powerful Probes for Glycosidases: Novel, Fluorescently Tagged Glycosidase Inhibitors. *Bioorg. Med. Chem. Lett.* 2001, 11, 1339-1342.

Holladay et al. Tetrahedron. Lett 24:4401-4404 (1983)

Holmes, C., Xianfeng, L., Pan, Y., Xu, C., Bhandari, A., Moody, C., Miguel, J., Ferla, S., De Francisco, N., Frederick, B., Zhou, S., Macher, N., Jang, L., Irvine, J., and Grove, J. Discovery and Structure-Activity Relationships of Novel Sulfonamides as Potent PTP1B Inhibitors. *Bioorg. Med. Chem. Lett.* 2005, 15, 4336-4341.

Hoogenboom et al., *J. Mol. Biol.,* 227:381, 1991; Marks et al., *J. Mol. Biol.,* 222:581, 1991).

Horishita, T., and Harris, R. A. n-Alcohols Inhibit, Voltage-Gated $Na^+$ Channels Expressed in *Xenopus* Oocytes. *JPET* 2008, 326, 270-277.

Hruby Life Sci 31:189-199 (1982)

Hudson, D. et al., Int J Pept Prot Res 14:177-185 (1979)

Hughes et al., *Cancer Research,* 49:6214-6220, (1989); and Litzinger and Huang, *Biochimica et Biophysica Acta,* 1104:179-187, (1992)

Huwe A, Mazitschek R, Giannis A. Small molecules as inhibitors of cyclin-dependent kinases. Angew Chem Int Ed Engl 2003; 42:2122-2138.

Ibba and Hennecke, Bio/technology, 12:678-682 (1994)

Ibba, Biotechnology & Genetic Enginerring Reviews 13:197-216 (1995)

Jaeger et al. *Methods Enzymol.* 183:281-306, 1989

Jaeger et al. *Proc. Natl. Acad. Sci. USA* 86:7706-7710, 1989

Jakobovits et al., *Nature,* 362:255-258 (1993)

Jakobovits et al., *Proc. Natl. Acad. Sci. USA,* 90:2551-255 (1993)

Janout, V., Lanier, M. and Regan, S. L. Molecular Umbrellas. *J. Am. Chem. Soc.* 1996, 118, 1573-1574.

Jennings-White et al. Tetrahedron Lett 23:2533 (1982)

Johnson, J. I., Decker, S., Zaharevitz, D., Rubinstein, L. V., Venditti, J. M., Schepartz, S., Kalyandrug, S., Christian, M., Arbuck, S., Hollingshead, M. and Sausville, E. A. Relationships Between Drug Activity in NCI Preclinical In Vitro and In Vivo Models and Early Clinical Trials. *British Journal of Cancer* 2001, 84, 1424-1431.

Jones et al., Nature, 321:522-525 (1986)

Jones, T. A.; Zou, J. Y.; Cowan, S. W.; Kjeldgaard, M. Improved methods for building protein models in electron density maps and the location of errors in these models. *Acta Cryst.* 1991, A47, 110-119.

Knockaert M, Gray N, Damiens E, Chang Y T, Grellier P, Grant K et al. Intracellular targets of cyclin-dependent kinase inhibitors: identification by affinity chromatography using immobilised inhibitors. Chem Biol 2000; 7:411-422.

Knockaert, M; Greengard, P.; Meijer, L. (2002). Pharmacological inhibitors of cyclin-dependent kinases. *Trends in Pharmacological Sciences.* 23, 417-425.

Ko, S. H.; Jochnowitz, N.; Lenkowski, P. W.; Batts, T. W.; Davis, G. C.; Martin, W. J.; Brown, M. L.; Patel, M. K., Reversal of neuropathic pain by alpha-hydroxyphenylamide: A novel sodium channel antagonist. *Neuropharmacology.* 2006, 50, 865-873.

Kohler and Milstein, *Nature,* 256:495 (1975)

Koopman G, Reutelingsperger C P, Kuijten G A, Keehnen R M, Pals S T, van Oers M H. Annexin V for flow cytometric detection of phosphatidylserine expression on B cells undergoing apoptosis. Blood 1994; 84:1415-1420.

Laniado M E, Lalani E-N, Fraser S P, et al. Expression and functional analysis of voltage-activated $Na^+$ channels in human prostate cancer cell lines and their contribution to invasion in vitro. Am J Pathol 1997; 150:1213-21.

Laniado, M. E.; Fraser, S. P.; Djamgoz, M. B. A. Voltage-gated K+ channel activity in human prostate cancer cell lines of markedly different metastatic potential: distinguishing characteristics of PC-3 and LNCaP cells. *Prostate* (N.Y., N.Y., U.S.). 2001, 46, 262-274.

Lansdell, M. I., Burring, D. J., Hepworth, D., Strawbridge, M., Graham, E., Guyot, T., Betson, M. S., and Hart, J. D. Design and Synthesis of Fluorescent SGLT2 Inhibitors. *Bioorg. Med. Chem. Lett.* 2008, 18, 4944-4947.

Lavis, L. D., and Raines, R. T. Bright Ideas for Chemical Biology. *ACS Chem. Biol.* 2008, 3, 142-155.

Lenkowski, P. W. et al. *Eur. J. Pharm. Sci.,* 2004, 21, 635-644

Lenkowski, P. W., Batts, T. W., Smith, M. D., Ko, S., Jones, P. J., Taylor, C. H., McCusker, A. K., Davis, G. C., Hartmann, H. A., White, H. S., Brown, M. L., and Patel, M. K. A Pharmacophore Derived Phenyloin Analogue with Increased Affinity for Slow Inactiviated Sodium Channels Exhibits a Desired Anticonvulsant Profile. *Neuropharmacology* 2007, 52, 1044-1054.

LePage, K. T.; Goeger, D.; Yokokawa, F.; Asano, T.; Shiori, T.; Gerwick, W. H.; Murray, T. F.; The neurotoxic lipopeptide kalkitoxin interacts with voltage-sensitive sodium channels in cerebellar granule neurons. *Toxicol. Lett.* 2005, 158, 133-139.

Letsinger et al., Proc. Natl. Acad. Sci. USA, 1989, 86, 6553-6556

Li H, Ahonen T J, Alanen K, et al. Activation of signal transducer and activator of transcription 5 in human prostate cancer is associated with high histological grade. Cancer Res 2004; 64:4774-82.

Li, W. l.; Berma, F. W.; Okino, T.; Yokokawa, F.; Shiori, T.; Gerwick, W. H.; Murray, T. F. Antillatoxin is a marine cyanobacterial toxin that potently activates voltage-gated sodium channels. *Proc. Natl. Acad. USA,* 2003, 98, 7599-7604.

Li, Y.; Chen, l.; Cao, X.-P. A Stereoselective Synthesis of (4E,7S)-(+7-Methoxydodec-4-enoic Acid. *Synlett* 2006, 320-324.

Linford, N. J.; Cantrell, A. R.; Qu, Y.; Scheuer, T.; Catterall, W. A., Interaction of batrachotoxin with the local anesthetic receptor site in transmembrane segment IVS6 of the voltage-gated sodium channel. *Proc. Natl. Acad. Sci. U.S.A.* 1998, 95, 13947-13952.

Lipkind, G. M.; Fozzard, H. A., Molecular modeling of local anesthetic drug binding by voltage-gated sodium channels. *Mol. Pharmacol.* 2005, 68, 1611-1622.

Liu, Y. M.; Liu, H.; Zhong, B. H.; Liu, K. L., Stereoselective synthesis of the optical isomers of a new muscarinic receptor antagonist, HL-031120. *Synth. Commun.* 2006, 36, 1815-1822.

Luo, N., Zhang, C., Hirt, D. E., and Husson, S. M. Adsorption of Fluorescently Labeled Protein Residues on Poly(ethylene-co-acrylic acid) Films Modified with Affinity Functionalities. *Colloids Surf B.* 2006, 50, 89-96.

Mattei et al., *J. Neurosci. Res.*, 1999, 55: 666-673)

McGrath, J. C., and Daly, C. J. Do Fluorescent Drugs Show You More Than You Wanted to Know?*Br. J. Pharmacol.* 2003, 139, 187-189.

Meijer L, Raymond E. Roscovitine and other purines as kinase inhibitors. From starfish oocytes to clinical trials. Acc Chem Res 2003; 36:417-425.

Minor, W.; Cymborowski, M.; Otwinowski, Z.; Chruszcz, M. HKL-3000: the integration of data reduction and structure solution—from diffraction images to an initial model in minutes. *Acta Cryst.* 2006, D62, 859-866.

Misaki, T.; Ureshino, S.; Nagase, R.; Oguni, Y.; Tanabe, Y., Improved Practical Asymmetric Synthesis of alpha-Alkylmandelic Acids Utilizing Highly Diastereoselective Alkylation of 5-Aryl-2-(1-naphthyl)-1,3-dioxolan-4-ones. *Org. Process Res. Dev.* 2006, 10, 500-504.

Mitani et al., *Hum. Gene Ther.* 5:941-948, 1994

Morgan D O. Cyclin-dependent kinases: engines, clocks, and microprocessors. Annu Rev Cell Dev Biol 1997; 13:261-291.

Morris, G. M., Goodsell, D. S., Holliday, R. S., Huey, R., Hart, W. E., Belew, R. K., and Olson, A. J. Automated Docking Using a Lamarckian Genetic Algorithm and Empirical Binding Free Energy Function. *J. Comput. Chem.* 1998, 19, 1639-1662.

Morrison et al., *Proc. Natl. Acad. Sci. USA*, 81:6851-6855 (1984

Mueller, C.; Voss, G.; Gerlach, H. Synthesis of (4E,7S)-(−)-methoxy-4-tetradecenoic acid, a major constituent of the marine cyanophyte *Lyngbya majuscula. Liebigs Ann. Chem.* 1995, 4, 673-676.

Mycielska M E, Fraser S P, Szatkowski M, Djamgoz M B A. Contribution of functional voltage-gated channel expression to cell behaviors involved in the metastatic cascade in rat prostate cancer: II. secretory membrane activity. J Cell Physiol 2003; 195:461-69.

Mycielska M E, Palmer C P, Brackenbury W J, Djamgoz M B A. Expression of $Na^+$-dependent citrate transport in a strongly metastatic human prostate cancer PC-3M cell line: regulation by voltage-gated $Na^+$ channel activity. J Physiol 2005; 563:393-408.

Nagase, R.; Oguni, Y.; Misaki, T.; Tanabe, Y., Practical and robust method for the preparation of Seebach and Frater's chiral template, cis-2-substituted 5-methyl(or phenyl)-1,3-dioxolan-4-ones. *Synthesis.* 2006, 22, 3915-3917.

Naidini et al., *Science* 272:263-267, 1996

Nau, C., and Wang, G. K. Interactions of Local Anesthetics with Voltage-Gated $Na^+$ Channels. *J. Membrane Biol.* 2004, 201, 1-8.

Needleman and Wunsch, J. Mol. Biol. 48: 443 (1970)

Nigg E A. Cyclin-dependent protein kinases: key regulators of the eukaryotic cell cycle. Bioessays 1995; 17:471-480.

Nigg E A. Targets of cyclin-dependent protein kinases. Curr Opin Cell Biol 1993; 5:187-193.

Otwinowski, Z.; Minor, W.; *Macromolecular Crystallography, part A*, C. W. Carter, Jr. & R. M. Sweet, Eds.; Academic Press.: New York, pp. 307-326, 1997.

Otwinowski, Z.; Borek, D.; Majewski, W.; Minor, W. 3-(1-Methylpiperidinio)-1-propanesulfonate. *Acta Cryst.* 2003, A59, 228-234.

Palmer, C. P., Mycielska, M. E., Burcu, H., Osman, K., Collins, T., Beckerman, R., Perrett, R., Johnson, H., Aydar, E., and Djamgoz, M. B. A. Single Cell Adhesion Measuring Apparatus (SCAMA): Application to Cancer Cell Lines of Different Metastatic Potential and Voltage-Gated $Na^+$ Channel Expression. *Eur. Biophys. J.* 2008, 37, 359-368.

Pastan et al., *Proc. Natl. Acad. Sci. U.S.A.* 85:4486, 1988; Miller et al., *Mol. Cell. Biol.* 6:2895, 1986

Pearson and Lipman, Proc. Natl. Acad. Sci. U.S.A. 85: 2444 (1988)

Poupaert, J. H., Vandervorst, D., Guiot, P., Moustafa, M. M. M., and Dumont, P. Structure-Activity Relationships of Phenyloin-like Anticonvulsant Drugs. *J. Med. Chem.* 1989, 27, 76-78.

Preussat, K.; Beetz, C.; Schrey, M.; Kraft, R.; Wolfl, S.; Kalff, R.; Patt, S. Expression of voltage-gated potassium channels Kv1.3 and Kv1.5 in human gliomas. *Neurosci. Lett.* 2003, 346, 33-36.

R. A, et al., Clinical Prostate Cancer. 2003, 2, 181-187

Ragsdale, D. S., McPhee, J. C., Scheuer, T., and Catterall, W. A. Molecular Determinants of State-Dependent Block of Sodium Channels by Local Anesthetics. *Science* 1994, 265, 1724-1728.

Reichmann et al., *Nature,* 332:323-327 (1988)

*Remington: The Science and Practice of Pharmacy* (19th ed.) ed. A. R. Gennaro, Mack Publishing Company, Easton, Pa. 1995

Rizo and Gierasch Ann. Rev. Biochem. 61:387 (1992)

Roberts R. W. and Szostak J. W. Proc. Natl. Acad. Sci. USA, 94(23)12997-302 (1997)

Robinson, D., Sandblom, G., Johansson, R., Garmo, H., Stattin, P., Mommsen, S., Varenhorst, E., and the Scandinavian Prostate Cancer Group (SPCG)-5. Prediction of Survival of Metastatic Prostate Cancer Based on Early Serial Measurements of Prostate Specific Antigen and Alkaline Phosphatase. *J. Urol.* 2008, 179, 117-123.

Roddam A W, Duffy M J, Hamdy F C, et al. Use of prostate-specific antigen (PSA) isoforms for the detection of prostate cancer in men with a PSA level of 2-10 ng/ml: systematic review and meta-analysis. Eur Urol 2005; 48:386-99.

Roger, S., Potier, M., Vandier, C., Besson, P., and Le Guennec, J. Y. Voltage-Gated Sodium Channels: New Targets in Cancer Therapy? *Curr. Pharm. Des.* 2006, 12, 3681-3695.

Roger, S., Rollin, J., Barascu, A., Besson, P., Raynal, P. I., Iochmann, S., Lei, M., Bougnoux, P., Gruel, Y., and Le Guennec, J. Y. Voltage-Gated Sodium Channels Potentiate the Invasive Capacities of Human Non-Small-Cell Lung Cancer Cell Lines. *The International Journal of Biochemistry & Cell Biology* 2007, 39, 774-786.

Rosania G R, Merlie J, Jr., Gray N, Chang Y T, Schultz P G, Heald R. A cyclin-dependent kinase inhibitor inducing cancer cell differentiation: biochemical identification using *Xenopus* egg extracts. Proc Natl Acad Sci USA 1999; 96:4797-4802.

Rossi A G, Sawatzky D A, Walker A, Ward C, Sheldrake T A, Riley N A, Caldicott A, Martinez-Losa M, Walker T R, Duffin R, Gray M, Crescenzi E, Martin M C, Brady H J, Savill J S, Dransfield I, Haslett C (2006). "Cyclin-dependent kinase inhibitors enhance the resolution of inflammation by promoting inflammatory cell apoptosis". *Nature Medicine* 12 (9): 1056-1064.

Rotivinen, et al., 1988 *Acta Pharmaceutica Fennica* 97, 159-166; Ripka, *New Scientist* 54-57 (Jun. 16, 1988); McKinaly and Rossmann, 1989 *Annu. Rev. Pharmacol: Toxiciol.* 29, 111-122; Perry and Davies, *QSAR: Quantitative Structure-Activity Relationships in Drug Design* pp. 189-193 (Alan R. Liss, Inc. 1989); Lewis and Dean, 1989 *Proc. R. Soc. Lond.* 236, 125-140 and 141-162; and, with respect to a model enzyme for nucleic acid components, Askew, et al., 1989 *J. Am. Chem. Soc.* 111, 1082-1090.

Sambrook et al., Molecular Cloning: A Laboratory Manual, 2nd Ed., Cold Spring Harbor Laboratory, Cold Spring Harbor, N.Y., 1989; Kunkel et al. Methods Enzymol. 1987: 154:367

Sambrook et al., *Molecular Cloning: A Laboratory Manual*, 2nd Edition (Cold Spring Harbor Laboratory Press, Cold Spring Harbor, N.Y., 1989) Chapters 5, 6) to purely synthetic methods, for example, by the cyanoethyl phosphoramidite method using a Milligen or Beckman System 1Plus DNA synthesizer (for example, Model 8700 automated synthesizer of Milligen-Biosearch, Burlington, Mass. or ABI Model 380B). Synthetic methods useful for making oligonucleotides are also described by Ikuta et al., *Ann. Rev. Biochem.* 53:323-356 (1984), (phosphotriester and phosphite-triester methods), and Narang et al., *Methods Enzymol.*, 65:610-620 (1980), (phosphotriester method). Protein nucleic acid molecules can be made using known methods such as those described by Nielsen et al., *Bioconjug. Chem.* 5:3-7 (1994)

Sankaranarayanan, S.; Sharma, A.; Chattopadhyay, S. Convenient synthesis of (±)- and (S)-antipode of (4E,7S)-7-methoxytetradec-4-enoic acid, the antimicrobial principle of marine cyanophyte. *Tetrahedron Asymm.* 1996, 7, 2639-2643.

Sausville, E. A., and Burger, A. M. Contributions of Human Tumor Xenografts to Anticancer Drug Development. *Cancer Res* 2006, 66, 3351-3354.

Schang L M, Rosenberg A, Schaffer P A (2000). "Roscovitine, a specific inhibitor of cellular cyclin-dependent kinases, inhibits herpes simplex virus DNA synthesis in the presence of viral early proteins". *J Virol.* 74 (5): 2107-20.

Schenck, H. A., Lenkowski, P. W., Choudhury-Mukherjee, I., Ko, S. H., Patel, M. K., and Brown, M. L. Design, Synthesis and Evaluation of Novel Hydroxyamides as Orally Available Anticonvulsants. *Bioorg. Med. Chem.* 2004, 12, 979-993.

Schnolzer, Metal. Science, 256:221 (1992)

Schwartzenberger et al., *Blood* 87:472-478, 1996

Schwartzenberger et al., *Blood* 87:472-478, 1996

Scott, D. F. *J. Hist. Neurosci.*, 1992, 1, 111-118

Seebach, D.; Sting, A. R.; Hoffmann, M. "Self-Regeneration of Stereocenters (SRS)—Applications, Limitations, and Abandonment of a Synthetic Principle." *Angewandte Chemie International Edition in English* 35. 1996, 23-24, 2708-2748.

Senderowicz A M. Small-molecule cyclin-dependent kinase modulators. Oncogene 2003; 22:6609-6620.

Senderowicz, A. M.; Sausville, E. A. (2000). Preclinical and clinical development of cyclin-dependent kinase modulators. *Journal of the National Cancer Institute*. 92, 376-387.

Senter, et al., *Bioconjugate Chem.*, 2:447-451, (1991); Bagshawe, K. D., *Br. J. Cancer*, 60:275-281, (1989); Bagshawe, et al., *Br. J. Cancer*, 58:700-703, (1988); Senter, et al., *Bioconjugate Chem.*, 4:3-9, (1993); Battelli, et al., *Cancer Immunol. Immunother.*, 35:421-425, (1992); Pietersz and McKenzie, *Immunolog. Reviews*, 129:57-80, (1992); and Roffler, et al., *Biochem. Pharmacol*, 42:2062-2065, (1991)

Shao, B., Vitory, S., Ilyin, V. I., Goehring, R. R., Sun, Q., Hogenkamp, D., Hodges, D. D., Islam, K., Sha, D., Zhang, C., Nguyen, P., Robledo, S., Sakellaropoulos, G., and Carter, R. B. Phenoxyphenyl Pyridines as Novel State-Dependent, High-Potency Sodium Channel Inhibitors. *J. Med. Chem.* 2004, 47, 4277-4285.

Shapiro G I. Cyclin-dependent kinase pathways as targets for cancer treatment. J Clin Oncol 2006; 24:1770-1783.

Sharpless, N. E., and DePinho, R. A. The Mighty Mouse: Genetically Engineered Mouse Models in Cancer Drug Development. *Nat. Rev. Drug. Discov.* 2006, 5, 741-754.

Sheldrick, G. M. A short history of SHELX. *Acta Cryst.* 2008, A64, 112-122.

Sherr C J. Cancer cell cycles. Science 1996; 274:1672-1677.

Sikes, R. A., Walls, A. M., Brennen, W. N., Anderson, J. D., Choudhury-Mukherjee, I., Schenck, H. A., and Brown, M. L. Therapeutic Approaches Targeting Prostate Cancer Progression Using Novel Voltage-Gated Ion Channel Blockers. *Clinical Prostate Cancer* 2003, 2, 181-187.

Simone, G., Fiore, A., Menshise, V., Pedone, C., Antel, J., Casini, A., Scozzafava, A., Wurl, M., and Supuran, C. Carbonic Anhydrase Inhibitors. Zonisamide as an Effective Inhibitor of the Cytosolic Isozyme II and Mitrochondrial Isozyme V: Solution and X-Ray Crystallographic Studies. *Bioorg. Med. Chem. Lett.* 2005, 15, 2315-2320.

Singer, E. A., Golijanin, D. J., Miyamoto, H., and Messing, E. M. Androgen Deprivation Therapy for Prostate Cancer. *Expert Opin. Pharmacother.* 2008, 9, 211-228.

Smith and Waterman Adv. Appl. Math. 2: 482 (1981)

Smith, P.; Rhodes, N. P.; Shortland, A. P.; Fraser, S. P.; Djamgoz, M. B. A.; Ke, Y.; Foster, C. S. Sodium channel protein expression enhances the invasiveness of rat and human prostate cancer cells. *FEBS Lett.* 1998, 423, 19-24.

Spatola et al. Life Sci 38:1243-1249 (1986)

Spatola et al. Life Sci 38:1243-1249 (1986)

Spatola, A. F. in Chemistry and Biochemistry of Amino Acids, Peptides, and Proteins, B. Weinstein, eds., Marcel Dekker, New York, p. 267 (1983)

Spatola, A. F., Vega Data (March 1983)

Stearns M E, Jenkins D P, Tew K D. Dansylated estramustine, a fluorescent probe for studies of estramustine uptake and identification of intracellular targets. Proc Natl Acad Sci USA 1985; 82:8483-8487.

Summerer D, Chen S, Wu N, Deiters A, Chin J W, Schultz P G. A genetically encoded fluorescent amino acid. Proc Natl Acad Sci USA 2006; 103:9785-9789.

Szatkowski M, Mycielska M, Knowles R, Kho A, Djamgoz M B A. Electrophysiological recordings from the rat prostate gland in vitro: identified single-cell and transepithelial (lumen) potentials. BJI Int 2000; 86:1068-75

Szelke et al. European Appln, EP 45665 CA (1982)

Szelke et al. European Appln, EP 45665 CA (1982)

Szostak, *TIBS* 19:89, 1992

T. E. Creighton, Proteins: Structure and Molecular Properties, W. H. Freeman & Co., San Francisco pp 79-86 [1983]

Tan, L. T.; Okino, T.; Gerwick, W. H. Hermitamides A and B, Toxic Malyngamide-Type Natural Products from the Marine Cyanobacterium *Lyngbya majuscula*. *J. Nat. Prod.* 2000, 63, 952-955.

The End of the Beginning? *Nat. Rev. Drug. Discov.* 2006, 5, 705.

Thompson, J. D.; Higgins, D. G.; Gibson, T. J. CLUSTAL W: improving the sensitivity of progressive multiple sequence alignment through sequence weighting, position-specific gap penalties and weight matrix choice. *Nucleic Acids Research.* 1994, 22, 4673-4680.

Thorson et al., Methods in Molec. Biol. 77:43-73 (1991)

Toledo-Aral J J, Moss B L, He Z-J, et al. Identification of PN1, a predominant voltage-dependent sodium channel expressed principally in peripheral neurons. *Proc. Natl. Acad. Sci.* 1997; 94:1527-32.

U.S. Food and Drug Administration, Center for Drug Evaluation and Research. http://www.accessdata.fda.gov/scripts/cder/drugsatfda/. (November 2008).

Uysal-Onganer, P., and Djamgoz, M. B. A. Epidermal Growth Factor Potentiates in vitro Metastatic Behaviour of Human Prostate Cancer PC-3M Cells: Involvement of Voltage-Gated Sodium Channel. *Molecular Cancer* 2007, 6, 76.

Van Krevelen, D. W., Properties of Polymers: Their Estimation and Correlation With Chemical Structure, $2^{nd}$ Ed. (1976, Elsevier), pp. 129-159

Vermeulen K, Van Bockstaele D R, Berneman Z N. The cell cycle: a review of regulation, deregulation and therapeutic targets in cancer. Cell Prolif 2003; 36:131-149.

Virolleaud, M.-A.; Menant, C.; Fenet, B.; Piva, O. Total and formal enantioselective synthesis of lyngbic acid and hermitamides A and B. *Tetrahedron Lett.* 2006, 47, 5127-5130.

Vol. 1, Issue 3, Peptide Backbone Modifications (general review); Morley, Trends Pharm Sci (1980) pp. 463-468

Wang, J.; Penna, K. D.; Wang, H.; Karczewski, J.; Connolly, T. M.; Koblan, K. S.; Bennett, P. B.; Salata, J. J.;. *Functional and pharmacological properties of canine ERG potassium channels*. Am J Physiol Heart Circ Physiol, 2003, 284: H256-H267.

Wang, X. T.; Nagaba, Y.; Cross, H. S.; Wrba, F.; Zhang, L.; Guggino, S. E. The mRNA of L-Type calcium channel elevated in colon cancer: Protein distribution in normal and cancerous colon. Am. J. Pathol. 2000, 157, 1549-1562.

Weber, G., and Farris, F. Synthesis and Spectral Properties of a Hydrophobic Fluorescent Probe: 6-Propionyl-2-(dimethylamino)naphthalene. *Biochemistry* 1979, 18, 3075-3078.

WO 94/29348 published Dec. 22, 1994 and U.S. Pat. No. 4,342,566.

Yale, and Forster and Altman, *Science* 238:407-409 (1990)

Yarov-Yarovoy, V., Brown, J., Sharp, E. M., Clare, J. J., Scheuer, T., and Catterall, W. A. Molecular Determinants of Voltage-Dependent Gating and Binding of Pore-Blocking Drugs in Transmembrane Segment IIIS6 of the Sodium Channel α-Subunit. *J. Biol. Chem.* 2001, 276, 20-27.

Yarov-Yarovoy, V., McPhee, J. C., Idsvoog, D., Pate, C., Scheuer, T., and Catterall, W. A. The Role of Amino Acid Residues in Transmembrane Segments IS6 and IIS6 of the Sodium Channel α-Subunit in Voltage-Dependent Gating and Drug Block. *J. Biol. Chem.* 2002, 277, 35393-35401.

Yu F H, Catterall W A. Overview of the voltage-gated sodium channel family. Genome Biol 2003; 4:207-14.

Yu F H, Westernbroek R E, Silos-Santiago I, et al. Sodium channel ☐4, a new disulfide-linked auxiliary subunit with similarity to ☐2. J Neuro 2003; 23:7577-85.

Yu, F. H., and Catterall, W. A. Overview of the Voltage-Gated Sodium Channel Family. *Genome Biology* 2003, 4, 207.

Yuan and Altman, *EMBO J* 14:159-168 (1995)

Yuan et al., *Proc. Natl. Acad. Sci. USA* 89:8006-8010 (1992)

Zha, C., Brown, G., and Brouillette, W. Synthesis and Structure-Activity Relationship Studies for Hydantoins and Analogues as Voltage-Gated Sodium Channel Ligands. *J. Med. Chem.* 2004, 47, 6519-6528.

Zheng, S., El-Naggar, A. K., Kim, E. S., Kurie, J. M., and Lozano, G. A Genetic Mouse Model for Metastatic Lung Cancer with Gender Differences in Survival. *Oncogene* 2007, 26, 6896-6904.

Zoller, Current Opinion in Biotechnology, 3:348-354 (1992)

Zuker, M. *Science* 244:48-52, 1989

What is claimed is:

1. A compound comprising:

a residue that can bind to one or more isoforms of an ion channel to modulate ion flow across said channel, wherein the residue is selected from the group consisting of hermitamide A, hermitamide B, diphenyl hydantoin, an enantiomer of 2-(3-chloro-phenyl)-2-hydroxy-nonanoic acid amide, and a N-(5-(4-(3-chlorophenyl)-2,5-dioxoimidazolidin-4-yl)pentyl)-species, a lipophilic linker or optionally a covalent bond, wherein the linker is a linear, branched or cyclic $C_1$-$C_{11}$ hydrocarbon residue, and wherein the backbone atoms of the linker are carbons, and a fluorophore moiety, wherein the fluorophore moiety is selected from the group consisting of dansyl, 4-(Diethylamino)azobenzene-4'-sulfonyl, fluorescein isothiocyanate (FITC), 5,6-carboxymethyl fluorescein, Texas red, nitrobenz-2-oxa-1,3-diazol-4-yl (NBD), coumarin, dansyl chloride, rhodamine, amino-methyl coumarin (AMCA), Eosin, Erythrosin, BODIPY®, Cascade Blue®, Oregon Green®, pyrene, lissamine, xanthenes, acridines, oxazines, phycoerythrin, macrocyclic chelates of lanthanide ions, quantum Dye™, fluorescent energy transfer dyes, thiazole orange-ethidium heterodimer, the cyanine dyes Cy3, Cy3.5, Cy5, Cy5.5 and Cy7,3-Hydroxypyrene 5,8,10-Tri Sulfonic acid, 5-Hydroxy Tryptamine (5-HT), Acid Fuchsin, Alizarin Complexon, Alizarin Red, Allophycocyanin, Aminocoumarin, Anthroyl Stearate, Astrazon Brilliant Red 4G, Astrazon Orange R, Astrazon Red 6B, Astrazon Yellow 7 GLL, Atabrine, Auramine, Aurophosphine, Aurophosphine G, BAO 9 (Bisaminophenyloxadiazole), BCECF, Berberine Sulphate, Bisbenzamide, Blancophor FFG Solution, Blancophor SV, Bodipy Fl, Brilliant Sulphoflavin FF, Calcien Blue, Calcium Green, Calcofluor RW Solution, Calcofluor White, Calcophor White ABT Solution, Calcophor White Standard Solution, Carbostyryl, Cascade Yellow, Catecholamine, Chinacrine, Coriphosphine O, Coumarin-Phalloidin, CY3.18, CY5.18, CY7, Dans (1-Dimethyl Amino Naphaline 5 Sulphonic Acid), Dansa (Diamino Naphtyl Sulphonic Acid), Dansyl NH—CH3, Diamino Phenyl Oxydiazole (DAO), Dimethylamino-5-Sulphonic acid, Dipyrromethenboron Difluoride, Diphenyl Brilliant Flavine 7GFF, Dopamine, Erythrosin ITC, Euchrysin, FIF (Formaldehyde Induced Fluorescence), Flazo Orange, Fluo 3, Fluorescamine, Fura-2, Genacryl Brilliant Red B, Genacryl Brilliant Yellow 10GF, Genacryl Pink 3G, Genacryl Yellow 5GF, Gloxalic Acid, Granular Blue, Haematoporphyrin, Indo-1, Intrawhite Cf Liquid, Leucophor PAF, Leucophor SF, Leucophor WS, Lissamine Rhodamine B200 (RD200), Lucifer Yellow CH, Lucifer Yellow VS, Magdala Red, Marina Blue, Maxilon Brilliant Flavin 10 GFF, Maxilon Brilliant Flavin 8 GFF, MPS (Methyl Green Pyronine Stilbene), Mithramycin, NBD Amine, Nitrobenzoxadidole, Noradrenaline, Nuclear Fast Red, Nuclear Yellow, Nylosan Brilliant Flavin E8G, Oxadiazole, Pacific Blue, Pararosaniline (Feulgen), Phorwite AR Solution, Phorwite BKL, Phorwite Rev, Phorwite RPA, Phosphine 3R, Phthalocyanine, Phycoerythrin R, Polyazaindacene Pontochrome Blue Black, Porphyrin, Primuline, Procion Yellow, Pyronine, Pyronine B, Pyrozal Brilliant Flavin 7GF, Quinacrine Mustard, Rhodamine 123, Rhodamine 5 GLD, Rhodamine 6G, Rhodamine B, Rhodamine B 200, Rhodamine B Extra, Rhodamine BB, Rhodamine BG, Rhodamine WT, Serotonin, Sevron Brilliant Red 2B, Sevron Brilliant Red 4G, Sevron Brilliant Red B, Sevron Orange, Sevron Yellow L, SITS (Primuline), SITS (Stilbene Isothiosulphonic acid), Stilbene, Snarf 1, sulpho Rhodamine B Can C, Sulpho Rhodamine G Extra, Tetracycline, Thiazine Red R, Thioflavin S, Thioflavin TCN, Thioflavin 5, Thiolyte, Thiozol Orange, Tinopol CBS, True Blue, Ultralite, Uranine B, Uvitex SFC, Xylene Orange, and XRITC, wherein the linker is covalently bonded to each of the residue and the fluorophore moiety.

2. A composition comprising any of the compounds of claim 1.

3. A method of treating prostate cancer comprising administering to a mammal in need thereof a composition according to claim 2.

4. A method of assessing the presence of prostate cancer in a mammalian patient, wherein the method comprises a step in which an ion channel containing tissue culture from the patient is treated with a composition containing a compound according to claim 1.

5. A method for investigating cell proliferation, electrical depolarization of a tissue, or another phenomenon mediated by ion migration across an ion channel, comprising treating a cell culture, tissue culture, or other sample containing an ion channel, with a composition comprising a compound according to claim 1, and assessing the location and intensity of fluorescence in the sample.

6. The compound of claim 1, wherein the linker has between 2 and 7 backbone atoms between the residue and the fluorophore moiety.

7. A pharmaceutical composition comprising a compound of claim 6.

8. A method of treating prostate cancer comprising administering to a mammal in need thereof a pharmaceutical composition according to claim 7.

9. A method of assessing the presence of prostate cancer in a mammalian patient, wherein the method comprises a step in which an ion channel containing tissue culture from the patient is treated with a composition containing a compound according to claim 6.

10. The compound of claim 1, wherein the ion channel is a voltage-gated sodium channel ($Na_v$).

11. The compound of claim 1, wherein the fluorophore moiety comprises an electron donating group in captodative communication with an electron withdrawing group.

12. The compound of claim 1, wherein the residue comprises hermitamide A.

13. The compound of claim 1, wherein the residue comprises hermitamide B.

14. The compound of claim 1, wherein the residue comprises an enantiomer of 2-(3-chloro-phenyl)-2-hydroxy-nonanoic acid amide.

15. The compound of claim 1, wherein the residue is a N-(5-(4-(3-chlorophenyl)-2,5-dioxoimidazolidin-4-yl)pentyl)-species.

16. The compound of claim 1, wherein the lipophilic side chain is further substituted with a moiety selected from the group consisting of halogen, $C_1$-$C_4$ organic group, $C_1$-$C_4$ ether, $C_1$-$C_4$ ester, $C_1$-$C_4$ sulfester, $C_1$-$C_4$ phosphoester, mono- or di-$C_1$-$C_4$ alkylamine, $C_1$-$C_4$ amide, $C_1$-$C_4$ sulfamide, $C_1$-$C_4$ phosphoamide, and imidazolidine-2,4-dilactone.

17. The compound of claim 1, wherein the residue is diphenyl hydantoin.

18. The compound of claim 1, wherein fluorophore moiety is 5-(dimethylamino)naphthalene sulfamide (dansyl).

19. The compound of claim 1, wherein the linker is alkyl, alkenyl, alkynyl, polyether, polyethylene glycol, polyethylene alkyl ether, polypropylene glycol, polypropylene glycol alkyl ether, polyalkylamine, and wherein the backbone is optionally substituted with an ester, sulfoester, phosphoester, amide, sulfamide, or phosphoamide moiety.

20. The compound of claim 1, wherein the linker has between 7 backbone atoms between the residue and the fluorophore moiety.

21. A compound comprising a residue that can bind to one or more isoforms of an ion channel to modulate ion flow across said channel, a lipophilic linker or optionally a covalent bond, and a fluorophore moiety, wherein the linker is covalently bonded to each of the residue and the fluorophore moiety, wherein the residue is selected from the group consisting of hermitamide A, hermitamide B, an enantiomer of 2-(3-chloro-phenyl)-2-hydroxy-nonanoic acid amide, and a N-(5-(4-(3-chlorophenyl)-2,5-dioxoimidazolidin-4-yl) pentyl)-species, wherein the linker is a linear, branched or cyclic $C_1$-$C_{11}$ hydrocarbon residue, and wherein the backbone atoms of the linker are carbons, and wherein the fluorophore moiety comprises an electron donating group in captodative communication with an electron withdrawing group.

* * * * *

UNITED STATES PATENT AND TRADEMARK OFFICE
CERTIFICATE OF CORRECTION

| | |
|---|---|
| PATENT NO. | : 8,816,095 B2 |
| APPLICATION NO. | : 13/059182 |
| DATED | : August 26, 2014 |
| INVENTOR(S) | : Milton L. Brown et al. |

It is certified that error appears in the above-identified patent and that said Letters Patent is hereby corrected as shown below:

In the Specification

Column 1, Lines 13-15, replace the following paragraph:
"This invention was developed using funds from federal NIH-ROI grant CA105534-04, 7CA105435 and NIH grant nos. NIH-ROI grant CA105534-04."

With the following paragraph:
--This invention was made with government support under grant numbers CA105537 and CA105534 awarded by the National Institutes of Health. The government has certain rights in the invention.--

Signed and Sealed this
Seventh Day of November, 2023

Katherine Kelly Vidal
*Director of the United States Patent and Trademark Office*